(12) United States Patent
Song et al.

(10) Patent No.: US 12,396,745 B2
(45) Date of Patent: Aug. 26, 2025

(54) SURGERY INSTRUMENT

(71) Applicant: LIVSMED INC., Seongnam-si (KR)

(72) Inventors: Youngjae Song, Seongnam-si (KR); Jaeyeong Lee, Seongnam-si (KR); Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/757,036

(22) Filed: Jun. 27, 2024

(65) Prior Publication Data

US 2024/0350160 A1 Oct. 24, 2024

Related U.S. Application Data

(63) Continuation of application No. PCT/KR2022/021631, filed on Dec. 29, 2022.

(30) Foreign Application Priority Data

Dec. 29, 2021 (KR) .......................... 10-2021-0191880

(51) Int. Cl.
*A61B 17/29* (2006.01)
*A61B 34/30* (2016.01)
*A61B 34/37* (2016.01)
*A61B 17/00* (2006.01)

(52) U.S. Cl.
CPC .............. *A61B 17/29* (2013.01); *A61B 34/37* (2016.02); *A61B 2017/00199* (2013.01); *A61B 2017/00212* (2013.01); *A61B 2017/00398* (2013.01); *A61B 2017/00477* (2013.01); *A61B 2017/2903* (2013.01); *A61B 2017/2929* (2013.01); *A61B 2017/294* (2013.01); *A61B 2017/2944* (2013.01); *A61B 2034/302* (2016.02); *A61B 2034/305* (2016.02)

(58) Field of Classification Search
CPC ......... A61B 34/71; A61B 34/70; A61B 34/30; A61B 34/37; A61B 2034/305; A61B 2017/00477

See application file for complete search history.

(56) References Cited

U.S. PATENT DOCUMENTS

| 6,331,181 | B1 | 12/2001 | Tierney et al. |
| 6,783,524 | B2 | 8/2004 | Anderson et al. |
| 2002/0111621 | A1 | 8/2002 | Wallace et al. |

(Continued)

FOREIGN PATENT DOCUMENTS

| CN | 112043394 A | 12/2020 |
| CN | 112617968 A | 4/2021 |

(Continued)

*Primary Examiner* — Katherine H Schwiker
(74) *Attorney, Agent, or Firm* — Bridgeway IP Law Group, PLLC; Sang Ho Lee; Hyun Woo Shin

(57) ABSTRACT

The present disclosure relates to an end tool of a surgical instrument, and more particularly, to an end tool of a surgical instrument capable of being mounted on a robot arm or operated manually for use in laparoscopic surgery or various surgeries, the multi-joint type surgical device capable of independently and smoothly performing a pitch motion and a yaw motion/actuation motion by compensating for jaw wire movement that occurs during the pitch motion.

27 Claims, 106 Drawing Sheets

(56) References Cited

U.S. PATENT DOCUMENTS

| | | |
|---|---|---|
| 2006/0079889 A1 | 4/2006 | Scott |
| 2014/0350570 A1 | 11/2014 | Lee |
| 2017/0172553 A1* | 6/2017 | Chaplin ................. A61B 34/30 |
| 2019/0328467 A1* | 10/2019 | Waterbury ............. A61B 34/30 |
| 2020/0305992 A1 | 10/2020 | Schuh et al. |

FOREIGN PATENT DOCUMENTS

| | | |
|---|---|---|
| JP | 2004-301275 A | 10/2004 |
| JP | 2011-200593 A | 10/2011 |
| JP | 2018-538065 A | 12/2018 |
| JP | 2021-153858 A | 10/2021 |
| KR | 10-2308205 B1 | 10/2021 |
| WO | 2022/231337 A1 | 11/2022 |

* cited by examiner

FIG. 14
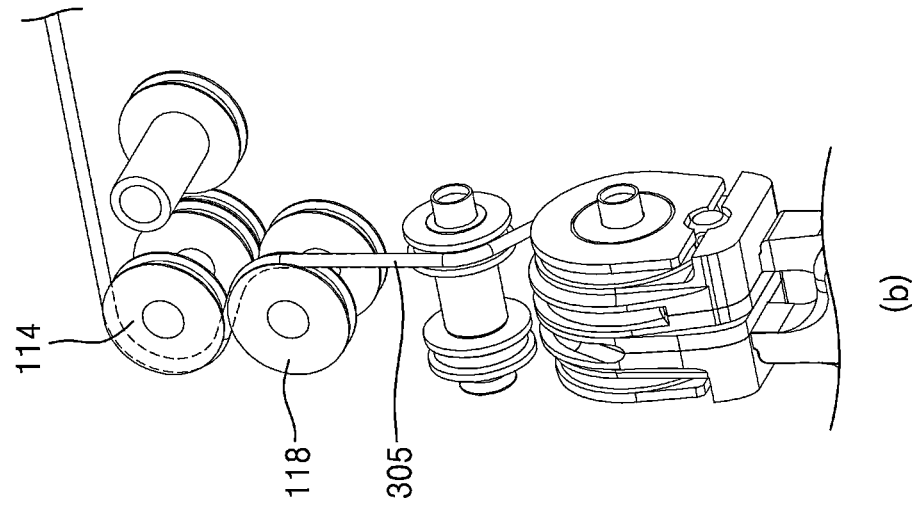
(b)
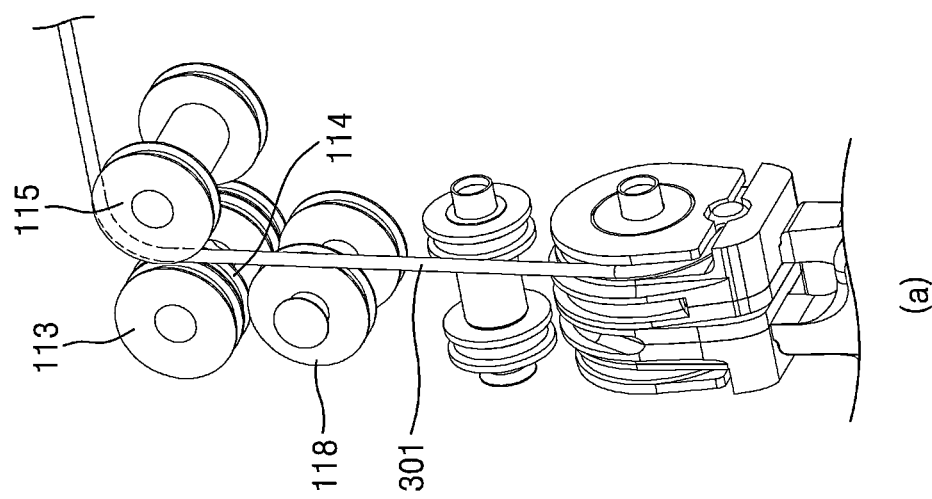
(a)

FIG. 70
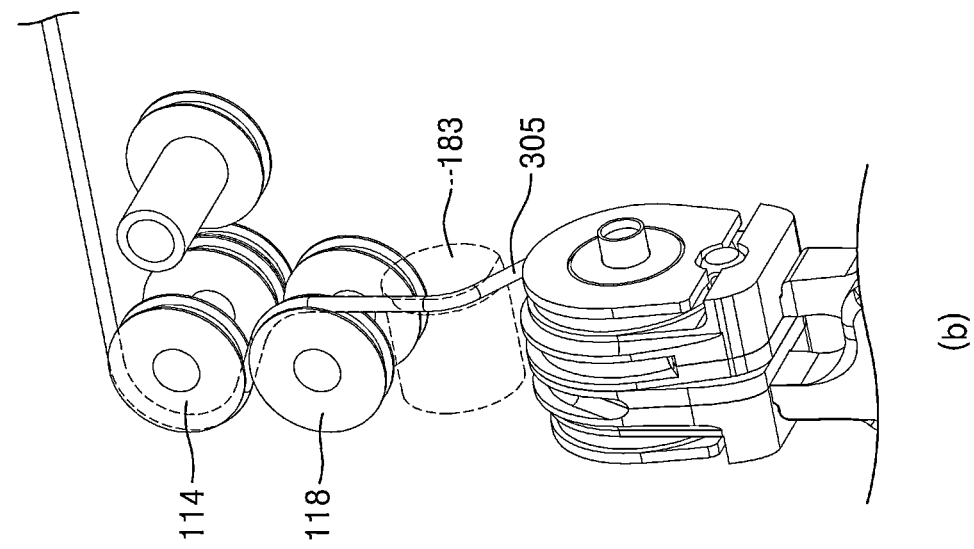
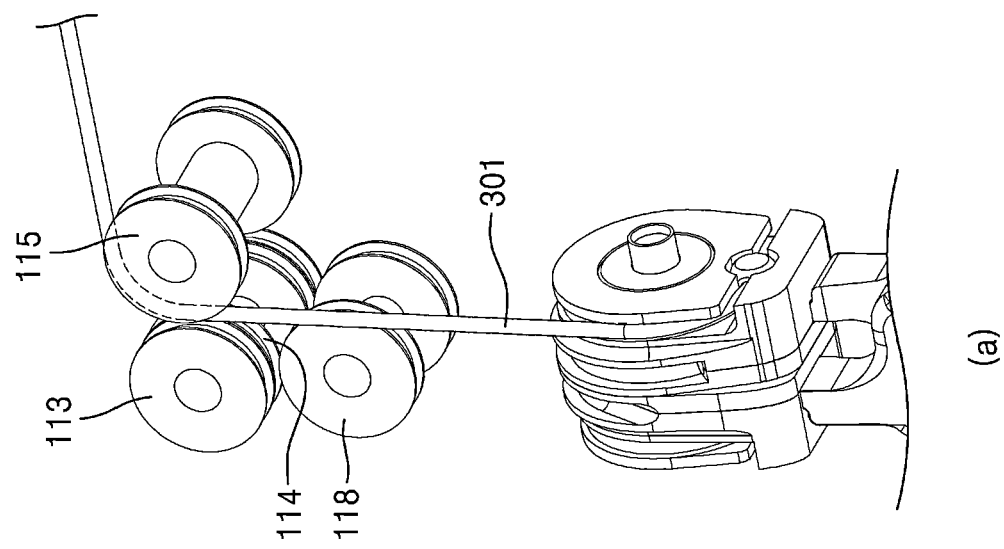

SURGERY INSTRUMENT

CROSS-REFERENCE TO RELATED APPLICATION

This application is a continuation application of International Application No. PCT/KR2022/021631, filed on Dec. 29, 2022, and claims priority to Korean Application No. 10-2021-0191880, filed on Dec. 29, 2021, in the Korean Intellectual Property Office, the entire disclosures of which are incorporated herein by reference.

TECHNICAL FIELD

The present disclosure relates to a surgical instrument, and more particularly, to a surgical instrument capable of being mounted on a robot arm or operated manually for use in laparoscopic surgery or various surgeries.

BACKGROUND ART

Medically, surgery refers to the treatment of diseases by cutting, slitting, or manipulating the skin, mucous membranes, or other tissues using medical devices In particular, open surgery in which the skin of the surgical site is incised and opened to treat, shape, remove organs or the like therein and the like cause problems such as bleeding, side effects, patient pain, scarring. Accordingly, recently, surgery performed by inserting only a medical device, for example, laparoscopic surgical instrument, microsurgical microscope, and the like by forming a predetermined hole in the skin or surgery using a robot has been spotlighted as an alternative.

Here, a surgical robot refers to a robot that has a function of replacing a surgical action performed by a surgeon. Advantageously, the surgical robot may operate more accurately and precisely as compared with a human and enable remote operation.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery using a laparoscope and small surgical instruments.

Laparoscopic surgery is a cutting-edge surgery technique that involves perforating one or more small holes in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, can be obtained and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) equipped on the master robot, a surgical tool coupled to or held by a robot arm on the slave robot may be manipulated to perform surgery.

DESCRIPTION OF EMBODIMENTS

Technical Problem

The present disclosure is directed to providing a multi-joint type surgical device capable of being mounted on a robot arm or operated manually for use in laparoscopic surgery or various surgeries, the multi-joint type surgical device capable of independently and smoothly performing a pitch motion and a yaw motion/actuation motion by compensating for jaw wire movement that occurs during the pitch motion.

Technical Solution to Problem

One aspect of the present disclosure provides a surgical instrument comprising: an end tool including one or more jaws, and an end tool jaw pulley coupled to the jaws and formed to be rotatable together with the jaws around a first shaft, the end tool being formed to allow at least a pitch rotation and a yaw rotation; a jaw wire coupled to the end tool jaw pulley and moved in response to rotation of the end tool jaw pulley; a connection part formed to extend in one direction, having the jaw wire passing therethrough, and having one end portion to which the end tool is coupled; and a driving part coupled to another end portion of the connection part and configured to control the pitch rotation and the yaw rotation of the end tool, wherein the driving part includes: a driving part jaw pulley formed to be rotatable around a second shaft and coupled to the jaw wire; and a driving part pitch pulley disposed adjacent to the driving part jaw pulley and formed to be rotatable around a third shaft different from the second shaft, and when the driving part pitch pulley is rotated for the pitch rotation of the end tool, the driving part jaw pulley is also rotated.

In an embodiment of the present disclosure, a relative position of the driving part pitch pulley and the driving part jaw pulley remains constant.

In an embodiment of the present disclosure, when the driving part pitch pulley is rotated around the third shaft, the driving part jaw pulley is rotated around the second shaft to change a length of the jaw wire in the driving part.

In an embodiment of the present disclosure, as the length of the jaw wire in the driving part is changed due to the rotation of the driving part jaw pulley, a length of the jaw wire in the end tool is changed.

In an embodiment of the present disclosure, even when the length of the jaw wire in the driving part is changed due to the rotation of the driving part jaw pulley, an overall length of the jaw wire remains constant.

In an embodiment of the present disclosure, the jaws include a first jaw and a second jaw formed to face the first jaw, the end tool jaw pulley includes a first jaw pulley coupled to the first jaw and formed to be rotatable around the first shaft, and a second jaw pulley coupled to the second jaw and formed to be rotatable around a shaft substantially equal to or parallel to the first shaft and to face the first jaw pulley, the jaw wire includes a first jaw wire coupled to the first jaw pulley to rotate the first jaw pulley, and a second jaw wire coupled to the second jaw pulley to rotate the second jaw pulley, and the driving part jaw pulley includes a driving part first jaw pulley coupled to the first jaw wire to move the first jaw wire, and a driving part second jaw pulley coupled to the second jaw wire to move the second jaw wire.

In an embodiment of the present disclosure, the end tool includes: a pair of first jaw pitch main pulleys formed on one side of the first jaw pulley and formed to be rotatable around a fourth shaft that forms a predetermined angle with the first shaft; a pair of second jaw pitch main pulleys formed on one side of the second jaw pulley and formed to be rotatable around a shaft substantially equal to or parallel to the fourth shaft; a first jaw pitch redundant pulley disposed between the first jaw pulley and the pair of first jaw pitch main pulleys and formed to be rotatable around a fifth shaft; and a second jaw pitch redundant pulley disposed between the second jaw pulley and the pair of second jaw pitch main pulleys and formed to be rotatable around a sixth shaft, wherein the first jaw wire is wound around at least some of the pair of first jaw pitch main pulleys, and the second jaw wire is wound around at least some of the pair of second jaw pitch main pulleys.

In an embodiment of the present disclosure, while moving from a proximal end of the end tool toward a distal end of the end tool, of two strands of the first jaw wire coupled to the first jaw pulley, one strand of the first jaw wire is wound in one direction of a clockwise direction and a counterclockwise direction around the first jaw pitch main pulley, and another strand of the first jaw wire is wound in another direction of the clockwise direction and the counterclockwise direction around the first jaw pitch main pulley.

In an embodiment of the present disclosure, based on a plane perpendicular to the first shaft and passing between the first jaw pulley and the second jaw pulley, of two strands of the first jaw wire coupled to the first jaw pulley, one strand of the first jaw wire comes into contact with an upper side of the first jaw pitch main pulley, and another strand of the first jaw wire comes into contact with a lower side of the first jaw pitch main pulley.

In an embodiment of the present disclosure, while moving from a proximal end of the end tool toward a distal end of the end tool, the first jaw wire sequentially comes into contact with the first jaw pitch main pulley and the first jaw pitch redundant pulley.

In an embodiment of the present disclosure, based on a plane perpendicular to the first shaft and passing between the first jaw pulley and the second jaw pulley, of two strands of the first jaw wire coupled to the first jaw pulley, one strand of the first jaw wire sequentially comes into contact with a lower side of the first jaw pitch main pulley and a lower side of the first jaw pitch redundant pulley, and of the two strands of the first jaw wire coupled to the first jaw pulley, another strand of the first jaw wire sequentially comes into contact with an upper side of the first jaw pitch main pulley and an upper side of the first jaw pitch redundant pulley.

In an embodiment of the present disclosure, a first jaw auxiliary pulley formed between the first jaw pulley and the first jaw pitch redundant pulley; and a second jaw auxiliary pulley formed between the second jaw pulley and the second jaw pitch redundant pulley.

In an embodiment of the present disclosure, the first jaw wire is located on a common internal tangent of the first jaw pulley and the first jaw auxiliary pulley, and a rotation angle of the first jaw pulley is increased by the first jaw auxiliary pulley.

In an embodiment of the present disclosure, further comprising: one or more first jaw pitch sub-pulleys formed on one side of the first jaw pitch main pulley and formed to be rotatable around a shaft substantially parallel to the fourth shaft; and one or more second jaw pitch sub-pulleys formed on one side of the second jaw pitch main pulley and formed to be rotatable around a shaft substantially parallel to the fourth shaft.

In an embodiment of the present disclosure, the first jaw pitch sub-pulley or the second jaw pitch sub-pulley includes only one pulley.

In an embodiment of the present disclosure, further comprising: an end tool hub formed to internally accommodate at least some of the first jaw and the second jaw; and a pitch hub formed to be rotatable relative to the end tool hub by being axially coupled to the end tool hub.

In an embodiment of the present disclosure, the first jaw and the second jaw are rotated around the first shaft to perform a yaw motion, and the end tool hub is rotated around the fourth shaft to perform a pitch motion.

In an embodiment of the present disclosure, further comprising: an end tool pitch pulley formed on an end portion of the end tool hub at a proximal end side; and a pitch wire coupled to the end tool pitch pulley to rotate the end tool pitch pulley.

In an embodiment of the present disclosure, when the end tool pitch pulley is rotated by the pitch wire, the end tool hub is rotated as a whole together with the end tool pitch pulley to change a length of the first jaw wire wound around the first jaw pitch main pulley and the second jaw pitch main pulley.

In an embodiment of the present disclosure, when the end tool pitch pulley is rotated by the pitch wire, the first jaw wire is moved to a certain degree by an external force in order to compensate for an amount of change in the length by which the first jaw wire is wound around the first jaw pitch main pulley and the second jaw pitch main pulley.

In an embodiment of the present disclosure, the first jaw pitch redundant pulley or the second jaw pitch redundant pulley is integrally formed with the end tool hub.

In an embodiment of the present disclosure, the fifth shaft and the sixth shaft are substantially parallel to the fourth shaft.

In an embodiment of the present disclosure, the fifth shaft and the sixth shaft are formed to be inclined with respect to the first shaft and the fourth shaft, respectively.

In an embodiment of the present disclosure, a groove of the first jaw pulley around which the first jaw wire is wound and a groove of the second jaw pulley around which the second jaw wire is wound are formed to be spaced apart from each other by a certain degree.

In an embodiment of the present disclosure, a groove of the first jaw pulley around which the first jaw wire is wound and a groove of the second jaw pulley around which the second jaw wire is wound are formed to be adjacent to each other.

In an embodiment of the present disclosure, the first jaw pitch redundant pulley or the second jaw pitch redundant pulley includes only one pulley.

In an embodiment of the present disclosure, when the driving part pitch pulley of the driving part is rotated for a pitch motion, a driving part first jaw pulley and a driving part second jaw pulley of the driving part are rotated together to compensate for the pitch motion.

In an embodiment of the present disclosure, an end tool hub formed to internally accommodate at least some of the first jaw and the second jaw; a pitch hub formed to be rotatable relative to the end tool hub by being axially coupled to the end tool hub; a first pin formed to be inserted through the end tool hub, and formed to extend in a first direction; a second pin inserted through the end tool hub, formed to be parallel to the first pin, and formed on one side of the first pin; a 2.5th pin inserted through the end tool hub, formed to extend in a second direction forming a predetermined angle with the first direction, and formed on one side of the second pin; a third pin inserted through the end tool hub and the pitch hub, formed to be parallel to the 2.5th pin, and formed on one side of the 2.5th pin; a fourth pin inserted through the pitch hub, formed to be parallel to the third pin, and formed on one side of the third pin; a first jaw auxiliary pulley formed on one side of the first jaw pulley, and formed to be rotatable around the second pin; a second jaw auxiliary pulley formed on one side of the second jaw pulley, and formed to be rotatable around the second pin; one or more first jaw pitch redundant pulleys formed on one side of the first jaw auxiliary pulley, and formed to be rotatable around the 2.5th pin; one or more second jaw pitch redundant pulleys formed on one side of the second jaw auxiliary pulley, and formed to be rotatable around the 2.5th pin; a pair of first jaw pitch main pulleys formed on one side of the first jaw pitch redundant pulley, and formed to be rotatable around the third pin; a pair of second jaw pitch main pulleys formed on one side of the second jaw pitch redundant pulley, and formed to be rotatable around the third pin; one or more first jaw pitch sub-pulleys formed on one side of the first jaw pitch main pulley, and formed to be rotatable around the fourth pin; and one or more second jaw pitch sub-pulleys formed on one side of the second jaw pitch main pulley, and formed to be rotatable around the fourth pin.

In an embodiment of the present disclosure, an end tool hub formed to internally accommodate at least some of the first jaw and the second jaw; a pitch hub formed to be rotatable relative to the end tool hub by being axially coupled to the end tool hub; a first pin formed to be inserted through the end tool hub, and formed to extend in a first direction; a second pin inserted through the end tool hub, formed to extend in a second direction forming a predetermined angle with the first direction, and formed on one side of the first pin; a third pin inserted through the end tool hub and the pitch hub, formed to extend in a third direction forming a predetermined angle with the first direction and the second direction, and formed on one side of the second pin; a fourth pin inserted through the pitch hub, formed to be parallel to the third pin, and formed on one side of the third pin; a first jaw auxiliary pulley formed on one side of the first jaw pulley, and formed to be rotatable around the second pin; a second jaw auxiliary pulley formed on one side of the second jaw pulley, and formed to be rotatable around the second pin; a pair of first jaw pitch main pulleys formed on one side of the first jaw auxiliary pulley, and formed to be rotatable around the third pin; a pair of second jaw pitch main pulleys formed on one side of the second jaw auxiliary pulley, and formed to be rotatable around the third pin; one or more first jaw pitch sub-pulleys formed on one side of the first jaw pitch main pulley, and formed to be rotatable around the fourth pin; and one or more second jaw pitch sub-pulleys formed on one side of the second jaw pitch main pulley, and formed to be rotatable around the fourth pin.

Advantageous Effects of Disclosure

According to the present disclosure, a pitch motion and a yaw motion/actuation motion can be smoothly performed independently by compensating for jaw wire movement occurring during the pitch motion.

BRIEF DESCRIPTION OF DRAWINGS

FIG. 14 is a side view illustrating a state in which the end tool of the surgical instrument of FIG. 5 is pitch-rotated by +90°.

FIG. 70 is a side view illustrating a state in which the end tool of the surgical instrument of FIG. 64 is pitch-rotated by +90°.

MODE OF DISCLOSURE

Figure 1:
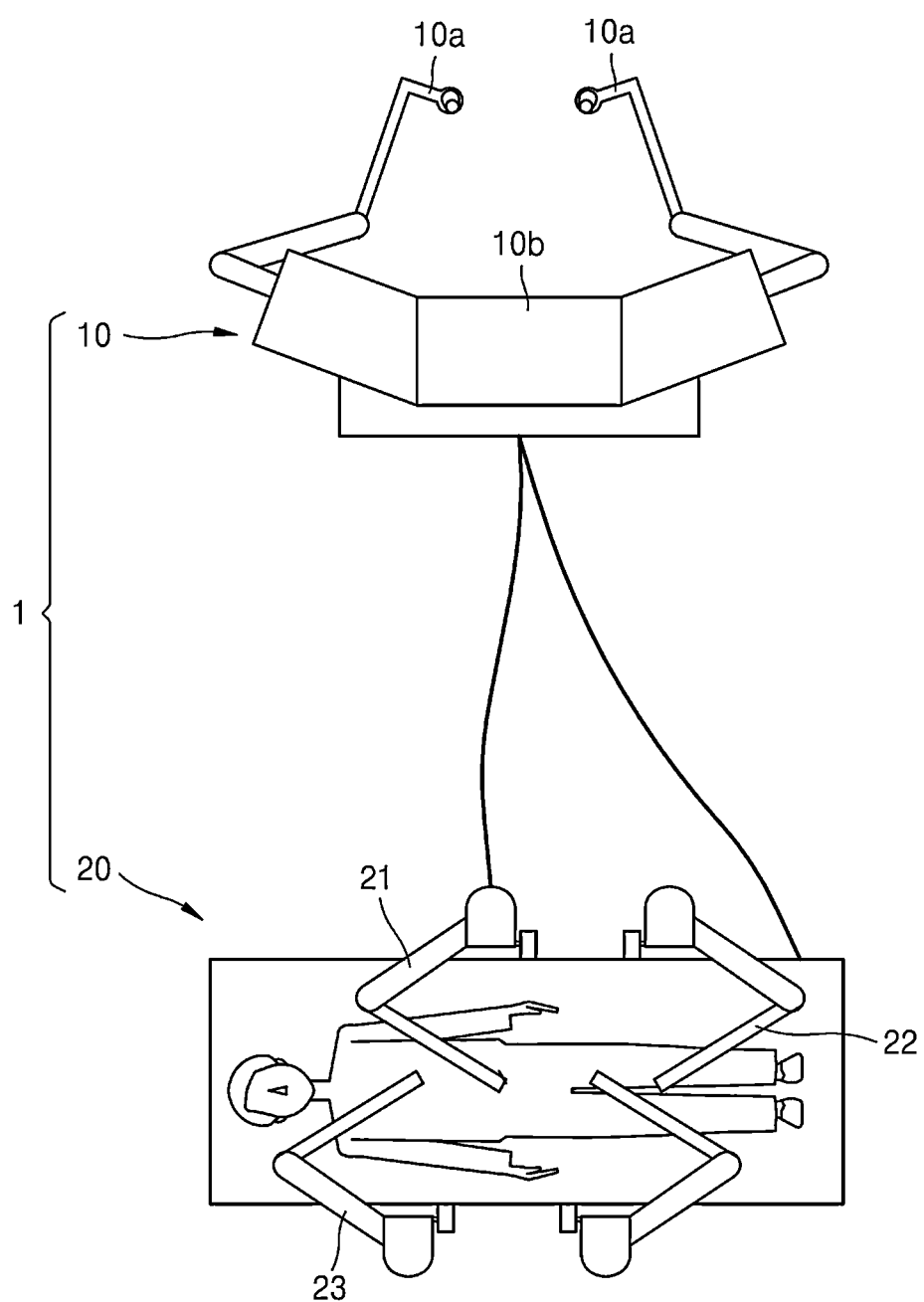
FIG. 1 is a conceptual view illustrating a surgical robot system to which a surgical instrument according to an embodiment of the present disclosure is mounted.

While the present disclosure is susceptible to various modifications and alternative forms, specific embodiments thereof are shown by way of example in the drawings and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, a detailed description of known related arts will be omitted when it is determined that the gist of the present disclosure may be unnecessarily obscured Although terms such as "first", "second", and the like may be used to describe various components, such components should not be limited to the above terms The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise", "comprising", "include", and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

Figure 2:
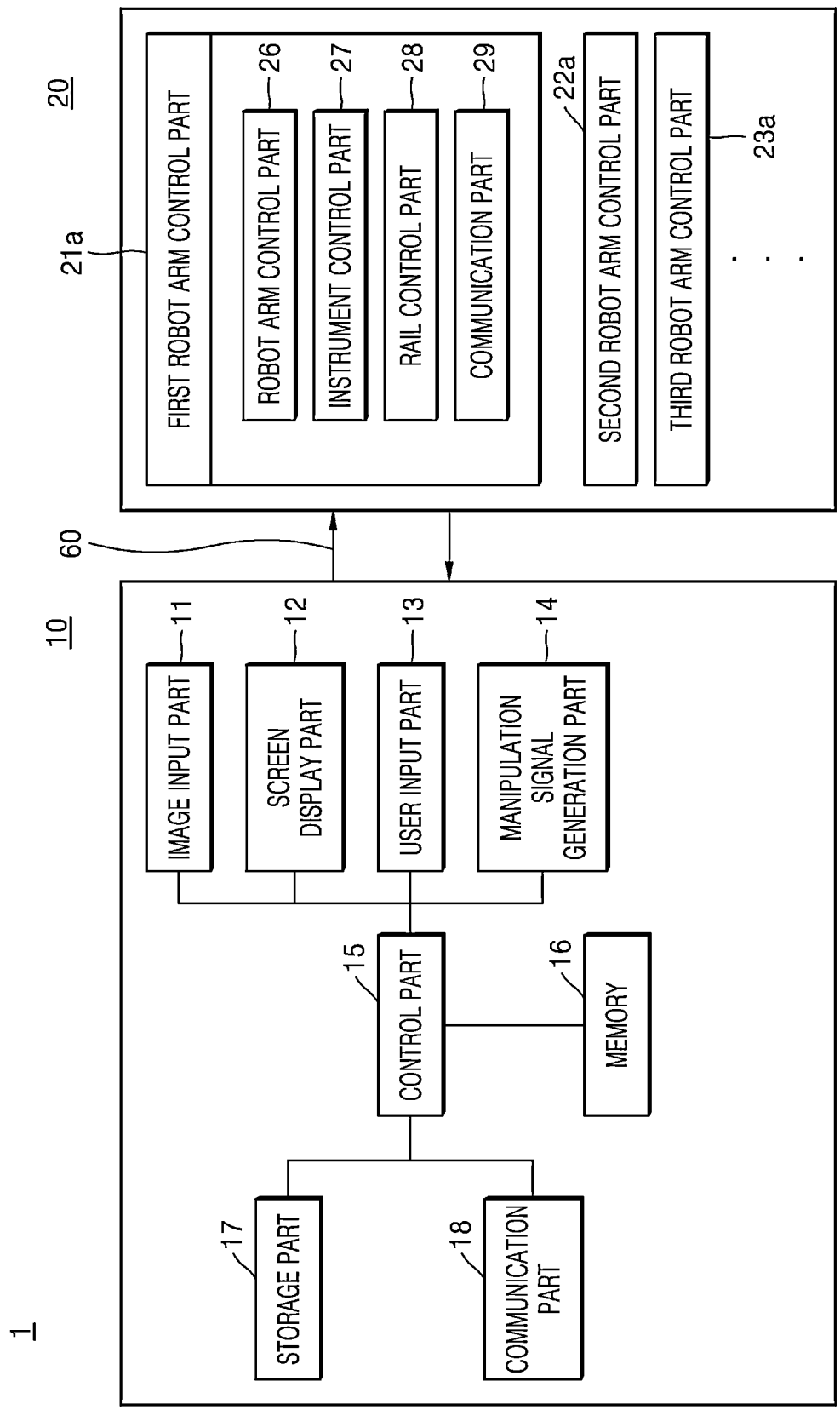
FIG. 2 is a block diagram illustrating an internal configuration of the surgical robot system of FIG. 1.
Figure 3:
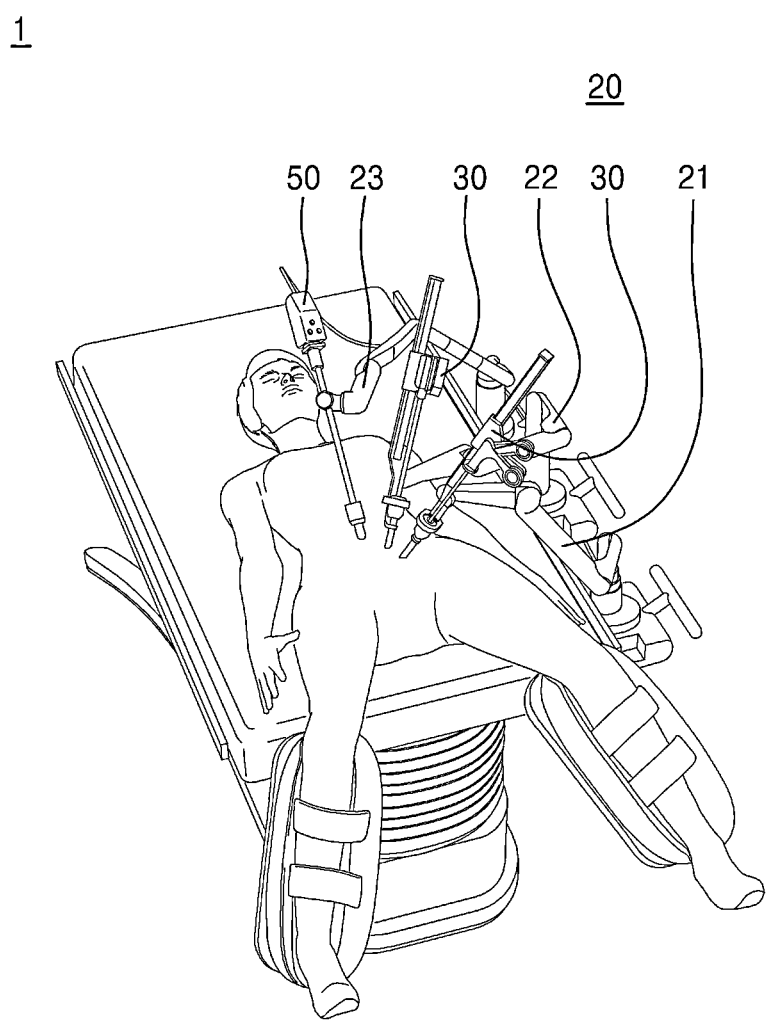
FIG. 3 is a perspective view illustrating a slave robot of the surgical robot system of FIG. 1.

FIG. 1 is a conceptual diagram illustrating a surgical robot system to which a multi-joint type surgical device according to an embodiment of the present disclosure is mounted, FIG. 2 is a block diagram illustrating an internal configuration of the surgical robot system of FIG. 1, and FIG. 3 is a perspective view illustrating a slave robot of the surgical robot system of FIG. 1 and the multi-joint type surgical device mounted thereto.

Referring to FIGS. 1 to 3, a surgical robot system 1 includes a master robot 10, a slave robot 20, and a multi-joint type surgical device 30.

The master robot 10 includes manipulating members 10a and a display member 10b, and the slave robot 20 includes one or more robot arm units 21, 22, and 23.

In detail, the master robot 10 includes the manipulating members 10a so that a surgical operator can grip and manipulate them respectively with both hands. The manipulating members 10a may be implemented as two or more handles as illustrated in FIG. 1, and manipulation signals according to the handle manipulation of the surgical operator are transmitted to the slave robot 20 through a wired or wireless communication network so that the robot arm units 21, 22, and 23 are controlled. That is, surgical motions such as positioning, rotation, and cutting operations of the robot arm units 21, 22, and 23 may be performed by the handle manipulation of the surgical operator.

For example, the surgical operator may manipulate the robot arm units 21, 22, and 23 using manipulation levers in the form of a handle. The manipulation lever as described above may have various mechanical configurations according to the manipulate method thereof, and may be provided in various configurations for operating the robot arm units 21, 22, and 23 of the slave robot 20 and/or other surgical instruments, such as a master handle manipulating the motion of each of the robot arm units 21, 22, and 23 and various input tools added to the master robot 10 for manipulating the functions of the entire system such as joystick, keypad, trackball, foot pedal, and touch screen. Here, the manipulating member 10*a* is not limited to the shape of a handle and can be applied without any limitation as long as it can control motions of the robot arm units 21, 22, and 23 through a network such as a wired or wireless communication network.

Alternatively, a voice input or a motion input may also be applied for user input. That is, a user may wear, on the head thereof, glasses or a head mount display (HMD), to which a sensor is attached, and a laparoscope 50 may move according to a direction in which the user's gaze. Alternatively, when the user issues a command with voice, such as "left", "right", "first arm", "second arm", and the like, the voice command may be recognized and the motion may be performed.

An image captured through the laparoscope 50 to be described later is displayed as a screen image on the display member 10*b* of the master robot 10. In addition, a predetermined virtual manipulation plate may be displayed independently or displayed together with the image captured by the laparoscope 50 on the display member 10*b*. A detailed description of the arrangement, configuration, and the like of such a virtual manipulation plate will be omitted.

Here, the display member 10*b* may include one or more monitors, each of which may individually display information necessary for surgery. The quantity of monitors may be variously determined depending on the type or kind of information that needs to be displayed.

Meanwhile, the slave robot 20 may include one or more robot arm units 21, 22, and 23. Here, each of the robot arm units 21, 22, and 23 may be provided in the form of a module that can operate independently of each other, and in this case, an algorithm for preventing a collision between the robot arm units 21, 22, and 23 may be applied to the surgical robot system 1.

In general, a robot arm refers to a device having a function similar to that of the arm and/or the wrist of a human being and having a wrist portion to which a predetermined tool may be attached. In the present specification, the robot arm units 21, 22, and 23 may each be defined as a concept encompassing all of the components such as an upper arm, a lower arm, a wrist, and an elbow, a multi-joint type surgical device coupled to the wrist portion, and the like. Alternatively, the robot arm unit may also be defined as a concept that includes only components for driving the multi-joint type surgical device, excluding the multi-joint type surgical device coupled to the wrist portion.

The robot arm units 21, 22, and 23 of the slave robot 20 described above may be implemented to be driven with multiple degrees of freedom. The robot arm units 21, 22, and 23 may include, for example, a surgical instrument inserted into a surgical site of a patient, a yaw driving part for rotating the surgical instrument in a yaw direction according to a surgical position, a pitch driving part for rotating the surgical instrument in a pitch direction perpendicular to a rotational driving of the yaw driving part, a transfer driving part for moving the surgical instrument in a length direction, a rotation driving part for rotating the surgical instrument, and a surgical instrument driving part for incising or cutting the surgical lesion by driving an end effector at an end of the surgical instrument. However, the configuration of the robot arm units 21, 22, and 23 is not limited thereto, and it should be understood that this example does not limit the scope of the present disclosure. Here, a detailed description of the actual control process, such as rotation and movement of the robot arm units 21, 22, and 23 in a corresponding direction by the surgical operator manipulating the manipulating member 10*a* will be omitted.

Here, two of the robot arm units 21, 22, and 23 may have the multi-joint type surgical device 30 attached thereto, and one of the robot arm units 21, 22, and 23 may have the laparoscope 50 attached thereto. In addition, the surgical operator may select the robot arm unit 21, 22, or 23 to be controlled via the master robot 10. As described above, by directly controlling a total of three or more surgical instruments through the master robot 10, the surgical operator may accurately and freely control various tools according to the intention of the surgical operator without a surgical assistant.

Meanwhile, one or more slave robots 20 may be provided to operate the patient, and the laparoscope 50 for allowing a surgical site to be displayed as a screen image through the display member 10*b* may be implemented as an independent slave robot 20. In addition, as described above, the embodiments of the present disclosure can be used universally for surgeries in which various surgical endoscopes other than laparoscopes (e.g., thoracoscopic, arthroscopic, rhinoscopic, and the like) are used.

Referring to FIG. 2, in an embodiment of the present disclosure, the master robot 10 may include an image input part 11, a screen display part 12, a user input part 13, a manipulation signal generation part 14, a control part 15, a memory 16, a storage part 17, and a communication part 18.

The image input part 11 may receive an image captured by a camera provided in the laparoscope 50 of the slave robot 20 through a wired or wireless communication network.

The screen display part 12 outputs a screen image corresponding to the image received through the image input part 11 as visual information. In addition, the screen display part 12 may further output information corresponding to biometric information of a subject to be treated, when the biometric information is input. In addition, the screen display part 12 may further output image data (e.g., an X-ray image, a CT image, an MRI image, or the like) associated with a patient for a surgical site. Here, the screen display part 12 may be implemented in the form of a display member (see 10*b* of FIG. 1), and an image processing process for allowing the received image to be output as a screen image through the screen display part 12 may be performed by the control part 15.

In the embodiment illustrated in FIG. 2, the image input part and the screen display part are illustrated as being included in the master robot 10, but the present disclosure is not limited thereto. That is, the display member may be provided as a separate member spaced apart from the master robot 10. Alternatively, the display member may be provided as one component of the master robot 10. In addition, in another embodiment, a plurality of display members may be provided, one of which may be disposed adjacent to the master robot 10, and others thereof may be disposed at some distance from the master robot 10.

Here, the screen display part 12 (that is, the display member 10*b* of FIG. 1) may be provided as a three-dimensional display device. In detail, the three-dimensional display device refers to an image display device in which depth information is added to a two-dimensional image by applying a stereoscopic technique, and this depth information is used to enable an observer to feel a three-dimensional living feeling and a sense of reality. The surgical robot system 1 according to an embodiment of the present disclosure may provide a more realistic virtual environment to a user by including a three-dimensional display device as the screen display part 12.

The user input part 13 is a member for allowing the surgical operator to manipulate the positions and functions of the robot arm units 21, 22, and 23 of the slave robot 20. The user input part 13 may be formed in the form of a handle-shaped manipulation member (see 10a of FIG. 1) as illustrated in FIG. 1, but the shape thereof is not limited thereto and may be implemented by being modified in various shapes to achieve the same purpose. In addition, for example, some of the user input part 13 may be formed in the shape of a handle, and the others may be formed in a different shape, such as a clutch button. In addition, a finger insertion tube or insertion ring may be further formed so as to allow the surgical operator's finger to be inserted therethrough and fixed to facilitate manipulation of the surgical tool.

When the surgical operator manipulates the user input part 13 to move the positions of robot arm units 21, 22, and 23 or manipulate surgical operations thereof, the manipulation signal generation part 14 may generate a corresponding manipulation signal, and transmit the manipulation signal to the slave robot 20 through the communication part 18. The manipulation signal may be transmitted and received via a wired or wireless communication network.

The control part 15 is a kind of central processing device, and controls the operation of each component so that the above-described functions can be performed. In an example, the control part 15 may perform a function of converting an image input through the image input part 11 into a screen image to be displayed through the screen display part 12.

The memory 16 may perform a function of temporarily or permanently storing data processed by the control part 15. Here, the memory 16 may include a magnetic storage medium or a flash storage medium, but the scope of the present disclosure is not limited thereto.

The storage part 17 may store data received from the slave robot 20. In addition, the storage part 17 may store various pieces of input data (e.g., patient data, device data, surgery data, and the like).

The communication part 18 interworks with a communication network 60 to provide a communication interface necessary for transmitting and receiving image data transmitted from the slave robot 20 and control data transmitted from the master robot 10.

The slave robot 20 includes a plurality of robot arm unit control parts 21a, 22a, and 23a. In addition, the robot arm unit control part 21a includes a robot arm control part 26, an instrument control part 27, and a communication part 29. In addition, the robot arm unit control part 21a may further include a rail control part 28.

The robot arm control part 26 may receive a manipulation signal generated by the manipulation signal generation part 14 of the master robot 10, and may serve to control the robot arm units 21, 22, and 23 so as to operate according to the manipulation signal.

The instrument control part 27 may receive a manipulation signal generated by the manipulation signal generation part 14 of the master robot 10, and may serve to control the multi-joint type surgical device 30 so as to operate according to the manipulation signal.

The communication part 29 interworks with the communication network 60 to provide a communication interface necessary for transmitting and receiving image data transmitted from the slave robot 20 and control data transmitted from the master robot 10.

Meanwhile, the communication network 60 serves to connect the master robot 10 and the slave robot 20. That is, the communication network 60 refers to a communication network for providing an access path so that data can be transmitted and received between the master robot 10 and the slave robot 20 after the master robot 10 and the slave robot 20 are connected. The communication network 60 may be, for example, a wired network such as local area networks (LANs), wired area networks (WANs), metropolitan area networks (MANs), and integrated service digital networks (ISDNs), or a wireless network such as wireless LANs, code division multiple access (CDMA), Bluetooth, and satellite communication, but the scope of the present disclosure is not limited thereto.

Figure 4:
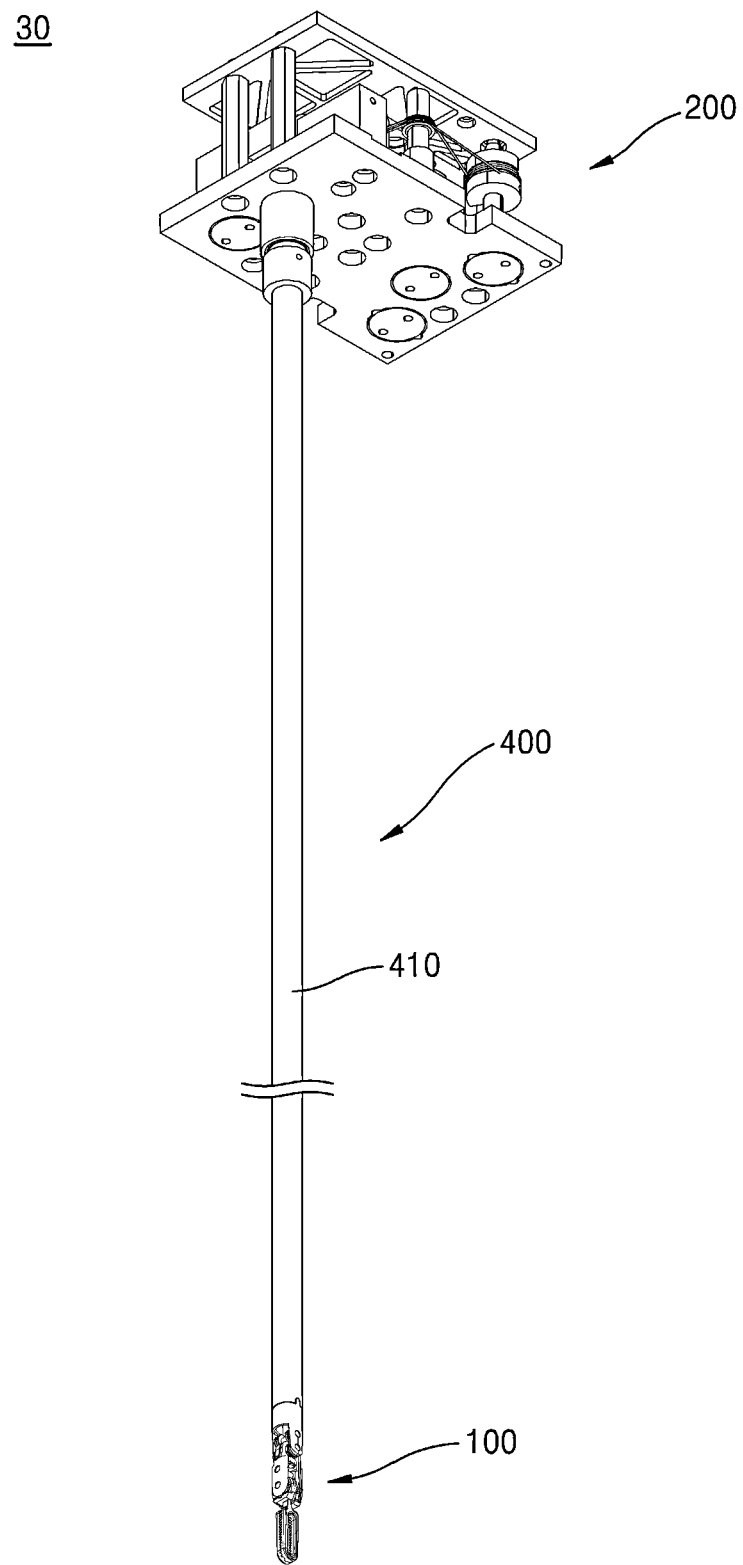
FIG. 4 is a perspective view illustrating a surgical instrument mounted to the slave robot of FIG. 1.

Continuing to refer to FIG. 4, the surgical instrument 30 of the surgical robot system 1 may include an end tool 100, a driving part 200, and a connection part 400.

Here, the connection part 400 is formed in the shape of a hollow shaft, in which one or more wires (to be described later) may be accommodated, and may have one end portion to which the driving part 200 is coupled and another end portion to which the end tool 100 is coupled and serve to connect the driving part 200 and the end tool 100.

The driving part 200 is formed at one end portion of the connection part 400 and provides an interface capable of being coupled to the robot arm units 21, 22, and 23. Accordingly, when a user operates the master robot 10, a motor (not shown) of the robot arm units 21, 22, and 23 is operated so that the end tool 100 of the surgical instrument 30 can perform a motion corresponding thereto, and a driving force of the motor (not shown) is transmitted to the end tool 100 through the driving part 200. In other words, it may be described that the driving part 200 itself becomes an interface that connects between the surgical instrument 30 and the slave robot 20.

The end tool 100 is formed on another end portion of the connection part 400, and performs necessary motions for surgery by being inserted into a surgical site. The end tool 100 will be described in more detail later with reference to FIG. 5.

The surgical instrument according to an embodiment of the present disclosure may be provided in the surgical instrument of the surgical robot system shown in FIGS. 1 to 4.

Hereinafter, the surgical instrument that may be provided in the surgical robot system will be described in more detail.

<First Embodiment of Surgical Instrument>

Figure 5:
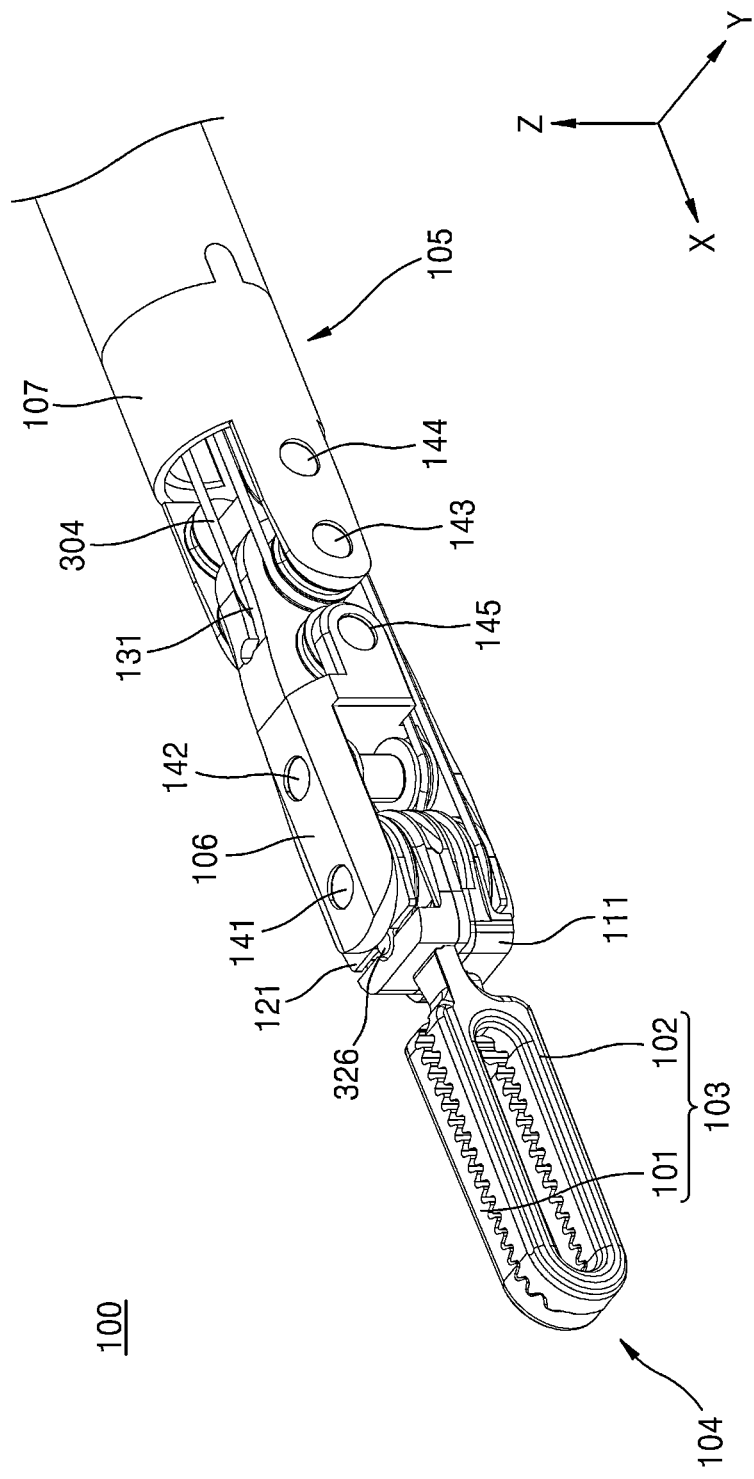
FIGS. 5 and 6 are perspective views illustrating an end tool of a surgical instrument according to a first embodiment of the present disclosure.
Figure 6:
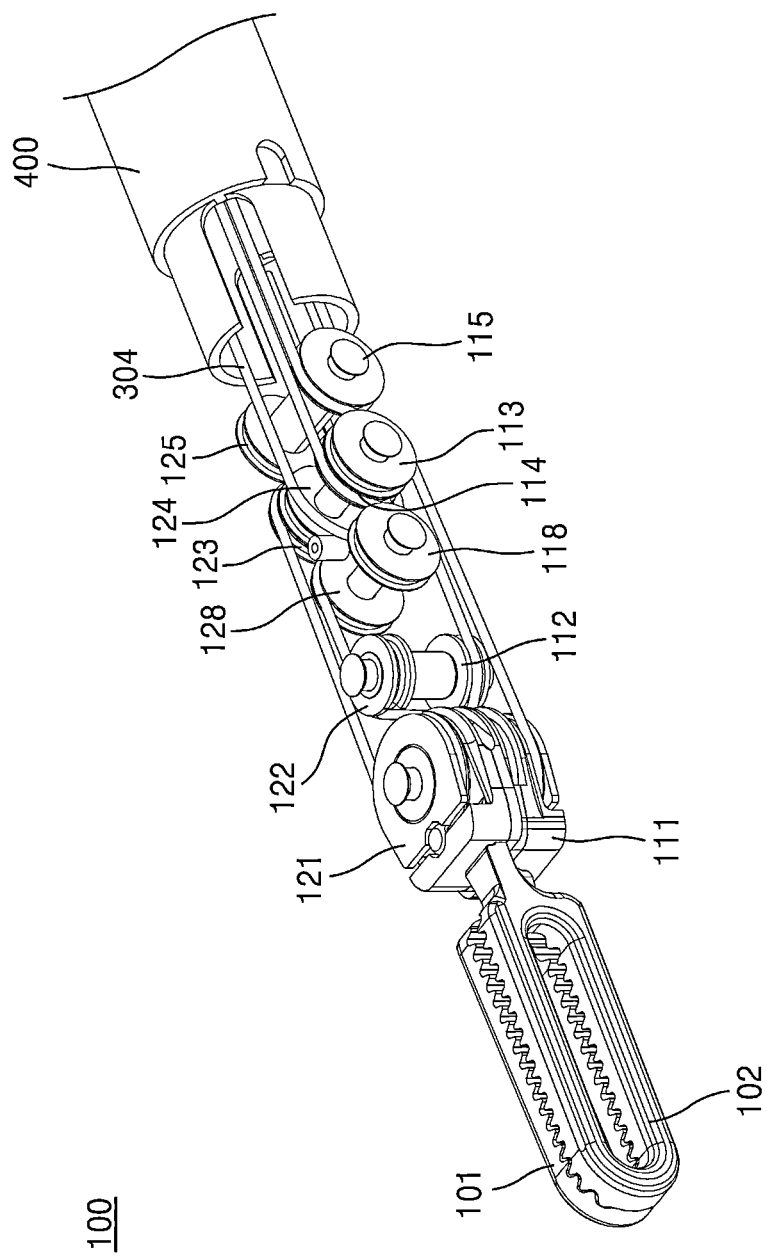
Figure 7:
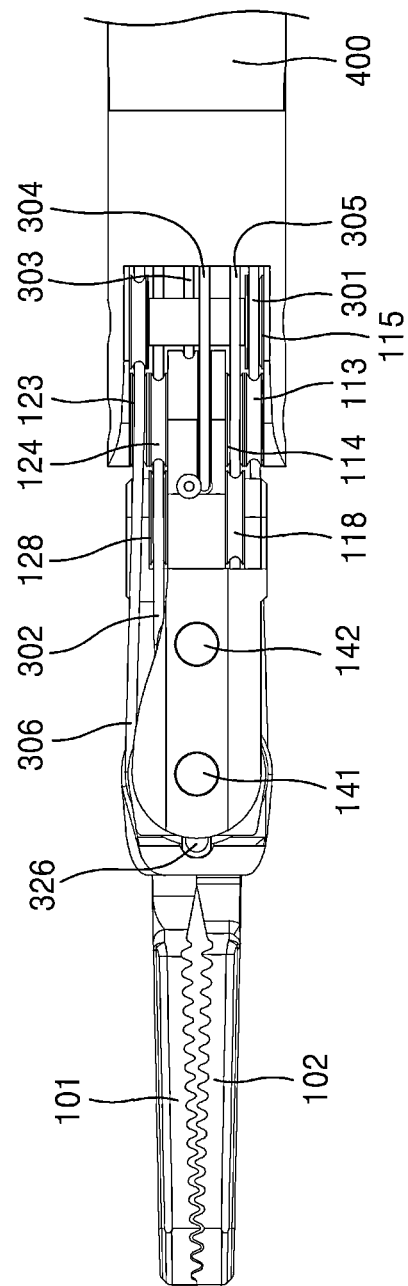
FIGS. 7 and 8 are plan views of the end tool of FIG. 5.
Figure 8:
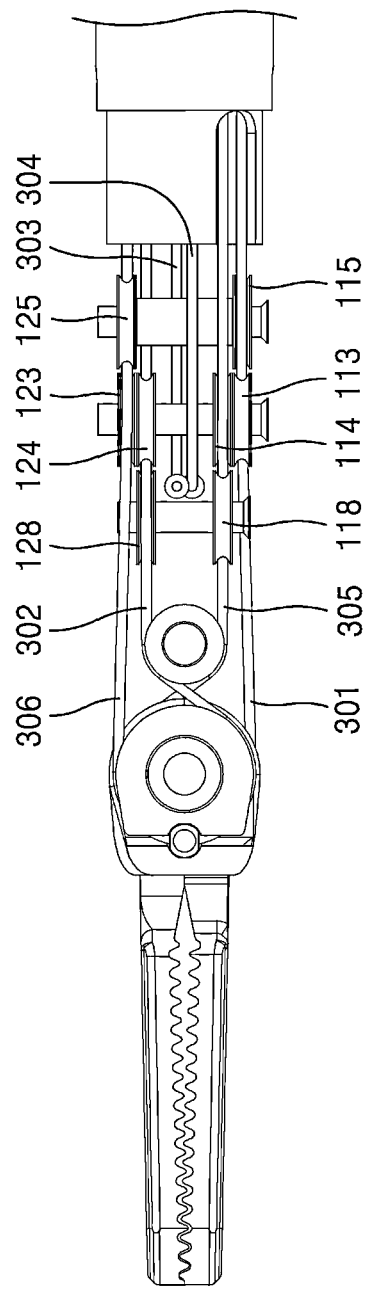
Figure 9:
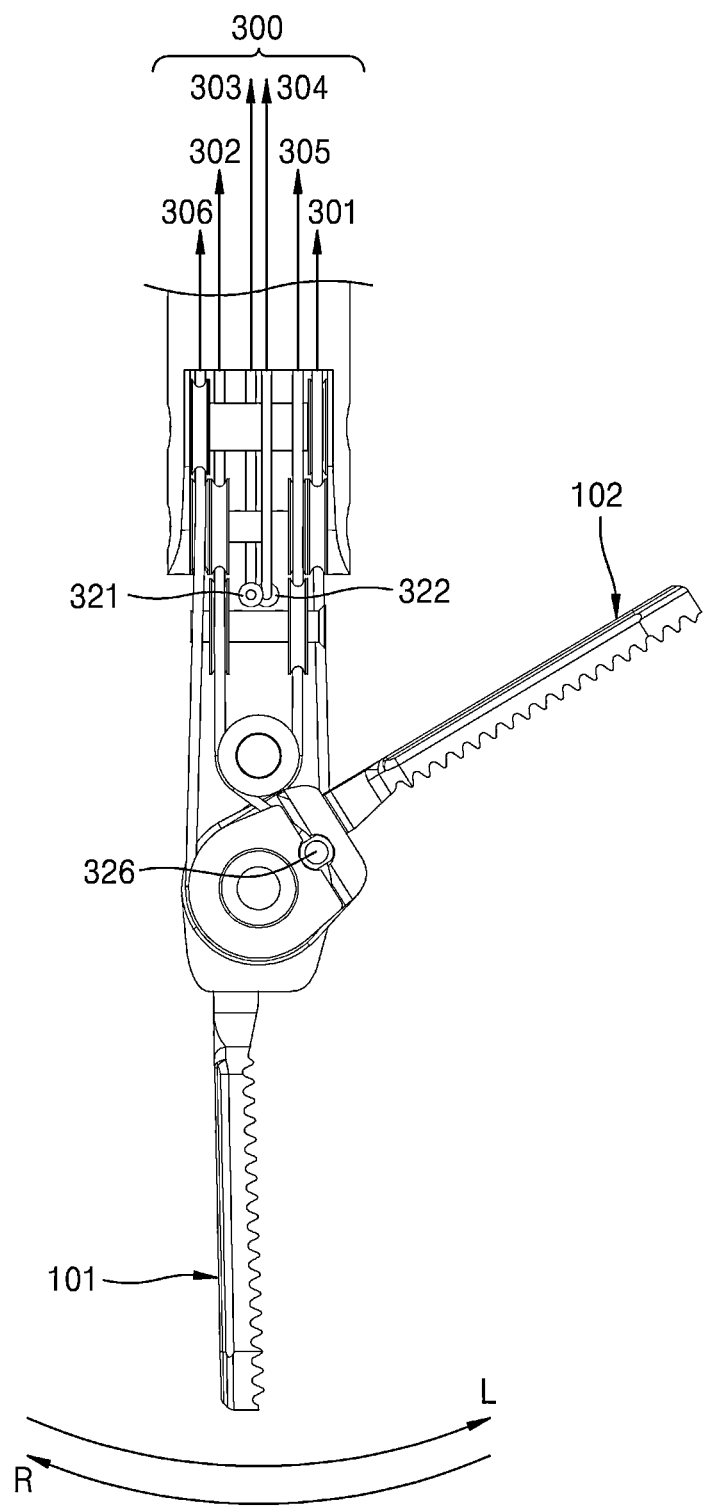
FIGS. 9 and 10 are plan views of the end tool of FIG. 5.
Figure 10:
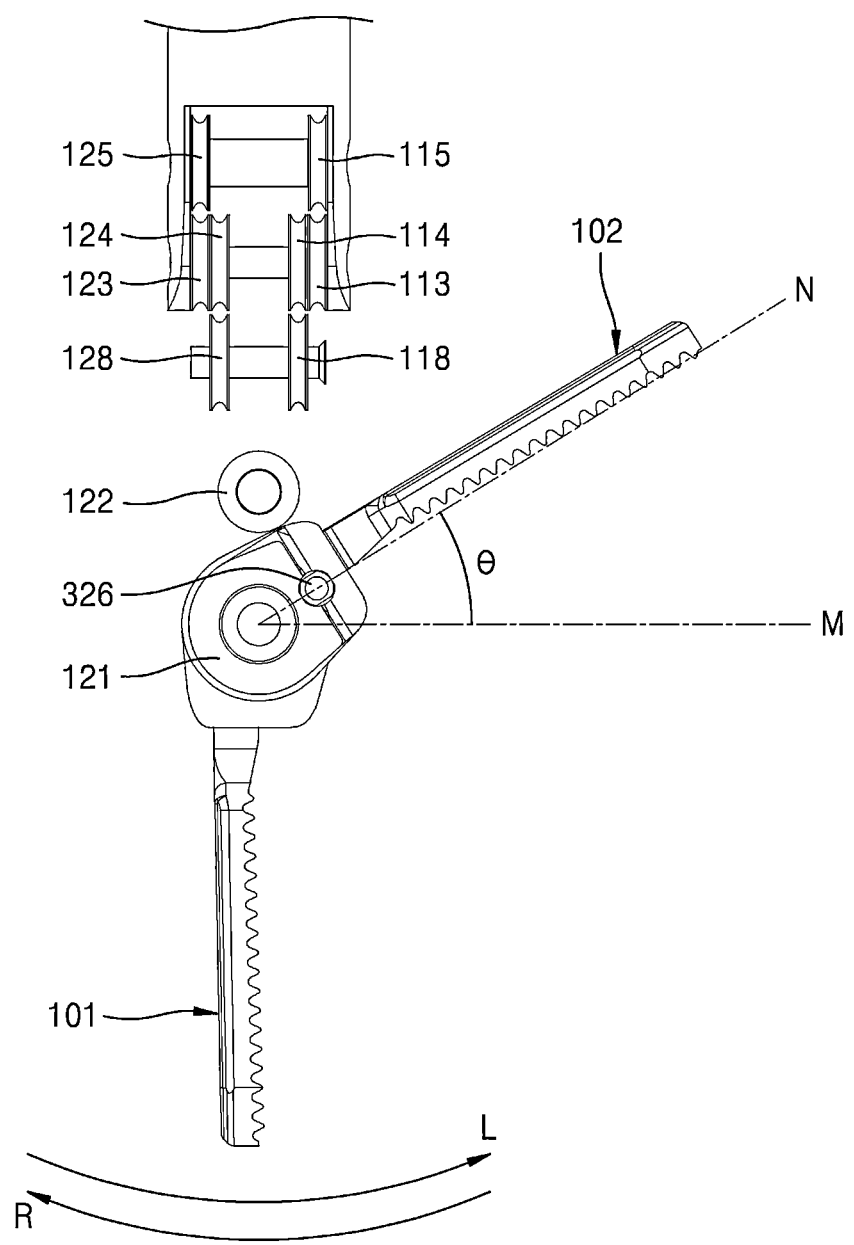
Figure 11:
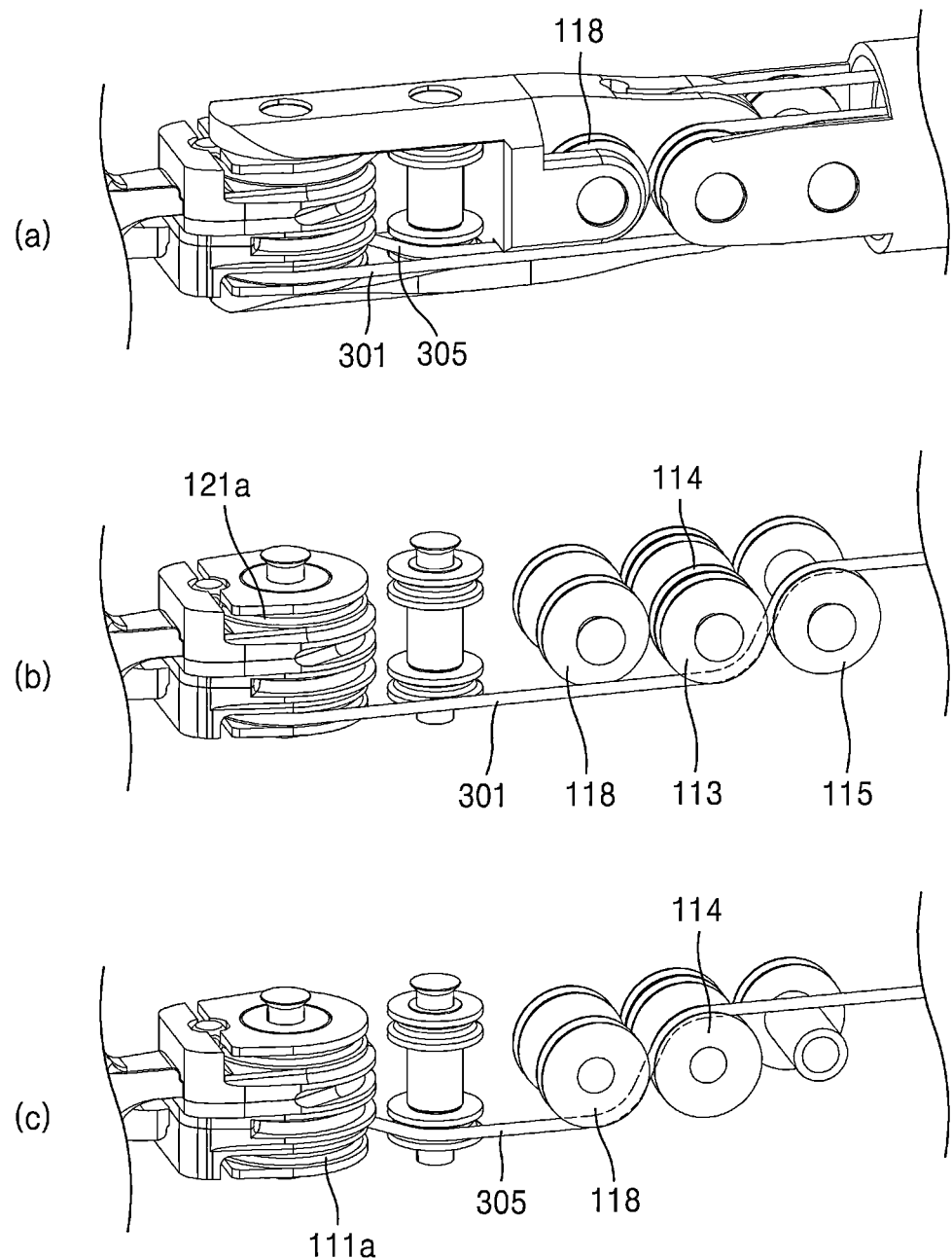
FIG. 11 is a perspective view of the end tool of FIG. 5.
Figure 12:
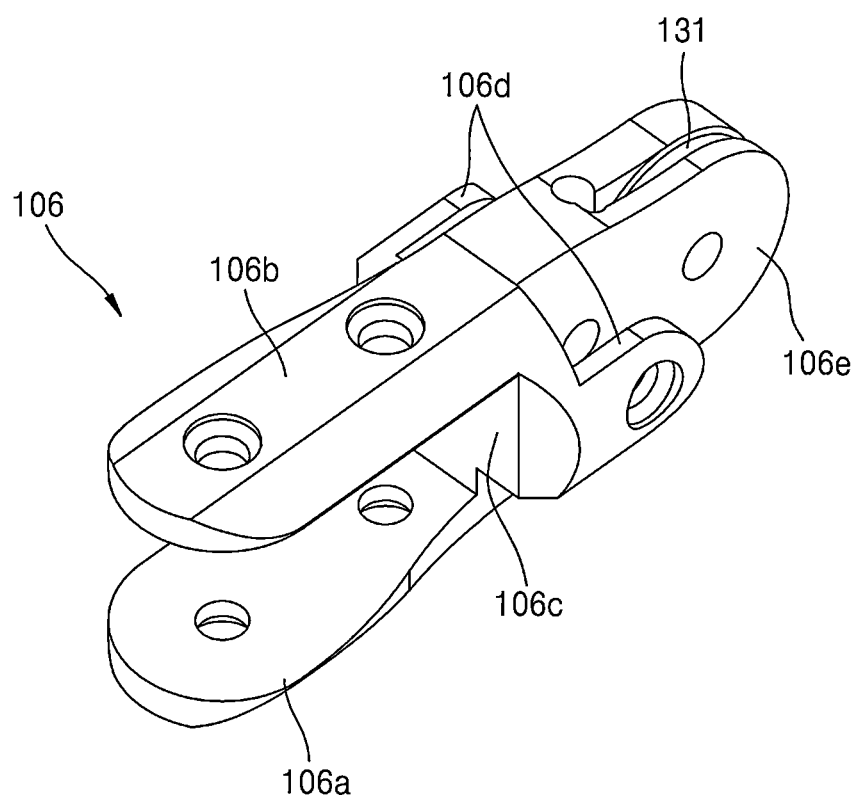
FIG. 12 is a perspective view of an end tool hub of the end tool of FIG. 5.

FIGS. 5 and 6 are perspective views illustrating an end tool of a surgical instrument according to a first embodiment of the present disclosure. FIGS. 7 and 8 are plan views of the end tool of FIG. 5. FIGS. 9 and 10 are plan views of the end tool of FIG. 5. FIG. 11 is a side perspective view of the end tool of FIG. 5. FIG. 12 is a perspective view of an end tool hub of the end tool of FIG. 5.

Figure 13:
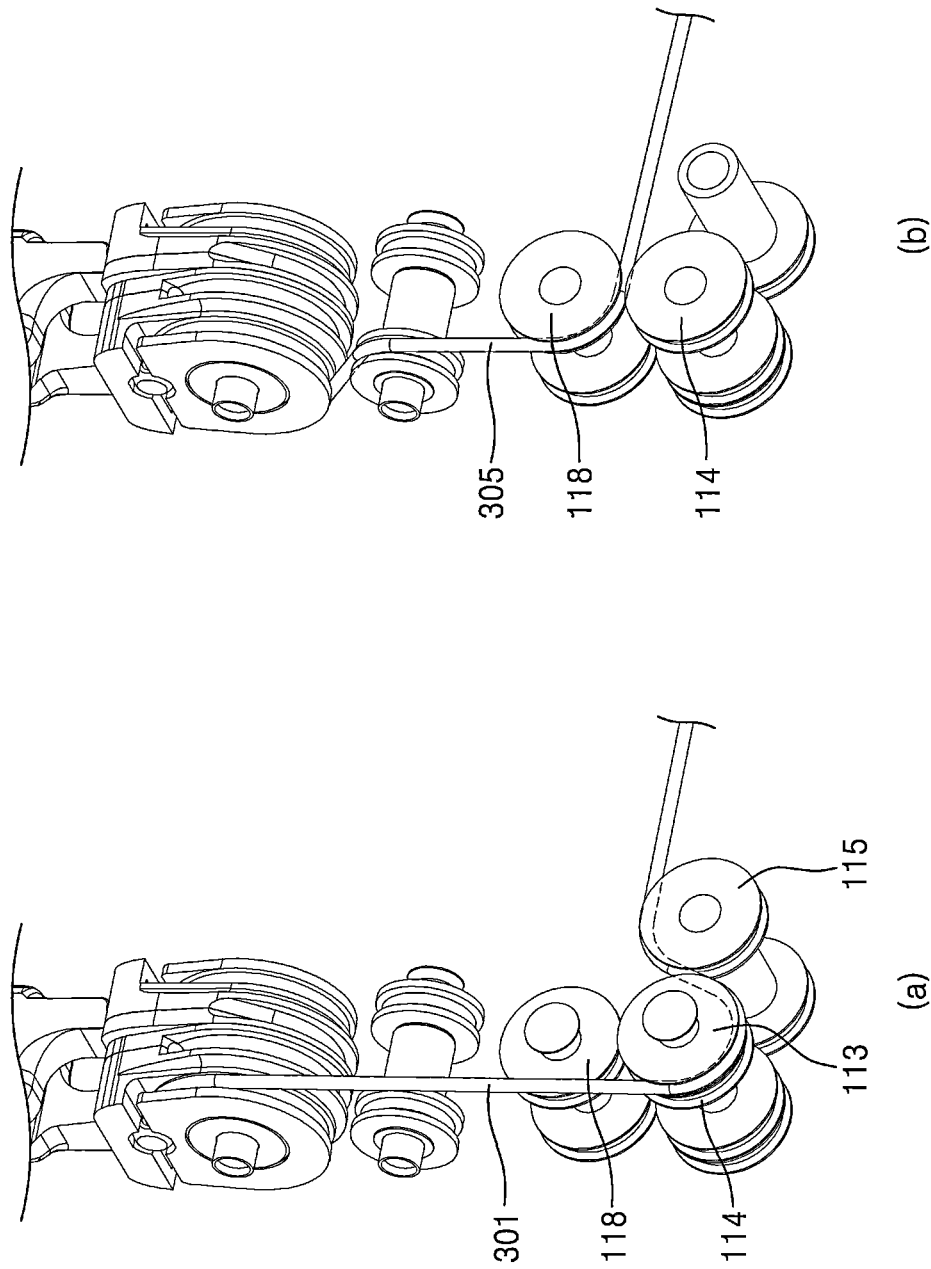
FIG. 13 is a perspective view illustrating a state in which the end tool of the surgical instrument of FIG. 5 is pitch-rotated by −90°.
Figure 15:
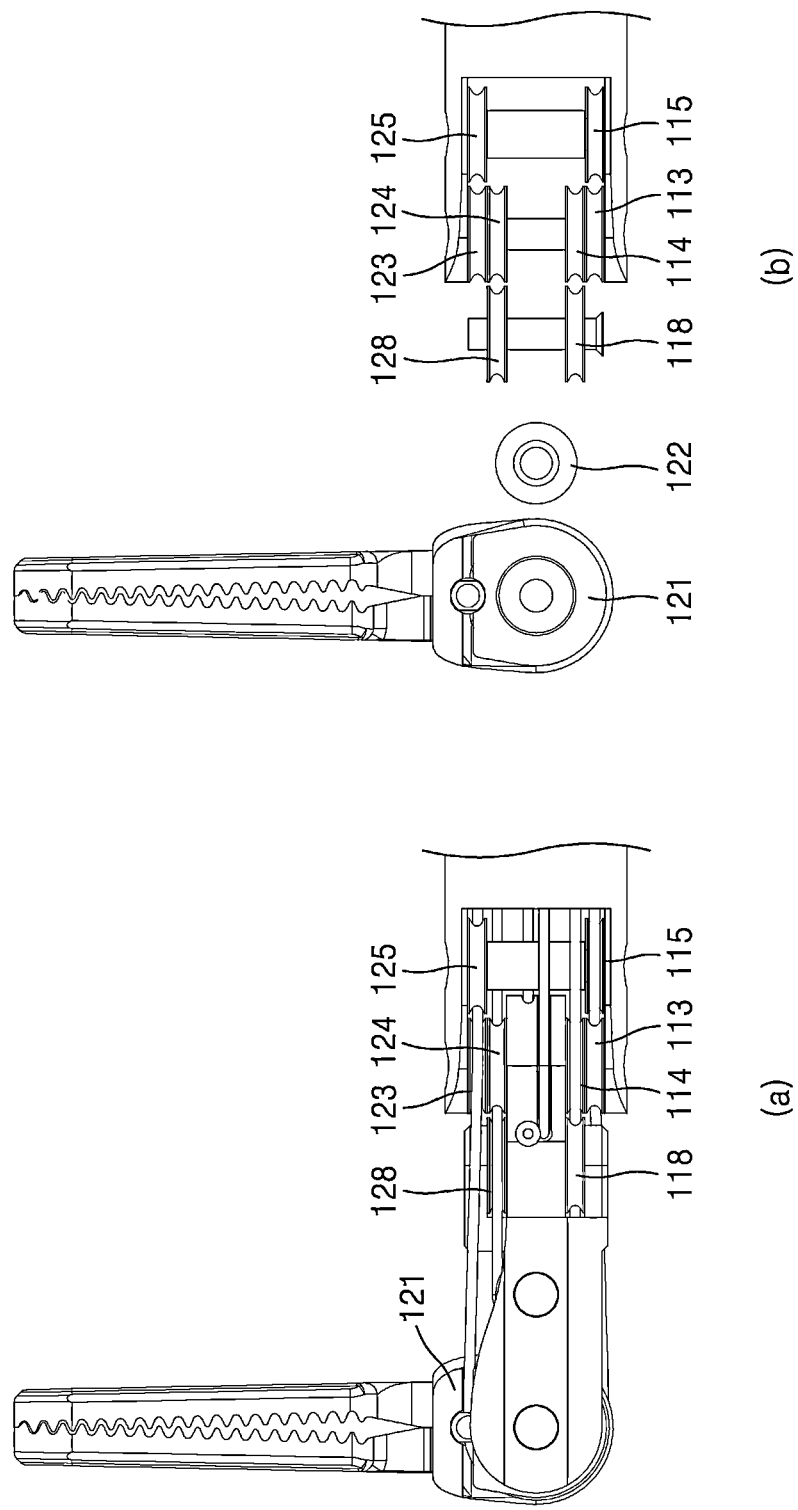
FIG. 15 is a perspective view illustrating a state in which the end tool of the surgical instrument of FIG. 5 is yaw-rotated by +90°.

In addition, FIG. 13 is a perspective view illustrating a state in which the end tool of the surgical instrument of FIG. 5 is pitch-rotated by −90°. FIG. 14 is a side view illustrating a state in which the end tool of the surgical instrument of FIG. 5 is pitch-rotated by +90°. In addition, FIG. 15 is a perspective view illustrating a state in which the end tool of the surgical instrument of FIG. 5 is yaw-rotated by +90°.

Figure 16:
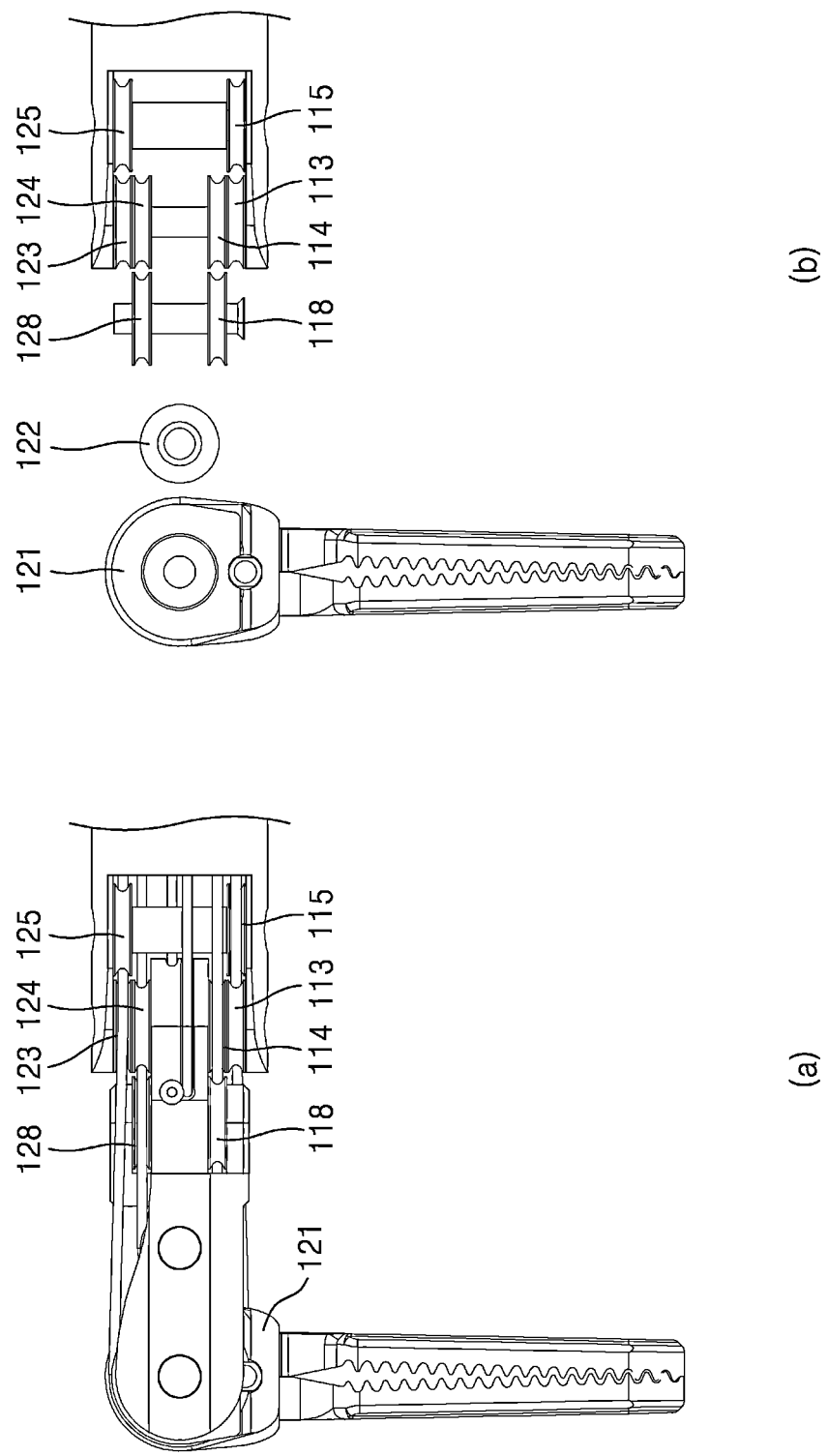
FIG. 16 is a side view illustrating a state in which the end tool of the surgical instrument of FIG. 5 is yaw-rotated by −90°.

FIG. 16 is a side view illustrating a state in which the end tool of the surgical instrument of FIG. 5 is yaw-rotated by −90°.

Here, FIG. 6 illustrates a state in which an end tool hub 106 and a pitch hub 107 are removed from the end tool of FIG. 5, and FIG. 8 illustrates a state in which the end tool hub 106 and the pitch hub 107 are removed from the end tool of FIG. 7. In addition, FIG. 9 is a view illustrating the end tool of FIG. 5, with a focus on wires, and FIG. 10 is a view illustrating the end tool of FIG. 5, with a focus on pulleys. In addition, FIG. 11A illustrates a state in which the end tool hub 106 and the pitch hub 107 are mounted, FIG. 11B illustrates a path of a wire 301 in a state in which the end tool hub 106 and the pitch hub 107 are removed, and FIG. 11C illustrates a path of a wire 305 in the state in which the end tool hub 106 and the pitch hub 107 are removed.

As described above with reference to FIGS. 1 to 4, a surgical instrument (see 30 of FIG. 4) according to the first embodiment of the present disclosure may include the end tool 100, a driving part (see 200 of FIG. 4), the power transmission part 300, and the connection part 400.

Referring to FIGS. 5 to 16, the end tool 100 is formed at an end portion of the connection part 400 and performs necessary motions for surgery by being inserted into a surgical site. As an example of the above-described end tool 100, as shown in FIG. 5, a pair of jaws 101 and 102 for performing a grip motion may be used. However, the concept of the present disclosure is not limited thereto, and various devices for performing surgery may be used as the end tool 100. For example, a configuration such as a one-armed cautery may also be used as the end tool. The above-described end tool 100 is connected to the driving part (see 200 of FIG. 4) by the power transmission part 300 and receives a driving force of the driving part (see 200 of FIG. 4) through the power transmission part 300 to perform motions necessary for surgery, such as a gripping motion, a cutting motion, a suturing motion, or the like.

Here, the end tool 100 of the surgical instrument 30 according to the first embodiment of the present disclosure is formed to be rotatable in at least two or more directions, for example, the end tool 100 may be formed to perform a pitch motion around a rotation shaft 143 of FIG. 5 and simultaneously perform a yaw motion and an actuation motion around a rotation shaft 141 of FIG. 5.

Here, each of the pitch, yaw, and actuation motions used in the present disclosure are defined as follows.

First, the pitch motion means a motion of the end tool 100 rotating in a vertical direction with respect to an extension direction of the connection part 400 (an X-axis direction of FIG. 5), that is, a motion rotating around a Y-axis of FIG. 5. In other words, the pitch motion means a motion of the end tool 100, which is formed to extend from the connection part 400, rotating vertically around the Y-axis with respect to the connection part 400.

Next, the yaw motion means a motion of the end tool 100 rotating in the left and right directions, that is, a motion rotating around the Z-axis of FIG. 5, with respect to the extension direction of the connection part 400 (the X-axis direction of FIG. 5). In other words, the yaw motion means a motion of the end tool 100, which is formed to extend from the connection part 400, rotating horizontally around the Z-axis with respect to the connection part 400. That is, the yaw motion means rotating motions of two jaws 101 and 102, which are formed on the end tool 100, around the Z-axis in the same direction.

Meanwhile, the actuation motion means a motion of the end tool 100 rotating around the same rotation shaft as that of the yaw motion, while the two jaws 101 and 102 rotate in the opposite directions so as to be closed or opened. That is, the actuation motion means rotating motions of the two jaws 101 and 102, which are formed on the end tool 100, in the opposite directions around the Z-axis.

Defining this from another perspective, the yaw rotation may be defined as a motion in which a jaw pulley to be described later is rotated around the rotation shaft 141, which is a jaw pulley rotation shaft, and the pitch rotation may be defined as a motion in which the jaw pulley revolves around the rotation shaft 143, which is a pitch main rotation shaft.

The power transmission part 300 may connect the driving part (see 200 of FIG. 4) to the end tool 100, transmit the driving force from the driving part (see 200 of FIG. 4) to the end tool 100, and include a plurality of wires, pulleys, links, sections, gears, or the like.

Hereinafter, the power transmission part 300 and the end tool 100 including the same will be described in more detail.

(Power Transmission Part)

Hereinafter, the power transmission part 300 of the end tool of the surgical instrument of FIG. 5 will be described in more detail.

Referring to FIGS. 5, 6, and 10 and the like, the power transmission part 300 of the end tool 100 of the surgical instrument according to an embodiment of the present disclosure may include the wire 301, a wire 302, a wire 303, a wire 304, the wire 305, and a wire 306.

Here, the wire 301 and the wire 305 may be paired to serve as first jaw wires. The wire 302 and the wire 306 may be paired to serve as second jaw wires. Here, the components encompassing the wire 301 and the wire 305, which are first jaw wires, and the wire 302 and the wire 306, which are second jaw wires, may be referred to as jaw wires. In addition, the wire 303 and the wire 304 may be paired to serve as pitch wires.

Here, in the drawings, a pair of wires are illustrated as being associated with a rotational motion of a first jaw 101, and a pair of wires are illustrated as being associated with a rotational motion of a second jaw 102, but the concept of the present disclosure is not limited thereto. For example, a pair of wires may be associated with a yaw motion, and a pair of wires may be associated with an actuation motion.

In addition, the power transmission part 300 of the surgical instrument according to an embodiment of the present disclosure may include a coupling member 321, a coupling member 322, a coupling member 323, a coupling member 324, a coupling member 325, a coupling member 326, a coupling member 327, a coupling member 328, a coupling member 329, a coupling member 330, and the like, which are coupled to respective end portions of wires to couple the wires to pulleys. Here, each of the coupling members may have various shapes as necessary, such as a ball shape, a tube shape, and the like.

Here, the coupling member 321, which is a pitch wire coupling member, may be coupled to the end portion of the wire 303, which is a pitch wire, at the end tool 100 side, the coupling member 322, which is a pitch wire coupling member, may be coupled to the end portion of the wire 304, which is a pitch wire, at the end tool 100 side, and the coupling member 321 and the coupling member 322 may serve as pitch wire-end tool coupling members. Meanwhile, the coupling member 329, which is a pitch wire-driving part coupling member, may be coupled to the end portion of the wire 303, which is a pitch wire, at the driving part side (see 200 of FIG. 4), and the coupling member 330, which is a pitch wire-driving part coupling member, may be coupled to the end portion of the wire 304 at the driving part side (see 200 of FIG. 4).

Meanwhile, the coupling member 323, which is a first jaw wire coupling member, may be coupled to the end portions of the wires 301 and 305, which are first jaw wires, at the end tool 100 side to serve as a first jaw wire-end tool coupling member. Meanwhile, the coupling member 324, which is a first jaw wire-driving part coupling member, may be coupled to the end portion of the wire 301, which is a first jaw wire, at the driving part side (see 200 of FIG. 4), and the coupling member 325, which is a first jaw wire-driving part coupling member, may be coupled to the end portion of the wire 305 at the driving part side (see 200 of FIG. 4).

Meanwhile, the coupling member 326, which is a second jaw wire coupling member, may be coupled to the end portions of the wires 302 and 306, which are second jaw wires, at the end tool 100 side to serve as a second jaw wire-end tool coupling member. Meanwhile, the coupling member 327, which is a second jaw wire-driving part coupling member, may be coupled to the end portion of the wire 302, which is a second jaw wire, at the driving part side (see 200 of FIG. 4), and the coupling member 328, which is a second jaw wire-driving part coupling member, may be coupled to the end portion of the wire 306 at the driving part side (see 200 of FIG. 4).

Here, each of the coupling members is classified as being included in the power transmission part 300, but the coupling members may be classified such that the coupling member at the end tool 100 side may be included in the end tool 100, and the coupling member at the driving part side (see 200 of FIG. 4) may be included in the driving part (see 200 of FIG. 4).

The coupling relationship between the wires, the coupling members, and the respectively pulleys will be described in detail as follows.

First, the wires 302 and 306, which are second jaw wires, may be a single wire. The coupling member 326, which is a second jaw wire-end tool coupling member, is inserted at an intermediate point of the second jaw wire, which is a single wire, and the coupling member 326 is crimped and fixed, and then, both strands of the second jaw wire centered on the coupling member 326 may be referred to as the wire 302 and the wire 306, respectively.

Alternatively, the wires 302 and 306, which are second jaw wires, may also be formed as separate wires, and connected to each other by the coupling member 326.

In addition, by coupling the coupling member 326 to a pulley 121, the wires 302 and 306 may be fixedly coupled to the pulley 121. This allows the pulley 121 to rotate as the wires 302 and 306 are pulled and released.

Meanwhile, the coupling member 327, which is a second jaw wire-driving part coupling member, may be coupled to the end portion of the wire 302, which is opposite to the end portion of the wire 302 to which the coupling member 326 is coupled, and the coupling member 328, which is a second jaw wire-driving part coupling member may be coupled to the end portion of the wire 306, which is opposite to the end portion of the wire 302 to which the coupling member 326 is coupled.

In addition, by coupling the coupling member 327, which is a second jaw wire-driving part coupling member coupled to the wire 302, to a pulley 221, and coupling the coupling member 328, which is a second jaw wire-driving part coupling member coupled to the wire 306, to a pulley 222, the wire 302 and the wire 306 may be fixedly coupled to the pulley 221 and the pulley 222, respectively. As a result, when the pulley 221 and the pulley 222 are rotated by a motor or a human force, the pulley 121 of the end tool 100 may be rotated as the wire 302 and the wire 306 are pulled or released.

Here, as shown in the drawings, the driving part second jaw pulley may include two pulleys of the pulley 221 and the pulley 222, the second jaw wire-driving part coupling member may also include the coupling member 327 and the coupling member 328, the wire 302 may be coupled to the coupling member 327, and the wire 306 may be coupled to the coupling member 328. Alternatively, although not shown in the drawings, the driving part second jaw pulley may include one pulley, the second jaw wire-driving part coupling member may also include one coupling member, and the wire 302 and the wire 306 may be coupled to one coupling member to be coupled to one driving part second jaw pulley.

In the same manner, the wire 301, which is a first jaw wire, is coupled to the first jaw wire-end tool coupling member 323 and the first jaw wire-driving part coupling member 324, and the wire 305 is coupled to the first jaw wire-end tool coupling member 323 and the first jaw wire-driving part coupling member 325. In addition, the first jaw wire-end tool coupling member 323 is coupled to a pulley 111, the first jaw wire-driving part coupling member 324 is coupled to a pulley 211, and the first jaw wire-driving part coupling member 325 is coupled to a pulley 212. As a result, when the pulley 211 and the pulley 212 are rotated by a motor or a human force, the pulley 111 of the end tool 100 may be rotated as the wire 301 and the wire 305 are pulled and released.

In the same manner, one end portion of the wire 303, which is a pitch wire, may be coupled to the coupling member 321, which is a pitch wire-end tool coupling member, and one end portion of the wire 304, which is a pitch wire, may be coupled the coupling member 322, which is a pitch wire-end tool coupling member. In addition, another end portion of the wire 303 may be coupled to the coupling member 329, which is a pitch wire-driving part coupling member, and another end portion of the wire 304 may be coupled to the coupling member 330, which is a pitch wire-driving part coupling member. In addition, the coupling member 321 and the coupling member 322 are each coupled to the pulley 131, and the coupling member 329 and the coupling member 330 are respectively coupled to the pulley 231/pulley 232 that are driving part pitch pulleys. As a result, when the pulley 231/pulley 232, which is a driving part pitch pulley, is rotated by a motor or a human force, the pulley 131 of the end tool 100 may be rotated as the wire 303 and the wire 304 are pulled and released.

As a result, the wire 301 and the wire 305, which are both strands of the first jaw wire, are coupled to the coupling member 323, which is a first jaw wire-end tool coupling member, and the coupling member 324/coupling member 325, which is a first jaw wire-driving part coupling member, to function as a closed loop as a whole. Similarly, the second jaw wire and the pitch wire may each be formed to function as a closed loop.

(End Tool)

Hereinafter, the end tool 100 of the surgical instrument of FIG. 5 will be described in more detail.

Continuing to refer to FIGS. 5 to 16, the end tool 100 of the first embodiment of the present disclosure includes a pair of jaws for performing a grip motion, that is, the first jaw 101 and the second jaw 102. Here, each of the first jaw 101 and the second jaw 102, or a component encompassing the first jaw 101 and the second jaw 102 may be referred to as a jaw 103.

Further, the end tool 100 may include the pulley 111, a pulley 112, a pulley 113, a pulley 114, a pulley 115, and a pulley 118 that are related to a rotational motion of the first jaw 101. In addition, the end tool 100 may include the pulley 121, a pulley 122, a pulley 123, a pulley 124, a pulley 125, and a pulley 128 that are related to a rotational motion of the second jaw 102.

Here, in the drawings, one group of pulleys is illustrated as being associated with a rotational motion of the first jaw 101, and one group of pulleys is illustrated as being associated with a rotational motion of the second jaw 102, but the concept of the present disclosure is not limited thereto. For example, one group of pulleys in the end tool may be associated with a yaw motion, and one group of pulleys in the end tool may be associated with an actuation motion. Here, the pulleys included in the end tool 100, including the pulleys described above, may be collectively referred to as end tool pulleys.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 100 of the first embodiment of the present disclosure may include the end tool hub 106 and the pitch hub 107.

The rotation shaft 141, a rotation shaft 142, and a rotation shaft 145, which will be described later, are inserted through the end tool hub 106. In addition, the end tool hub 106 may internally accommodate at least some of the pulley 111 and the pulley 121 that are axially coupled to the rotation shaft 141. In addition, the end tool hub 106 may internally accommodate at least some of the pulley 112 and the pulley 122 that are axially coupled to the rotation shaft 142. In addition, the pulley 118 and the pulley 128, which are axially coupled to the rotation shaft 145, may be coupled to the end tool hub 106.

In detail, referring to FIG. 12 or the like, the end tool hub 106 includes the first jaw pulley coupling part 106a, the second jaw pulley coupling part 106b, a guide part 106c, a pitch redundant pulley accommodation part 106d, and a pitch pulley coupling part 106e.

In detail, the first jaw pulley coupling part 106a and the second jaw pulley coupling part 106b are formed to face each other, and the pulley 111 and the pulley 121 are accommodated therein. In addition, a through hole is formed in each of the first jaw pulley coupling part 106a and the second jaw pulley coupling part 106b such that the rotation shaft 141 passes through and axially couples the first jaw pulley coupling part 106a, the pulley 111, the pulley 121, and the second jaw pulley coupling part 106b. In addition, the rotation shaft 142 passes through and axially couples the first jaw pulley coupling part 106a, the pulley 112, the pulley 122, and the second jaw pulley coupling part 106b.

The first jaw pulley coupling part 106a and the second jaw pulley coupling part 106b are connected to each other by the guide part 106c. That is, the first jaw pulley coupling part 106a and the second jaw pulley coupling part 106b parallel to each other are coupled to each other by the guide part 106c formed in a direction substantially perpendicular thereto, so that the first jaw pulley coupling part 106a, the second jaw pulley coupling part 106b, and the guide part 106c form a substantially "C-shape," in which the pulley 111, the pulley 112, the pulley 121, and the pulley 122 are accommodated.

Here, the pulley 111, which is a first jaw pulley, is disposed close to the first jaw pulley coupling part 106a of the end tool hub 106, and the pulley 121, which is a second jaw pulley, is disposed close to the second jaw pulley coupling part 106b of the end tool hub 106, and thus a predetermined space may be formed between the wire 301/wire 305, which is a first jaw wire, and the wire 302/wire 306, which is a second jaw wire.

Meanwhile, the pitch redundant pulley accommodation part 106d may be formed on the guide part 106c of the end tool hub 106 at the proximal end side. In addition, the pulley 118 and the pulley 128, which are pitch redundant pulleys, may be accommodated in the pitch redundant pulley accommodation part 106d, and these pitch redundant pulleys may be axially coupled to the end tool hub 106 by the rotation shaft 145.

Meanwhile, the pulley 131 serving as an end tool pitch pulley may be formed on the pitch pulley coupling part 106e at one end portion of the end tool hub 106. Here, the pulley 131 may be integrally formed with the end tool hub 106 as one body. That is, one end portion of the end tool hub 106 may be formed in a disk shape or a semi-circular shape, and a groove around which a wire may be wound may be formed on an outer circumferential surface of the end tool hub 106, thereby forming a kind of guide channel. Alternatively, the pulley 131 may be formed as a separate member from the end tool hub 106 to be coupled to the end tool hub 106. The wires 303 and 304 described above are coupled to the pulley 131 serving as an end tool pitch pulley, and a pitch motion is performed as the pulley 131 is rotated around the rotation shaft 143.

The rotation shaft 143 and a rotation shaft 144, which will be described later, may be inserted through the pitch hub 107, and the pitch hub 107 may be axially coupled to the end tool hub 106 and the pulley 131 by the rotation shaft 143. Thus, the end tool hub 106 and the pulley 131 (coupled thereto) may be formed to be rotatable around the rotation shaft 143 with respect to the pitch hub 107.

Further, the pitch hub 107 may internally accommodate at least some of the pulley 113, the pulley 114, the pulley 123, and the pulley 124 that are axially coupled to the rotation shaft 143. In addition, the pitch hub 107 may internally accommodate at least some of the pulley 115 and the pulley 125 that are axially coupled to the rotation shaft 144.

Further, the end tool 100 of the first embodiment of the present disclosure may include the rotation shaft 141, the rotation shaft 142, the rotation shaft 145, the rotation shaft 143, and the rotation shaft 144. As described above, the rotation shaft 141 and the rotation shaft 142 may be inserted through the end tool hub 106, and the rotation shaft 143 and the rotation shaft 144 may be inserted through the pitch hub 107.

The rotation shaft 141, the rotation shaft 142, the rotation shaft 145, the rotation shaft 143, and the rotation shaft 144 may be arranged sequentially from a distal end 104 of the end tool 100 toward a proximal end 105. Accordingly, starting from the distal end 104, the rotation shaft 141 may be referred to as a first pin, the rotation shaft 142 may be referred to as a second pin, the rotation shaft 145 may be referred to as a 2.5th pin, the rotation shaft 143 may be referred to as a third pin, and the rotation shaft 144 may be referred to as a fourth pin.

Here, the rotation shaft 141 may function as a jaw pulley rotation shaft, the rotation shaft 142 may function as a jaw auxiliary pulley rotation shaft, the rotation shaft 143 may function as a pitch main rotation shaft, and the rotation shaft 144 may function as a pitch-serve rotation shaft of the end tool 100. In addition, the rotation shaft 145 disposed between the rotation shaft 142 and the rotation shaft 143 may function as a pitch redundant rotation shaft of the end tool 100.

Each of the rotation shafts 141, 142, 143, 144, and 145 may be fitted into one or more pulleys, which will be described in detail later.

The pulley 111 functions as a first jaw pulley, and the pulley 121 functions as a second jaw pulley, and these two components may be collectively referred to as jaw pulleys.

The pulley 111 and the pulley 121, which are jaw pulleys, are formed to face each other, and are formed to be rotatable independently of each other around the rotation shaft 141, which is a jaw pulley rotation shaft. Here, in the drawings, it is illustrated that the pulley 111 and the pulley 121 are formed to rotate around one rotation shaft 141, but it is of course possible that each jaw pulley may be formed to be rotatable around a separate shaft. Here, the first jaw 101 may be fixedly coupled to the pulley 111 and rotated together with the pulley 111, and the second jaw 102 may be fixedly coupled to the pulley 121 and rotated together with the pulley 121. Yaw and actuation motions of the end tool 100 are performed in response to the rotation the pulley 111 and the pulley 121. That is, when the pulley 111 and the pulley 121 are rotated in the same direction around the rotation shaft 141, the yaw motion is performed, and when the pulley 111 and the pulley 121 are rotated in opposite directions around the rotation shaft 141, the actuation motion is performed.

Here, the first jaw 101 and the pulley 111 may be formed as separate members and coupled to each other, or the first jaw 101 and the pulley 111 may be integrally formed as one body. Similarly, the second jaw 102 and the pulley 121 may be formed as separate members and coupled to each other, or the second jaw 102 and the pulley 121 may be integrally formed as one body.

Here, a groove 111a around which the wire 301/wire 305, which is a first wire, is wound is disposed in the pulley 111, which is a first jaw pulley, to be adjacent to the first jaw pulley coupling part 106a of the end tool hub 106, and a groove 121a around which the wire 302/wire 306, which is a second wire, is wound is disposed in the pulley 121, which is a second jaw pulley, to be adjacent to the first jaw pulley coupling part 106a of the end tool hub 106. Accordingly, a predetermined space may be formed between the wire 301/wire 305, which is a first jaw wire, and the wire 302/wire 306, which is the second jaw wire. As described above, by disposing the wire 301/wire 305, which is a first jaw wire, and the wire 302/wire 306, which is a second jaw wire, to be spaced apart from each other, the wires may be wound around the respective pulleys while maintaining a straight line.

The pulley 112 functions as a first jaw auxiliary pulley, and the pulley 122 functions as a second jaw auxiliary pulley, and these two components may be collectively referred to as jaw auxiliary pulleys.

In detail, the pulley 112 and the pulley 122, which are jaw auxiliary pulleys, may be additionally provided on one side of the pulley 111 and one side of the pulley 121, respectively. In other words, the pulley 112, which is a jaw auxiliary pulley, may be disposed between the pulley 111 and the pulley 113/pulley 114. In addition, the pulley 122, which is a jaw auxiliary pulley, may be disposed between the pulley 121 and the pulley 123/pulley 124. The pulley 112 and the pulley 122 may be formed to be rotatable independently of each other around the rotation shaft 142. Here, in the drawings, it is illustrated that the pulley 112 and the pulley 122 are formed to rotate around one rotation shaft 142, but it is of course possible that each of the pulley 112 and the pulley 122 may be formed to be rotatable around a separate shaft. Such auxiliary pulleys will be described in more detail later.

The pulley 113 and the pulley 114 function as first jaw pitch main pulleys, and the pulley 123 and the pulley 124 function as second jaw pitch main pulleys, and these two components may be collectively referred to as pitch main pulleys.

The pulley 115 functions as a first jaw pitch sub-pulley, and the pulley 125 functions as a second jaw pitch sub-pulley, and these two components may be collectively referred to as pitch sub-pulleys.

Meanwhile, in the present disclosure, the pulley 118 and the pulley 128, which are pitch redundant pulleys, are further disposed between the pulleys 112 and 122, which are jaw auxiliary pulleys, and the pulleys 113, 114, 123, and 124, which are pitch main pulleys.

The pulley 118 functions as a first jaw pitch redundant pulley, and the pulley 128 functions as a second jaw pitch redundant pulley, and these two components may be collectively referred to as pitch redundant pulleys.

In addition, the rotation shaft 145 functioning as a pitch redundant rotation shaft may be further provided, and the rotation shaft 145 may be inserted through the end tool hub 106. Here, the rotation shaft 145 may be formed to be substantially parallel to the rotation shaft 143, which is a pitch main rotation shaft, and the rotation shaft 144, which is a pitch-serve rotation shaft. In this case, the rotation shaft 145 is disposed between the rotation shaft 142, which is a second pin, and the rotation shaft 143, which is a third pin, and thus may be referred to as a 2.5th pin due to a position thereof.

Such a pitch redundant pulley may serve to change an entry/exit path of the jaw wire, through which the jaw wire enters from the proximal end of the end tool to the distal end or exits from the distal end to the proximal end. This will be described in more detail later.

As a result, the rotation shaft 141, the rotation shaft 142, the rotation shaft 145, the rotation shaft 143, and the rotation shaft 144 may be arranged sequentially from the distal end 104 of the end tool 100 toward the proximal end 105.

In addition, the pulley 111, the pulley 112, the pulley 118, the pulley 113/pulley 114, and the pulley 115, which are pulleys associated with the rotation of the first jaw 101, may be arranged sequentially from the distal end 104 of the end tool 100 toward the proximal end 105.

In addition, the pulley 121, the pulley 122, the pulley 128, the pulley 123/pulley 124, and the pulley 125, which are pulleys associated with the rotation of the second jaw 102, may be arranged sequentially from the distal end 104 of the end tool 100 toward the proximal end 105.

Hereinafter, the pulley 112 and the pulley 122 serving as auxiliary pulleys will be described in more detail.

The pulley 112 and the pulley 122 may serve to enlarge rotation angles of the first jaw 101 and the second jaw 102, respectively, by coming into contact with the wire 305, which is a first jaw wire, and the wire 302, which is a second jaw wire, to change the arrangement path of the wires 305 and 302 to a certain extent.

That is, when the auxiliary pulleys are not disposed, each of the first jaw and the second jaw may be rotated up to a right angle, but in an embodiment of the present disclosure, the pulley 112 and the pulley 122, which are auxiliary pulleys, are additionally provided, so that the maximum rotation angle may be increased by θ as shown in FIG. 10. This enables a motion of the two jaws of the end tool 120 being opened for an actuation motion while the two jaws are yaw-rotated by 90° in an L direction. This is because the second jaw 102 is rotated by the additional angle θ as shown in FIG. 10. Similarly, an actuation motion is possible even when the two jaws are yaw-rotated in an R direction. In other words, a feature of increasing the range of a yaw rotation in which the actuation motion is possible may be obtained through the pulley 112 and the pulley 122.

This will be described below in more detail.

When the auxiliary pulleys are not disposed, since the first jaw wire is fixedly coupled to the first jaw pulley, and the second jaw wire is fixedly coupled to the second jaw pulley, each of the first jaw pulley and the second jaw pulley may be rotated up to 90°. In this case, when the actuation motion is performed while the first jaw and the second jaw are located at a 90° line, the first jaw may be spread, but the second jaw may not be rotated beyond 90°. Accordingly, when the first jaw and the second jaw perform a yaw motion over a certain angle, there was a problem that the actuation motion is not smoothly performed.

In order to address such a problem, in the end tool 100 of the surgical instrument of the present disclosure, the pulley 112 and the pulley 122, which are auxiliary pulleys, are additionally disposed on one side of the pulley 111 and one side of the pulley 121, respectively. As described above, as the arrangement paths of the wire 305, which is a first jaw wire, and the wire 302, which is a second jaw wire, are changed to a certain extent by disposing the pulley 112 and the pulley 122, a tangential direction of the wires 305 and 302 is changed, and accordingly, the coupling member 326 for coupling the wire 302 and the pulley 121 may be rotated up to a line N of FIG. 10. That is, the coupling member 326, which is a coupling part of the wire 302 and the pulley 121, is rotatable until the coupling member 326 is located on a common internal tangent of the pulley 121 and the pulley 122. Similarly, the coupling member 323, which is a coupling part of the wire 305 and the pulley 111, is rotatable until the coupling member 323 is located on a common internal tangent of the pulley 111 and the pulley 112, so that the range of rotation in the L direction may be increased.

In other words, due to the pulley 112, the wires 301 and 305, which are two strands of the first jaw wire wound around the pulley 111, are disposed on one side with respect to a plane perpendicular to the Y-axis and passing through the X-axis. Simultaneously, due to the pulley 122, the wires 302 and 306, which are two strands of the second jaw wire wound around the pulley 121, are disposed at another side with respect to the plane perpendicular to the Y-axis and passing through the X-axis.

In other words, the pulley 113 and the pulley 114 are disposed on one side with respect to the plane perpendicular to the Y-axis and passing through the X-axis, and the pulley 123 and the pulley 124 are disposed at another side with respect to the plane perpendicular to the Y-axis and passing through the X-axis.

In other words, the wire 305 is located on the internal tangent of the pulley 111 and the pulley 112, and the rotation angle of the pulley 111 is increased by the pulley 112. In addition, the wire 302 is located on the internal tangent of the pulley 121 and the pulley 122, and a rotation angle of the pulley 121 is increased by the pulley 122.

As the rotation radii of the jaw 101 and the jaw 102 increase as described above according to the present disclosure, an effect of increasing a yaw motion range over which a normal opening/closing actuation motion is performed may be obtained.

Hereinafter, components related to the rotation of the pulley 111 will be described.

The pulley 113 and the pulley 114 are paired to function as first jaw pitch main pulleys. That is, the pulley 113 and the pulley 114 function as main rotation pulleys for a pitch motion of the first jaw 101. Here, the wire 301, which is a first jaw wire, is wound around the pulley 113, and the wire 305, which is a first jaw wire, is wound around the pulley 114.

The pulley 115 functions as a first jaw pitch sub-pulley. That is, the pulley 115 functions as a sub rotation pulley for a pitch motion of the first jaw 101. Here, the wire 301, which is a first jaw wire, is wound around the pulley 115.

The pulley 118 functions as a first jaw redundant pulley. That is, the pulley 118 function as a redundant rotation pulley for a pitch motion of the first jaw 101. Here, the wire 305, which is a first jaw wire, is wound around the pulley 118.

Here, the pulley 118 is disposed on one side of the pulley 111 and the pulley 112. Here, the pulley 118 is formed to be rotatable around the rotation shaft 145, which is a pitch redundant rotation shaft. Further, the pulley 113 and the pulley 114 are disposed on one side of the pulley 118 to face each other. Here, the pulley 113 and the pulley 114 are formed to be rotatable independently of each other around the rotation shaft 143 that is a pitch main rotation shaft. In addition, the pulley 115 are disposed on one side of each of the pulley 113 and the pulley 114. Here, the pulley 115 is formed to be rotatable around the rotation shaft 144, which is a pitch-serve rotation shaft. Here, in the drawings, it is illustrated that the pulley 118, the pulley 113, the pulley 114, and the pulley 115 are all formed to be rotatable around the Y-axis direction, but the concept of the present disclosure is not limited thereto, and the rotation shafts of the respective pulleys may be formed in various directions according to configurations thereof.

The wire 301, which is a first jaw wire, is sequentially wound to make contact with at least portions of the pulley 115, the pulley 113, and the pulley 111. In addition, the wire 305 connected to the wire 301 by the coupling member 323 is sequentially wound to make contact with at least portions of the pulley 111, the pulley 112, the pulley 118, and the pulley 114.

In other words, the wire 301 and the wire 305, which are first jaw wires, are sequentially wound to make contact with at least portions of the pulley 115, the pulley 113, the pulley 111, the pulley 112, the pulley 118, and the pulley 114 and are formed to move along the above pulleys while rotating the above pulleys.

Accordingly, when the wire 301 is pulled in the direction of an arrow 301 of FIG. 9, a coupling member 323 to which the wire 301 is coupled and the pulley 111 coupled to the coupling member 323 are rotated in an arrow L direction of FIG. 9. In contrast, when the wire 305 is pulled in the direction of an arrow 305 of FIG. 9, the coupling member 323 to which the wire 305 is coupled and the pulley 111 coupled to the coupling member 323 are rotated in an arrow R direction of FIG. 9.

Next, components related to the rotation of the pulley 121 will be described.

The pulley 123 and the pulley 124 are paired to function as second jaw pitch main pulleys. That is, the second jaw 102 functions as a main rotation pulley for a pitch motion of the second jaw 102. Here, the wire 306, which is a second jaw wire, is wound around the pulley 123, and the wire 302, which is a second jaw wire, is wound around the pulley 124.

The pulley 125 functions as a second jaw pitch sub-pulley. That is, the pulley 125 functions as a sub rotation pulley for a pitch motion of the second jaw 102. Here, the wire 306, which is a second jaw wire, is wound around the pulley 125.

The pulley 128 functions as a second jaw pitch redundant pulley. That is, the pulley 128 functions as a redundant rotation pulley for a pitch motion of the second jaw 102. Here, the wire 302, which is a second jaw wire, is wound around the pulley 128.

Here, the pulley 128 is disposed on one side of the pulley 121 and the pulley 122. Here, the pulley 128 is formed to be rotatable around the rotation shaft 145, which is a pitch redundant rotation shaft. Further, the pulley 123 and the pulley 124 are disposed on one side of the pulley 128 to face each other. Here, the pulley 123 and the pulley 124 are formed to be rotatable independently of each other around the rotation shaft 143 that is a pitch main rotation shaft. In addition, the pulley 125 is disposed on one side of each of the pulley 123 and the pulley 124. Here, the pulley 125 is formed to be rotatable around the rotation shaft 144, which is a pitch-serve rotation shaft. Here, in the drawings, it is illustrated that all of the pulley 128, pulley 123, the pulley 124, and the pulley 125 are formed to be rotatable around the Y-axis direction, but the concept of the present disclosure is not limited thereto, and the rotation shafts of the respective pulleys may be formed in various directions according to configurations thereof.

The wire 306, which is a second jaw wire, is sequentially wound to make contact with at least portions of the pulley 125, the pulley 123, and the pulley 121. In addition, the wire 302 connected to the wire 306 by the coupling member 326 is sequentially wound to make contact with at least portions of the pulley 121, the pulley 122, the pulley 128, and the pulley 124.

In other words, the wires 306 and 302, which are second jaw wires, are sequentially wound to make contact with at least portions of the pulley 125, the pulley 123, the pulley 121, the pulley 122, the pulley 128, and the pulley 124, and are formed to move along the above pulleys while rotating the above pulleys.

Accordingly, when the wire 306 is pulled in the direction of an arrow 306 of FIG. 9, the coupling member 326 to which the wire 306 is coupled and the pulley 121 coupled to the coupling member 326 are rotated in the arrow R direction of FIG. 9. In contrast, when the wire 302 is pulled in the direction of an arrow 302 of FIG. 9, the coupling member 326 to which the wire 302 is coupled and the pulley 121 coupled to the coupling member 326 are rotated in the arrow L direction of FIG. 9.

Here, in the present disclosure, two strands of the jaw wire, which are wound around one jaw pulley, are wound around the pitch main pulley in opposite directions to each other, thereby facilitating control of the pitch motion.

In detail, when defining a +Z-axis direction and a −Z-axis direction as upper and lower sides, respectively, based on a plane (i.e., an XY plane) passing between the pulley 111, which is a first jaw pulley, and the pulley 121, which is a second jaw pulley, of two strands of the first jaw wire, one strand (e.g., the wire 301) may enter the pulley 113, which is a first jaw pitch main pulley, at the lower side of the XY plane, and another strand (e.g., the wire 305) may exit from the pulley 114, which is a first jaw pitch main pulley, at the upper side of the XY plane. In other words, it may be said that the jaw wire is structured to enter the lower side of the first jaw pitch main pulley and exit the upper side of the first jaw pitch main pulley. (It is the structure in which the second jaw wire enters the upper side of the second jaw pitch main pulley and exits from the lower side thereof).

In other words, the wire 301, which is one strand of the first jaw wire sequentially comes into contact with an upper side of the pulley 115 and a lower side of the pulley 113, and then comes into contact with the pulley 111. Subsequently, the wire 305, which is another strand of the first jaw wire, is wound around the pulley 111 and the pulley 112, and then exits from the connection part 400 after sequentially coming into contact with an upper side of the pulley 114 and a lower side of the pulley 118. As a result, the first jaw wire exits from the connection part 400, enters the lower side of the pulley 113, and then proceeds through each of the pulleys, and re-enters the connection part 400 via the upper side of the pulley 114.

Likewise, the wire 306, which is one strand of the second jaw wire, sequentially come into contact with a lower side of the pulley 125 and an upper side of the pulley 123, and then comes into contact with the pulley 121. Subsequently, the wire 302, which is another strand of the second jaw wire, is wound around the pulley 121 and the pulley 122, and then exits from the connection part 400 after sequentially coming into contact with an upper side of the pulley 128 and a lower side of the pulley 124. As a result, the second jaw wire exits from the connection part 400, enters the upper side of the pulley 123, and then proceeds through each of the pulleys, and re-enters the connection part 400 via the lower side of the pulley 124.

In other words, it may be expressed that, of the two strands of first jaw wire, one wire is wound around the first jaw pitch main pulley in one of the clockwise and counter-clockwise directions, and another wire is wound around the first jaw pitch main pulley in the other one of the clockwise and counterclockwise directions. That is, when viewed in FIG. 11, the wire 301 is wound in the clockwise direction while entering from the connection part 400 toward the end tool 100, and the wire 305 is wound in the counterclockwise direction while entering from the connection part 400 toward the end tool 100.

Likewise, it may be expressed that, of the two strands of first second jaw wire, one wire is wound around the second jaw pitch main pulley in one of the clockwise and counter-clockwise directions, and another wire is wound around the second jaw pitch main pulley in the other one of the clockwise and counterclockwise directions. That is, when viewed in FIG. 10, the wire 302 is wound in the clockwise direction while entering from the connection part 400 toward the end tool 100, and the wire 306 is wound in the counterclockwise direction while entering from the connection part 400 toward the end tool 100.

As described above, by winding two strands of the jaw wire, which are wound around one jaw pulley, around the pitch main pulley in opposite directions to each other, it is possible to easily control the pitch motion. This will be described in more detail later.

Meanwhile, when viewed from the perspective of an XZ plane, the two strands of each jaw wire are disposed on the same side with respect to the XZ plane. In detail, when defining a +Y-axis direction and a −Y-axis direction with respect to a plane (i.e., the XZ plane) passing between the pulley 114, which is a first jaw pitch main pulley, and the pulley 124, which is a second jaw pitch main pulley, as a first side and a second side, respectively, of the two strands of the first jaw wire, one strand (e.g., the wire 301) may be disposed on the first side of the XZ plane, and another strand (e.g., the wire 305) may also be disposed on the same first side. Likewise, of the two strands of the second jaw wire, one strand (e.g., the wire 306) may be disposed on the second side of the XZ plane and another strand (e.g., the wire 302) may also be disposed on the same second side. That is, it may be said that it is structured so that one jaw wire enters the first side and exits from the first side. (In addition, it may be said that it is structured so that another jaw wire enters the second side and exits from the second side).

(Driving Part)

Hereinafter, the driving part 200 of the surgical instrument 30 of FIG. 4 will be described in more detail.

Figure 17:
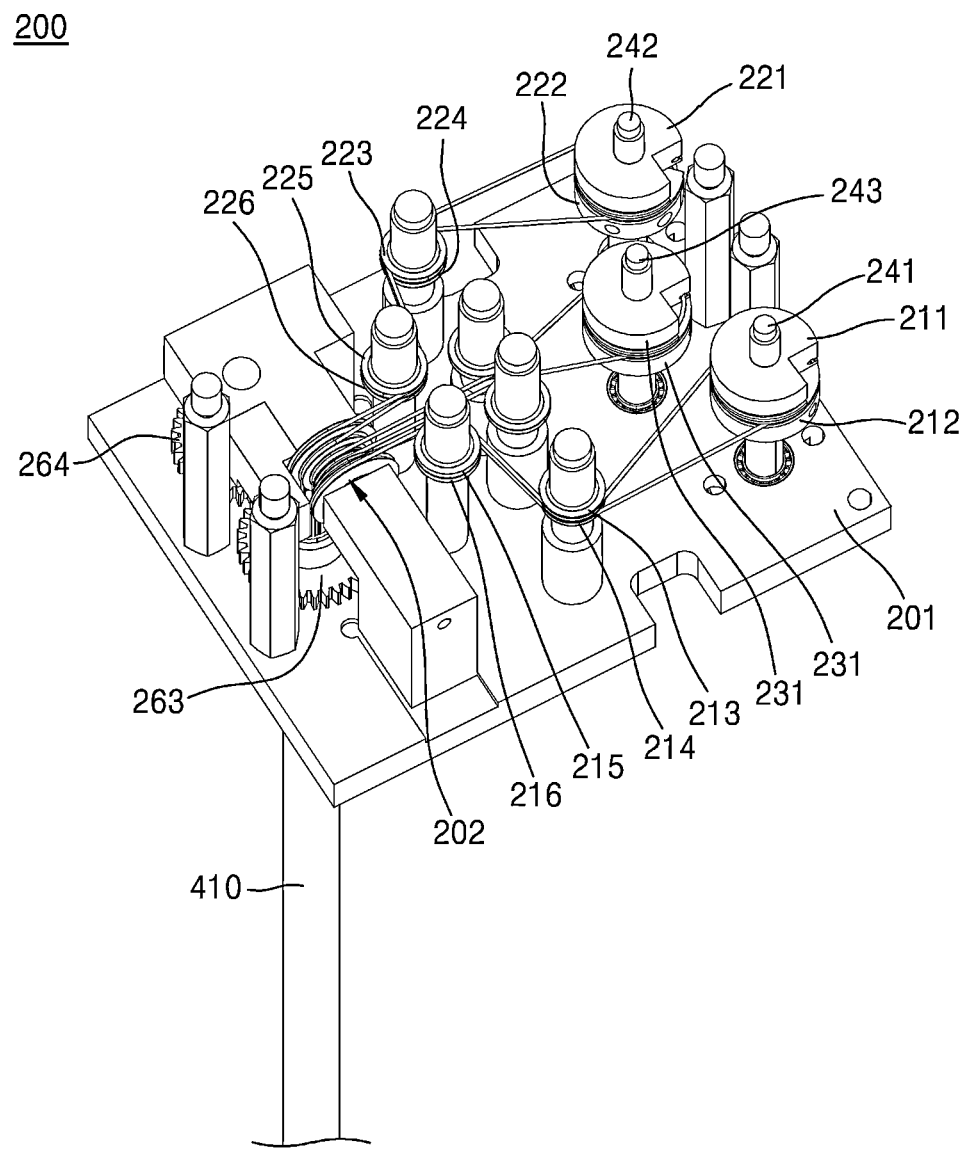
FIG. 17 is a perspective view of a driving part of the surgical instrument of FIG. 4.
Figure 18:
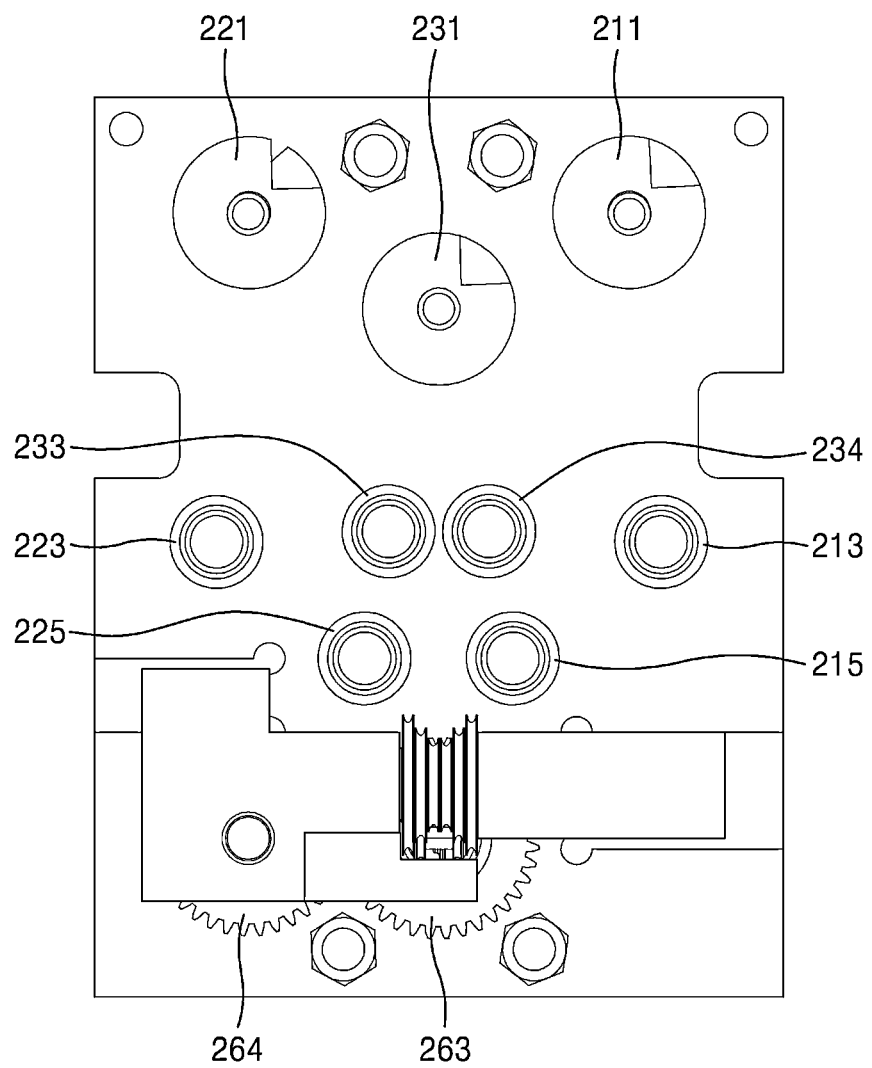
FIG. 18 is a plan view of the driving part of the surgical instrument of FIG. 17.
Figure 19:
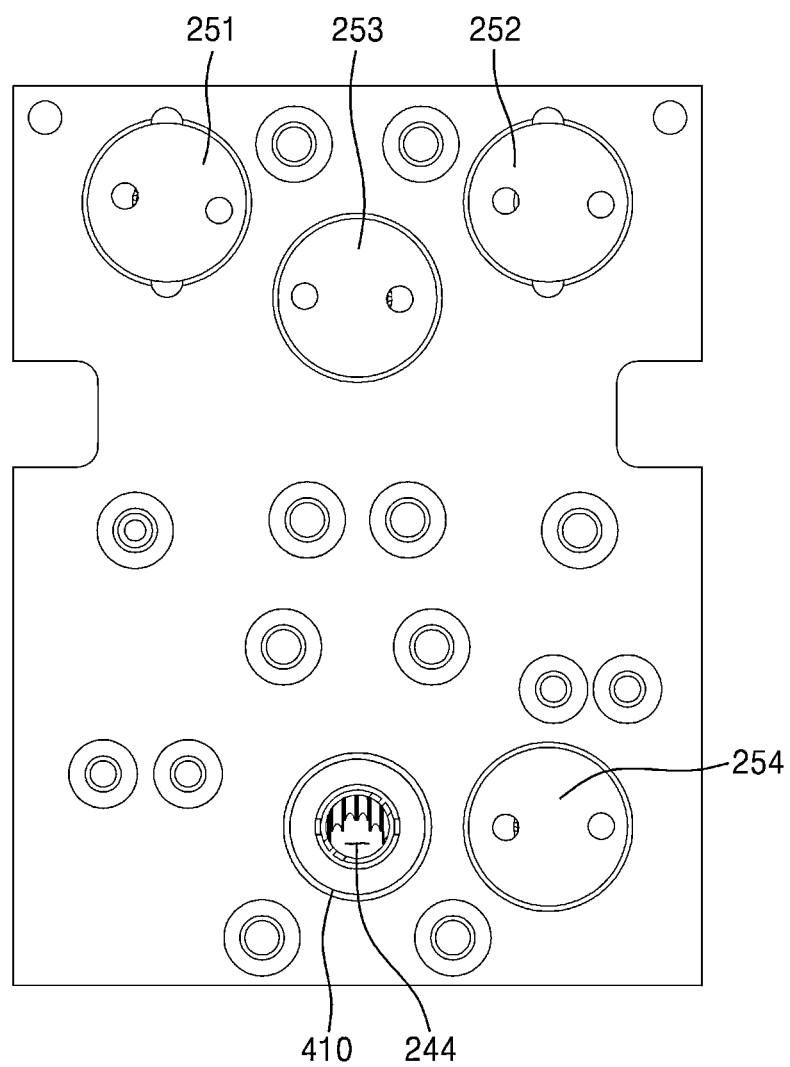
FIG. 19 is a rear view of the driving part of the surgical instrument of FIG. 17.
Figure 20:
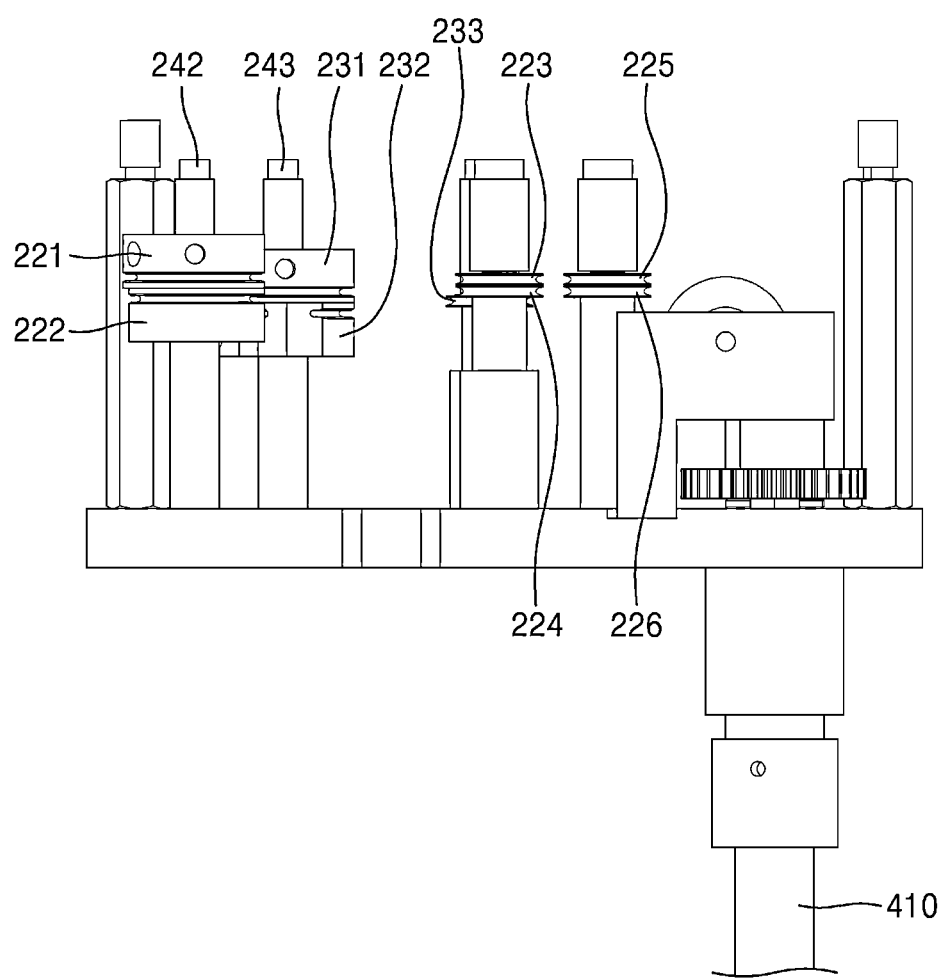
FIG. 20 is a side view of the driving part of the surgical instrument of FIG. 17.
Figure 21:
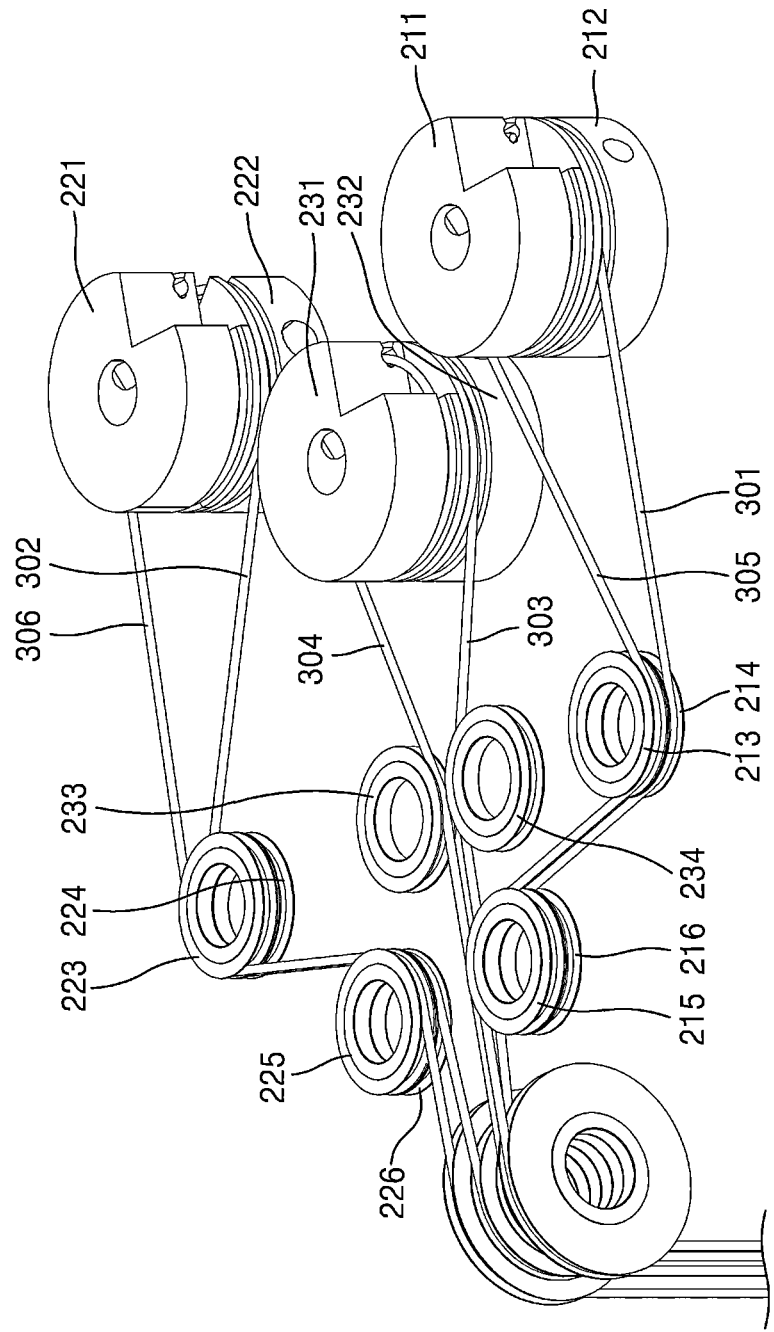
FIG. 21 is a view illustrating the configuration of pulleys and wires of the surgical instrument of FIG. 17 in detail.

FIG. 17 is a perspective view of the driving part of the surgical instrument of FIG. 4, FIG. 18 is a plan view of the driving part of the surgical instrument of FIG. 17, FIG. 19 is a rear view of the driving part of the surgical instrument of FIG. 17, and FIG. 20 is a side view of the driving part of the surgical instrument of FIG. 17.

Referring to FIGS. 17 to 20, the driving part 200 of the surgical instrument 30 according to the first embodiment of the present disclosure may include the pulley 211, the pulley 212, a pulley 213, a pulley 214, a pulley 215, and a pulley 216, which are related to a rotational motion of the first jaw 101. In addition, the driving part 200 may include the pulley 221, the pulley 222, a pulley 223, a pulley 224, a pulley 225, and a pulley 226 that are related to a rotational motion of the second jaw 102.

Here, the pulleys facing each other are illustrated in the drawings as being formed parallel to each other, but the concept of the present disclosure is not limited thereto, and each of the pulleys may be variously formed with a position and a size suitable for the configuration of the driving part.

In addition, the driving part 200 of the surgical instrument 30 according to the first embodiment of the present disclosure may further include the pulley 231 and the pulley 232, which serve as driving part pitch pulleys.

Further, the driving part 200 of the first embodiment of the present disclosure may include a rotation shaft 241, a rotation shaft 242, a rotation shaft 243, and a rotation shaft 244. Here, the rotation shaft 241 may function as a driving part first jaw rotation shaft, and the rotation shaft 242 may function as a driving part second jaw rotation shaft. In addition, the rotation shaft 243 may function as a driving part pitch rotation shaft, and the rotation shaft 244 may function as a driving part roll rotation shaft. Each of the rotation shafts 241, 242, 243, and 244 may be fitted into one or more pulleys, which will be described in detail later.

In addition, the driving part 200 of the first embodiment of the present disclosure may include a motor coupling part 251, a motor coupling part 252, a motor coupling part 253, and a motor coupling part 254. Here, the motor coupling part 251 may function as a first jaw driving motor coupling part, the motor coupling part 252 may function as a second jaw driving motor coupling part, the motor coupling part 253 may function as a pitch driving motor coupling part, and the motor coupling part 254 may function as a roll driving motor coupling part. Here, each of the motor coupling parts 251, 252, 253, and 254 may be formed in the form of a rotatable flat plate, in which one or more coupling holes to which a motor (not shown) may be coupled may be formed.

The motor coupling parts 251, 252, 253, and 254 of the driving part 200 described above are coupled to motors (not shown) formed in the robot arm units 21, 22, and 23, respectively, so that the driving part 200 is operated by driving the motors (not shown).

In addition, the driving part 200 of the first embodiment of the present disclosure may include a gear 263 and a gear 264. Here, the gear 263 and the gear 264 may function as roll driving gears.

Hereinafter, each component will be described in more detail.

The pulley 211 and the pulley 212 may function as driving part first jaw pulleys, and the pulley 221 and the pulley 222 may function as driving part second jaw pulleys, and these components may be collectively referred to as driving part jaw pulleys.

Here, it is illustrated in the drawings that the pulley 211 and the pulley 212 are associated with a rotational motion of the first jaw 101 of the end tool 100, and the pulley 221 and the pulley 222 are associated with a rotational motion of the second jaw 102 of the end tool 100, but the concept of the present disclosure is not limited thereto. For example, one group of pulleys in the driving part may be associated with a yaw motion, and one group of pulleys in the driving part may be associated with an actuation motion. Accordingly, the pulley 211, the pulley 212, the pulley 221, and the pulley 222 may be collectively referred to as driving part driving pulleys. In addition, for the other pulleys, one group of pulleys may be associated with a yaw motion, and one group of pulleys may be associated with an actuation motion.

The pulley 213, the pulley 214, the pulley 215, and the pulley 216 may function as driving part first jaw auxiliary pulleys, and the pulley 223, the pulley 224, the pulley 225, and the pulley 226 may function as driving part second jaw auxiliary pulley, and] these components may be collectively referred to as driving part jaw auxiliary pulleys.

A plurality of rotation shafts including the rotation shaft 241, the rotation shaft 242, the rotation shaft 243, and the rotation shaft 244 may be formed on a first surface of a base plate 201. In addition, a plurality of relay pulleys 202 are formed on the first surface of the base plate 201, and may serve to redirect the wires 301, 302, 303, 304, 305, and 306 entering the driving part 200 via a shaft 410 toward the pulley 231/pulley 232.

Further, the shaft 410 in the form of a shaft is coupled to a second surface of the base plate 201 opposite to the first surface, and the motor coupling part 251, the motor coupling part 252, the motor coupling part 253, and the motor coupling part 254, to which the motors (not shown) for driving the pulleys are coupled, may be formed on the second surface.

Here, the rotation shaft may be connected to the respective motor coupling part either directly or indirectly via a gear.

In an example, by directly coupling the motor coupling part 251, which is a first jaw driving motor coupling part, to the rotation shaft 241 that is a driving part first jaw rotation shaft, when the motor coupling part 251 coupled to a first jaw driving motor (not shown) is rotated, the rotation shaft 241 directly coupled to the motor coupling part 251 may be rotated together with the motor coupling part 251. Similarly, by directly coupling the motor coupling part 252, which is a second jaw driving motor coupling part, to the rotation shaft 242 that is a driving part second jaw rotation shaft, when the motor coupling part 252 coupled to a second jaw driving motor (not shown) is rotated, the rotation shaft 242 directly coupled to the motor coupling part 252 may be rotated together with the motor coupling part 252. Similarly, by directly coupling the motor coupling part 253, which is a pitch driving motor coupling part, to the rotation shaft 243 that is a driving part pitch rotation shaft, when the motor coupling part 253 coupled to a pitch driving motor (not shown) is rotated, the rotation shaft 243 directly coupled to the motor coupling part 253 may be rotated together with the motor coupling part 253.

In another example, when viewed from a plane perpendicular to the rotation shaft 244, the motor coupling part 254, which is a roll driving motor coupling part, and the rotation shaft 244, which is a driving part roll rotation shaft, may be disposed to be spaced apart from each other by a certain degree. In addition, the motor coupling part 254 and the rotation shaft 244 may be connected by the gears 263 and 264, which are roll driving gears.

As such, some motor coupling parts are configured to be directly connected to the rotation shafts, respectively, and the remaining motor coupling parts are configured to be indirectly connected to the rotation shafts, respectively, because the coupling position and direction between the surgical instrument 30 and the slave robot 20 should be considered. That is, the rotation shaft unaffected by the coupling position with the slave robot 20 may be directly connected to the motor coupling part, while the rotation shaft that may interfere with the coupling position with the slave robot 20 may be indirectly connected to the motor coupling part.

It is illustrated in the drawings that the motor coupling part 251, the motor coupling part 252, and the motor coupling part 253 are directly connected to the rotation shafts, respectively, and the motor coupling part 254 is indirectly connected, respectively, through the gears, but the concept of the present disclosure is not limited thereto, and various configurations are possible according to the coupling position and direction with the slave robot 20.

The pulleys 211 and 212, which are driving part first jaw pulleys, may be coupled to the rotation shaft 241, which is a driving part first jaw rotation shaft. Here, the pulleys 211 and 212 may be formed to rotate together with the rotation shaft 241.

Here, it is illustrated in the drawings that the driving part first jaw pulley is formed of two pulleys 211 and 212, the wire 301 is coupled to one pulley 211, and the wire 305 is coupled to the other pulley 212. However, the concept of the present disclosure is not limited thereto, and the driving part first jaw pulley may be formed of one pulley, and both the wires 301 and 305 may be coupled to the one pulley.

As described above, the rotation shaft 241 is coupled to the first jaw driving motor (not shown) by the motor coupling part 251, and thus, when the first jaw driving motor (not shown) rotates for driving the first jaw 101, the wires 301 and 305, which are first jaw wires, are pulled or released as the pulleys 211 and 212, which are driving part first jaw pulleys, are rotated together with the rotation shaft 241.

In addition, one or more driving part first jaw auxiliary rotation shafts may be disposed in a region adjacent to the rotation shaft 241. In addition, to these rotation shafts, the pulley 213, the pulley 214, the pulley 215, and the pulley 216 may be coupled. The pulley 213, the pulley 214, the pulley 215, and the pulley 216 may serve to guide paths of the wires 301 and 305, which are first jaw wires.

The pulleys 221 and 222, which are driving part second jaw rotation shafts, may be coupled to the rotation shaft 242 that is a driving part second jaw pulley. Here, the pulley 221 and the pulley 222 may be formed to rotate together with the rotation shaft 242.

Here, it is illustrated in the drawings that the driving part second jaw pulley is formed of two pulleys 221 and 222, the wire 302 is coupled to one pulley 221, and the wire 306 is coupled to the other pulley 222. However, the concept of the present disclosure is not limited thereto, and the driving part second jaw pulley may be formed of one pulley, and both the wires 302 and 306 may be coupled to the one pulley.

As described above, the rotation shaft 242 is coupled to the second jaw driving motor (not shown) by the motor coupling part 252, and thus, when the second jaw driving motor (not shown) rotates for driving the second jaw 102, that the wires 302 and 306, which are second jaw wires, are pulled or released as the pulley 221 and the pulley 222, which are driving part second jaw pulleys, are rotated together with the rotation shaft 242.

In addition, one or more driving part second jaw auxiliary rotation shafts may be disposed in a region adjacent to the rotation shaft 242. In addition, to these rotation shafts, the pulley 223, the pulley 224, the pulley 225, and the pulley 226, which are driving part second jaw auxiliary pulleys, may be coupled. The pulley 223, the pulley 224, the pulley 225, and the pulley 226 may serve to guide paths of the wires 302 and 306, which are second jaw wires.

The pulley 231 and the pulley 232, which are driving part pitch pulleys, may be coupled to the rotation shaft 243 that is a driving part pitch rotation shaft. Here, the pulley 231 and the pulley 232 may be formed to rotate together with the rotation shaft 243.

Here, it is illustrated in the drawings that the driving part pitch pulley is formed of two pulleys 231 and 232, the wire 304 is coupled to one pulley 231, and the wire 303 is coupled to the other pulley 232. However, the concept of the present disclosure is not limited thereto, and the driving part pitch pulley may be formed of one pulley, and both the wire 303 and the wire 304 may be coupled to the one pulley.

As described above, the rotation shaft 243 is coupled to a pitch driving motor (not shown) by the motor coupling part 253, and thus, when the pitch driving motor (not shown) rotates for a pitch motion, the wires 303 and 304, which are pitch wires, are pulled or released as the pulley 231 and the pulley 232, which are driving part pitch pulleys, are rotated together with the rotation shaft 243.

In addition, one or more driving part pitch auxiliary rotation shafts may be disposed in a region adjacent to the rotation shaft 243. In addition, a pulley 233 and a pulley 234, which are driving part pitch auxiliary pulleys, may be coupled to the driving part pitch auxiliary rotation shafts. The pulley 233 and the pulley 234 may serve to guide paths of the wire 304 and the wire 303, which are pitch wires.

The wire 305, which is a first jaw wire, is connected to the end tool 100 via the shaft 410 after being sequentially wound to make contact with at least portions of the pulley 211, the pulley 213, and the pulley 215 in a state in which one end portion of the wire 305 is coupled to the pulley 211 by the first jaw wire-driving part coupling member 325.

In other words, the wire 305, which is a first jaw wire, sequentially passes through the driving part first jaw pulley 211, the driving part first jaw auxiliary pulley 213, and the driving part first jaw auxiliary pulley 215, and then is connected to the end tool 100 via the shaft 410.

In other words, the wire 305, which is a first jaw wire, enters the driving part 200 after passing through the end tool 100 and the shaft 410, and then is fixedly coupled to the pulley 211, which is a driving part first jaw pulley, after being sequentially wound around the pulley 215 and the pulley 213.

Meanwhile, the wire 301, which is a first jaw wire, is connected to the end tool 100 through the shaft 410 after being sequentially wound to make contact with at least portions of the pulley 212, the pulley 214, and the pulley 216 in a state in which one end portion of the wire 301 is coupled to the pulley 212 by the first jaw wire-driving part coupling member 324.

The wire 306, which is a second jaw wire, is connected to the end tool 100 via the shaft 410 after being sequentially wound to make contact with at least portions of the pulley 221, the pulley 223, and the pulley 225 in a state in which one end portion of the wire 306 is coupled to the pulley 221 by the second jaw wire-driving part coupling member 327.

Meanwhile, the wire 302, which is a second jaw wire, is connected to the end tool 100 via the shaft 410 after being sequentially wound to make contact with at least portions of the pulley 222, the pulley 224, and the pulley 226 in a state in which one end portion of the wire 302 is coupled to the pulley 222 by the second jaw wire-driving part coupling member 328.

(Pitch Motion)

The end tool 100 of the surgical instrument of the present disclosure may include the pulley 131, which is an end tool pitch pulley, the driving part (see 200 of FIG. 17) may include the pulley 231 and the pulley 232, which are driving part pitch pulleys, and the power transmission part 300 may further include the wire 303 and the wire 304, which are pitch wires.

In detail, the pulley 131 of the end tool 100 is rotatable around the rotation shaft 143, which is a pitch main rotation shaft, and may be integrally formed with the end tool hub 106 (or fixedly coupled to the end tool hub 106) as one body. In addition, the wire 303 and the wire 304 may serve to connect the pulley 131 of the end tool 100 to the pulley 231/pulley 232, which is a driving part pitch pulley, of the driving part (see 200 of FIG. 17).

Thus, when the pulley 231/pulley 232, which is a driving part pitch pulley, of the driving part (see 200 of FIG. 17) rotates, the rotation of the pulley 231/pulley 232, which is a driving part pitch pulley, is transmitted to the pulley 131 of the end tool 100 through the wire 303 and the wire 304, so that the pulley 131 is also rotated together with the pulley 231/pulley 232, and as a result, the end tool 100 perform a pitch motion while rotating.

However, if the driving part does not perform separate pitch compensation for the jaw wire when the pulley 231/pulley 232, which is a driving part pitch pulley, is rotated to perform a pitch motion as described above, in the end tool, along with the pitch motion, the jaws are rotated around the rotation shaft 141, which is a jaw pulley rotation shaft, and as a result, a pure pitch motion could not be performed.

This pitch compensation will be described in more detail later.

Figure 22:
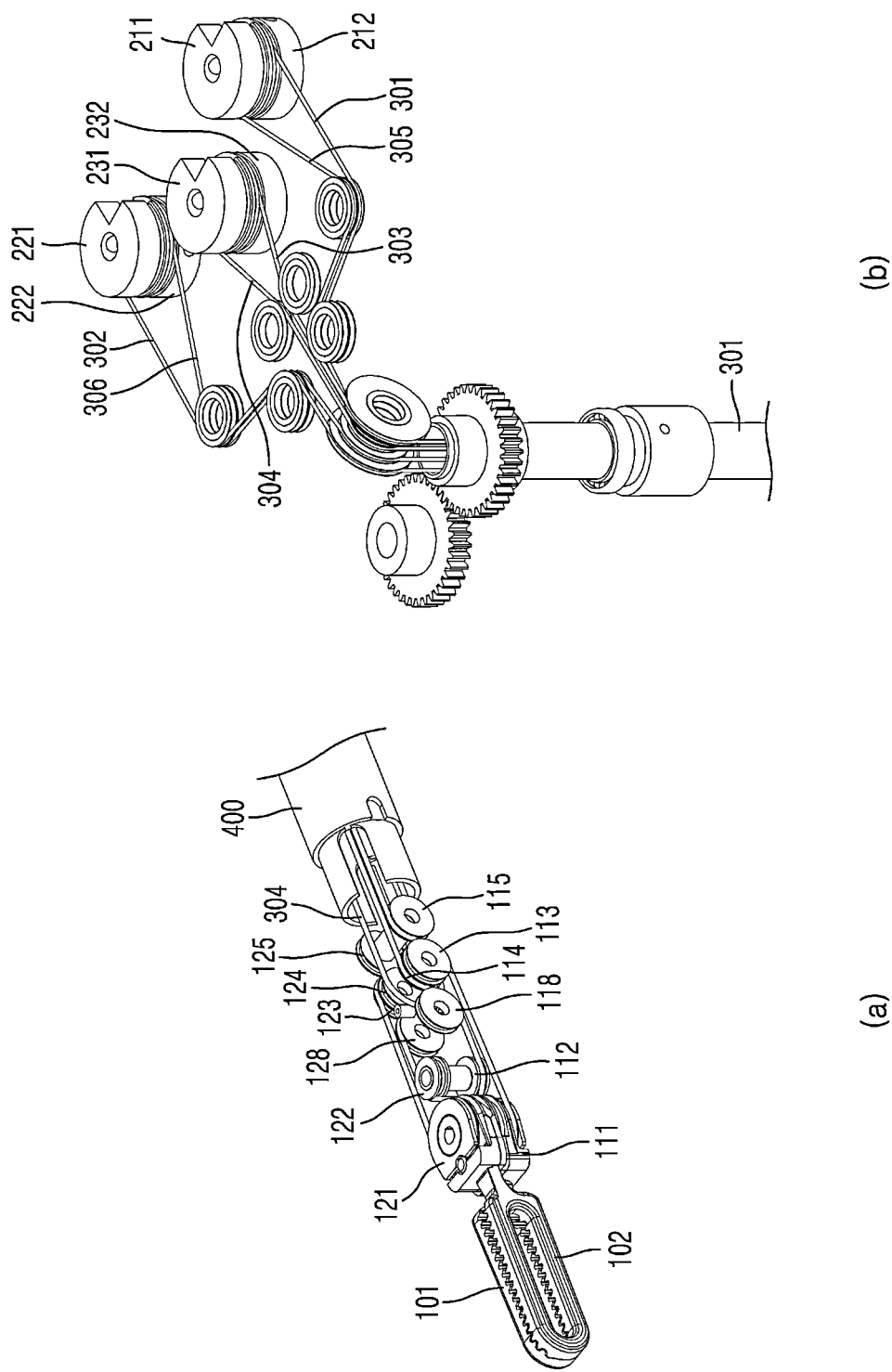
FIGS. 22 and 23 are views illustrating the surgical instrument of FIG. 17 in a neutral state.
Figure 23:
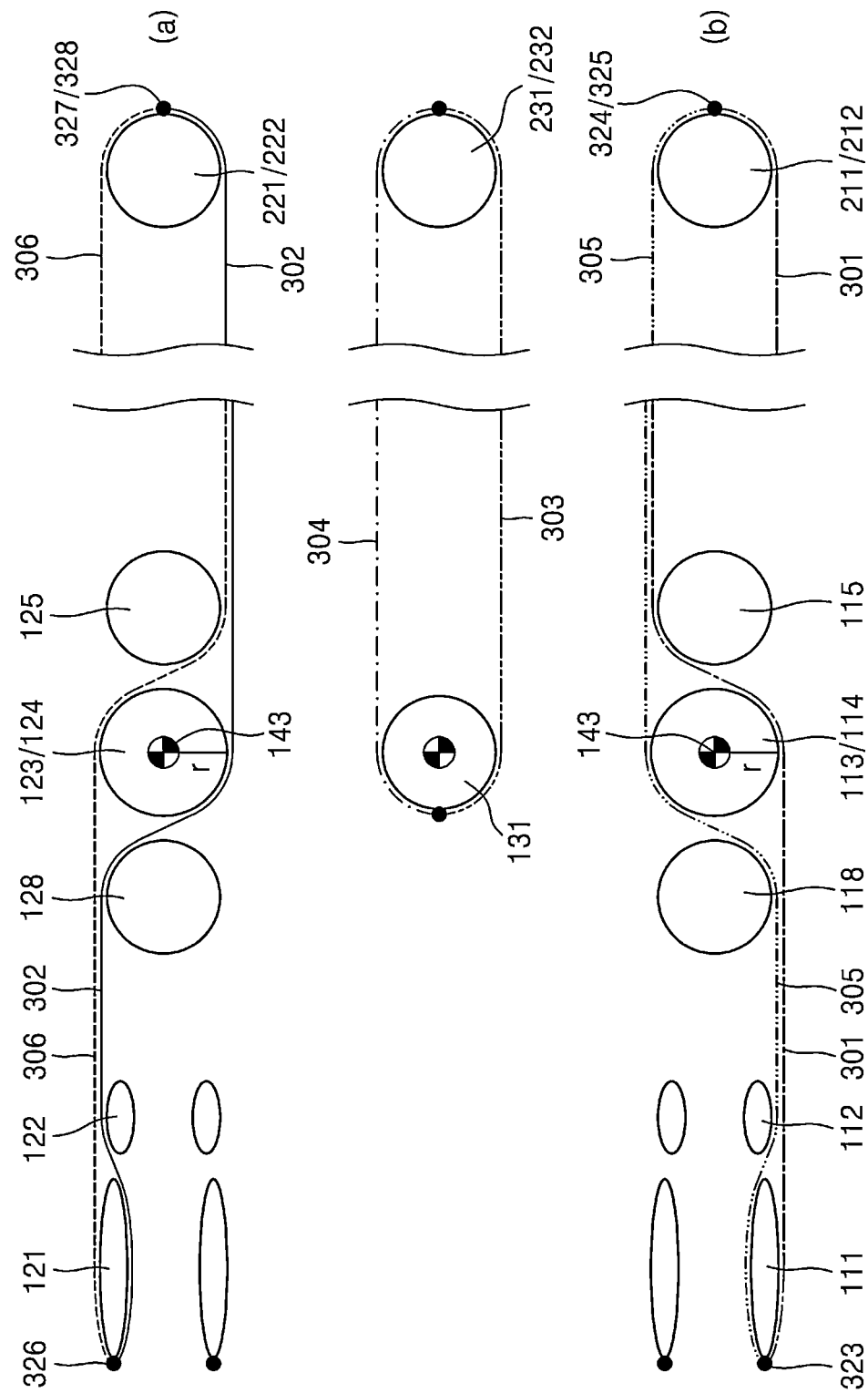
Figure 24:
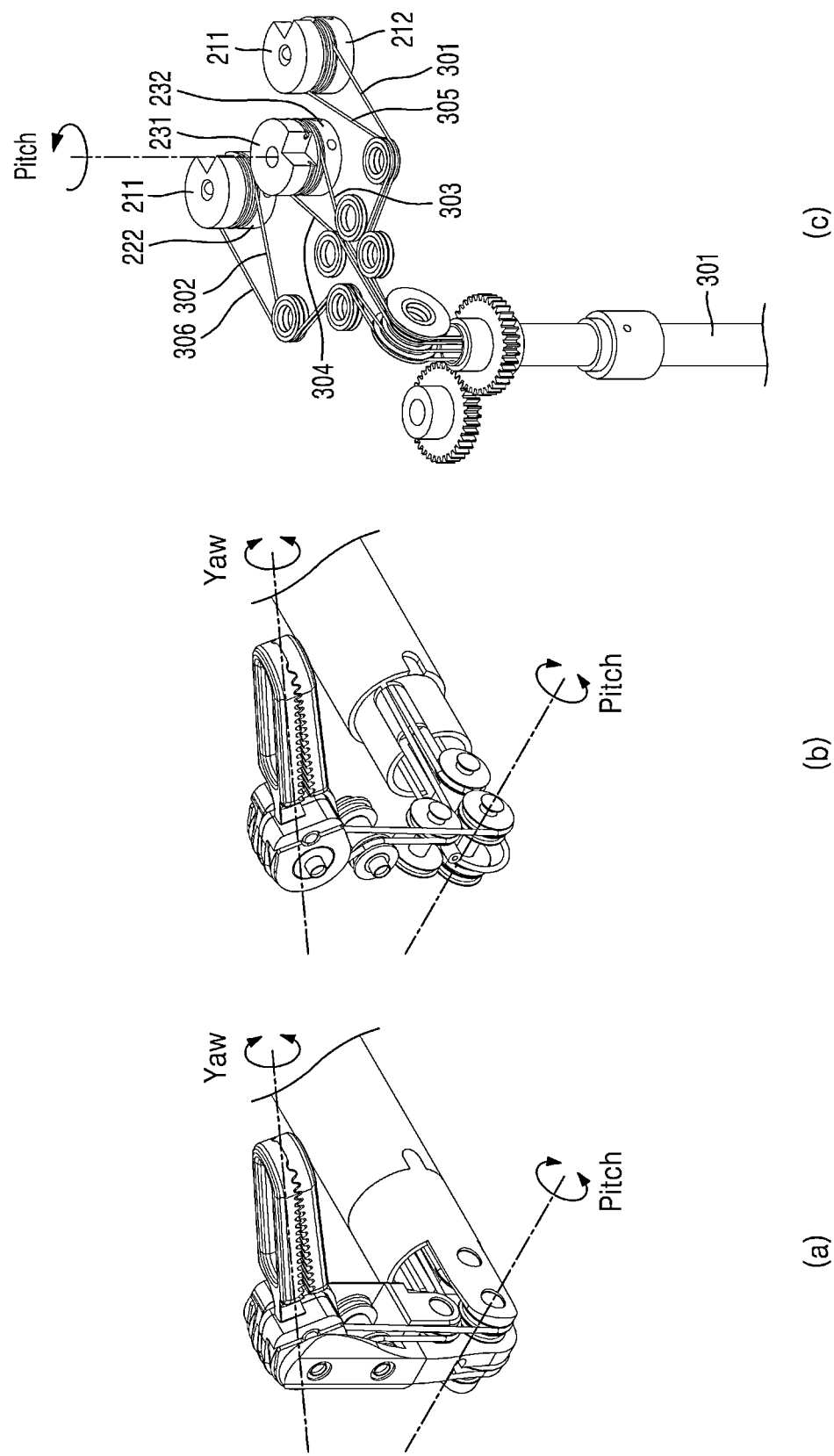
FIGS. 24, 25, 26A, and 26B are views illustrating the surgical instrument of FIG. 17 when pitch compensation is not performed.
Figure 25:
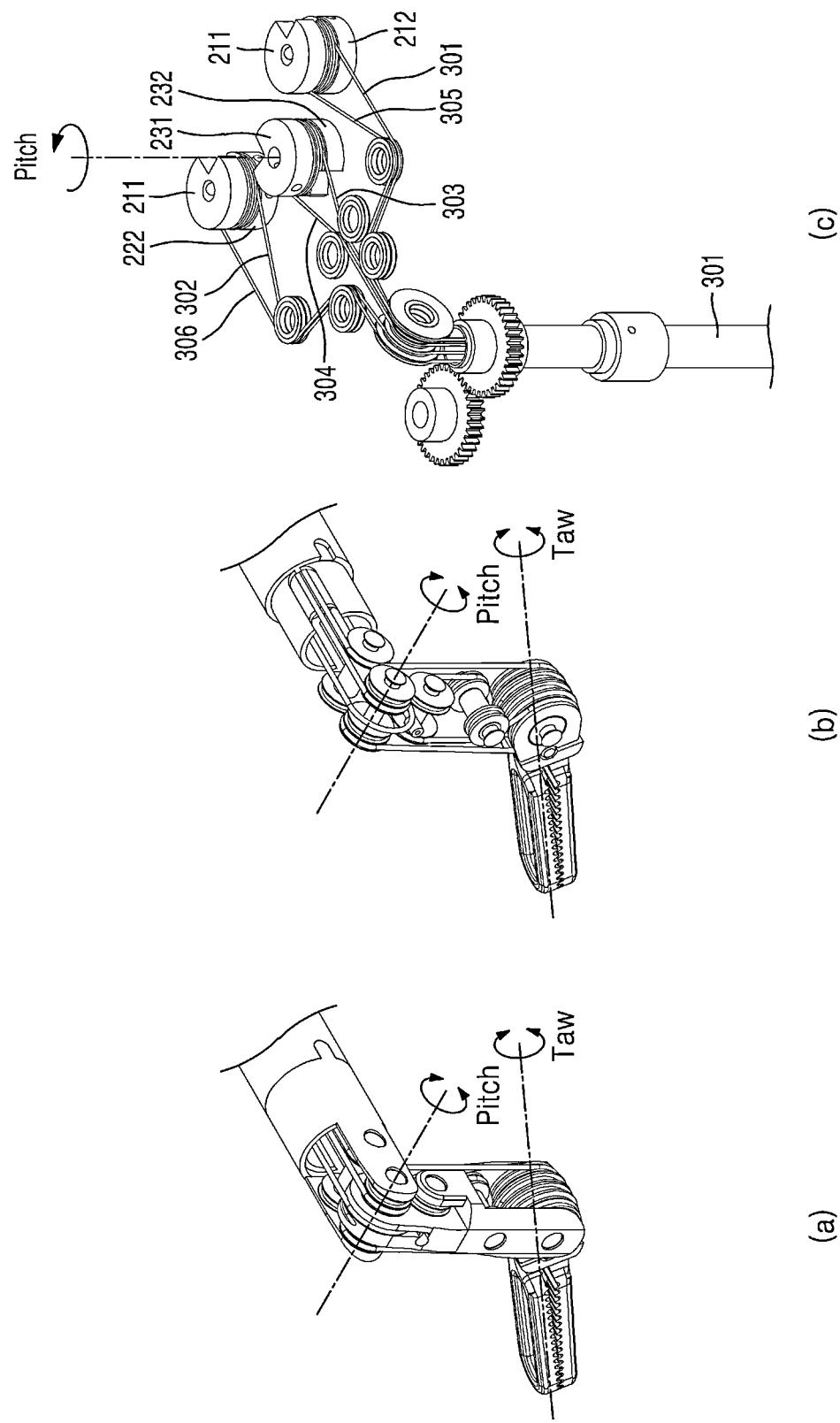
Figure 26A:
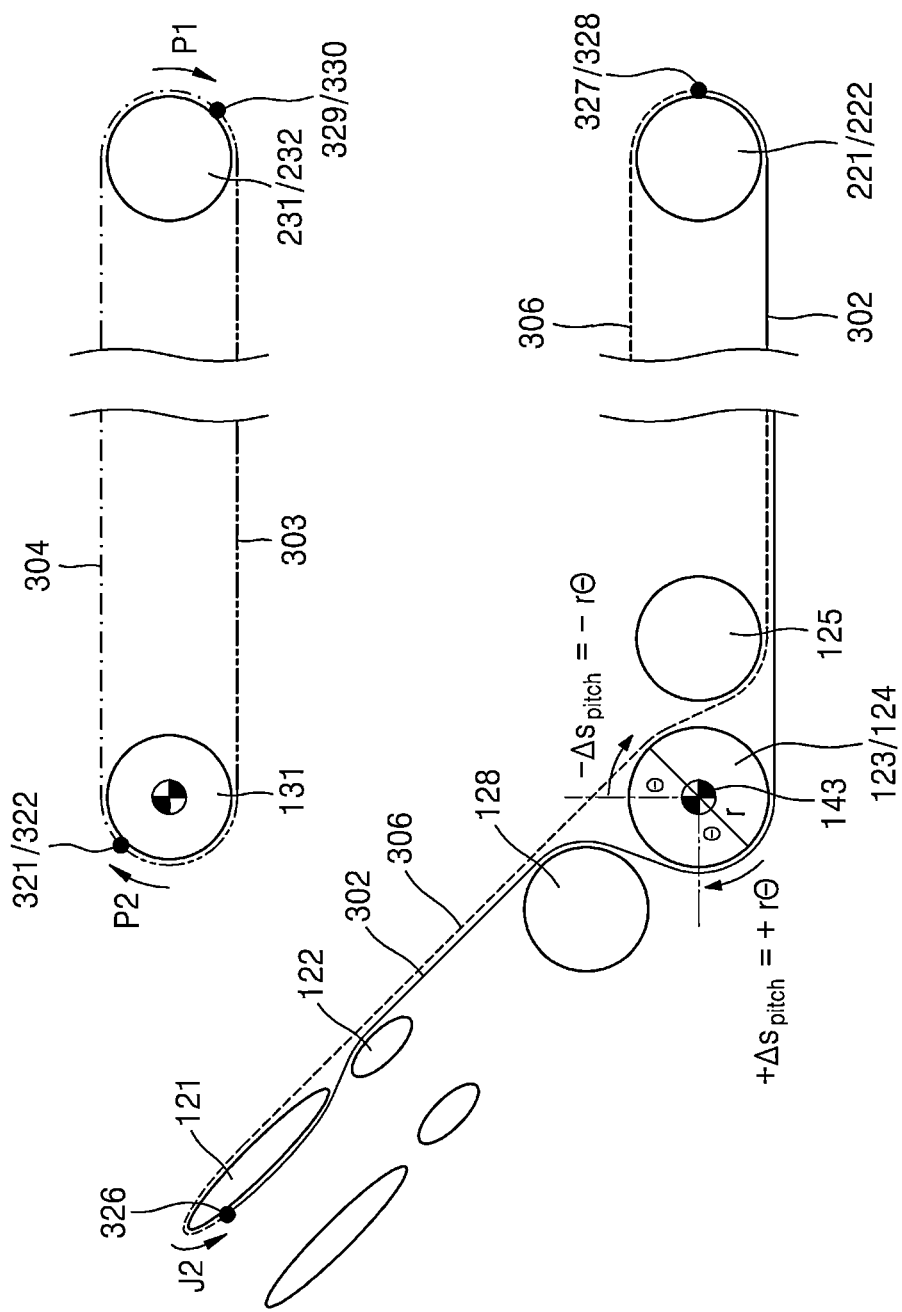
Figure 26B:
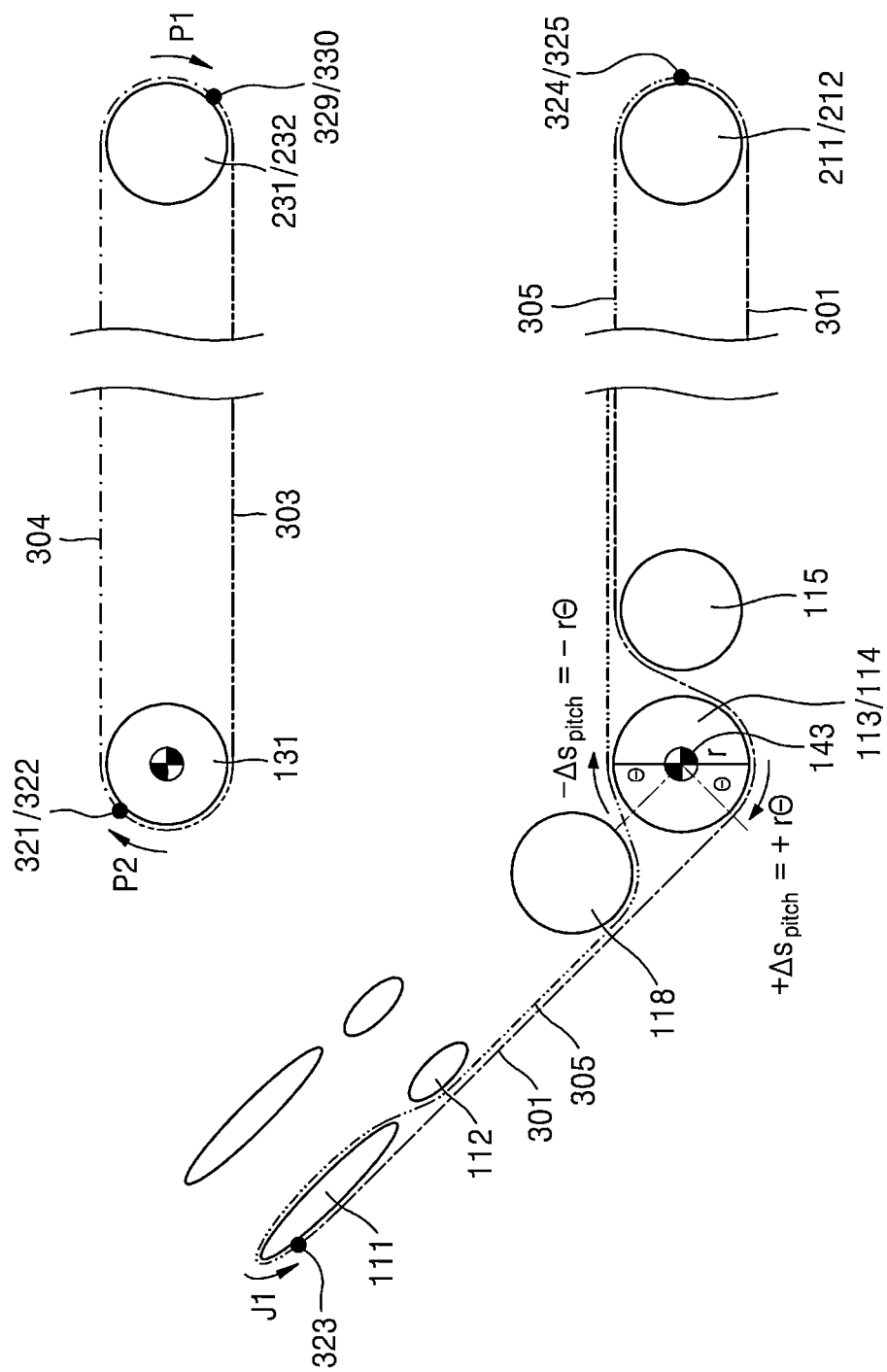
Figure 27:
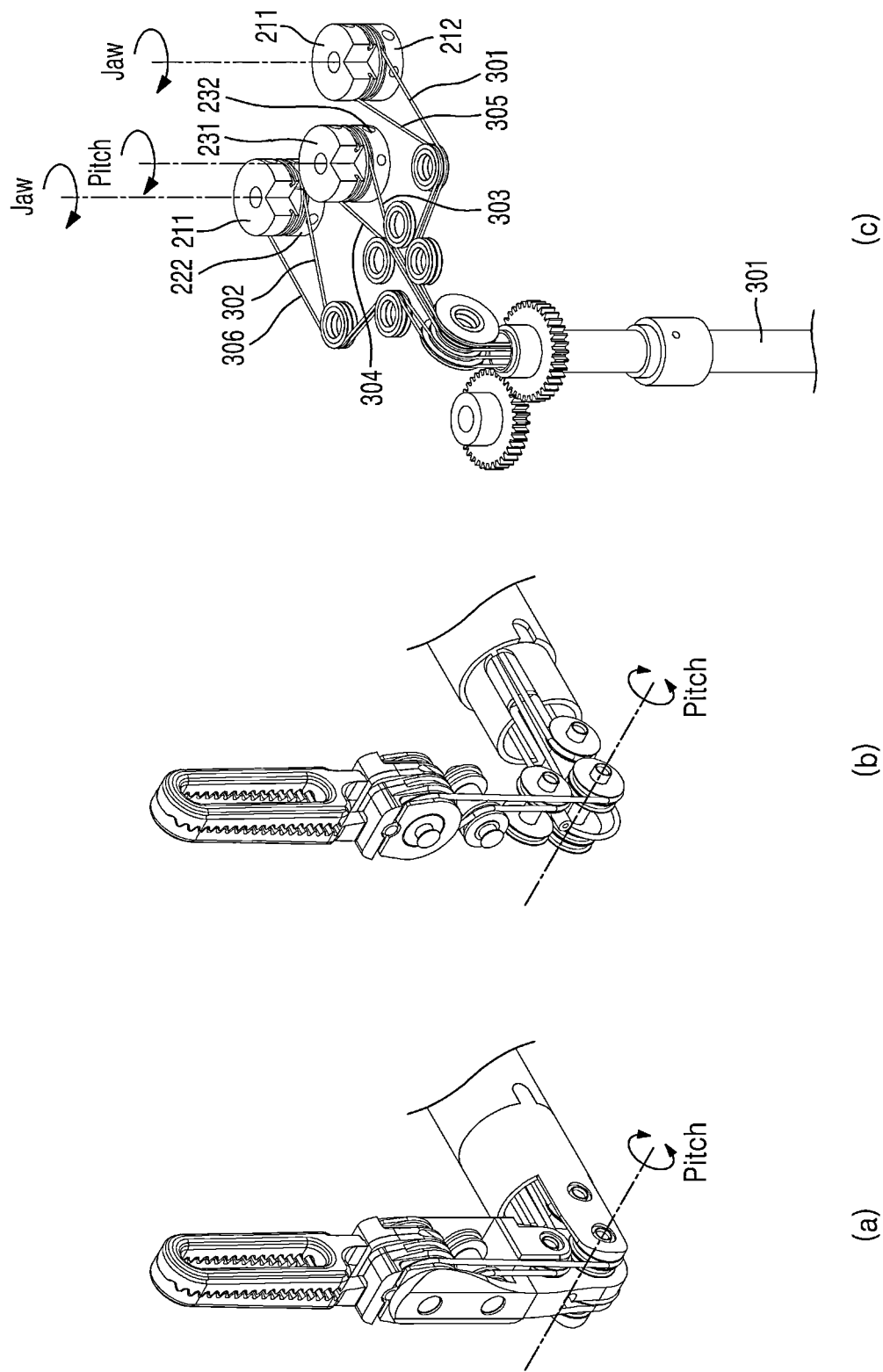
FIGS. 27, 28, 29A, and 29B are views illustrating the surgical instrument shown in FIG. 17 when pitch compensation is performed.
Figure 28:
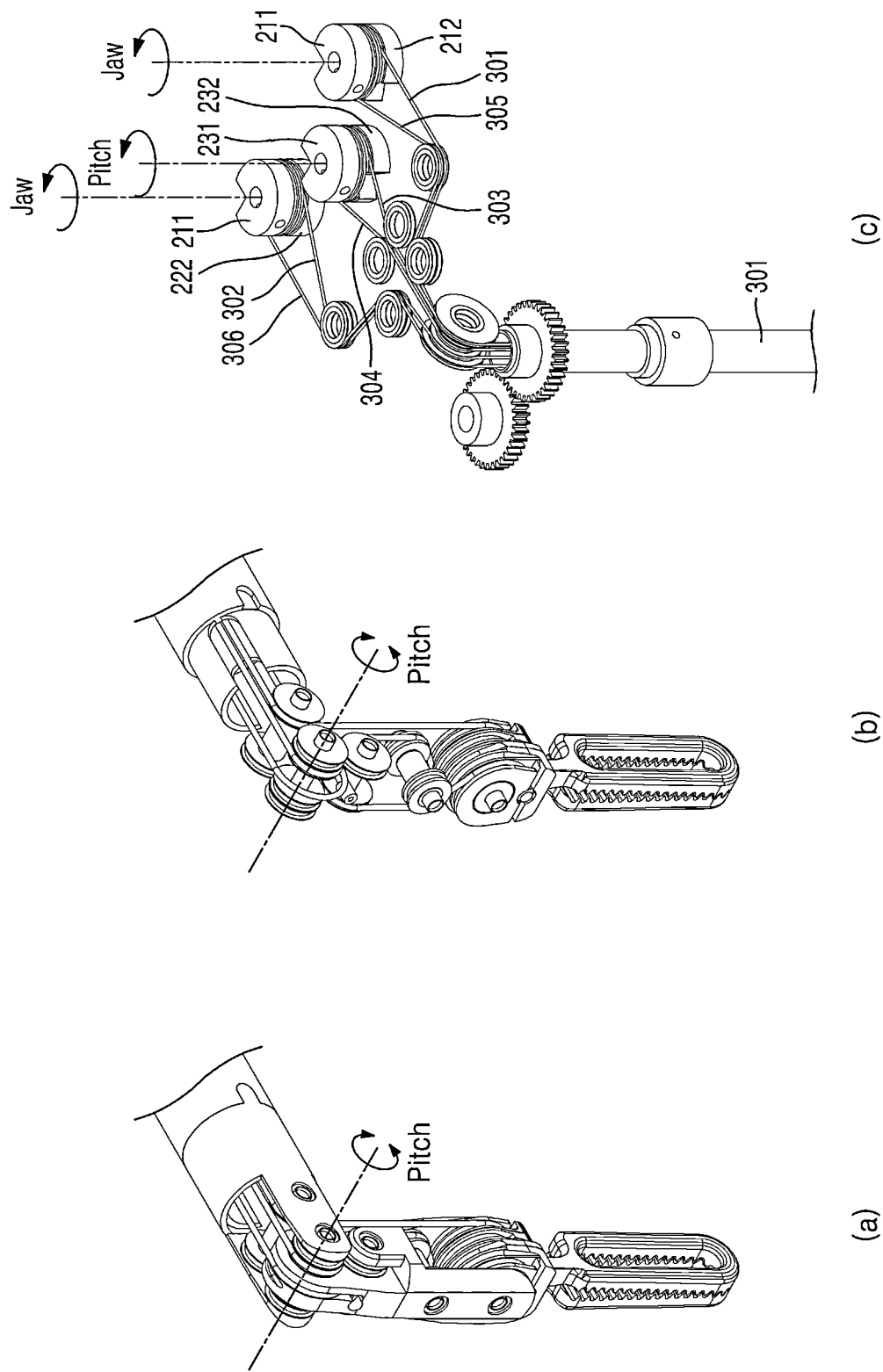
Figure 29A:
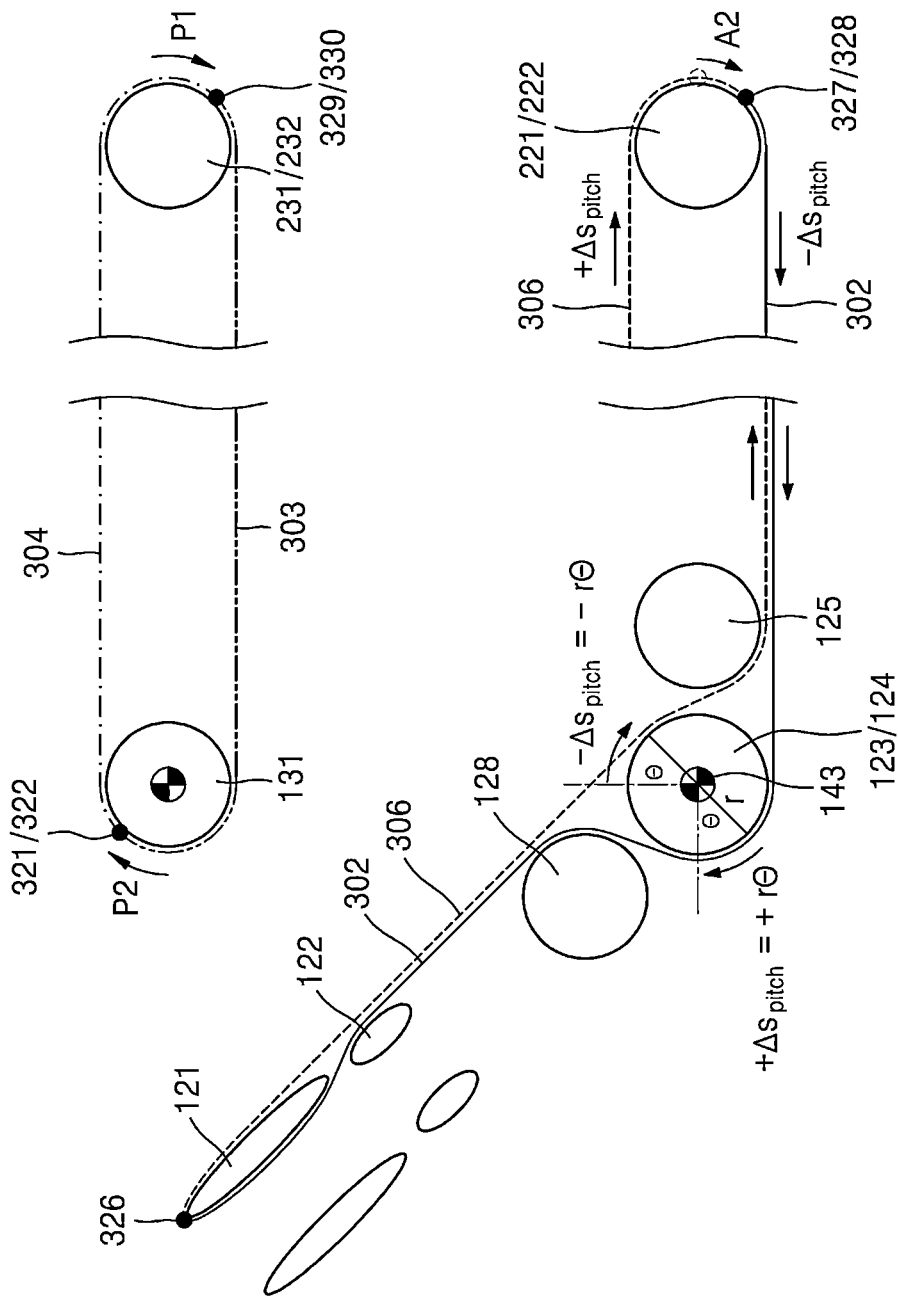
Figure 29B:
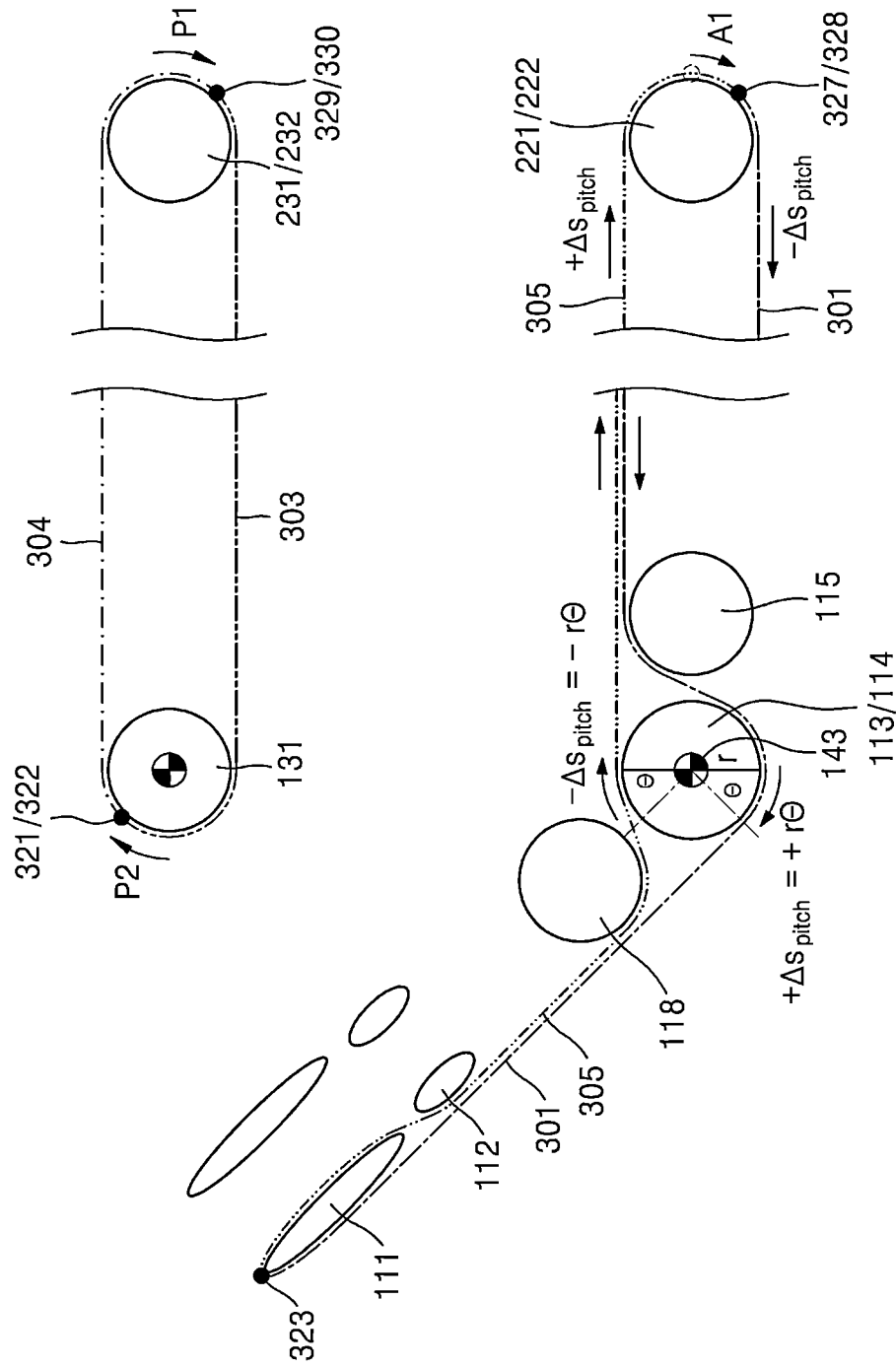

FIGS. 22 to 29 are conceptual views illustrating a pitch motion of the surgical instrument shown in FIG. 4. In detail, FIGS. 22 and 23 are views illustrating the surgical instrument in a neutral state, FIGS. 24, 25, and 26 are views illustrating the surgical instrument when pitch compensation is not performed, and FIGS. 27, 28, and 29 are views illustrating the surgical instrument when pitch compensation is performed. Here, for convenience of description, the pulleys and the wires associated with the rotation of the first jaw are mainly shown in FIGS. 23A, 26A, and 29A, and the pulleys and the wires associated with the rotation of the second jaw are mainly shown in FIGS. 23B, 26B, and 29B.

Here, in the surgical instrument according to an embodiment of the present disclosure, a pitch motion of the end tool 100 may be performed by rotating the pulley 211/pulley 212, which is a driving part first jaw pulley, and the pulley 221/pulley 222, which is a driving part second jaw pulley, to wind or unwind the jaw wires during the pitch motion.

As described above, if the driving part does not perform separate pitch compensation for the jaw wire when the pulley 231/pulley 232, which is a driving part pitch pulley, is rotated to perform a pitch motion as described above, in the end tool, along with the pitch motion, the jaws are rotated around the rotation shaft 141, which is a jaw pulley rotation shaft, and as a result, a pure pitch motion could not be performed.

In detail, referring to FIGS. 22 to 26, when the pulley 231/pulley 232, which is a driving part pitch pulley, of the driving part 200 is rotated to perform the pitch motion of the end tool, the rotation of the pulley 231/pulley 232, which is a driving part pitch pulley, is transmitted to the pulley 131 of the end tool 100 through the wire 303 and the wire 304, so that the pulley 131 is rotated together with the pulley 231/pulley 232, and as a result, the end tool 100 performs the pitch motion while rotating.

That is, when the pulley 231/pulley 232, which is a driving part pitch pulley, is rotated in the direction of an arrow P1 of FIG. 26A, the rotation of the pulley 231/pulley 232, which is a driving part pitch pulley, is transmitted to the pulley 131 of the end tool 100 through the wire 303 and the wire 304 so that the pulley 131 is rotated in the direction of an arrow P2 of FIG. 26A, and accordingly, the end tool hub (see 106 of FIG. 5) is rotated with respect to the pitch hub (see 107 of FIG. 5). In addition, the first jaw 101, the second jaw 102, the first jaw pulley 111, the second jaw pulley 122, the first jaw auxiliary pulley 112, and the second jaw auxiliary pulley 122, which are coupled to the end tool hub (see 106 of FIG. 5), are also rotated together with the end tool hub (see 106 of FIG. 5) with respect to the pitch hub (see 107 of FIG. 5).

However, in this case, the wire 301 and the wire 302, which are jaw wires, are wound further around the pulley 113/pulley 114 by $\Delta S_{pitch}$, and the wire 305 and the wire 306 are unwound further around the pulley 114/pulley 114 by $\Delta S_{pitch}$.

Thus, if this is not compensated for, the first jaw pulley 111 is rotated by a certain degree in the direction of an arrow J1 of FIG. 26B, and the second jaw pulley 121 is rotated by a certain degree in the direction of an arrow J2 of FIG. 26A.

Thus, when the movement of the jaw wire is not compensated for, in the end tool, along with the pitch motion, the jaws are also rotated around the rotation shaft 141, which is a jaw pulley rotation shaft, and as a result, the pure pitch motion may not be performed, and the pitch motion and a yaw motion may be mixed.

In order to perform motion compensation for the pitch motion as described above, in the surgical instrument according to an embodiment of the present disclosure, during the pitch motion, the jaw wires are wound or unwound as the pulley 211/pulley 212, which is a driving part first jaw pulley, and the pulley 221/pulley 222, which is a driving part second jaw pulley, are rotated together with the driving part pitch pulley, so that a kind of compensation for the pitch motion is performed, allowing the pitch motion of the end tool 100 to be performed.

That is, during the pitch motion, the pulley 211/pulley 212, which is a driving part first jaw pulley, is rotated by a certain degree in the direction of an arrow A1 of FIG. 29B. Then, the wire 301 is unwound from the pulley 211/pulley 212, which is a driving part first jaw pulley, by a certain degree (e.g., by $\Delta S_{pitch}$), thereby being wound around the first jaw pitch main pulley 113 to the extent of the unwinding. At the same time, the wire 305 is wound around the pulley 211/pulley 212, which is a driving part first jaw pulley, by a certain degree (e.g., by $\Delta S_{pitch}$), thereby being unwound from the first jaw pitch main pulley 114 to the extent of the winding.

Likewise, during the pitch motion, the pulley 221/pulley 222, which is a driving part second jaw pulley, is rotated by a certain degree in the direction of an arrow A2 of FIG. 29A. Then, the wire 302 is unwound from the pulley 221/pulley 222, which is a driving part second jaw pulley, by a certain degree (e.g., by $\Delta P_{pitch}$), thereby being wound around the second jaw pitch main pulley 123 to the extent of the unwinding. At the same time, the wire 306 is wound around the pulley 221/pulley 222, which is a driving part second jaw pulley, by a certain degree (e.g., by $\Delta S_{pitch}$) thereby being unwound from the second jaw pitch main pulley 124 to the extent of the winding.

In other words, when the pulley 231/pulley 232, which is a driving part pitch pulley, is rotated, the pulley 211/pulley 212, which is a driving part first jaw pulley, and the pulley 221/pulley 222, which is a driving part second jaw pulley, are also rotated, and accordingly, lengths of the jaw wires respectively wound around the pulley 211/pulley 212, which is a driving part first jaw pulley, and the pulley 221/pulley 222, which is a driving part second jaw pulley, are changed. That is, due to the rotation of the pulley 231/pulley 232, which is a driving part pitch pulley, the jaw wire wound at the end tool 100 side is unwound by the same amount at the driving part 200 side, and the jaw wire unwound at the end tool 100 side is wound by the same amount at the driving part 200 side, so that the pitch motion does not affect the yaw motion.

In other words, due to the rotation of the pulley 231/pulley 232, which is a driving part pitch pulley, when the end tool 100 performs a pitch motion, the jaw wires (responsible for the yaw motion and the actuation motion) are also moved by the pitch motion. That is, as the pitch rotation is performed around the rotation shaft 143 of the end tool 100, in the jaw wire coupled to one jaw, one strand is pulled and another strand is released. At the same time, in the jaw wire coupled to another jaw, one strand is pulled and another strand is released. Accordingly, it may be described that, in the present disclosure, in order to compensate for this movement of the jaw wire, when the pulley 231/pulley 232, which is a driving part pitch pulley, is rotated for a pitch motion of the end tool, the pulley 211/pulley 212, which is a driving part first jaw pulley, and the pulley 221/pulley 222, which is a driving part second jaw pulley, are also rotated to change the length of the respective jaw wire in the driving part, so that as much as the jaw wire is pulled (or released) at the end tool side, the jaw wire is released (or pulled) at the driving part side, thereby compensating for the movement of the jaw wire during the pitch motion of the end tool.

As described above, the end tool 100 of the surgical instrument according to an embodiment of the present disclosure can easily control a pitch motion by winding the two strands of the jaw wire, which are wound around one jaw pulley, around the pitch main pulley in opposite directions. That is, during the pitch motion, the pulley 211/pulley 212, which is a driving part first jaw pulley, and the pulley 221/pulley 222, which is a driving part second jaw pulley, are rotated to wind and unwind the jaw wires, which enables a kind of compensation for the pitch motion, allowing the pitch motion of the end tool 100 to be performed.

Figure 30:
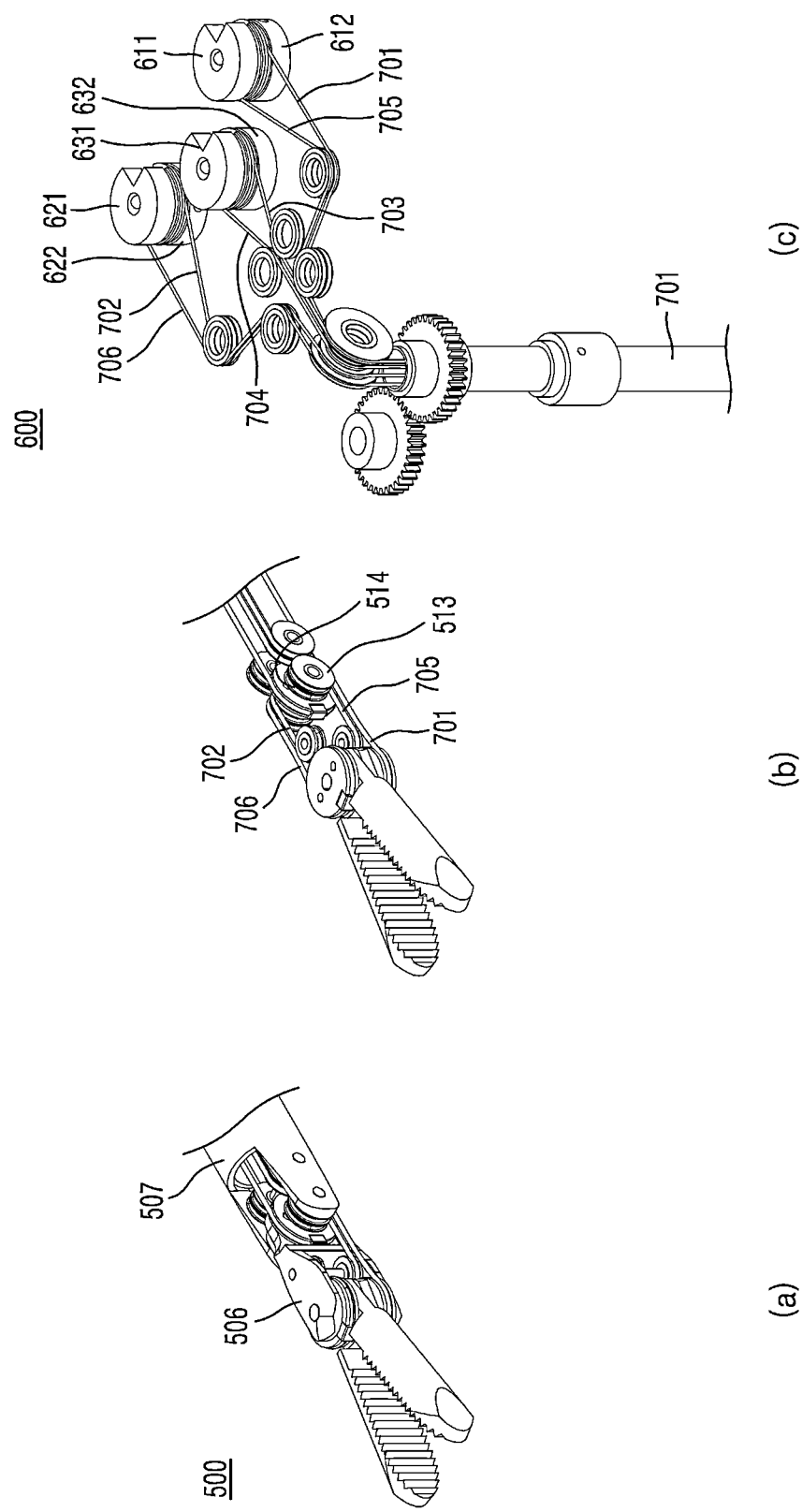
FIG. 30 is a view illustrating a neutral state of a surgical instrument according to a comparative example of the present disclosure.
Figure 31:
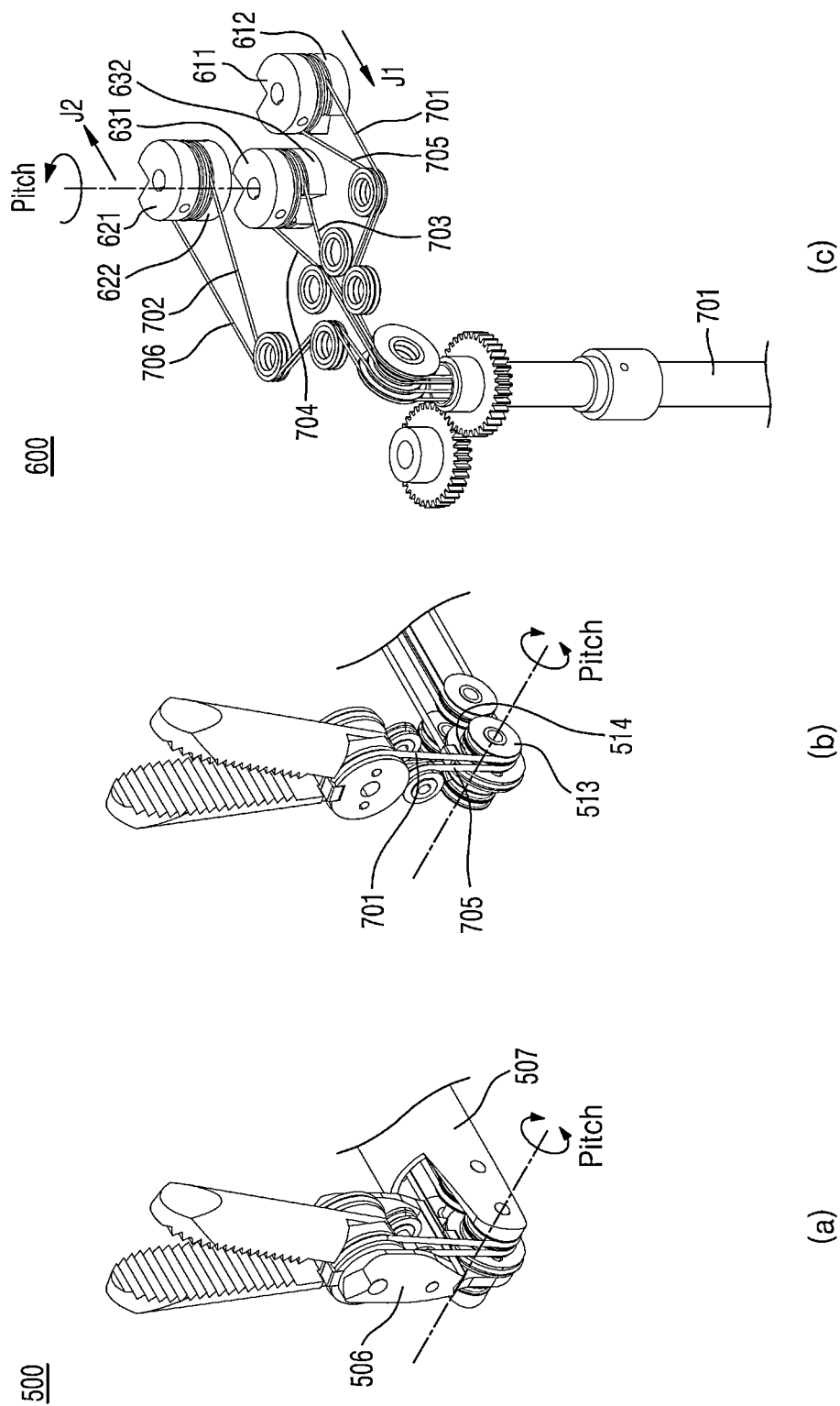
FIGS. 31, 32, and 33 are views illustrating the surgical instrument of FIG. 30 when pitch compensation is performed.
Figure 32:
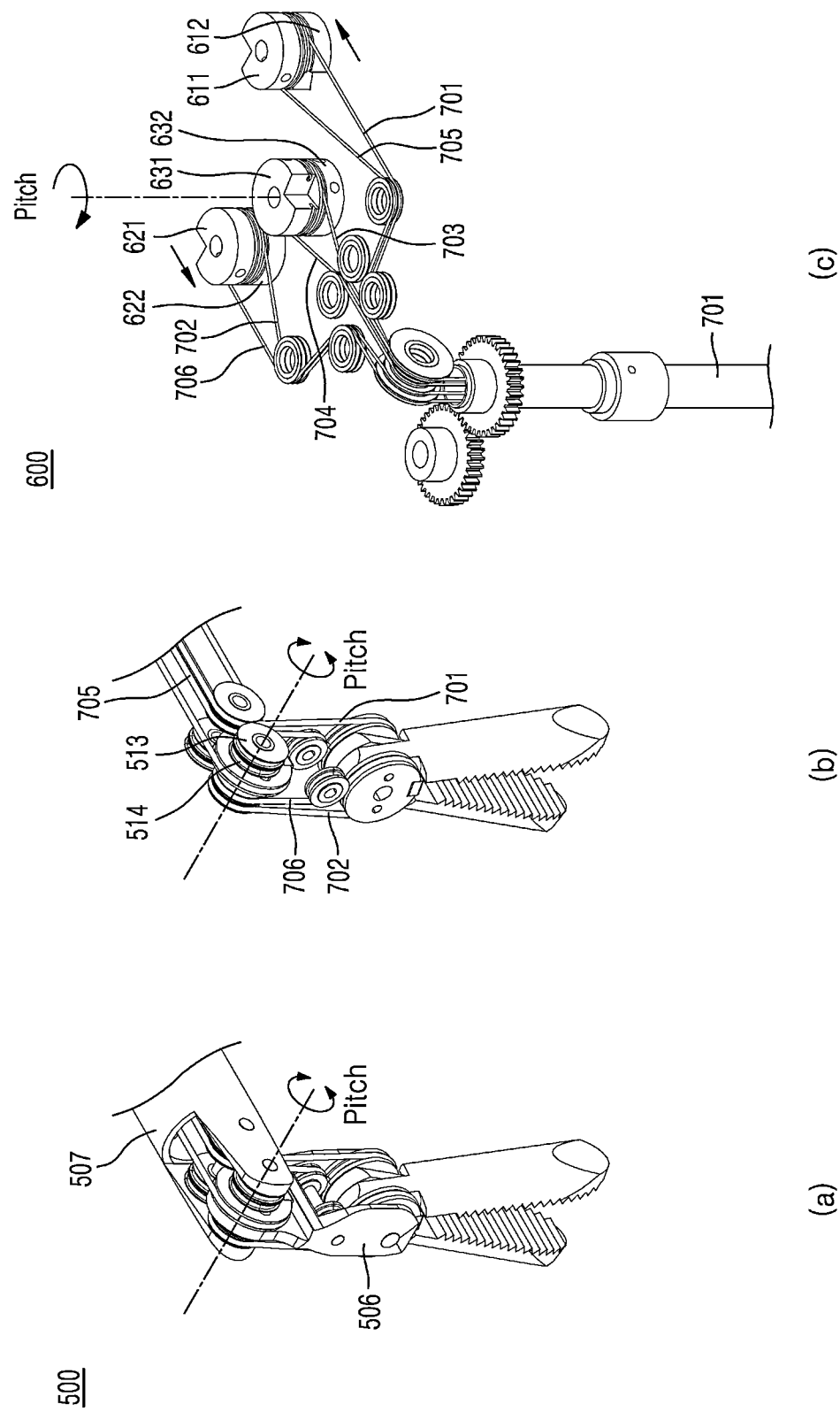
Figure 33:
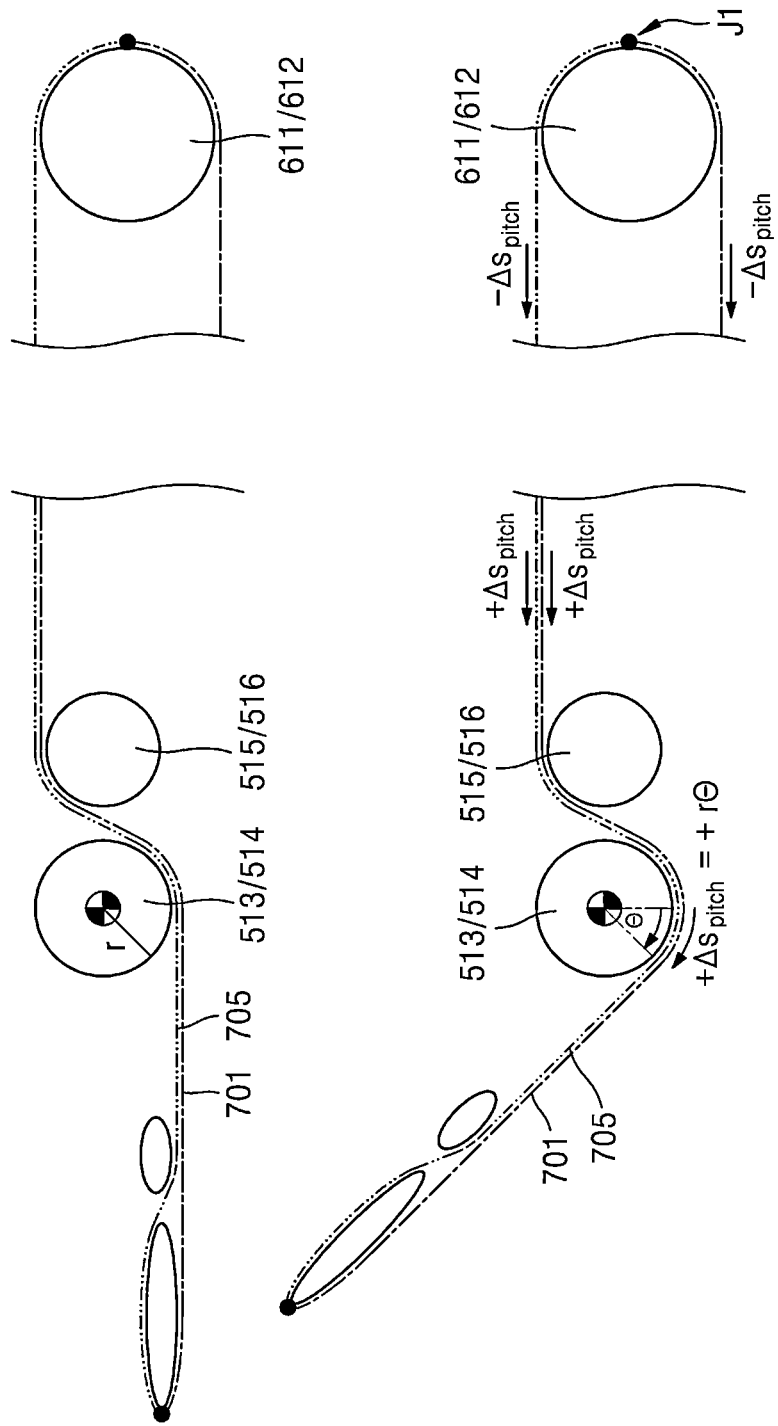

FIG. 30 is a view illustrating a neutral state of a surgical instrument according to a comparative example of the present disclosure, and FIGS. 31, 32, and 33 are views illustrating the surgical instrument of FIG. 30 when pitch compensation is performed.

Here, for convenience of description, a state of an end tool to which an end tool hub and a pitch hub are coupled is shown in FIGS. 30A, 31A, and 32A, and a state of the end tool from which the end tool hub and the pitch hub are removed is shown in FIGS. 30B, 31B, and 32B, and a driving part corresponding to the state of the end tool is shown in FIGS. 30C, 31C, and 32C.

In the case of the surgical instrument according to the comparative example of the present disclosure shown in FIG. 30, pitch redundant pulleys (see 118 and 128 of FIG. 6) are not provided. Thus, two strands of the jaw wire wound around one jaw pulley are wound around a pitch main pulley in the same direction.

For example, of two strands of the first jaw wire, one strand (e.g., a wire 701) may enter a pulley 513, which is a first jaw pitch main pulley, at a lower side of the XY plane, and another strand (e.g., a wire 705) may exit from a pulley 514, which is the first jaw pitch main pulley, at the lower side of the XY plane. In other words, it may be said that the first jaw wire is structured to enter a lower side of the first jaw pitch main pulley and exit from the lower side of the first jaw pitch main pulley. (It is the structure in which a second jaw wire enters an upper side of a second jaw pitch main pulley and exits from the upper side thereof).

Accordingly, when a pitch motion is performed by rotating a pulley 631/pulley 632, which is a driving part pitch pulley, a wire 701 and a wire 705, which are first jaw wires, move in the same direction.

For example, as shown in FIGS. 31 and 33, when the pulley 631/pulley 632, which is a driving part pitch pulley, is rotated in the direction of an arrow P of FIG. 31, the wire 701 and the wire 705 are pulled by $\Delta S_{pitch}$ shown in FIG. 33.

When the wire 701 and the wire 705 move in the same direction as described above, compensation for the pitch motion may not be performed just by rotating a pulley 611/pulley 612, which is a driving part first jaw pulley.

Thus, as shown in FIGS. 31 and 33, pitch compensation may be performed by moving the position of the pulley 611/pulley 612, which is driving part first jaw pulley, to change a path length of the first jaw wire in a driving part 600 and simultaneously moving the position of the a pulley 621/pulley 622, which is a driving part second jaw pulley, to change a path length of the second jaw wire in the driving part 600.

That is, in order to compensate for the movement of the jaw wires during pitch driving, the pulley 611/pulley 612, which is a driving part first jaw pulley, is moved by a certain degree in the direction of an arrow J1. In addition, by the same principle, the pulley 621/pulley 622, which is a driving part second jaw pulley, is moved by a certain degree in the direction of an arrow J2.

In this case, in order to move the positions of the driving part first jaw pulley and the driving part second jaw pulley for pitch compensation, various and complex instrument structures are required in the driving part.

In comparison, the end tool 100 of the surgical instrument according to an embodiment of the present disclosure can easily control the pitch motion by winding the two strands of the jaw wire, which are wound around one jaw pulley, around the pitch main pulley in opposite directions.

(Yaw Motion)

FIGS. 15 and 16 are views illustrating a yaw motion of the surgical instrument shown in FIG. 4.

Referring to FIGS. 15, 16, 17, and 21 and the like, when the pulley 211/pulley 212, which is a driving part first jaw pulley, is rotated in one direction for a yaw motion, one side of the wires 301 and 305, which are first jaw wires, is wound around the pulley 211/pulley 212 in response to the rotation of the pulley 211/pulley 212, and another side thereof is unwound from the pulley 211/pulley 212. Accordingly, the pulley 111, which is an end tool first jaw pulley connected to the opposite side of the wires 301 and 305, is rotated in one direction, so that the yaw motion is performed.

At this time, the driving part pitch pulley 231/pulley 232 is not rotated, and the wire 303 and the wire 304, which are pitch wires, remain in their positions without being wound or unwound.

Likewise, when the pulley 221/pulley 222, which is a driving part second jaw pulley, is rotated in one direction for the yaw motion, one side of the wire 302 and the wire 306, which are second jaw wires, is wound around the pulley 221/pulley 222 in response to the rotation the pulley 221/pulley 222, and another side thereof is unwound from the pulley 221/pulley 222. Accordingly, the pulley 121, which is an end tool second jaw pulley connected to the opposite side of the wires 302 and 306, is rotated in one direction, so that the yaw motion is performed.

At this time, the driving part pitch pulley 231/pulley 232 is not rotated, and the wire 303 and the wire 304, which are pitch wires, remain in their positions without being wound or unwound.

As a result, the overall lengths of the wire 301, the wire 302, the wire 305, and the wire 306, which are jaw wires, in the driving part 200 remain constant even when the pulley 211/pulley 212 or the pulley 221/pulley 222, which are driving part jaw pulleys, are rotated for the yaw or actuation motion.

As described above, in the surgical instrument 30 according to an embodiment of the present disclosure, when the driving part pitch pulley is rotated, the driving part jaw pulley is rotated together with the driving part pitch pulley to change the path length of the jaw wire wound around the driving part jaw pulley, so that the jaw wire is wound or unwound in response to the rotation of the driving part pitch pulley to offset or compensate for the movement of the jaw wire according to the pitch driving, thereby resulting in an effect of separating the pitch motion and the yaw motion.

MODES OF THE INVENTION

First Modified Example of First Embodiment

Hereinafter, an end tool 100 of a surgical instrument according to a first modified example of the first embodiment of the present disclosure will be described. Here, the end tool 100 of the surgical instrument according to the first modified example of the first embodiment of the present disclosure is different from the end tool of the surgical instrument according to the first embodiment of the present disclosure described above in that some pulleys are added. Hereinafter, the configuration that is different from that of the first embodiment will be described in detail.

Figure 34:
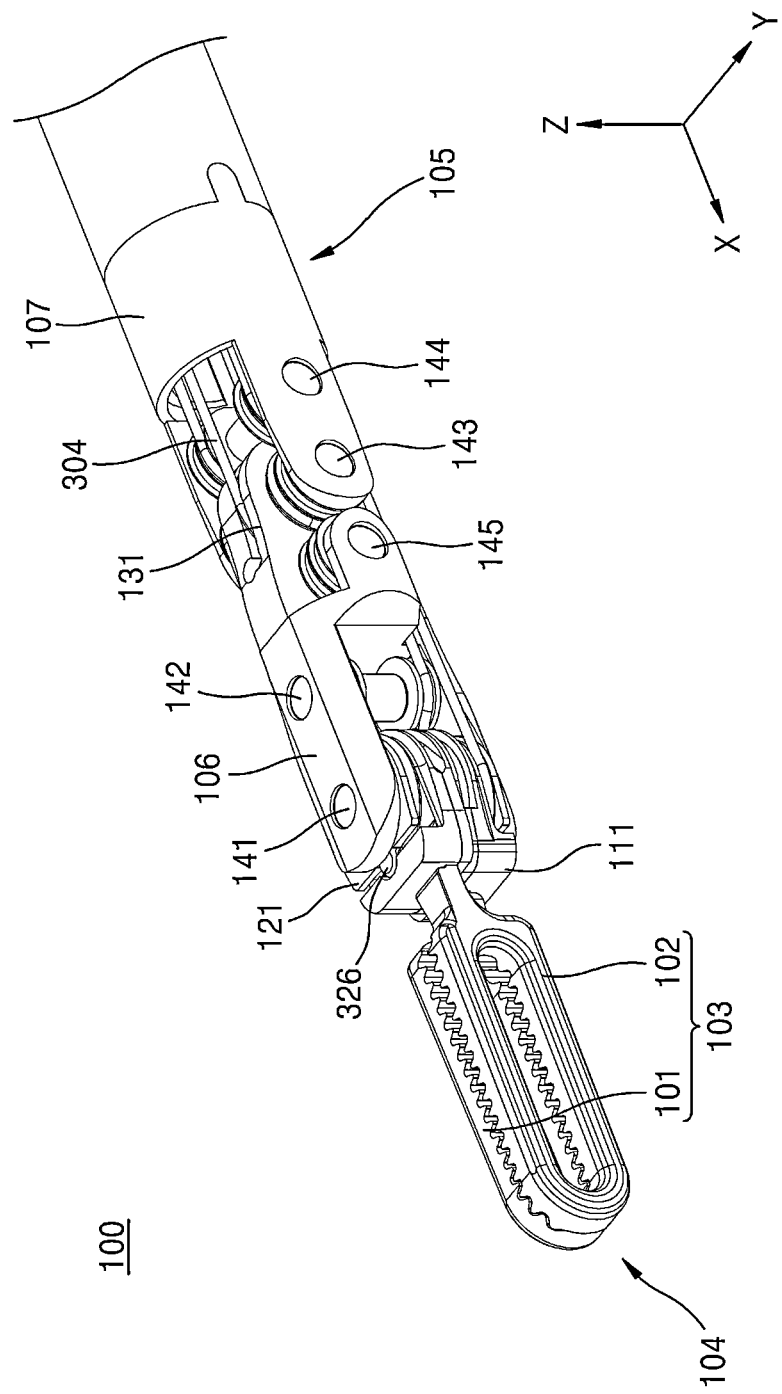
FIGS. 34 and 35 are perspective views illustrating an end tool of a surgical instrument according to a first modified example of the first embodiment of the present disclosure.
Figure 35:
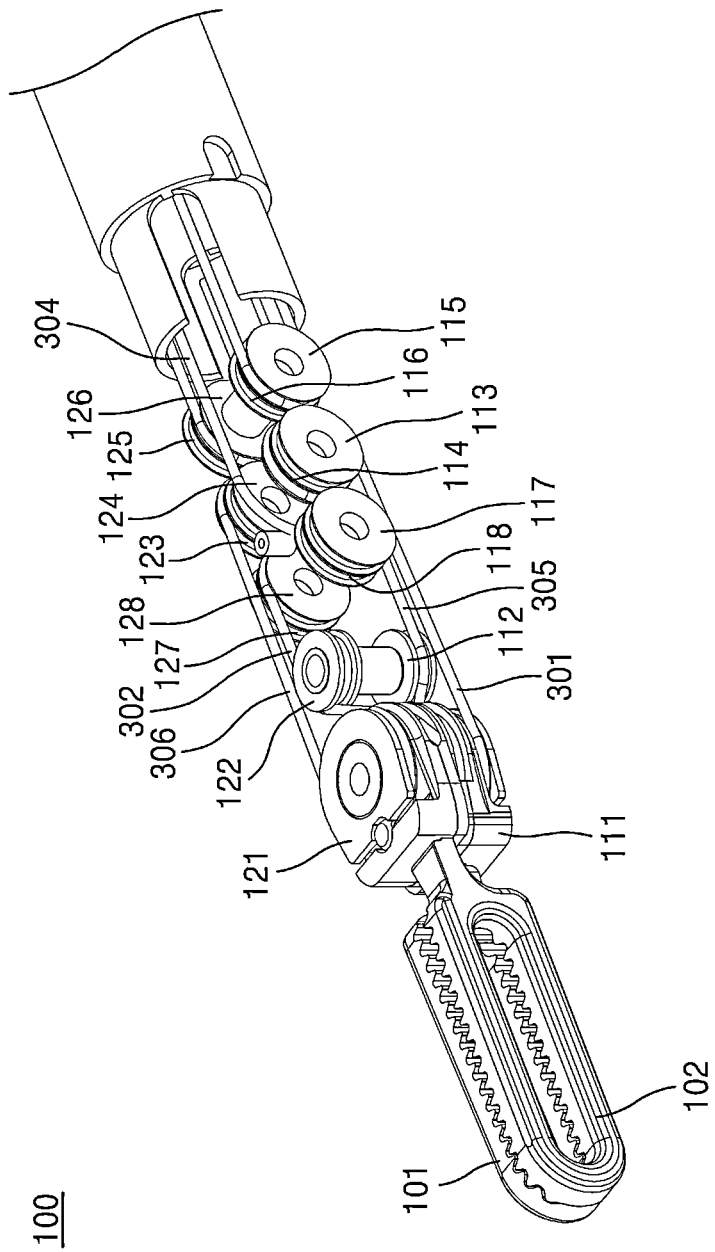
Figure 36:
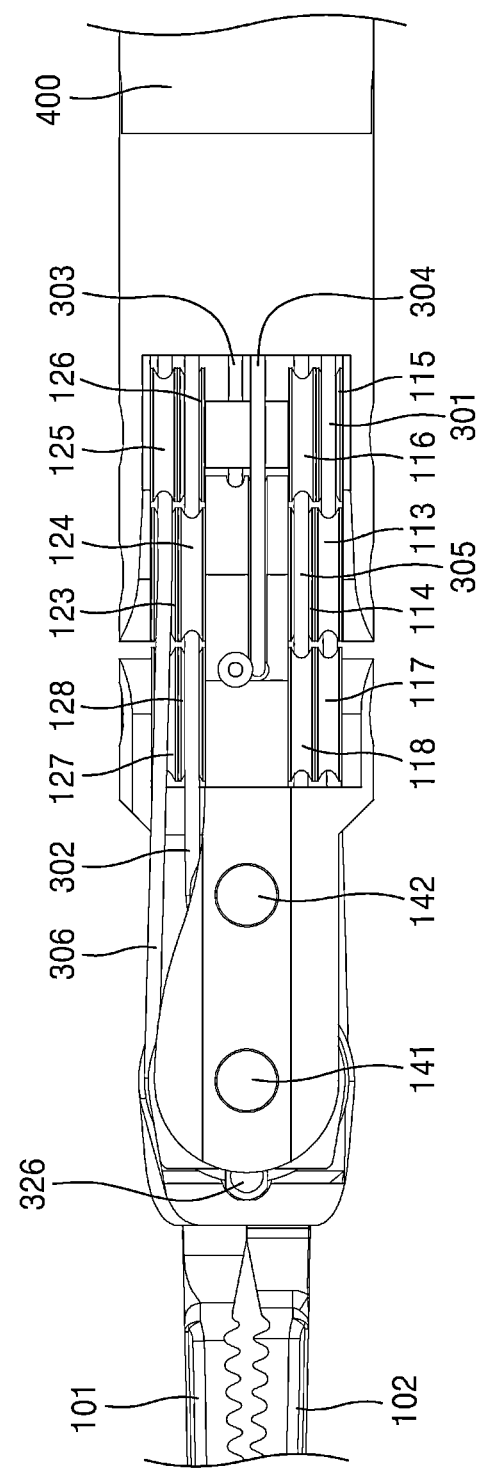
FIG. 36 is a plan view of the end tool of FIG. 34.
Figure 37:
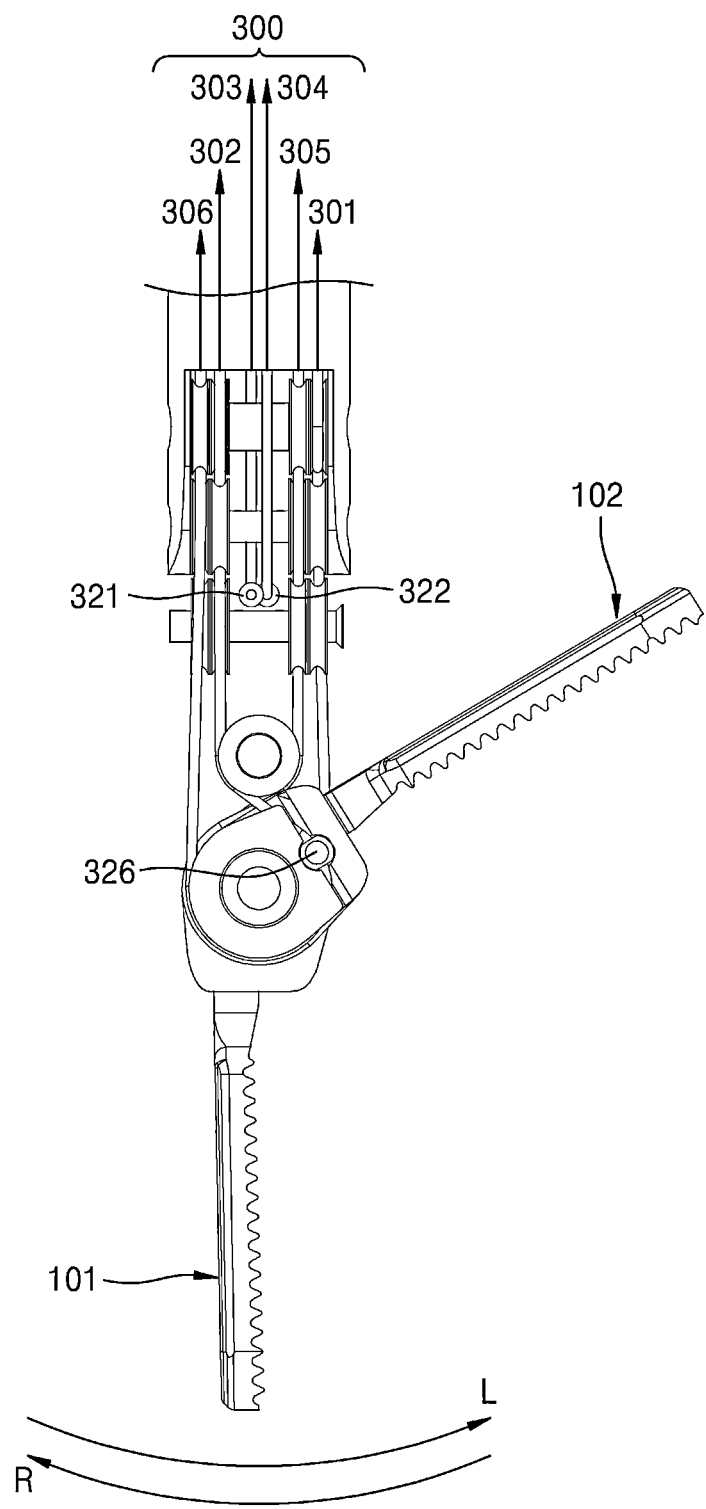
FIGS. 37 and 38 are plan views of the end tool of FIG. 34.
Figure 38:
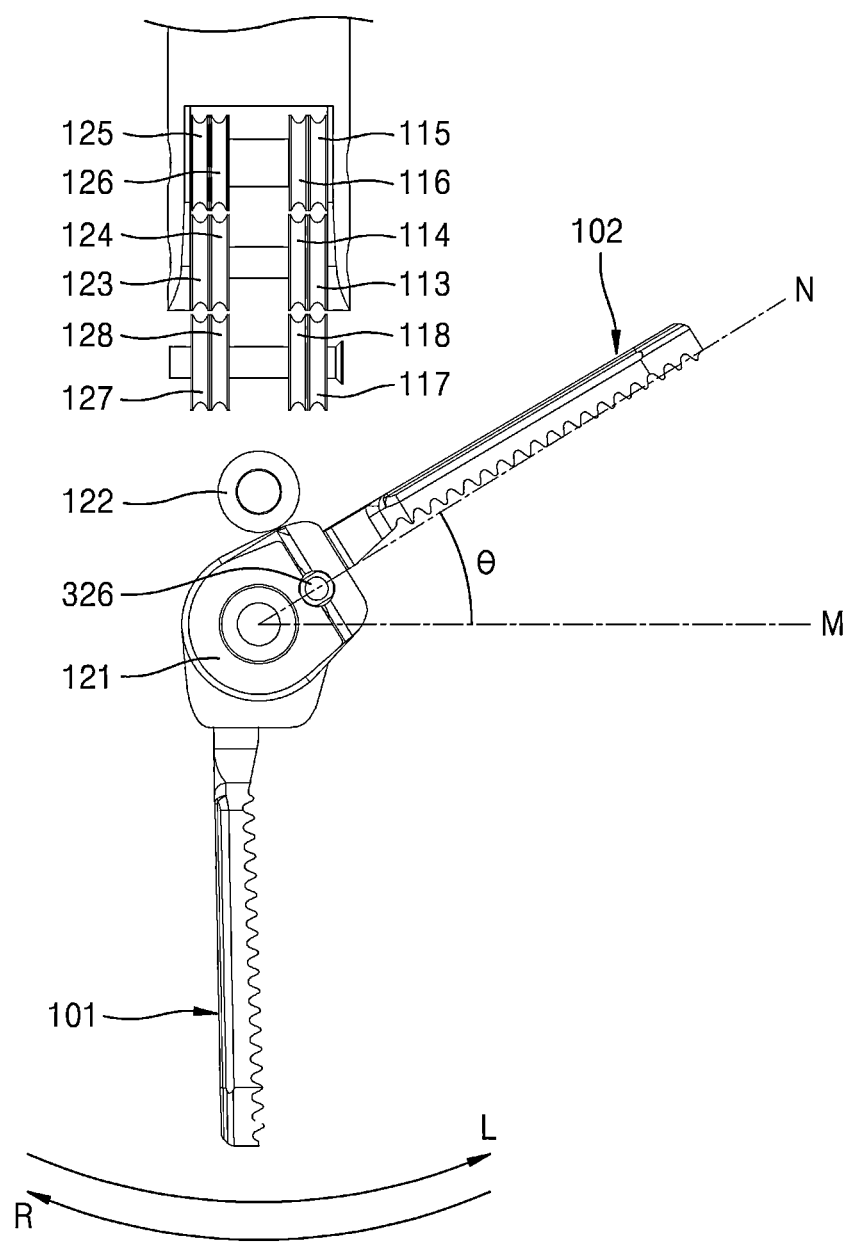
Figure 39:
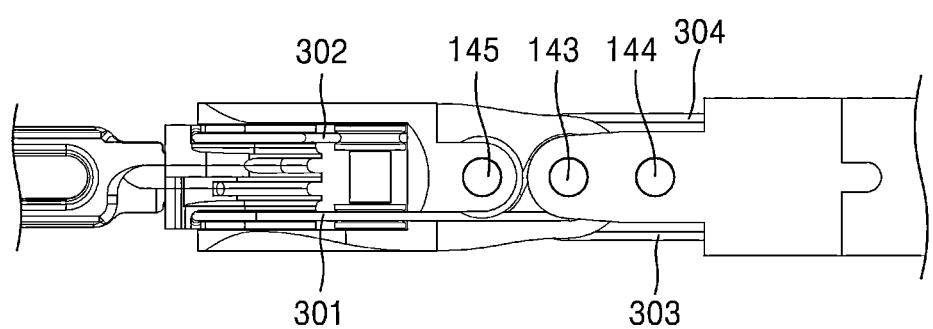
FIG. 39 is a perspective view of the end tool of FIG. 34.
Figure 40:
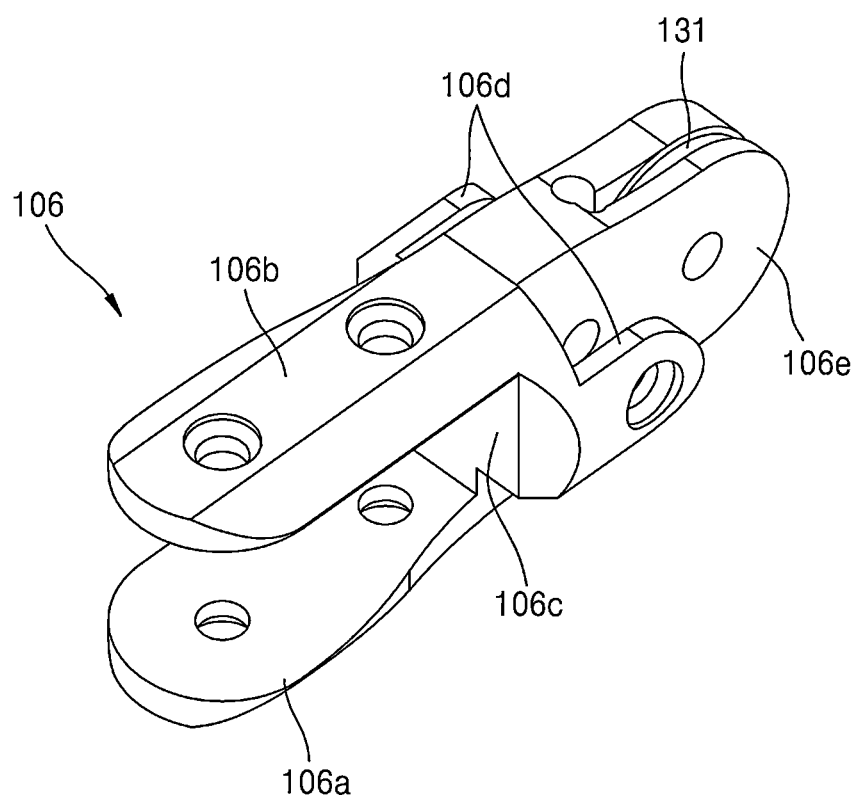
FIG. 40 is a perspective view of an end tool hub of the end tool of FIG. 34.

FIGS. 34 and 35 are perspective views illustrating the end tool of the surgical instrument according to the first modified example of the first embodiment of the present disclosure. FIG. 36 is a plan view of the end tool of FIG. 34. FIGS. 37 and 38 are plan views of the end tool of FIG. 34. FIG. 39 is a perspective view of the end tool of FIG. 34. FIG. 40 is a perspective view of an end tool hub of the end tool of FIG. 34.

Referring to FIGS. 34 to 40, the end tool 100 according to the first modified example of the first embodiment of the present disclosure includes a pair of jaws for performing a grip motion, that is, a first jaw 101 and a second jaw 102. Here, each of the first jaw 101 and the second jaw 102, or a component encompassing the first jaw 101 and the second jaw 102 may be referred to as a jaw 103.

Further, the end tool 100 of the first embodiment of the present disclosure may include an end tool hub 106 and a pitch hub 107.

Further, the end tool 100 of the first modified example of the first embodiment of the present disclosure may include a rotation shaft 141, a rotation shaft 142, a rotation shaft 145, a rotation shaft 143, and a rotation shaft 144. As described above, the rotation shaft 141, the rotation shaft 142, and the rotation shaft 145 may be inserted through the end tool hub 106, and the rotation shaft 143 and the rotation shaft 144 may be inserted through the pitch hub 107.

The end tool hub 106, the pitch hub 107, and each of the rotation shafts 141, 142, 143, 144, and 145 in the present modified example are substantially the same as the end tool hub 106, pitch hub 107, and each of the rotation shafts 141, 142, 143, 144, and 145 described in the first embodiment with reference to FIG. 5 or the like, and thus, detailed description thereof will be omitted herein.

Meanwhile, the end tool 100 may include a pulley 111, a pulley 112, a pulley 113, a pulley 114, a pulley 115, a pulley 116, a pulley 117, and a pulley 118 that are related to a rotational motion of the first jaw 101. In addition, the end tool 100 may include a pulley 121, a pulley 122, a pulley 123, a pulley 124, a pulley 125, a pulley 126, a pulley 127, and a pulley 128 that are related to a rotational motion of the second jaw 102.

Here, in the end tool 100 of the surgical instrument according to the first modified example of the first embodiment of the present disclosure, each of a first jaw pitch redundant pulley and a second jaw pitch redundant pulley includes two pulleys, and each of a first jaw pitch sub-pulley and a second jaw pitch sub-pulley includes two pulleys In detail, in the end tool 100 of the surgical instrument according to the first embodiment of the present disclosure shown in FIG. 6 or the like, one pulley 118 is provided as a first jaw pitch redundant pulley, and only one pulley 128 is provided as a second jaw pitch redundant pulley.

In contrast, the end tool 100 of the surgical instrument according to the first modified example of the first embodiment of the present disclosure is different from the first embodiment of the present disclosure illustrated with reference to FIG. 6 or the like in that the end tool 100 of the surgical instrument according to the first modified example of the first embodiment of the present disclosure includes a pair of pulleys 117 and 118 as first jaw pitch redundant pulleys and a pair of pulleys 127 and 128 as second jaw pitch redundant pulleys.

In addition, in the end tool 100 of the surgical instrument according to the first embodiment of the present disclosure illustrated with reference to FIG. 6 or the like, only one pulley 115 is provided as a first jaw pitch sub-pulley and only one pulley 125 as a second jaw pitch sub-pulley.

In contrast, the end tool 100 of the surgical instrument according to the first modified example of the first embodiment of the present disclosure is different from the first embodiment of the present disclosure illustrated with reference to FIG. 6 or the like in that the end tool 100 of the surgical instrument according to the first modified example of the first embodiment of the present disclosure includes a pair of pulleys 115 and 116 as first jaw pitch sub-pulleys and a pair of pulleys 125 and 126 as second jaw pitch sub-pulleys.

As a result, the pulley 111, the pulley 112, the pulley 117/pulley 118, the pulley 113/pulley 114, and the pulley 115/pulley 116, which are pulleys associated with the rotation of the first jaw 101, may be arranged sequentially from a distal end 104 of the end tool 100 toward a proximal end 105.

In addition, the pulley 121, the pulley 122, the pulley 127/pulley 128, the pulley 123/pulley 124, and the pulley 125/pulley 126, which are pulleys associated with the rotation of the second jaw 102, may be arranged sequentially from the distal end 104 of the end tool 100 toward the proximal end 105.

In other words, in the first embodiment of the present disclosure, the first jaw pitch redundant pulley and the second jaw pitch redundant pulley are each configured in one row, whereas, in the first modified example of the first embodiment of the present disclosure, the first jaw pitch redundant pulleys and the second jaw pitch redundant pulleys are each configured in two rows. In addition, in the first embodiment of the present disclosure, the first jaw pitch sub-pulley and the second jaw pitch sub-pulley are each configured in one row, whereas, in the first modified example of the first embodiment of the present disclosure, the first jaw pitch sub-pulleys and the second jaw pitch sub-pulleys are each configured in two rows.

Here, the pulley 117/pulley 118 are disposed on one side of the pulley 111 and the pulley 112 to face each other. Here, the pulley 117 and the pulley 118 are formed to be rotatable independently of each other around the rotation shaft 145 that is a pitch redundant rotation shaft. In addition, the pulley 113 and the pulley 114 are disposed on one side of the pulley 117 and one side of the pulley 118, respectively, to face each other. Here, the pulley 113 and the pulley 114 are formed to be rotatable independently of each other around the rotation shaft 143 that is a pitch main rotation shaft. In addition, the pulley 115 and the pulley 116 are disposed on one side of the pulley 113 and on one side of the pulley 114, respectively, to face each other. Here, the pulley 115 and the pulley 116 are formed to be rotatable independently of each other around the rotation shaft 144 that is a pitch-serve rotation shaft. Here, in the drawings, it is illustrated that the pulley 117, the pulley 118, the pulley 113, the pulley 114, the pulley 115, and the pulley 116 are all formed to be rotatable around a Y-axis direction, but the concept of the present disclosure is not limited thereto, and the rotation axes of the respective pulleys may be formed in various directions according to configurations thereof.

The wire 301, which is a first jaw wire, is sequentially wound to make contact with at least portions of the pulley 115, the pulley 113, the pulley 117, and the pulley 111. In addition, the wire 305 connected to the wire 301 by the coupling member 323 is sequentially wound to make contact with at least portions of the pulley 111, the pulley 112, the pulley 118, the pulley 114, and the pulley 116.

In other words, the wires 301 and 305, which are first jaw wires, are sequentially wound to make contact with at least portions of the pulley 115, the pulley 113, the pulley 117, the pulley 111, the pulley 112, the pulley 118, the pulley 114, and the pulley 116 and are formed to move along the above pulleys while rotating the above pulleys.

Meanwhile, the pulley 127/pulley 128 are disposed on one side of the pulley 121 and the pulley 122 to face each other. Here, the pulley 127 and the pulley 128 are formed to be rotatable independently of each other around the rotation shaft 145 which is a pitch redundant rotation shaft. Further, the pulley 123 and the pulley 124 are disposed on one side of the pulley 127 and the pulley 128, respectively, to face each other. Here, the pulley 123 and the pulley 124 are formed to be rotatable independently of each other around the rotation shaft 143 that is a pitch main rotation shaft. In addition, the pulley 125 and the pulley 126 are disposed on one side of the pulley 123 and one side of the pulley 124, respectively, to face each other. Here, the pulley 125 and the pulley 126 are formed to be rotatable independently of each other around the rotation shaft 144 that is a pitch-serve rotation shaft. Here, in the drawings, it is illustrated that all of the pulley 127, the pulley 128, the pulley 123, the pulley 124, the pulley 125, and the pulley 126 are formed to be rotatable around the Y-axis direction, but the concept of the present disclosure is not limited thereto, and the rotation shafts of the respective pulleys may be formed in various directions according to configurations thereof.

The wire 306, which is a second jaw wire, is sequentially wound to make contact with at least portions of the pulley 125, the pulley 123, the pulley 127, and the pulley 121. In addition, the wire 302 connected to the wire 306 by the coupling member 326 is sequentially wound to make contact with at least portions of the pulley 121, the pulley 122, the pulley 128, the pulley 124, and the pulley 126.

In other words, the wire 306 and the wire 302, which are second jaw wires, are sequentially wound to make contact with at least portions of the pulley 125, the pulley 123, the pulley 127, the pulley 121, the pulley 122, the pulley 128, the pulley 124, and the pulley 126 are formed to move along the above pulleys while rotating the above pulleys.

As a result, in the first embodiment of the present disclosure, the first jaw pitch redundant pulley, the second jaw pitch redundant pulley, the first jaw pitch sub-pulley, and the second jaw pitch sub-pulley are each configured in one row, but in the first modified example of the first embodiment of the present disclosure, the first jaw pitch redundant pulleys, the second jaw pitch redundant pulleys, the first jaw pitch sub-pulleys, and the second jaw pitch sub-pulleys are each configured in two rows, so that the effect of supporting the wire more stably can be achieved.

Second Modified Example of First Embodiment

Hereinafter, the end tool 100 of the surgical instrument according to a second modified example of the first embodiment of the present disclosure will be described. In this regard, the end tool 100 of the surgical instrument according to the second modified example of the first embodiment of the present disclosure is different from the end tool of the surgical instrument according to the first modified example of the first embodiment of the present disclosure described above in that some of the pulleys are omitted. Hereinafter, the configuration that is different from that the first modified example of the first embodiment will be described in detail.

Figure 41:
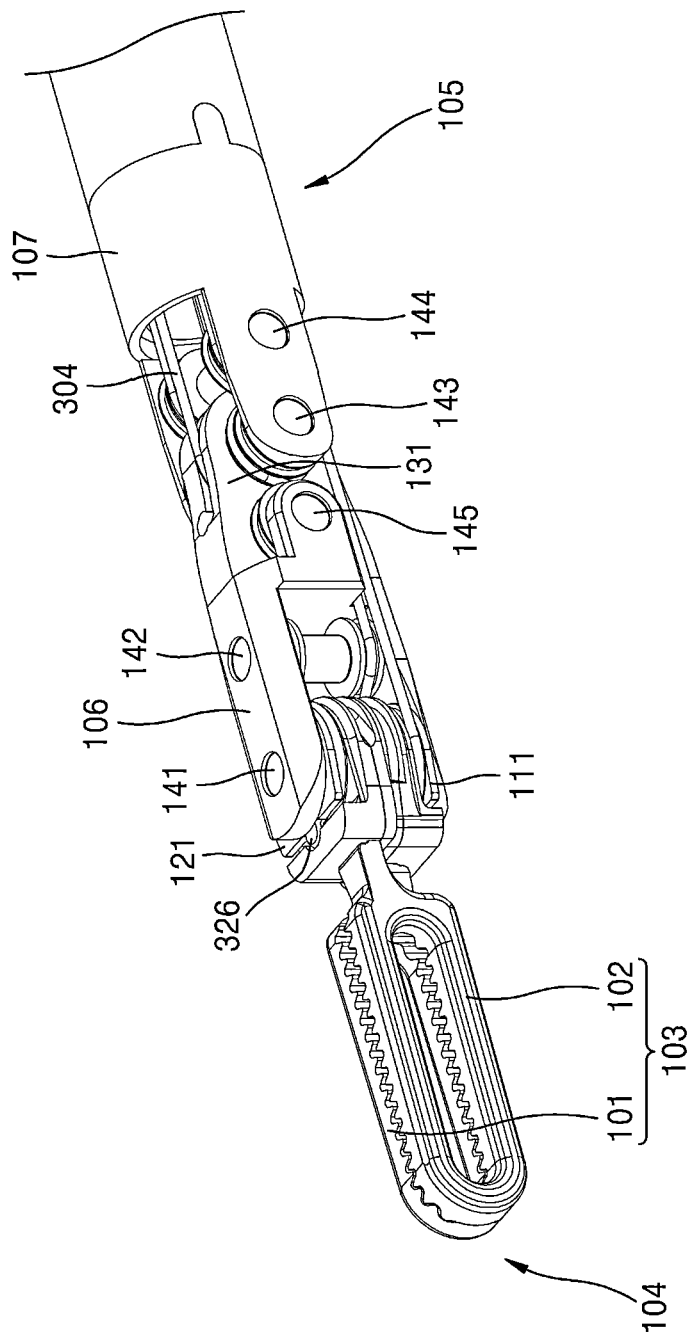
FIGS. 41 and 42 are perspective views illustrating an end tool of a surgical instrument according to a second modified example of the first embodiment of the present disclosure.
Figure 42:
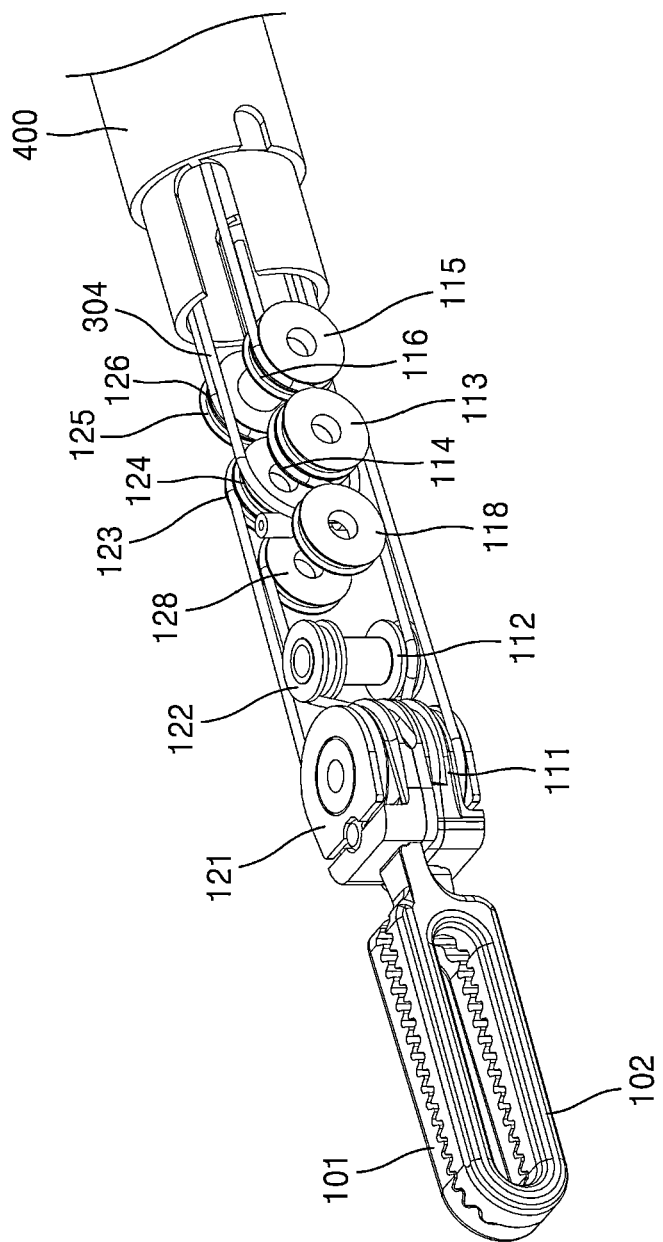
Figure 43:
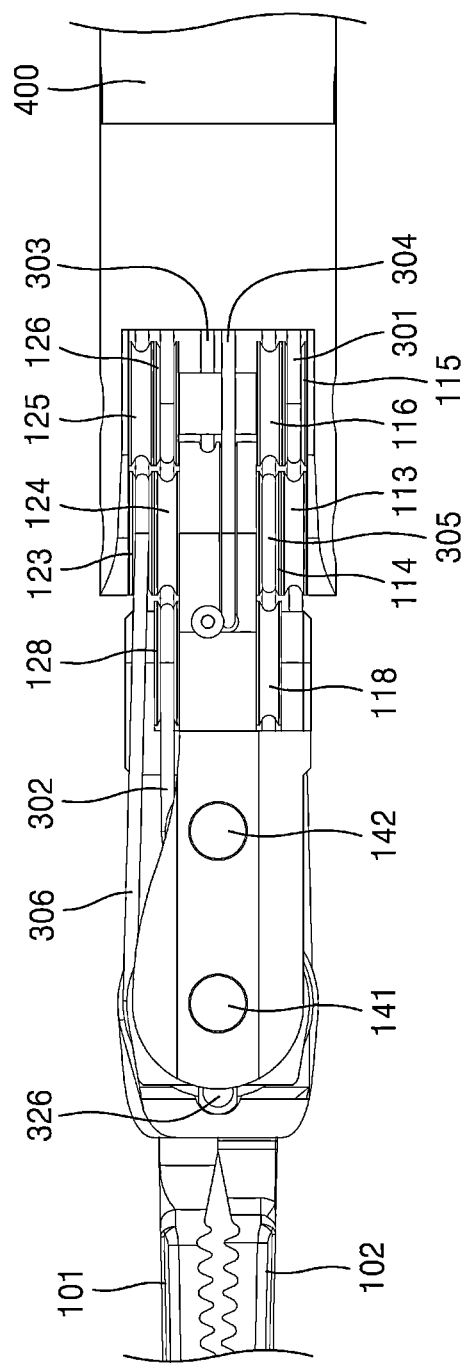
FIG. 43 is a plan view of the end tool of FIG. 41.

FIGS. 40 and 42 are perspective views illustrating an end tool of a surgical instrument according to a second modified example of the first embodiment of the present disclosure. FIG. 43 is a plan view of the end tool of FIG. 41.

Referring to FIGS. 41 to 43, the end tool 100 according to the second modified example of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as the jaw 103.

In addition, the end tool 100 of the first embodiment of the present disclosure may include the end tool hub 106 and the pitch hub 107.

In addition, the end tool 100 of the second modified example of the first embodiment of the present disclosure may include the rotation axis 141, the rotation axis 142, the rotation axis 145, the rotation axis 143, and the rotation axis 144. As described above, the rotation axis 141, the rotation axis 142, and the rotation axis 145 may be inserted through the end tool hub 106, and the rotation axis 143 and the rotation axis 144 may be inserted through the pitch hub 107.

In the present modified example, the end tool hub 106, the pitch hub 107, and the rotation axes 141, 142, 143, 144, and 145 are substantially the same as the end tool hub 106, the pitch hub 107, and the rotation axes 141, 142, 143, 144, and 145 that are described above with reference to FIG. 2 and the like, respectively, and thus, detailed descriptions thereof will be omitted.

Meanwhile, the end tool 100 may include the pulley 111, the pulley 112, the pulley 113, the pulley 114, the pulley 115, the pulley 116, and the pulley 118, which are associated with a rotational motion of the first jaw 101. In addition, the end tool 100 may include the pulley 121, the pulley 122, the pulley 123, the pulley 124, the pulley 125, the pulley 126, and the pulley 128, which are associated with a rotational motion of the second jaw 102.

In this regard, in the end tool 100 of the surgical instrument according to the second modified example of the first embodiment of the present disclosure, each of the first jaw pitch redundant pulley and the second jaw pitch redundant pulley includes only one pulley.

In detail, the end tool 100 of the surgical instrument according to the first modified example of the first embodiment of the present disclosure illustrated in FIG. 34 and the like includes a pair of pulleys 117 and 118 as first jaw pitch redundant pulleys, and a pair of pulleys 127 and 128 as second jaw pitch redundant pulleys.

On the contrary, the end tool 100 of the surgical instrument according to the second modified example of the first embodiment of the present disclosure is different from the first modified example of the first embodiment of the present disclosure illustrated in FIG. 34 and the like, in that it includes a single pulley 118 as a first jaw pitch redundant pulley, and a single pulley 128 as a second jaw pitch redundant pulley.

Accordingly, the pulley 111, the pulley 112, the pulley 118, the pulley 113/pulley 114, and the pulley 115/pulley 116, which are associated with rotation of the first jaw 101, may be sequentially arranged from the distal end 104 of the end tool 100 toward the proximal end 105.

In addition, the pulley 121, the pulley 122, the pulley 128, the pulley 123/pulley 124, and the pulley 125/pulley 126, which are associated with rotation of the second jaw 102, may be sequentially arranged from the distal end 104 of the end tool 100 toward the proximal end 105.

In this regard, the pulley 117 and pulley 127 of the end tool 100 of the first modified example of the first embodiment of the present disclosure illustrated in FIG. 34 and the like are not pulleys around which wires are wound, but pulleys through which the wires pass in a straight line, and thus may be omitted as in the present modified example.

In other words, in the first modified example of the first embodiment of the present disclosure, two rows of first jaw pitch redundant pulleys and two rows of second jaw pitch redundant pulleys are provided, whereas in the second modified example of the first embodiment of the present disclosure, one row of a first jaw pitch redundant pulley and one row of a second jaw pitch redundant pulley are provided.

In this regard, the pulley 118 is arranged on one side of the pulley 111 and the pulley 112. In this regard, the pulley 118 is formed to be rotatable around the rotation axis 145, which is a pitch redundant rotation axis. In addition, the pulley 113 and the pulley 114 are arranged on one side of the pulley 118 to face each other. In this regard, the pulley 113 and the pulley 114 are formed to be rotatable independently of each other around the rotation axis 143, which is a pitch main rotation axis. In addition, the pulley 115 and the pulley 116 are arranged on one sides of the pulley 113 and the pulley 114, respectively, to face each other. In this regard, the pulley 115 and the pulley 116 are formed to be rotatable independently of each other around the rotation axis 144, which is a pitch sub-rotation axis. In this regard, the drawings illustrate that the pulley 118, the pulley 113, the pulley 114, the pulley 115, and the pulley 116 are formed to be rotatable around the Y-axis direction, but the concept of the present disclosure is not limited thereto, and the rotation axes of the respective pulleys may be formed in various directions according to their configurations.

The wire 301, which is a first jaw wire, is wound to sequentially come into contact with at least portions of the pulley 115, the pulley 113, and the pulley 111. In addition, the wire 305 connected to the wire 301 by the coupling member 323 is wound to sequentially come into contact with at least portions of the pulley 111, the pulley 112, the pulley 118, the pulley 114, and the pulley 116.

In other words, the wire 301 and the wire 305, which are first jaw wires, are wound to sequentially come into contact with at least portions of the pulley 115, the pulley 113, the pulley 111, the pulley 112, the pulley 118, the pulley 114, and the pulley 116, and are formed to move along the above pulleys while rotating the above pulleys.

Meanwhile, the pulley 128 is arranged on one side of the pulley 121 and the pulley 122. In this regard, the pulley 128 is formed to be rotatable around the rotation axis 145, which is a pitch redundant rotation axis. In addition, the pulley 123 and the pulley 124 are arranged on one side of the pulley 128 to face each other. In this regard, the pulley 123 and the pulley 124 are formed to be rotatable independently of each other around the rotation axis 143, which is a pitch main rotation axis. In addition, the pulley 125 and the pulley 126 are arranged on one sides of the pulley 123 and the pulley 124, respectively, to face each other. In this regard, the pulley 125 and the pulley 126 are formed to be rotatable independently of each other around the rotation axis 144, which is a pitch sub-rotation axis. In this regard, the drawings illustrate that the pulley 128, the pulley 123, the pulley 124, the pulley 125, and the pulley 126 are formed to be rotatable around the Y-axis direction, but the concept of the present disclosure is not limited thereto, and the rotation axes of the respective pulleys may be formed in various directions according to their configurations.

The wire 306, which is a second jaw wire, is wound to sequentially come into contact with at least portions of the pulley 125, the pulley 123, and the pulley 121. In addition, the wire 302 connected to the wire 306 by the coupling member 326 is wound to sequentially come into contact with at least portions of the pulley 121, the pulley 122, the pulley 128, the pulley 124, and the pulley 126.

In other words, the wire 306 and the wire 302, which are second jaw wires, are wound to sequentially come into contact with at least portions of the pulley 125, the pulley 123, the pulley 121, the pulley 122, the pulley 128, the pulley 124, and the pulley 126, and are formed to move along the above pulleys while rotating the above pulleys.

Accordingly, in the first modified example of the first embodiment of the present disclosure, two rows of first jaw pitch redundant pulleys and two rows of second jaw pitch redundant pulleys are provided, whereas in the second modified example of the first embodiment of the present disclosure, one row of a first jaw pitch redundant pulley and one row of a second jaw pitch redundant pulley are provided, and thus, an effect of reducing the number of parts and simplifying a manufacturing process may be achieved.

Third Modified Example of First Embodiment

Hereinafter, the end tool 100 of the surgical instrument according to a third modified example of the first modified example of the first embodiment of the present disclosure will be described. In this regard, the end tool 100 of the surgical instrument according to the second modified example of the first embodiment of the present disclosure is different from the end tool of the surgical instrument according to the first embodiment of the present disclosure described above, in the configuration of the end tool hub. Hereinafter, the configuration that is different from that of the first modified example of the first embodiment will be described in detail.

Figure 44:
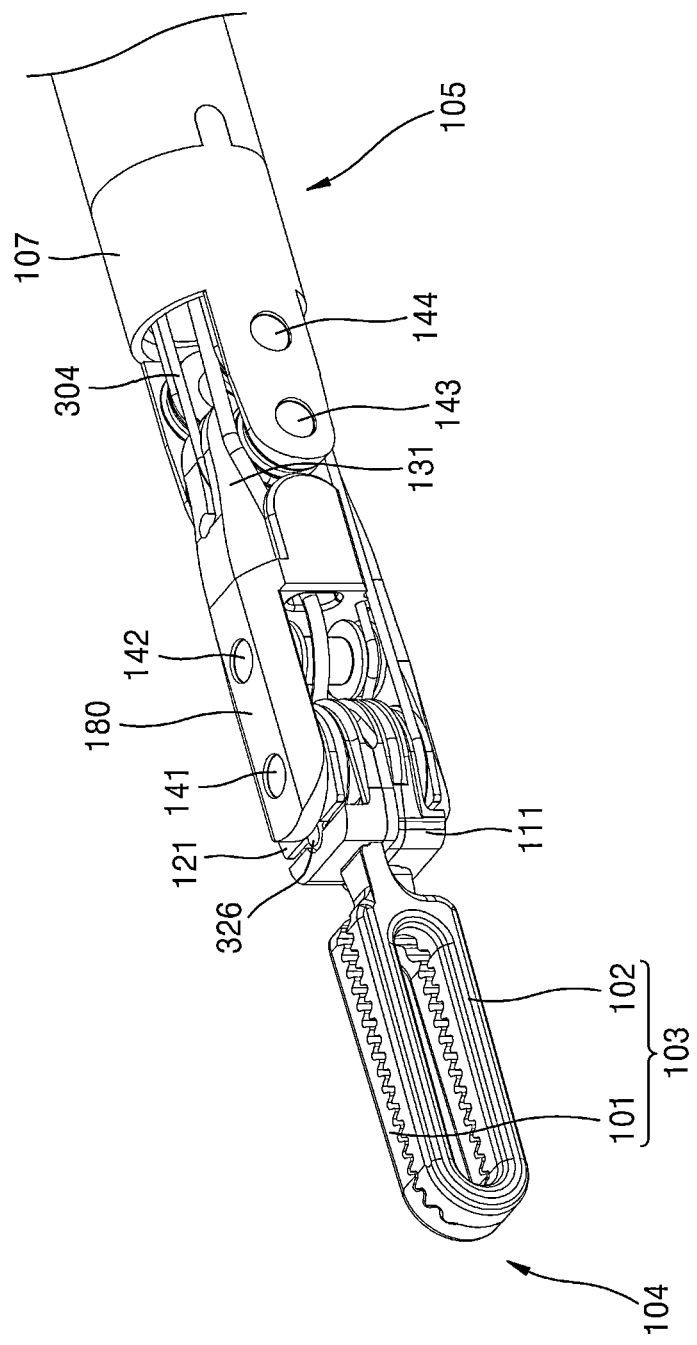
FIGS. 44 and 45 are perspective views illustrating an end tool of a surgical instrument according to a third modified example of the first embodiment of the present disclosure.
Figure 45:
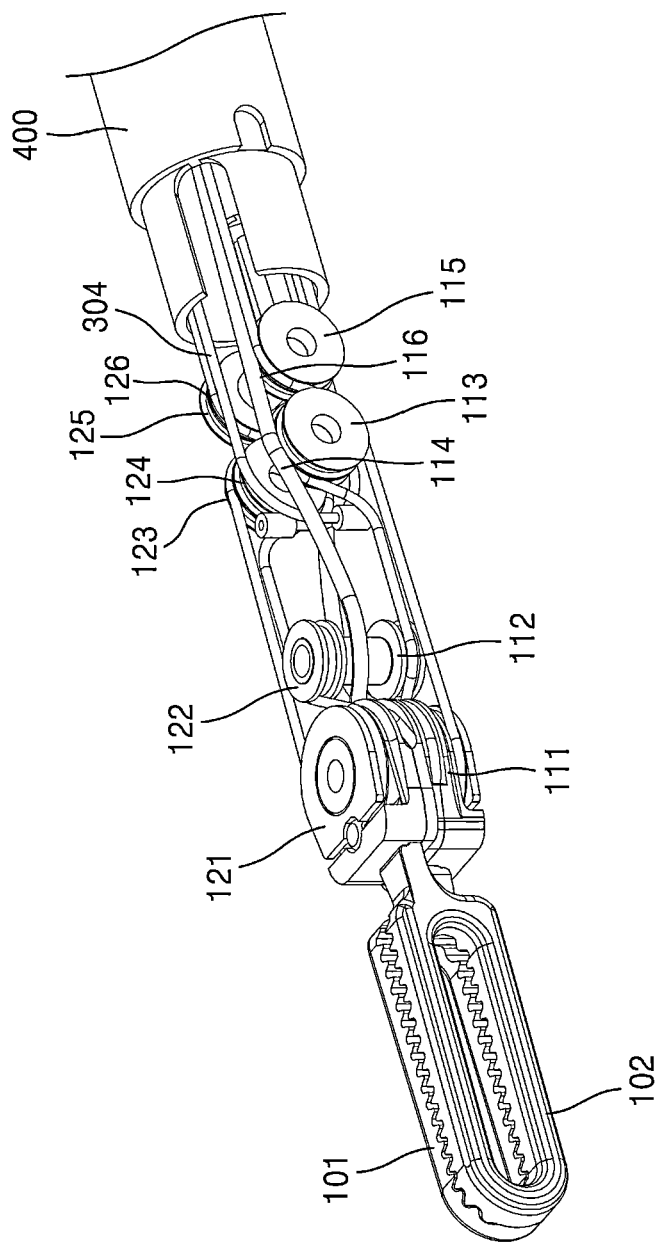
Figure 46:
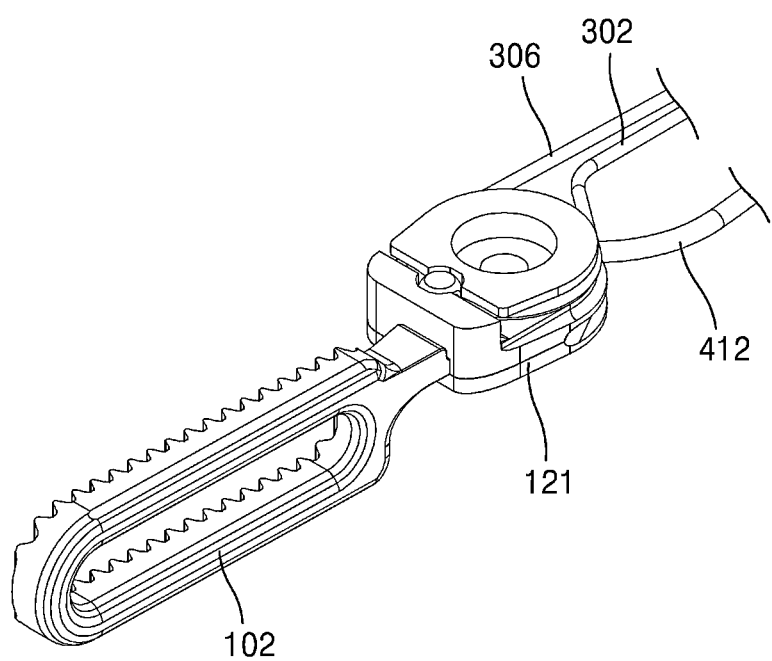
FIG. 46 is a coupled perspective view illustrating a second jaw of the end tool of FIG. 44.
Figure 47:
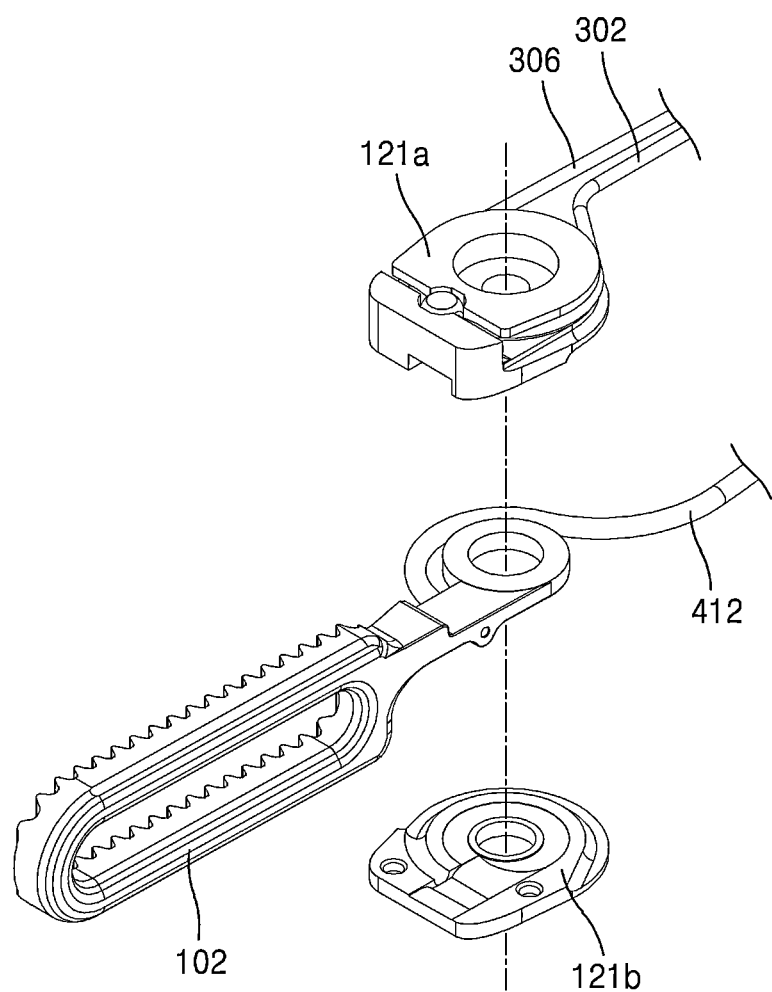
FIG. 47 is an exploded perspective view illustrating the second jaw of the end tool of FIG. 44.
Figure 48:
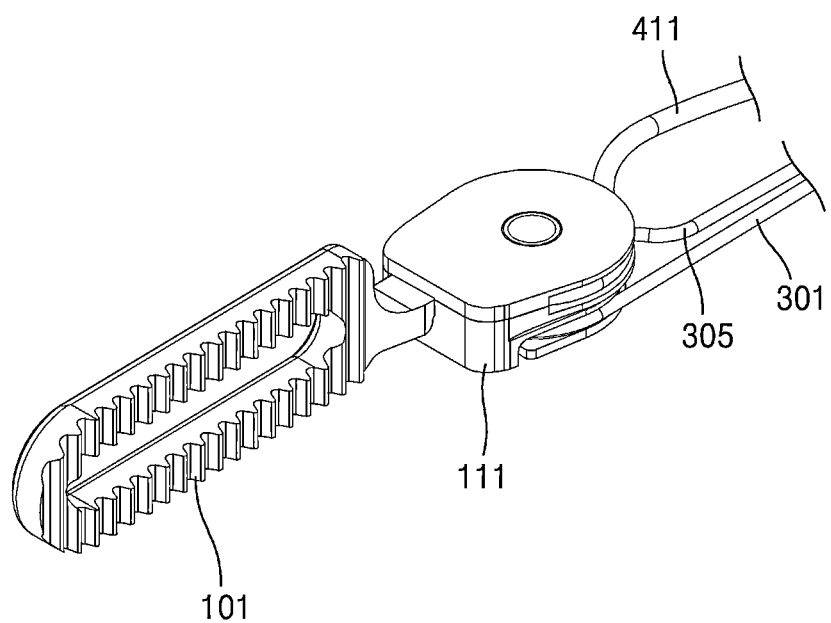
FIG. 48 is a coupled perspective view illustrating a first jaw of the end tool of FIG. 44.
Figure 49:
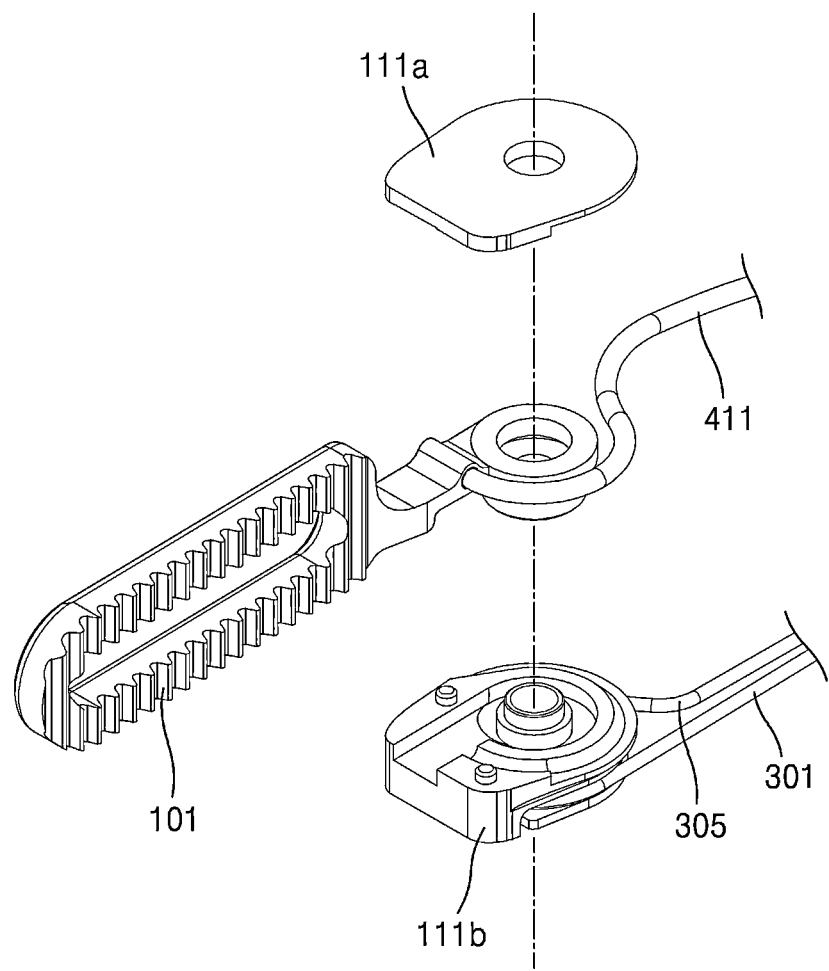
FIG. 49 is an exploded perspective view illustrating the first jaw of the end tool of FIG. 44.
Figure 50:
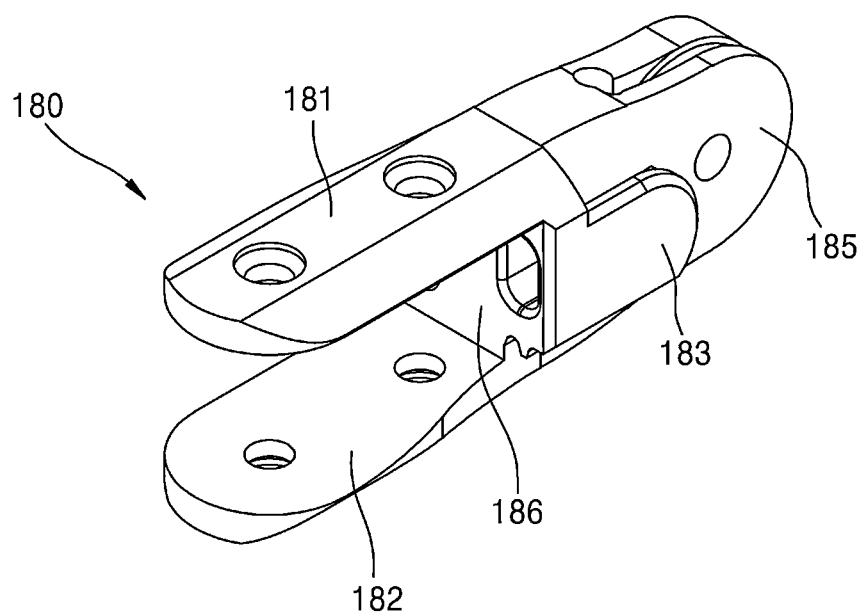
FIGS. 50 and 51 are perspective views illustrating an end tool hub of FIG. 44.
Figure 51:
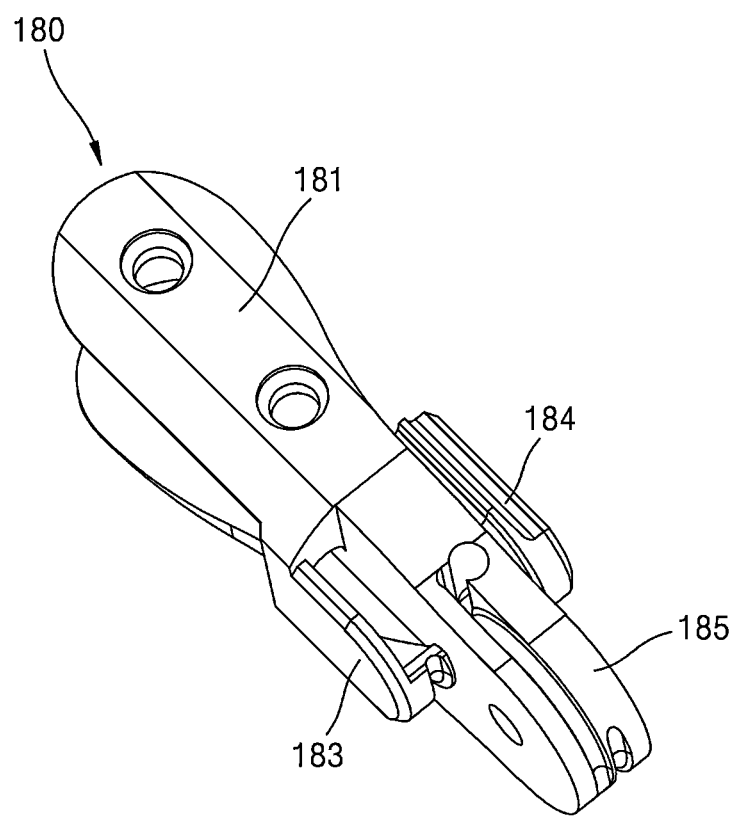
Figure 52:
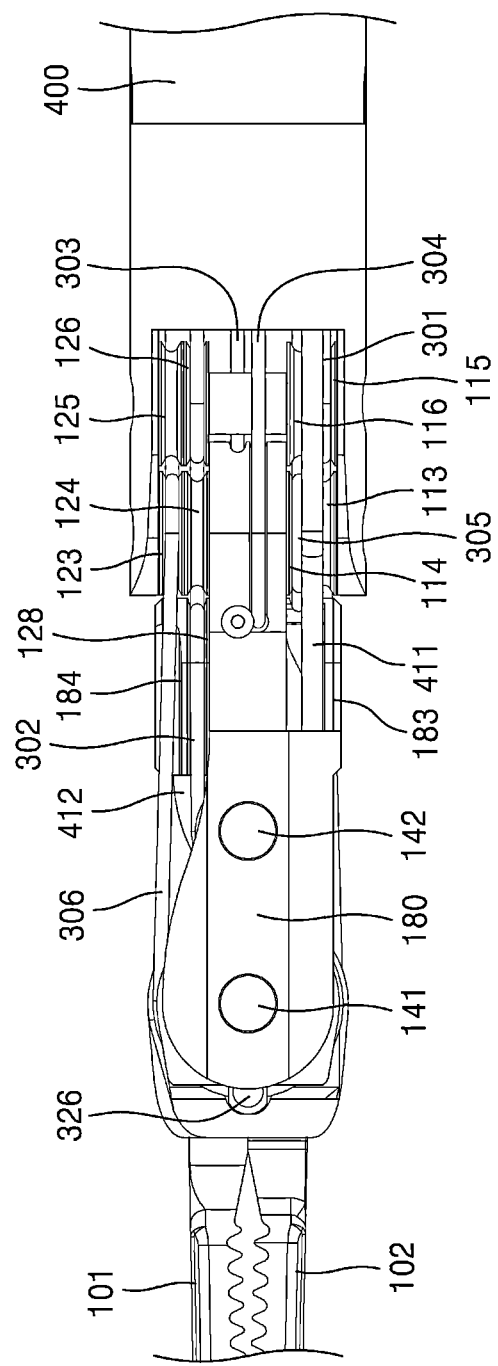
FIG. 52 is a plan view of the end tool of FIG. 44.
Figure 53:
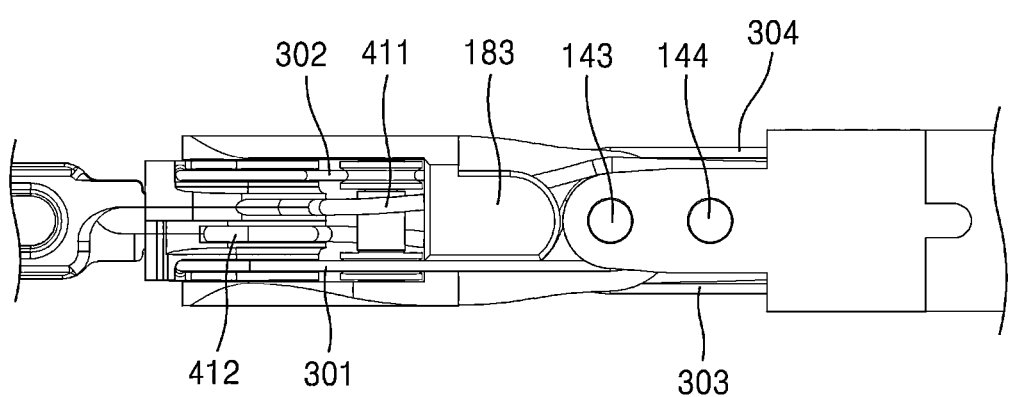
FIGS. 53 and 54 are side views of the end tool of FIG. 44.
Figure 54:
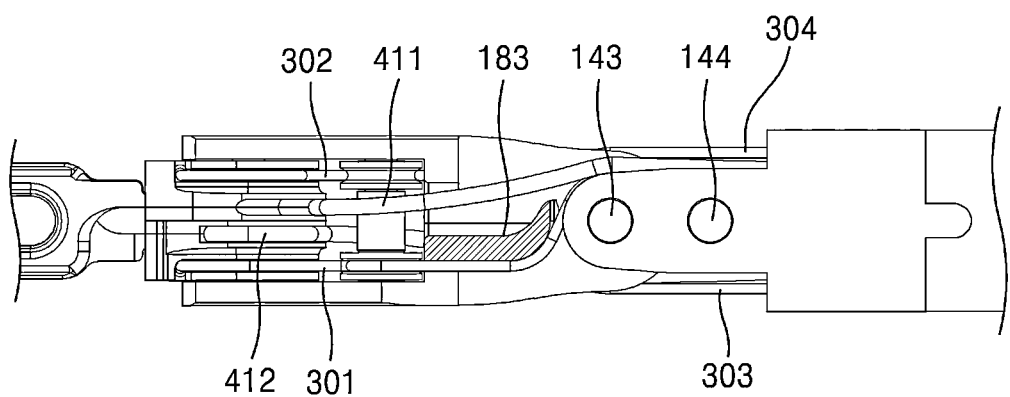

FIGS. 44 and 45 are perspective views illustrating the end tool of the surgical instrument according to the third modified example of the first embodiment of the present disclosure. FIG. 46 is a combined perspective view illustrating a second jaw of the end tool of FIG. 44. FIG. 47 is an exploded perspective view illustrating the second jaw of the end tool of FIG. 44. FIG. 48 is a combined perspective view illustrating a first jaw of the end tool of FIG. 44. FIG. 49 is an exploded perspective view illustrating the first jaw of the end tool of FIG. 44. FIGS. 50 and 51 are perspective views illustrating an end tool hub of the end tool of FIG. 44. FIG. 52 is a plan view of the end tool of FIG. 44. FIGS. 53 and 54 are side views of the end tool of FIG. 44.

Referring to FIGS. 44 to 54, the end tool 100 according to the third modified example of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as the jaw 103.

Meanwhile, an electric wire 411 may be coupled to the first jaw 101, and an electric wire 412 may be coupled to the second jaw 102.

In addition, the end tool 100 of the third modified example of the first embodiment of the present disclosure may include an end tool hub 180 and the pitch hub 107. The end tool hub 180 will be described in more detail below.

In addition, the end tool 100 of the third modified example of the first embodiment of the present disclosure may include the rotation axis 141, the rotation axis 142, the rotation axis 143, and the rotation axis 144. As described above, the rotation axis 141 and the rotation axis 142 may be inserted through the end tool hub 106, and the rotation axis 143 and the rotation axis 144 may be inserted through the pitch hub 107.

Meanwhile, the end tool 100 may include the pulley 111, the pulley 112, the pulley 113, the pulley 114, the pulley 115, and the pulley 116, which are associated with a rotational motion of the first jaw 101. In addition, the end tool 100 may include the pulley 121, the pulley 122, the pulley 123, the pulley 124, the pulley 125, and the pulley 126, which are associated with a rotational motion of the second jaw 102.

In the present modified example, the first jaw 101, the second jaw 102, the pitch hub 107, the respective pulleys, the respective rotation axes, and the like are substantially the same as those of the end tool 100 of the first embodiment described above with reference to FIG. 5 and the like, and thus, detailed descriptions thereof will be omitted.

Hereinafter, the end tool hub 180 of the third modified example of the first embodiment of the present disclosure will be described in more detail, and in particular, a first pitch redundant pulley part 183 and a second pitch redundant pulley part 184 of the end tool hub 180, which serve as pitch redundant pulleys, will be mainly described.

The end tool hub 180 includes a first jaw pulley coupling part 181, a second jaw pulley coupling part 182, the first pitch redundant pulley part 183, the second pitch redundant pulley part 184, and a pitch pulley coupling part 185.

In detail, the first jaw pulley coupling part 181 and the second jaw pulley coupling part 182 are formed to face each other such that the pulley 111, the pulley 112, the pulley 121, and the pulley 122 are accommodated therein. In addition, a through hole is formed in each of the jaw pulley coupling parts 181 and 182 such that the rotation axis 141 passes through and axially couples the jaw pulley coupling parts 181 and 182, the pulley 111, and the pulley 121. In addition, a through hole is formed in each of the jaw pulley coupling parts 181 and 182 such that the rotation axis 142 passes through and axially couples the jaw pulley coupling parts 181 and 182, the pulley 112, and the pulley 122.

The first jaw pulley coupling part 181 and the second jaw pulley coupling part 182 are connected to each other by a guide part 186. That is, the first jaw pulley coupling part 181 and the second jaw pulley coupling part 182 parallel to each other are coupled by the guide part 186 formed in a direction substantially perpendicular thereto, such that the first jaw pulley coupling part 181, the second jaw pulley coupling part 182, and the guide part 186 form a substantially "C" shape in which the pulley 111, the pulley 112, the pulley 121, and the pulley 122 are accommodated.

In other words, it may also be described that the first jaw pulley coupling part 181 and the second jaw pulley coupling part 182 are formed to extend in the X-axis direction from both ends of the guide part 186 that is elongated in the Z-axis direction.

The first pitch redundant pulley part 183 may be formed on one side surface of the guide part 186, and the second pitch redundant pulley part 184 may be formed on the other side surface.

In detail, the first pitch redundant pulley part 183 and the second pitch redundant pulley part 184, each of which is formed in the shape of a disk like a pulley and has a groove formed on the outer circumferential surface thereof, around which a wire may be wound, may be formed on both side surfaces of the guide part 186, respectively.

In addition, the wire 305, which is a first jaw wire, may be wound around the first pitch redundant pulley part 183, and the wire 302, which is a second jaw wire, may be wound around the second pitch redundant pulley part 184.

Meanwhile, the wire 301, which is a first jaw wire, may pass through a side surface of the first pitch redundant pulley part 183, and the wire 306, which is a second jaw wire, may pass through a side surface of the second pitch redundant pulley part 184.

Meanwhile, the pulley 131 that serves as an end tool pitch pulley may be formed in the pitch pulley coupling part 185 at one end of the end tool hub 180. In this regard, the pulley 131 may be formed with the end tool hub 180 as one body. That is, one end of the end tool hub 180 may be formed in a disk shape or a semicircular shape, and a groove around which a wire may be wound may be formed on an outer circumferential surface of the groove, such that a kind of guide channel is formed. Alternatively, the pulley 131 may be formed as a separate member from the end tool hub 180 and coupled to the end tool hub 180. The wire 303 and the wire 304 described above are coupled to the pulley 131 serving as an end tool pitch pulley, and a pitch motion is performed as the pulley 131 is rotated around the rotation axis 143.

As such, as the first pitch redundant pulley part 183 and the second pitch redundant pulley part 184 is formed in the existing end tool hub 180 without adding a separate structure such as a pitch redundant pulley, it is possible to increase the range of rotation without adding additional parts or manufacturing processes.

Fourth Modified Example of First Embodiment

Hereinafter, the end tool 100 of the surgical instrument according to a fourth modified example of the first embodiment of the present disclosure will be described. In this regard, the end tool 100 of the surgical instrument according to the fourth modified example of the first embodiment of the present disclosure is different from the end tool of the surgical instrument according to the first modified example of the first embodiment of the present disclosure described above in that some of the pulleys are omitted. Hereinafter, the configuration that is different from that of the first modified example of the first embodiment will be described in detail.

Figure 55:
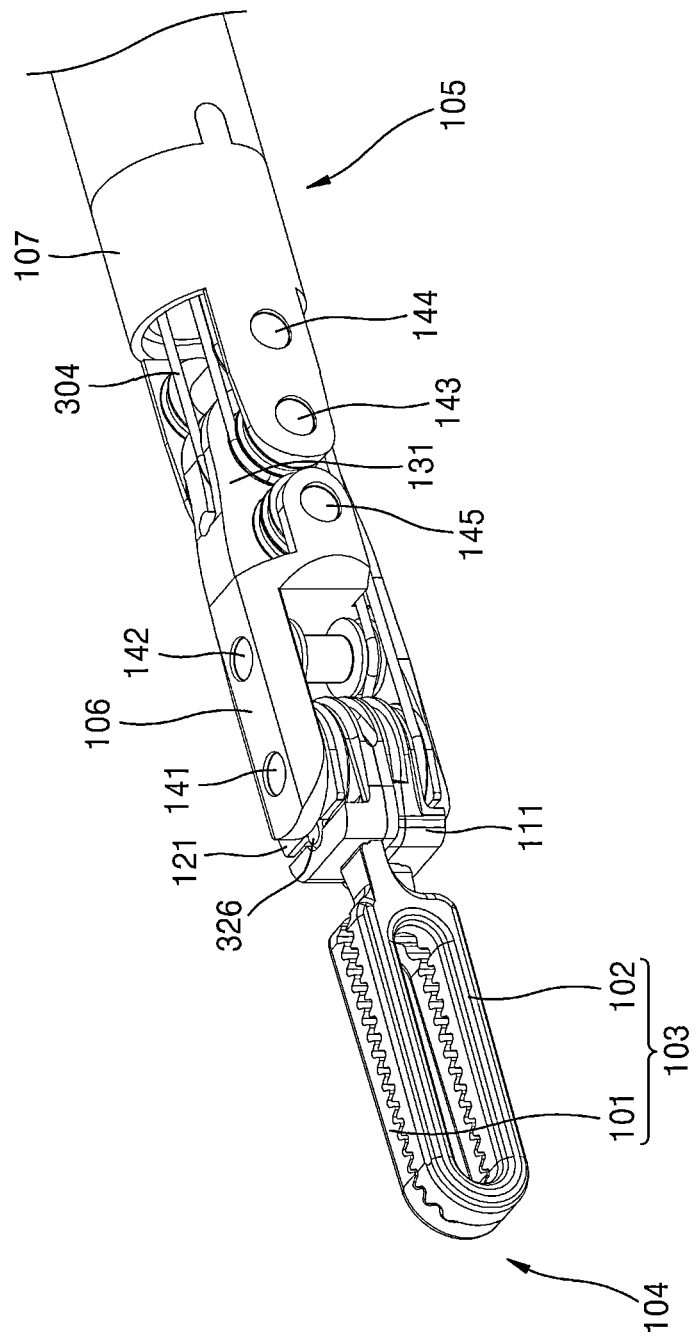
FIGS. 55 and 56 are perspective views illustrating an end tool of a surgical instrument according to a fourth modified example of the first embodiment of the present disclosure.
Figure 56:
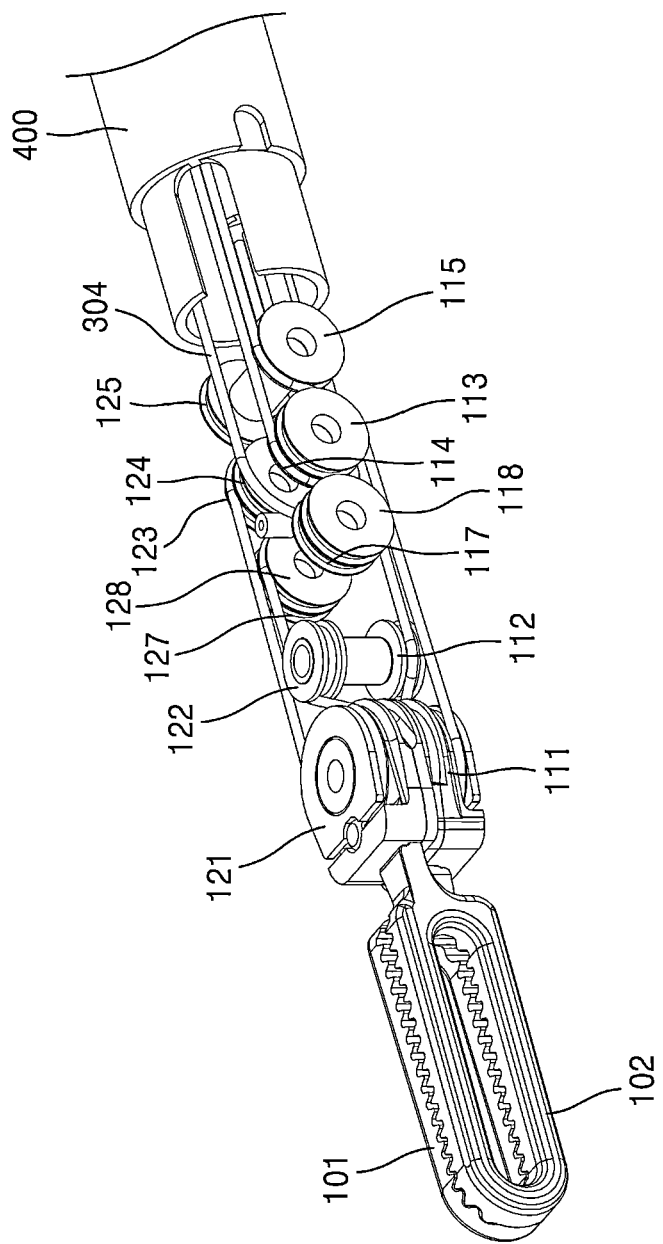
Figure 57:
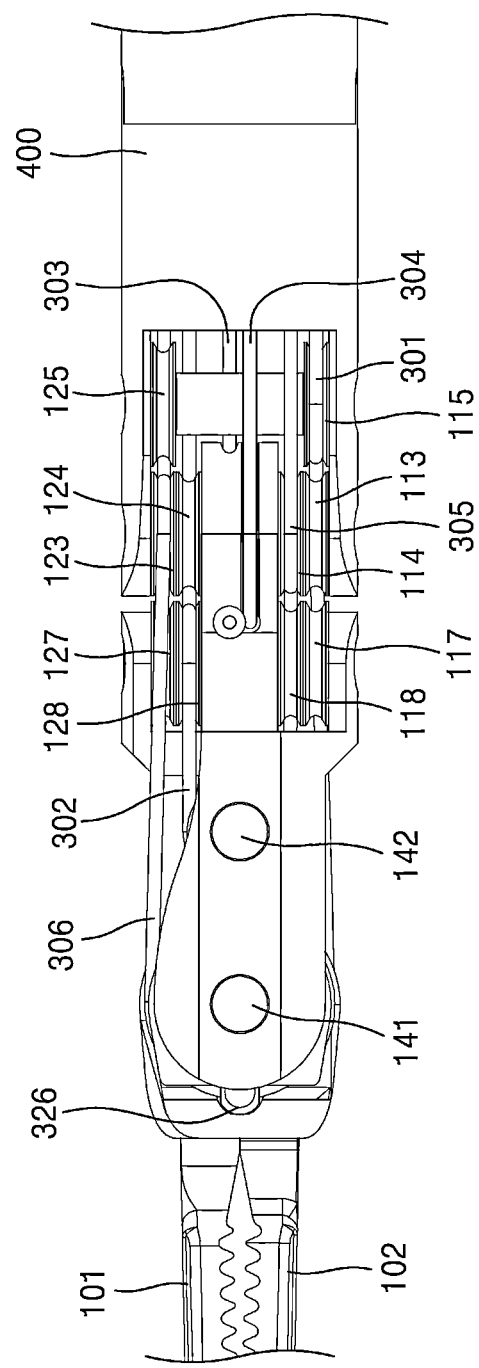
FIGS. 57 and 58 are plan views of the end tool of FIG. 55.
Figure 58:
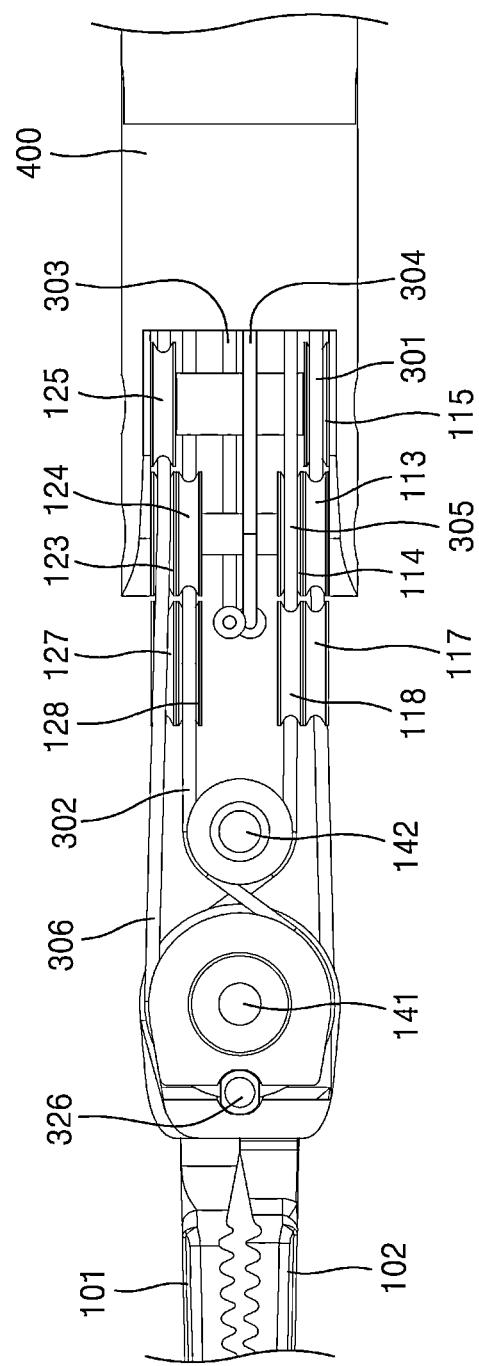
Figure 59:
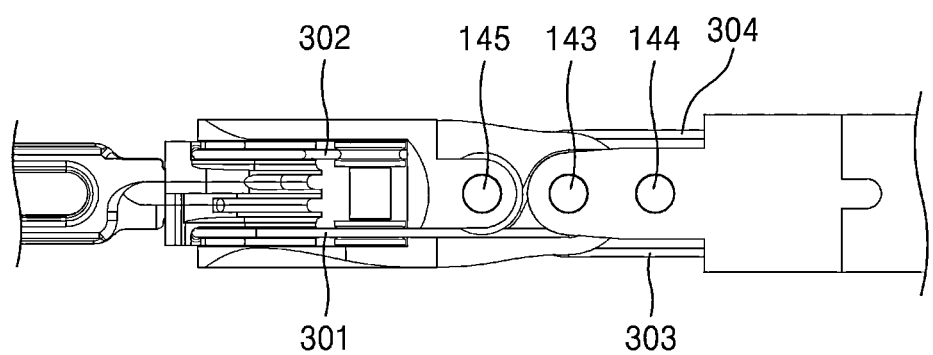
FIGS. 59, 60, and 61 are side views of the end tool of FIG. 55.
Figure 60:
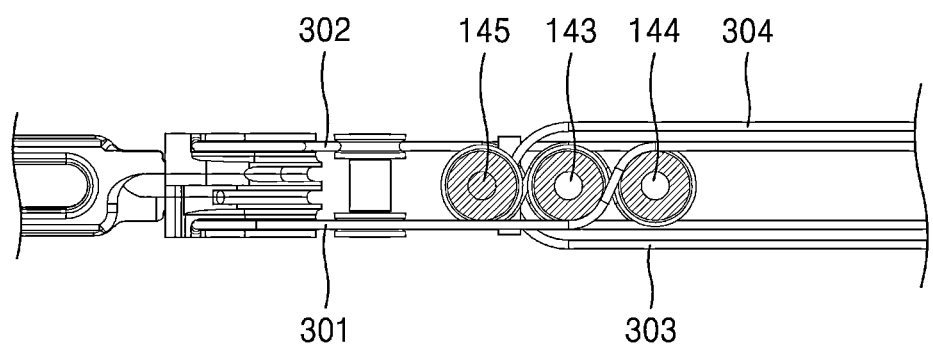
Figure 61:
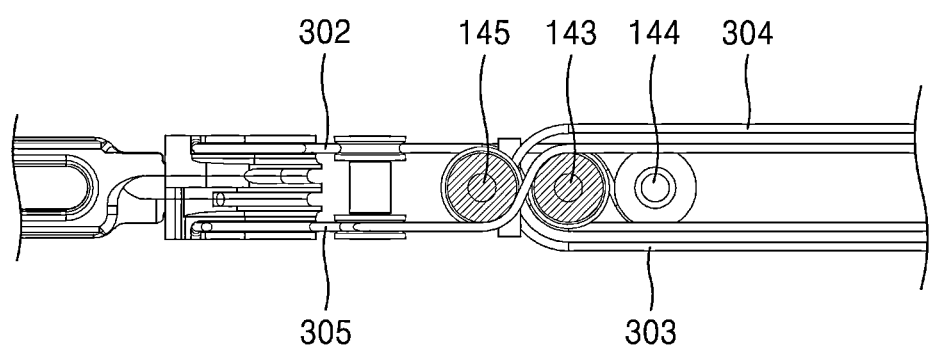
Figure 62:
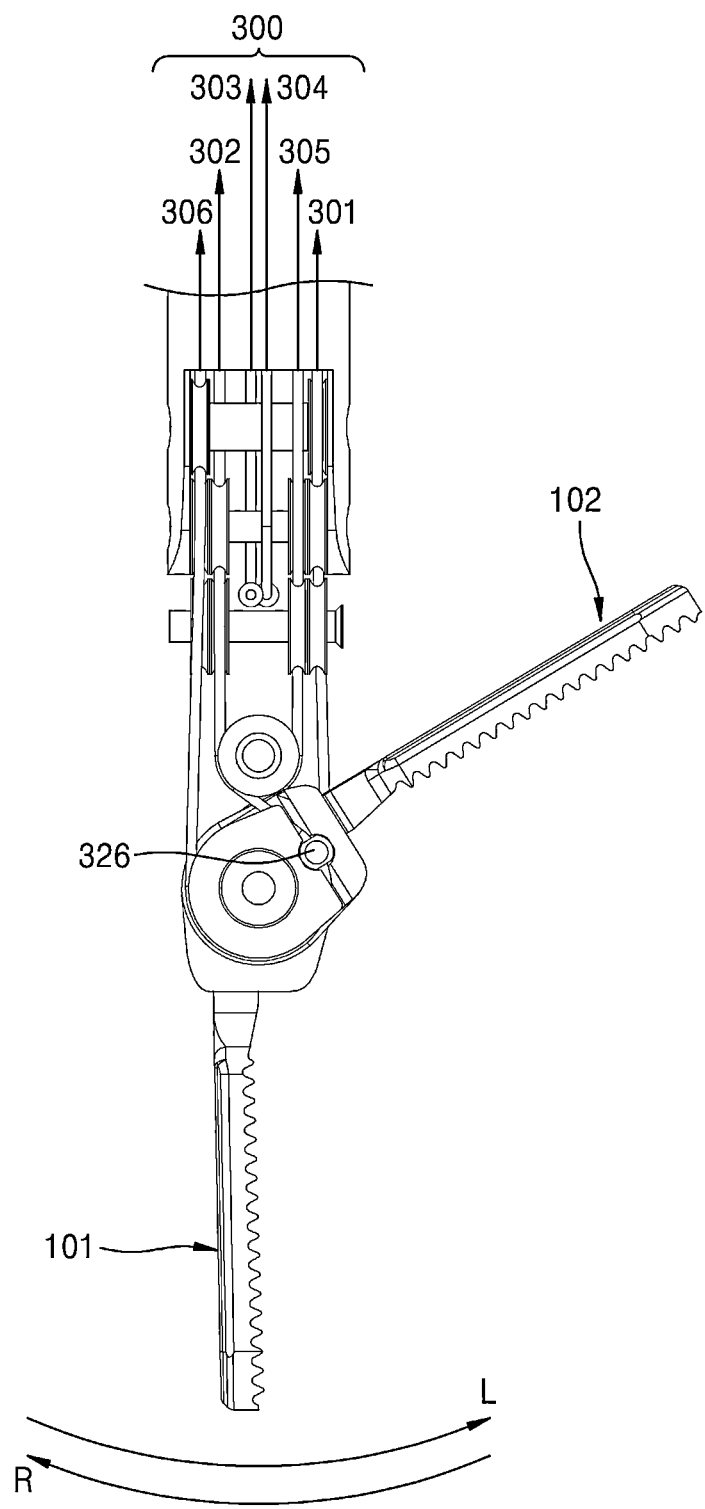
FIGS. 62 and 63 are plan views of the end tool of FIG. 55.
Figure 63:
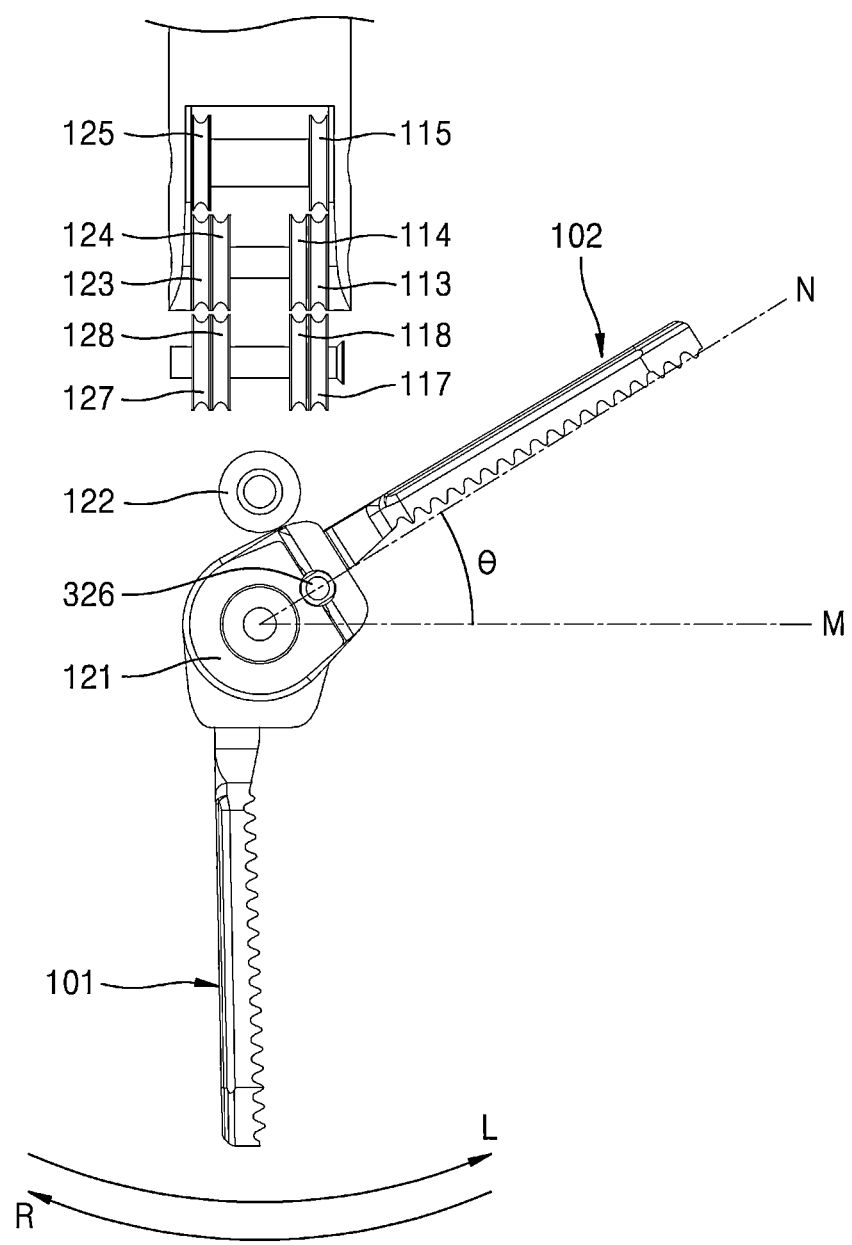

FIGS. 55 and 56 are perspective views illustrating the end tool of the surgical instrument according to the fourth modified example of the first embodiment of the present disclosure. FIGS. 57 and 58 are plan views of the end tool of FIG. 55. FIGS. 59, 60, and 61 are side views of the end tool of FIG. 55. FIGS. 62 and 63 are plan views of the end tool of FIG. 55.

Referring to FIGS. 55 to 63, the end tool 100 according to the third modified example of the first embodiment of the present disclosure includes a pair of jaws for performing a grip motion, that is, the first jaw 101 and the second jaw 102. In this regard, a component encompassing each of the first jaw 101 and the second jaw 102 or both the first jaw 101 and the second jaw 102 may be referred to as the jaw 103.

In addition, the end tool 100 of the fourth modified example of the first embodiment of the present disclosure may include the end tool hub 106 and the pitch hub 107.

In addition, the end tool 100 of the fourth modified example of the first embodiment of the present disclosure may include the rotation axis 141, the rotation axis 142, the rotation axis 145, the rotation axis 143, and the rotation axis 144. As described above, the rotation axis 141, the rotation axis 142, and the rotation axis 145 may be inserted through the end tool hub 106, and the rotation axis 143 and the rotation axis 144 may be inserted through the pitch hub 107.

In the present modified example, the end tool hub 106, the pitch hub 107, and the rotation axes 141, 142, 143, 144, and 145 are substantially the same as the end tool hub 106, the pitch hub 107, and the rotation axes 141, 142, 143, 144, and 145 that are described above with reference to FIG. 5 and the like, respectively, and thus, detailed descriptions thereof will be omitted.

Meanwhile, the end tool 100 may include the pulley 111, the pulley 112, the pulley 113, the pulley 114, the pulley 115, the pulley 117, and the pulley 118, which are associated with a rotational motion of the first jaw 101. In addition, the end tool 100 may include the pulley 121, the pulley 122, the pulley 123, the pulley 124, the pulley 125, the pulley 127, and the pulley 128, which are associated with a rotational motion of the second jaw 102.

In this regard, in the end tool 100 of the surgical instrument according to the fourth modified example of the first embodiment of the present disclosure, each of the first jaw pitch sub-pulley and the second jaw pitch sub-pulley includes only one pulley.

In detail, the end tool 100 of the surgical instrument according to the first modified example of the first embodiment of the present disclosure illustrated in FIG. 34 and the like includes a pair of pulleys 115 and 116 as first jaw pitch sub-pulleys, and a pair of pulleys 125 and 126 as second jaw pitch sub-pulleys.

On the contrary, the end tool 100 of the surgical instrument according to the fourth modified example of the first embodiment of the present disclosure is different from the first modified example of the first embodiment of the present disclosure illustrated in FIG. 34 and the like, in that it includes a single pulley 115 as a first jaw pitch sub-pulley, and a single pulley 125 as a second jaw pitch sub-pulley.

Accordingly, the pulley 111, the pulley 112, the pulley 117/pulley 118, the pulley 113/pulley 114, and the pulley 115, which are associated with rotation of the first jaw 101, may be sequentially arranged from the distal end 104 of the end tool 100 toward the proximal end 105.

In addition, the pulley 121, the pulley 122, the pulley 127/pulley 128, the pulley 123/pulley 124, and the pulley 125, which are associated with rotation of the second jaw 102, may be sequentially arranged from the distal end 104 of the end tool 100 toward the proximal end 105.

In this regard, the pulley 116 and pulley 126 of the end tool 100 of the first modified example of the first embodiment of the present disclosure illustrated in FIG. 34 and the like are not pulleys around which wires are wound, but pulleys through which the wires pass in a straight line, and thus may be omitted as in the present modified example.

In other words, in the first modified example of the first embodiment of the present disclosure, two rows of first jaw pitch sub-pulleys and two rows of second jaw pitch sub-pulleys are provided, whereas in the fourth modified example of the first embodiment of the present disclosure, one row of a first jaw pitch sub-pulley and one row of a second jaw pitch sub-pulley are provided.

In this regard, the pulley 117/pulley 118 are arranged on one side of the pulley 111 and the pulley 112. In this regard, the pulley 117/pulley 118 are formed to be rotatable around the rotation axis 145, which is a pitch redundant rotation axis. In addition, the pulley 113 and the pulley 114 are arranged on one side of the pulley 117/pulley 118 to face each other. In this regard, the pulley 113 and the pulley 114 are formed to be rotatable independently of each other around the rotation axis 143, which is a pitch main rotation axis. In addition, the pulley 115 is arranged on one side of each of the pulley 113 and the pulley 114. In this regard, the pulley 115 is formed to be rotatable around the rotation axis 144, which is a pitch sub-rotation axis. In this regard, the drawings illustrate that the pulley 117, the pulley 118, the pulley 113, the pulley 114, and the pulley 115 are formed to be rotatable around the Y-axis direction, but the concept of the present disclosure is not limited thereto, and the rotation axes of the respective pulleys may be formed in various directions according to their configurations.

The wire 301, which is a first jaw wire, is wound to sequentially come into contact with at least portions of the pulley 115, the pulley 113, the pulley 117, and the pulley 111. In addition, the wire 305 connected to the wire 301 by the coupling member 323 is wound to sequentially come into contact with at least portions of the pulley 111, the pulley 112, the pulley 118, and the pulley 114.

In other words, the wire 301 and the wire 305, which are first jaw wires, are wound to sequentially come into contact with at least portions of the pulley 115, the pulley 113, the pulley 117, the pulley 111, the pulley 112, the pulley 118, and the pulley 114, and are formed to move along the above pulleys while rotating the above pulleys.

Meanwhile, the pulley 127/pulley 128 are arranged on one side of the pulley 121 and the pulley 122. In this regard, the pulley 127/pulley 128 are formed to be rotatable around the rotation axis 145, which is a pitch redundant rotation axis. In addition, the pulley 123 and the pulley 124 are arranged on one side of the pulley 127/pulley 128 to face each other. In this regard, the pulley 123 and the pulley 124 are formed to be rotatable independently of each other around the rotation axis 143, which is a pitch main rotation axis. In addition, the pulley 125 is arranged on one side of the pulley 123 and the pulley 124. In this regard, the pulley 125 is formed to be rotatable around the rotation axis 144, which is a pitch sub-rotation axis. In this regard, the drawings illustrate that the pulley 127, the pulley 128, the pulley 123, the pulley 124, the pulley 125, and the pulley 126 are formed to be rotatable around the Y-axis direction, but the concept of the present disclosure is not limited thereto, and the rotation axes of the respective pulleys may be formed in various directions according to their configurations.

The wire 306, which is a second jaw wire, is wound to sequentially come into contact with at least portions of the pulley 125, the pulley 123, the pulley 127, and the pulley 121. In addition, the wire 302 connected to the wire 306 by the coupling member 326 is wound to sequentially come into contact with at least portions of the pulley 121, the pulley 122, the pulley 128, and the pulley 124.

In other words, the wire 306 and the wire 302, which are second jaw wires, are wound to sequentially come into contact with at least portions of the pulley 125, the pulley 123, the pulley 127, the pulley 121, the pulley 122, the pulley 128, and the pulley 124, and are formed to move along the above pulleys while rotating the above pulleys.

Accordingly, in the first modified example of the first embodiment of the present disclosure, two rows of first jaw pitch sub-pulleys and two rows of second jaw pitch sub-pulleys are provided, whereas in the fourth modified example of the first embodiment of the present disclosure, one row of a first jaw pitch sub-pulley and one row of a second jaw pitch sub-pulley are provided, and thus, an effect of reducing the number of parts and simplifying a manufacturing process may be achieved.

Fifth Modified Example of First Embodiment

Hereinafter, an end tool 100 of a surgical instrument according to a fifth modified example of the first embodiment of the present disclosure will be described. Here, the end tool 100 of the surgical instrument according to the fifth modified example of the first embodiment of the present disclosure is different from the end tool of the surgical instrument according to the first embodiment of the present disclosure described above in that the configuration of the end tool hub 180 serving as an auxiliary pulley is different. Such a configuration that is changed from that of the first embodiment will be described in detail later.

Figure 64:
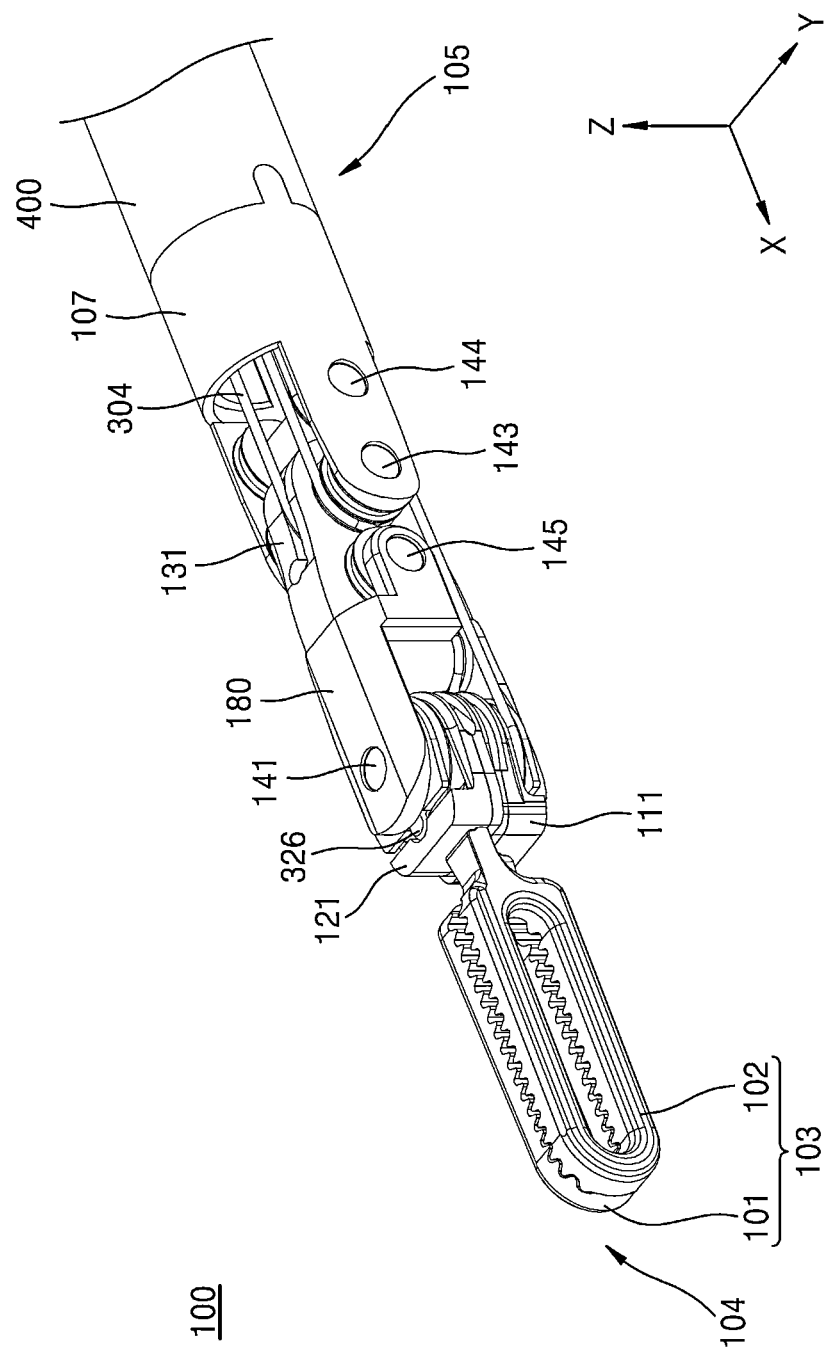
FIGS. 64 and 65 are perspective views illustrating an end tool of a surgical instrument according to a fifth modified example of the first embodiment of the present disclosure.
Figure 65:
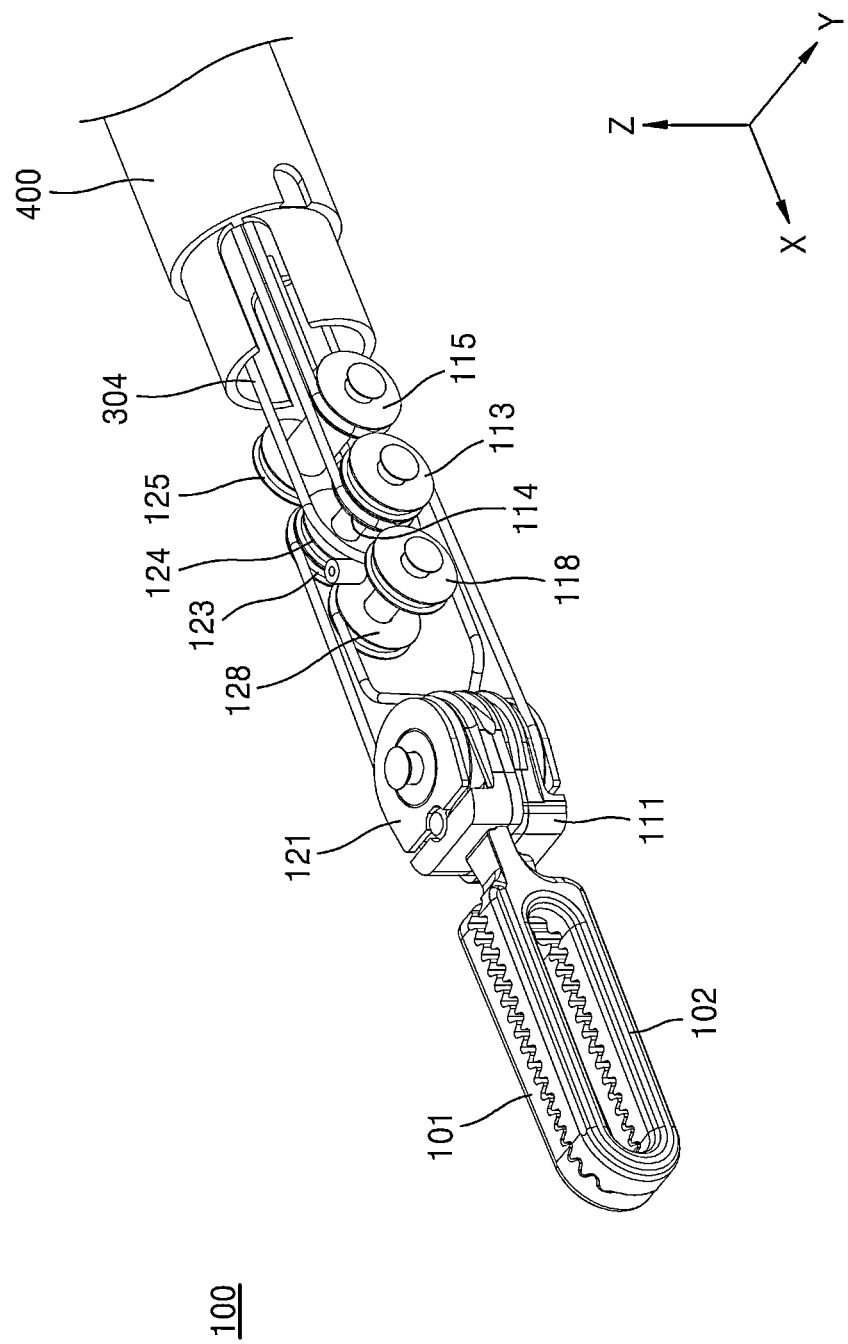
Figure 66:
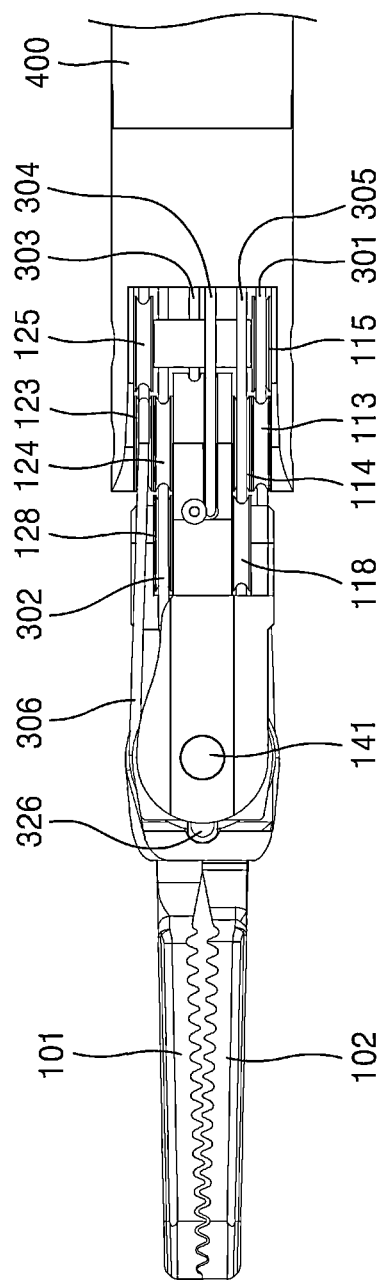
FIG. 66 is a plan view of the end tool of FIG. 64.
Figure 67:
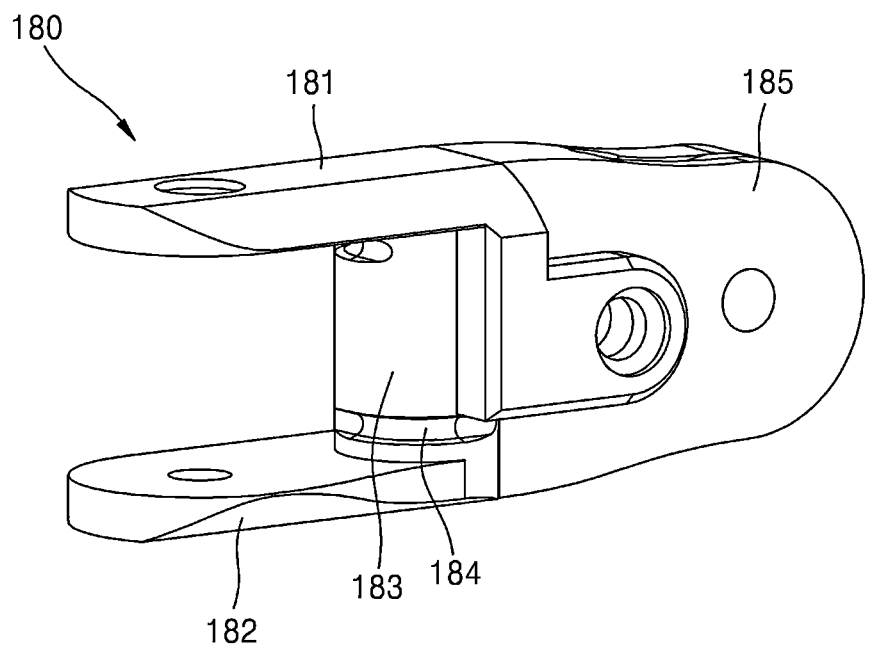
FIG. 67 is a perspective view of an end tool hub of the end tool of FIG. 64.
Figure 68:
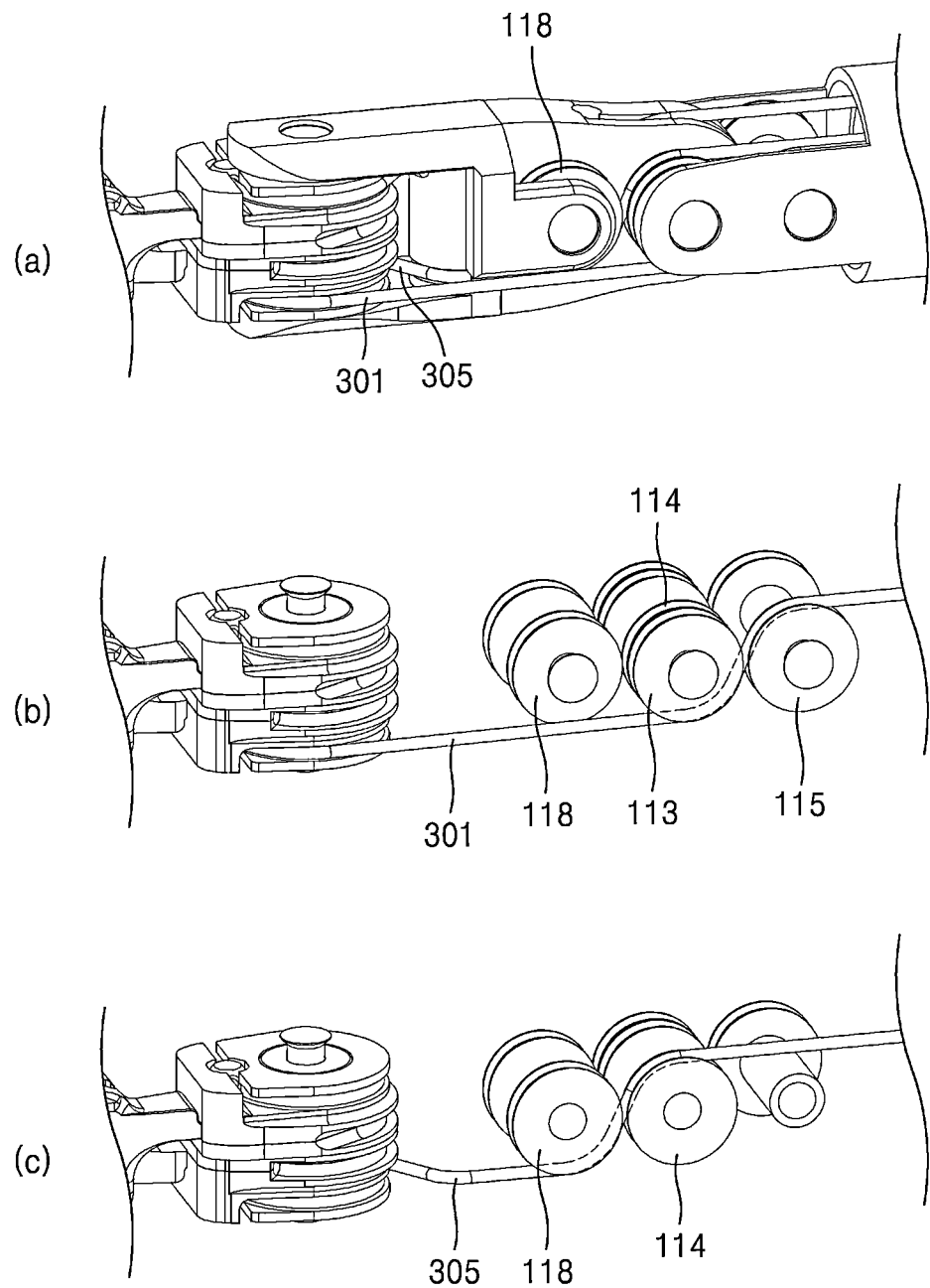
FIG. 68 is a side view of the end tool of FIG. 64.
Figure 69:
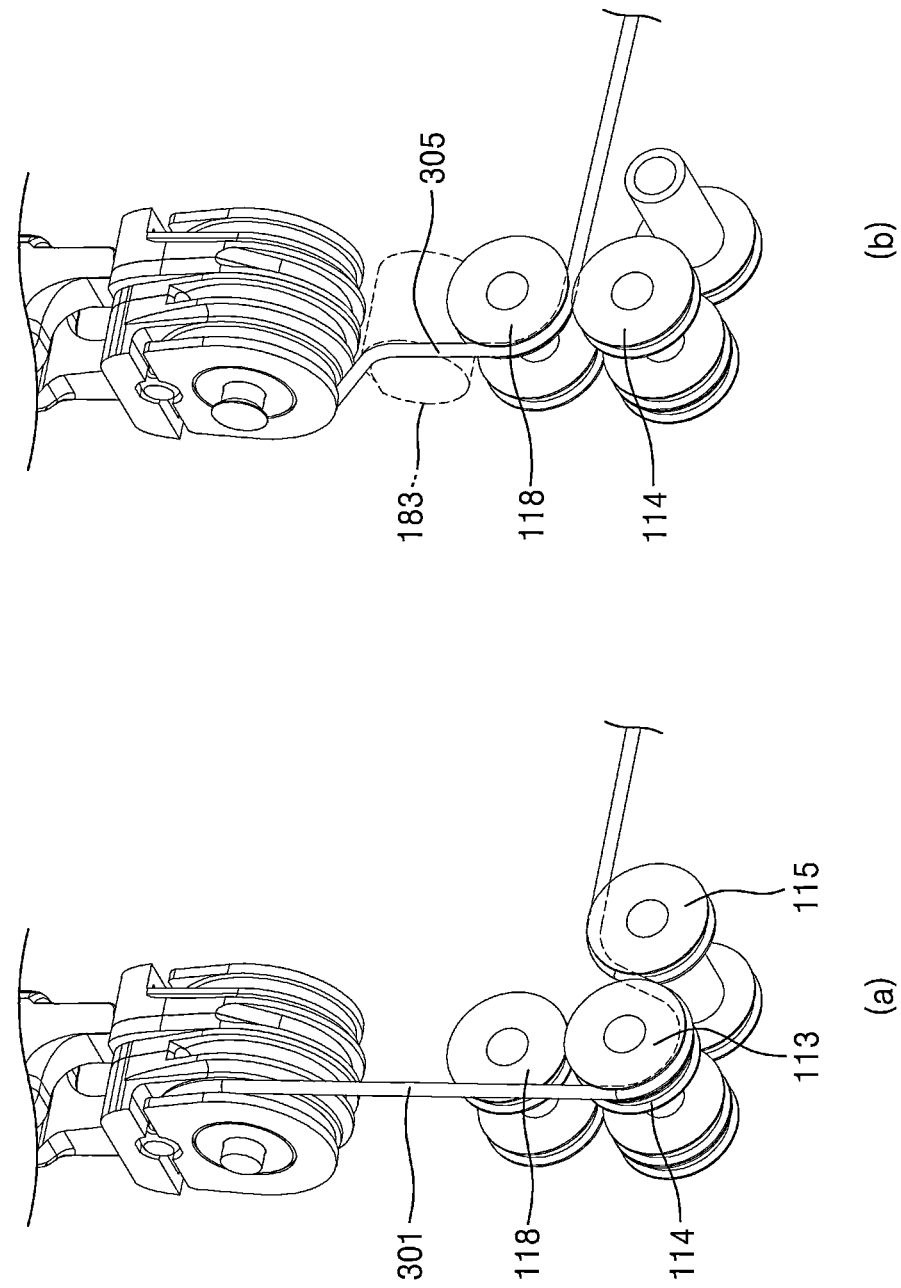
FIG. 69 is a perspective view illustrating a state in which the end tool of the surgical instrument of FIG. 64 is pitch-rotated by −90°.
Figure 71:
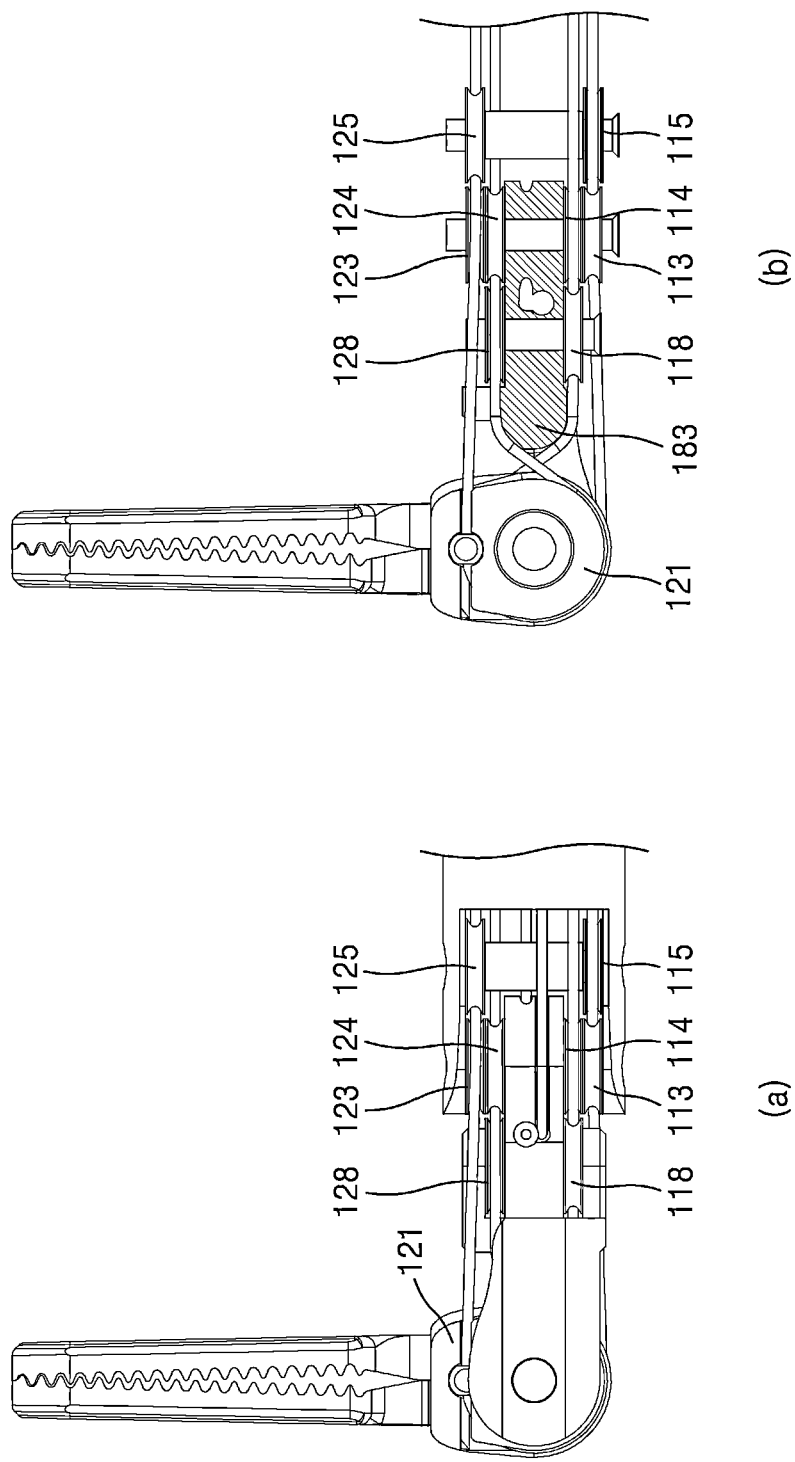
FIG. 71 is a perspective view illustrating a state in which the end tool of the surgical instrument of FIG. 64 is yaw-rotated by +90°.
Figure 72:
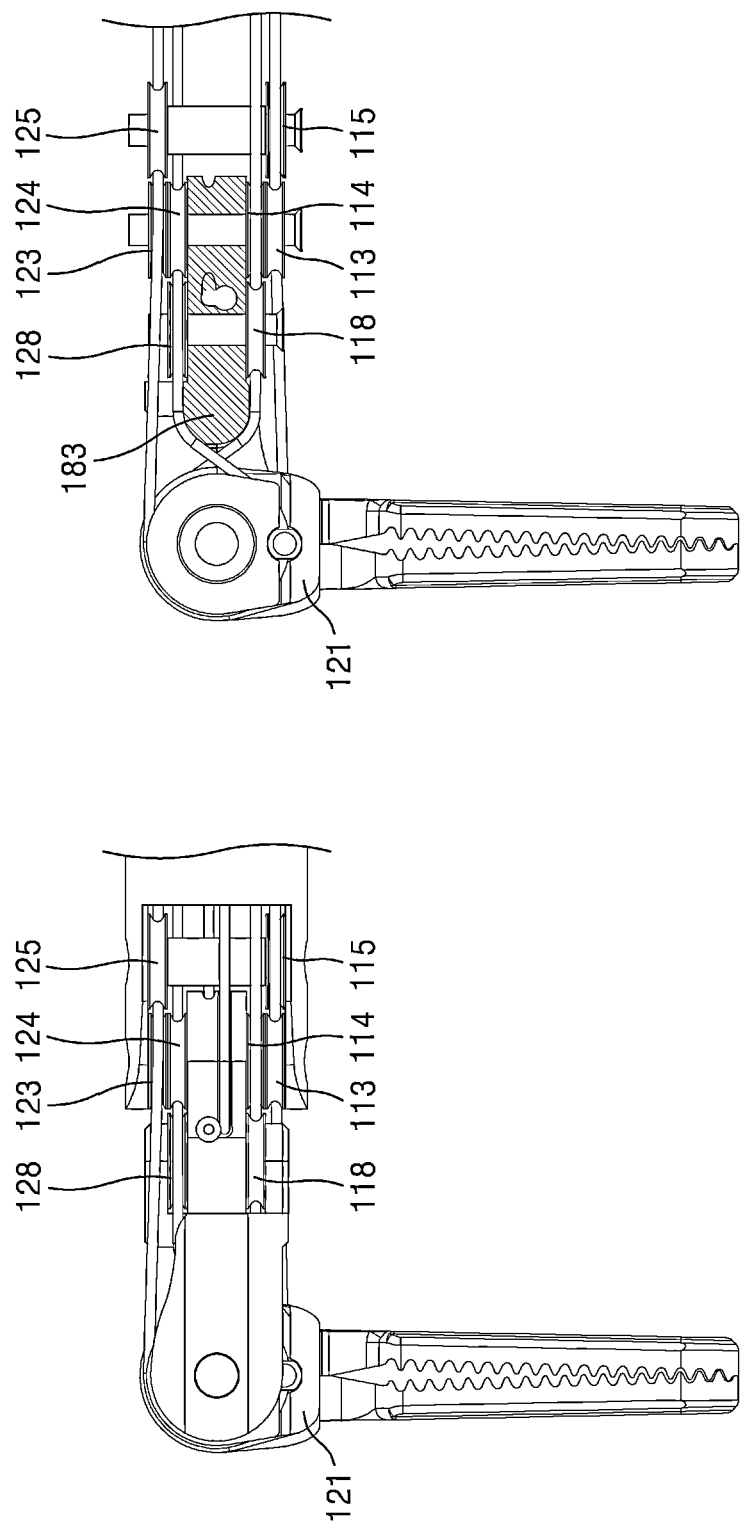
FIG. 72 is a side view illustrating a state in which the end tool of the surgical instrument of FIG. 64 is yaw-rotated by −90°.

FIGS. 64 and 65 are perspective views illustrating the end tool of the surgical instrument according to the fifth modified example of the first embodiment of the present disclosure. FIG. 66 is a plan view of the end tool of FIG. 64. FIG. 67 is a perspective view of an end tool hub of the end tool of FIG. 64. FIG. 68 is a side view of the end tool of FIG. 64. FIG. 69 is a perspective view illustrating a state in which the end tool of the surgical instrument of FIG. 64 is pitch-rotated by −90°. FIG. 70 is a side view illustrating a state in which the end tool of the surgical instrument of FIG. 64 is pitch-rotated by +90°. FIG. 71 is a perspective view illustrating a state in which the end tool of the surgical instrument of FIG. 64 is yaw-rotated by +90°. FIG. 72 is a side view illustrating a state in which the end tool of the surgical instrument of FIG. 64 is yaw-rotated by −90°.

Referring to FIGS. 64 to 72, the end tool 100 of the first embodiment of the present disclosure includes a pair of jaws for performing a grip motion, that is, a first jaw 101 and a second jaw 102. Here, each of the first jaw 101 and the second jaw 102, or a component encompassing the first jaw 101 and the second jaw 102 may be referred to as a jaw 103.

Meanwhile, the end tool 100 includes a plurality of pulleys including a pulley 111 related to a rotational motion of the first jaw 101. The pulleys related to the rotational motion of the first jaw 101 described in the present modified example are substantially the same as the pulley 111, the pulley 112, the pulley 113, the pulley 114, the pulley 115, and the pulley 118 described with reference to FIG. 5 or the like of the first embodiment, and thus, detailed descriptions thereof will be omitted herein.

Meanwhile, the end tool 100 includes a plurality of pulleys including a pulley 121 related to a rotational motion of the second jaw 102. The pulleys related to the rotational motion of the second jaw 102 described in the present modified example are substantially the same as the pulley 121, the pulley 122, the pulley 123, the pulley 124, the pulley 125, and the pulley 128 described with reference to FIG. 5 or the like of the first embodiment, and thus, detailed descriptions thereof will be omitted herein.

Further, the end tool 100 of the first embodiment of the present disclosure may include an end tool hub 180 and a pitch hub 107. The end tool hub 180 will be described in more detail later.

Further, the end tool 100 of the fifth modified example of the first embodiment of the present disclosure may include a rotation shaft 141, a rotation shaft 145, a rotation shaft 143, and a rotation shaft 144. As described above, the rotation shaft 141 and the rotation shaft 145 may be inserted through the end tool hub 180, and the rotation shaft 143 and the rotation shaft 144 may be inserted through the pitch hub 107.

In the present modified example, the pitch hub 107 and each of the rotation shafts 141, 143, 144, and 145 are substantially the same as the pitch hub 107 and each of the rotation shafts 141, 143, 144, and 145 described in the first embodiment with reference to FIG. 5 or the like, and thus detailed descriptions thereof will be omitted herein.

Also, the end tool 100 of the fifth modified example of the first embodiment of the present disclosure may include the end tool hub 180 and the pitch hub 107.

The rotation shaft 141 is inserted through the end tool hub 180, and the pulley 111 and the pulley 121, which are axially coupled to the rotation shaft 141, and at least some of the first jaw 101 and the second jaw 102 coupled the pulley 111 and the pulley 121 may be accommodated inside the end tool hub 180. Here, in an embodiment of the present disclosure, a guide part 183 serving as an auxiliary pulley is formed in the end tool hub 180. That is, the guide part 183 configured to guide paths of wires 305 and 302 may be formed in the end tool hub 180. The guide part 183 of the end tool hub 180 described above may serve as a kind of auxiliary pulley to reroute the wire, and the guide part 183 of the end tool hub 180 serving as an auxiliary pulley will be described in more detail later.

Meanwhile, a pulley 131 serving as an end tool pitch pulley may be formed at one end portion of the end tool hub 180. As shown in FIG. 64, the pulley 131 may be integrally formed with the end tool hub 180 as one body. In this case, the pulley 131 may be formed inside the end tool hub 180 in the form of a kind of guide channel to guide paths of the wire 303 and the wire 304. Alternatively, the pulley 131 may be formed as a separate member from the end tool hub 180 to be coupled to the end tool hub 180. In addition, the wire 303 and the wire 304 are coupled to the pulley 131 serving as an end tool pitch pulley, and a pitch motion is performed as the pulley 131 is rotated around the rotation shaft 143.

The rotation shaft 143 and the rotation shaft 144 are inserted through the pitch hub 107, and the pitch hub 107 may be axially coupled to the end tool hub 180 and the pulley 131 by the rotation shaft 143. Thus, the end tool hub 180 and the pulley 131 may be formed to be pitch-rotatable around the rotation shaft 143 with respect to the pitch hub 107.

Further, the pitch hub 107 may internally accommodate at least some of the pulley 113, the pulley 114, the pulley 123, and the pulley 124 that are axially coupled to the rotation shaft 143. In addition, the pitch hub 107 may internally accommodate at least some of the pulley 115 and the pulley 125 that are axially coupled to the rotation shaft 144.

Hereinafter, the end tool hub 180 of an embodiment of the present disclosure will be described in more detail, and in particular, the guide part 183 of the end tool hub 180 serving as an auxiliary pulley will be mainly described.

The end tool hub 180 includes a pair of jaw pulley coupling parts 181 and 182, the guide part 183, a guide groove 184, and a pitch pulley part 185.

In detail, the pair of jaw pulley coupling parts 181 and 182 are formed to face each other, and accommodate the pulley 111 and the pulley 121 therein. In addition, a through hole is formed in each of the jaw pulley coupling parts 181 and 182 such that the rotation shaft 141 passes through and axially couples the jaw pulley coupling parts 181 and 182, the pulley 111, and the pulley 121.

The pair of jaw pulley coupling parts 181 and 182 are connected to each other by the guide part 183. That is, the pair of jaw pulley coupling parts 181 and 182 parallel to each other are coupled by the guide part 183 formed in a direction substantially perpendicular to the pair of jaw pulley coupling parts 181 and 182, so that the pair of jaw pulley coupling parts 181 and 182 and the guide part 183 form a substantially C-shape, and accommodate the pulley 111 and the pulley 121 therein.

In other words, it may be expressed that the pair of jaw pulley coupling parts 181 and 182 are formed to extend in the X-axis direction from both end portions of the guide part 183 formed to be elongated in the Z-axis direction.

Here, the guide part 183 may be formed in a cylindrical shape with a cross section that is approximately semi-circular. In addition, the semi-circular portion may be disposed to protrude toward the pulley 111 and the pulley 121. In other words, it may be said that the guide part 183 is formed to protrude toward a space formed by the pair of jaw pulley coupling parts 181 and 182 and the guide part 183. In other words, it may be said that a region of the guide part 183 adjacent to the jaw pulley coupling parts 181 and 182 is formed such that a cross section thereof is curved with a predetermined curvature.

Alternatively, in other words, it may be also said that the wire guide part 183 serves as a kind of pulley member, which guides the paths of the wire 305 and the wire 302 by winding the wire 305 and the wire 302 around an outer circumferential surface thereof. However, here, the guide part 183 is not a member that is rotated around a predetermined axis like the original meaning pulley does, and it may be said that the guide part 183 is formed to be fixed as a portion of the end tool hub 180 and performs some similar functions of a pulley configured to guide a path of a wire by winding the wire therearound.

Here, the guide part 183 is illustrated in the drawing as being formed in a cylindrical shape with a cross section that is approximately semi-circular. That is, at least a portion of the cross section of the guide part 183 on the XY plane is illustrated as having a certain arc shape. However, the concept of the present disclosure is not limited thereto, and the cross section may have a predetermined curvature like an elliptical shape or a parabola, or a corner of a polygonal column is rounded to a certain extent, so that the cross section may have various shapes and sizes suitable for guiding the paths of the wire 305 and the wire 302.

Here, the guide groove 184 for guiding the paths of the wire 305 and the wire 302 well may be further formed in a portion of the guide part 183, which is in contact with the wire 305 and the wire 302. The guide groove 184 may be formed in the form of a groove recessed to a certain extent from a protruding surface of the guide part 183.

Here, although the guide groove 184 is illustrated in the drawing as being formed in the entire arc surface of the guide part 183, the concept of the present disclosure is not limited thereto, and the guide groove 184 may be formed only in a portion of the arc surface of the guide part 183 as necessary.

As described above, by further forming the guide groove 184 in the guide part 183, unnecessary friction between the wires is reduced, so that durability of the wires may be improved.

The pitch pulley part 185 may be further formed in a direction opposite to a direction of formation of the jaw pulley coupling parts 181 and 182 in the guide part 183. In addition, the pulley 131, which is a pitch pulley around which the wire 303 and the wire 304 that are pitch wires may be wound, may be formed in the pitch pulley part 185. However, here, the pulley 131 is not a member that is rotated around a predetermined axis like the original meaning pulley does, and it may be said that the pulley 131 is formed to be fixed as a portion of the end tool hub 180 and performs some similar functions of a pulley by winding a wire therearound. That is, the pulley 131 may be formed as a kind of groove in the pitch pulley part 185 of the end tool hub 180, and the pulley 131 may serve as guide channels of the wire 303 and the wire 304. Here, the pitch pulley part 185 may be formed on the XZ plane. In addition, a through hole through which the rotation shaft 143 may be inserted may be formed in the pitch pulley part 185.

Meanwhile, although not shown in the drawings, the pitch pulley part and the pitch pulley may be formed as separate members and may be coupled to each other, and the rotation shaft 143 may be formed to pass through the pitch pulley part and the pulley.

Hereinafter, the role and function of the guide part 183 will be described in more detail.

The guide part 183 may be in contact with the wire 305 and the wire 302 and may change the arrangement path of the wires 305 and 302 to a certain extent to serve to increase a rotation radius of each of the first jaw 101 and the second jaw 102.

That is, when the auxiliary pulley or the guide part 183 is not disposed, each of the pulley 111, which is a first jaw pulley, and the pulley 121, which is a second jaw pulley, may rotate up to a right angle, but in an embodiment of the present disclosure, by additionally providing the guide part 183 in the end tool hub 180, the maximum rotation angle of each pulley may be increased.

This enables a motion that two jaws of the end tool 100 have to open for an actuation motion in a state in which the two jaws of the end tool 100 are yaw-rotated by 90°. In other words, a feature of increasing the range of a yaw rotation in which an actuation motion is possible may be obtained through the configuration of the guide part 183 of the end tool hub 180.

Furthermore, by forming the guide part 183 in the end tool hub 180, which already exists, without adding a separate structure such as an auxiliary pulley, the range of rotation may be increased without adding a component and a manufacturing process.

As described above, since there is no need to additionally dispose a separate structure for increasing the rotation angle, the number of components is decreased and the manufacturing process is simplified, and also, the length of the end tool is reduced by as much as the size of the auxiliary pulley, so that the length of the end tool is shortened during a pitch motion. Accordingly, a surgical motion may be more easily performed in a narrow space.

This will be described below in more detail.

In the end tool 100 of the surgical instrument according to an embodiment of the present disclosure, the arrangement path of the wires may be changed without a separate structure by forming the guide part 183 capable of changing the path of the wire on an inner side wall of the end tool hub 180. As described above, as the arrangement path of the wire 305 and the wire 302 is changed to a certain degree by forming the guide part 183 in the end tool hub 180, a tangential direction of the wire 305 and the wire 302 is changed, and accordingly, rotation angles of a coupling member 323 and a coupling member 326 that couple respective wires and pulleys may be increased.

That is, the coupling member 326 that couples the wire 302 to the pulley 121 is rotatable until being located on a common internal tangent of the pulley 121 and the guide part 183. Similarly, a coupling member (see 323 of FIG. 11) that couples the wire 305 to the pulley 111 is rotatable until being located on a common internal tangent of the pulley 111 and the guide part 183, so that a rotation angle of the coupling member (see 323 of FIG. 11) may be increased.

In other words, due to the guide part 183, the wire 301 and the wire 305 wound around the pulley 111 are disposed on one side with respect to a plane perpendicular to the Y-axis and passing through the X-axis. Simultaneously, due to the guide part 183, the wires 302 and 306 wound around the pulley 121 are disposed on another side with respect to the plane perpendicular to the Y-axis and passing through the X-axis.

In other words, the pulley 113 and the pulley 114 are disposed on one side with respect to the plane perpendicular to the Y-axis and passing through the X-axis, and the pulley 123 and the pulley 124 are disposed on another side with respect to the plane perpendicular to the Y-axis and passing through the X-axis.

In other words, the wire 305 is located on the internal tangent of the pulley 111 and the guide part 183, and the rotation angle of the pulley 111 is increased by the guide part 183. In addition, the wire 302 is located on the internal tangent of the pulley 121 and the guide part 183, and a rotation angle of the pulley 121 is increased by the guide part 183.

In the present embodiment in which an auxiliary pulley is not formed and the guide part 183 capable of changing the path of the wire is formed on the inner side wall of the end tool hub 180, the length of the end tool of the surgical instrument may be reduced as compared to the surgical instrument in which a separate auxiliary pulley is formed. Since the length of the end tool is reduced as described above, a surgical operator may easily manipulate a surgical instrument, and side effects of surgery may be reduced when the surgery is performed in a narrow surgical space in the human body.

According to the present disclosure as described above, the rotation radii of the pulley 111, which is a first jaw pulley, and the pulley 121, which is a second jaw pulley, increase, so that a yaw motion range in which a normal opening/closing actuation motion can be performed may be increased.

<Second Embodiment of End Tool of Surgical Instrument>

Hereinafter, an end tool 1100 of a surgical instrument according to a second embodiment of the present disclosure will be described. In this regard, the end tool 1100 of the surgical instrument according to the second embodiment of the present disclosure is different from the end tool (see 100 of FIG. 5 and the like) of the surgical instrument according to the first embodiment of the present disclosure described above, in the arrangement of the jaw pulleys and the jaw wires. The configuration that is different from that of the first embodiment will be described in detail below.

Figure 73:
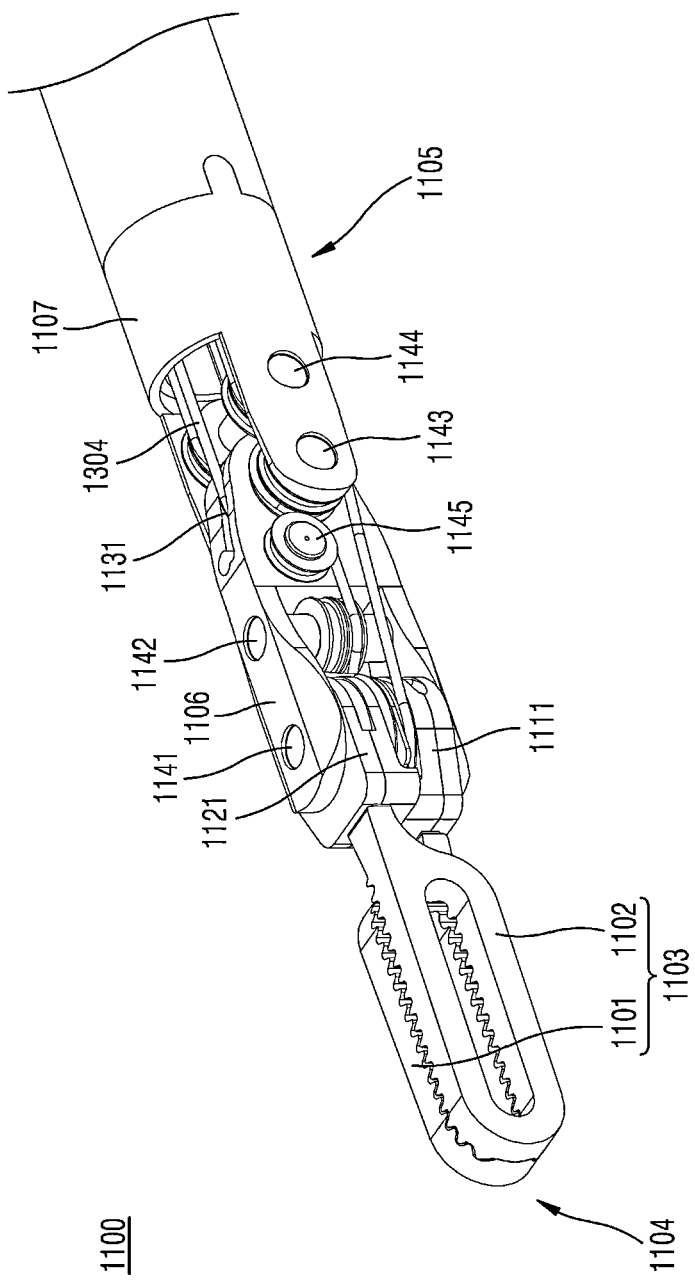
FIGS. 73 and 74 are perspective views illustrating an end tool of a surgical instrument according to a second embodiment of the present disclosure.
Figure 74:
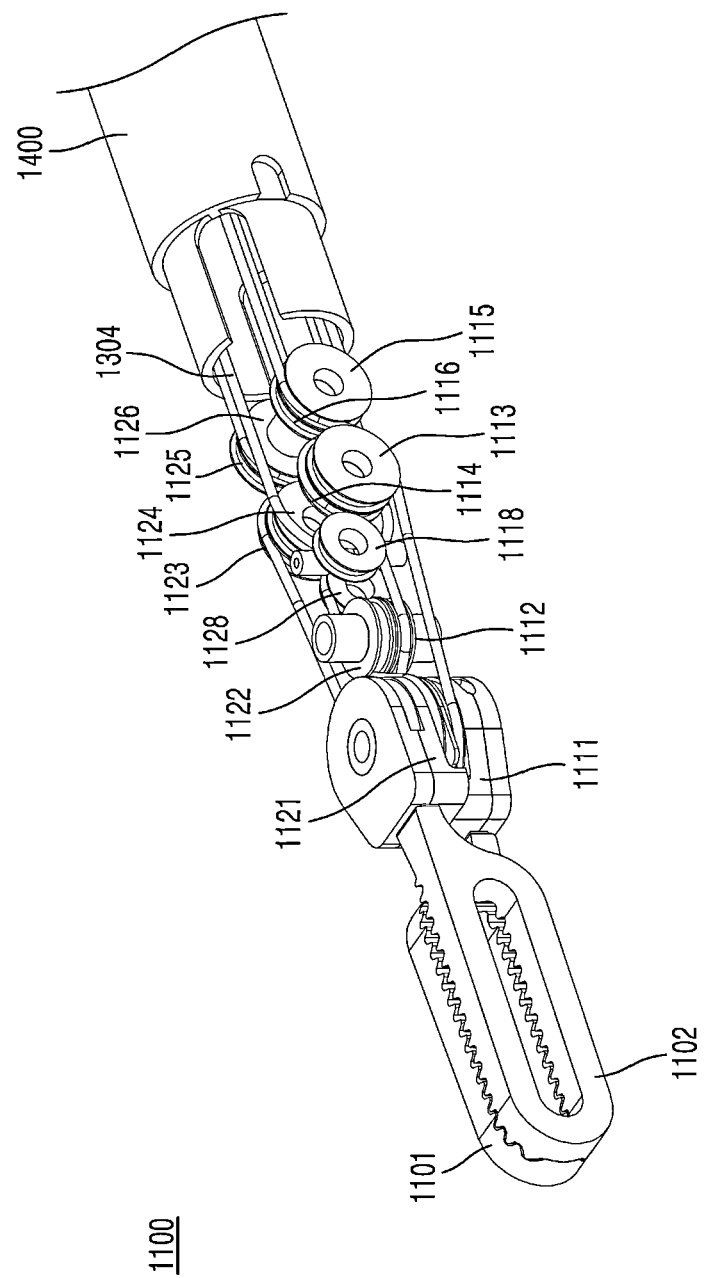
Figure 75:
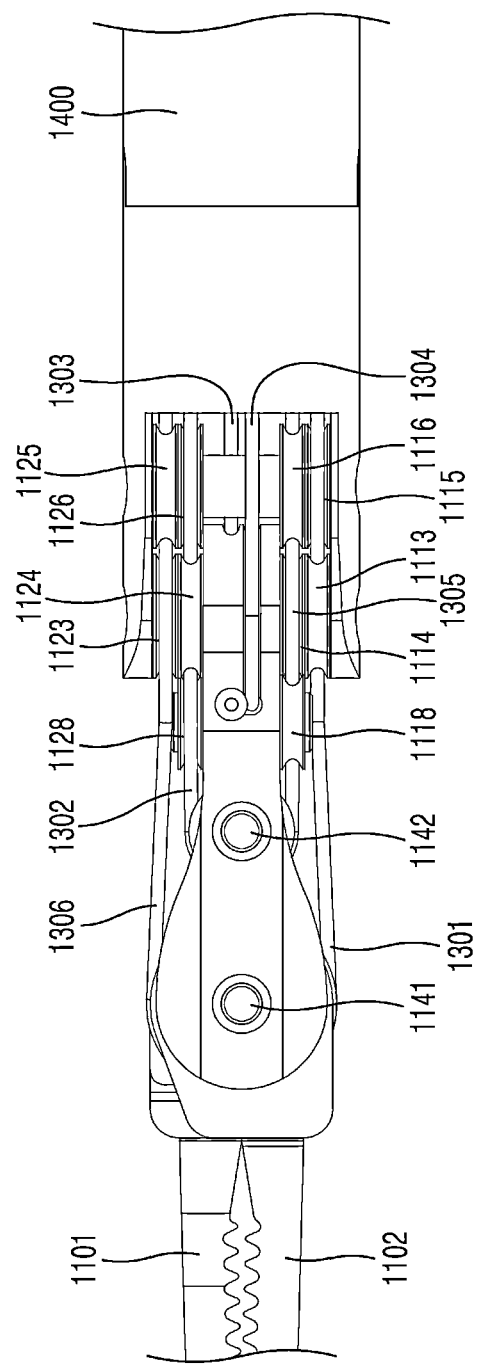
FIGS. 75, 76, 77, and 78 are plan views of the end tool of FIG. 73.
Figure 76:
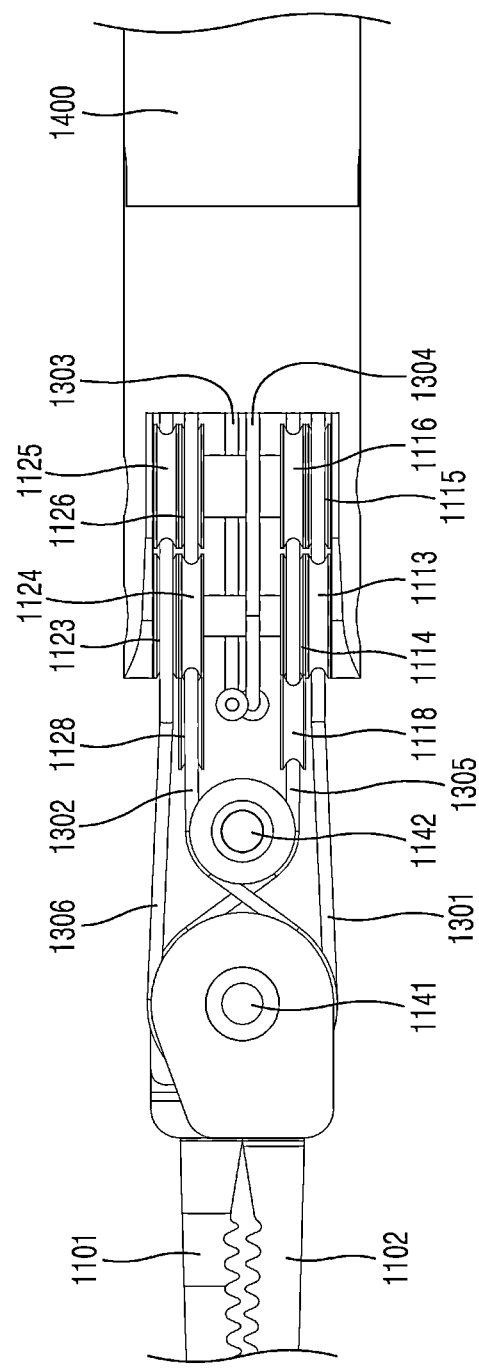
Figure 79:
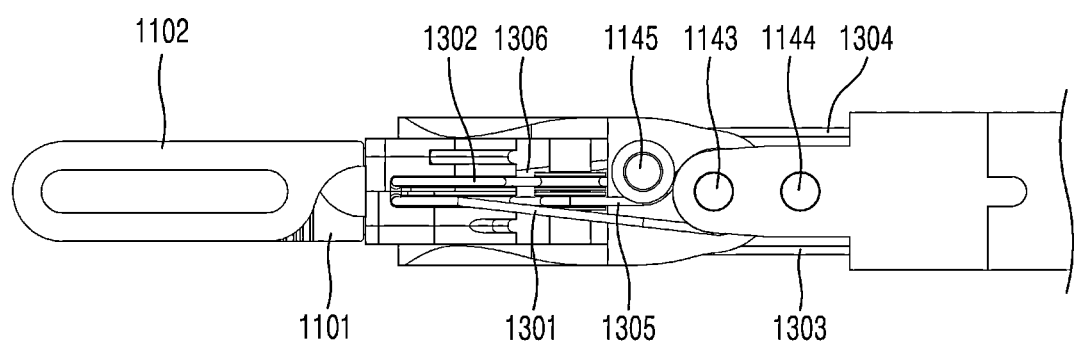
FIGS. 79, 80, and 81 are side views of the end tool of FIG. 73.
Figure 80:
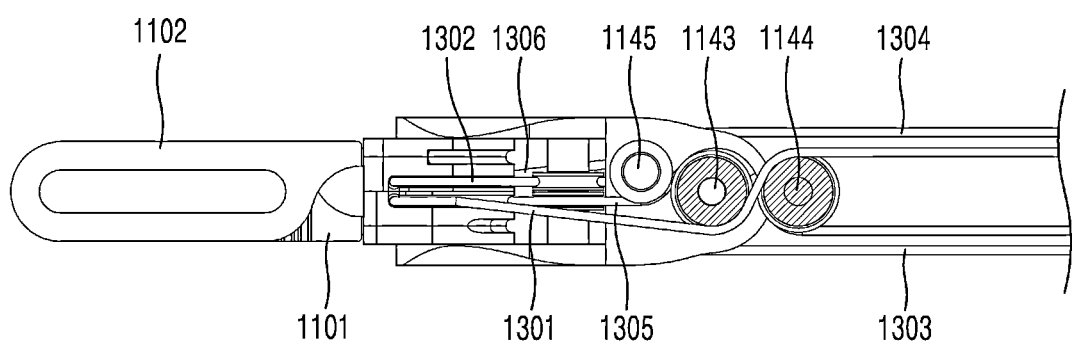
Figure 81:
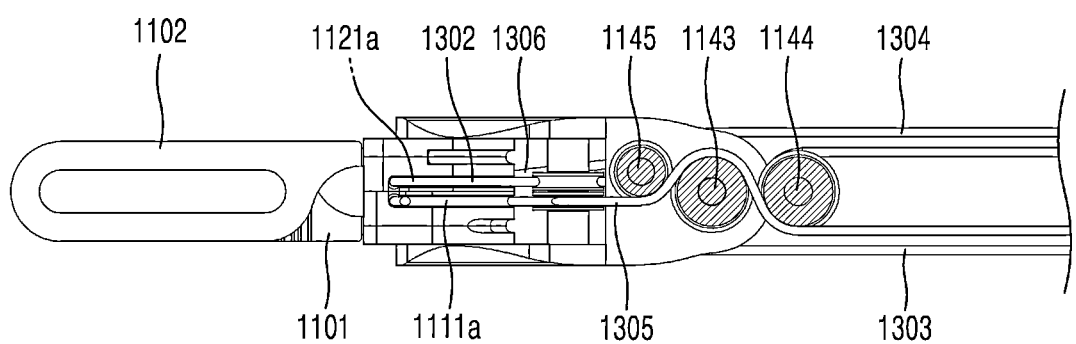

FIGS. 73 and 74 are perspective views illustrating the end tool of the surgical instrument according to the second embodiment of the present disclosure. FIGS. 75, 76, 77, and 78 are plan views of the end tool of FIG. 73. FIGS. 79, 80, and 81 are side views of the end tool of FIG. 73.

Referring to FIGS. 73 to 81, a power transmission part 1300 of the end tool 1100 of the surgical instrument according to the second embodiment of the present disclosure may include a wire 1301, a wire 1302, a wire 1303, a wire 1304, a wire 1305, and a wire 1306. In the present embodiment, the wires are substantially the same as the wire 301, the wire 302, the wire 303, the wire 304, the wire 305, and the wire 306 of the first embodiment described above with reference to FIG. 5 and the like, and thus, detailed descriptions thereof will be omitted.

In addition, the power transmission part 1300 of the end tool 1100 of the surgical instrument according to the second embodiment of the present disclosure may include a coupling member 1321, a coupling member 1322, a coupling member 1323, a coupling member 1324, a coupling member 1326, a coupling member 1327, a coupling member 1329, and the like, which are coupled to ends of the respective wires to combine the wires with the pulleys. In this regard, each of the coupling members may have various shapes as necessary, such as a ball shape, a tube shape, or the like. In the present embodiment, the coupling members are substantially the same as the coupling member 321, the coupling member 322, the coupling member 323, the coupling member 324, the coupling member 326, and the coupling member 327 of the first embodiment described above with reference to FIG. 9 and the like, and thus, detailed descriptions thereof will be omitted.

(End Tool)

Hereinafter, the end tool 1100 of the surgical instrument of FIG. 73 will be described in more detail.

Continuing to refer to FIGS. 73 to 81, the end tool 1100 of the second embodiment of the present disclosure includes a pair of jaws for performing a grip motion, that is, a first jaw 1101 and a second jaw 1102. In this regard, a component encompassing each of the first jaw 1101 and the second jaw 1102 or both the first jaw 1101 and the second jaw 1102 may be referred to as a jaw 1103.

In addition, the end tool 1100 may include a pulley 1111, a pulley 1112, a pulley 1113, a pulley 1114, a pulley 1115, a pulley 1116, and a pulley 1118, which are associated with a rotational motion of the first jaw 1101. In addition, the end tool 1100 may include a pulley 1121, a pulley 1122, a pulley 1123, a pulley 1124, a pulley 1125, a pulley 1126, and a pulley 1128, which are associated with a rotational motion of the second jaw 102. These pulleys will be described in more detail below.

In addition, the end tool 1100 of the second embodiment of the present disclosure may include an end tool hub 1106 and a pitch hub 1107.

A rotation axis 1141, a rotation axis 1142, and a rotation axis 1145 are inserted through the end tool hub 1106. In addition, the end tool hub 1106 may internally accommodate at least portions of the pulley 1111 and the pulley 1121 that are axially coupled to the rotation axis 1141. In addition, the end tool hub 1106 may internally accommodate at least portions of the pulley 1112 and the pulley 1122 that are axially coupled to the rotation axis 1142. In addition, the pulley 1118 and the pulley 1128 that are axially coupled to the rotation axis 1145 may be coupled to the end tool hub 1106.

The rotation axis 1143 and a rotation axis 1144 may be inserted through the pitch hub 1107, and the pitch hub 1107 may be axially coupled to the end tool hub 1106 and a pulley 1131 by the rotation axis 1143. Thus, the end tool hub 1106 and the pulley 1131 (formed with the end tool hub 1106 as one body) may be formed to be rotatable around the rotation axis 1143 with respect to the pitch hub 1107.

In addition, the pitch hub 1107 may internally accommodate at least portions of the pulley 1113, the pulley 1114, the pulley 1123, and the pulley 1124 that are axially coupled to the rotation axis 1143. In addition, the pitch hub 1107 may internally accommodate at least portions of the pulley 1115, the pulley 1116, the pulley 1125, and the pulley 1126 that are axially coupled to the rotation axis 1144.

In addition, the end tool 1100 of the second embodiment of the present disclosure may include the rotation axis 1141, the rotation axis 1142, the rotation axis 1145, the rotation axis 1143, and the rotation axis 1144. As described above, the rotation axis 1141, the rotation axis 1142, and the rotation axis 1145 may be inserted through the end tool hub 1106, and the rotation axis 1143 and the rotation axis 1144 may be inserted through the pitch hub 1107.

The rotation axis 1141, the rotation axis 1142, the rotation axis 1145, the rotation axis 1143, and the rotation axis 1144 may be arranged sequentially from a distal end 1104 of the end tool 1100 toward a proximal end 1105. Accordingly, starting from the distal end 1104, the rotation axis 1141 may be referred to as a first pin, the rotation axis 1142 may be referred to as a second pin, the rotation axis 1145 may be referred to as a two-and-a-halfth pin, the rotation axis 1143 may be referred to as a third pin, and the rotation axis 1144 may be referred to as a fourth pin.

In this regard, the rotation axis 1141 may function as a jaw pulley rotation axis, the rotation axis 1142 may function as a jaw auxiliary pulley rotation axis, the rotation axis 1143 may function as a pitch main rotation axis, and the rotation axis 1144 may function as a pitch sub-rotation axis of the end tool 1100. In addition, the rotation axis 1145 arranged between the rotation axis 1142 and the rotation axis 1143 may function as a pitch redundant rotation axis of the end tool 1100.

In the present embodiment, the end tool hub 1106, the pitch hub 1107, and the rotation axes 1141, 1142, 1143, 1144, and 1145 are substantially the same as the end tool hub 106, the pitch hub 107, and the rotation axes 141, 142, 143, 144, and 145 that are described above with reference to FIG. 5 and the like, respectively, and thus, detailed descriptions thereof will be omitted.

Meanwhile, one or more pulleys may be fit into each of the rotation axes 1141, 1142, 1143, 1144, and 1145, and this will be described in detail below.

The pulley 1111 functions as a first jaw pulley, the pulley 1121 functions as a second jaw pulley, and these two components may be collectively referred to as a jaw pulley.

The pulley 1111 and the pulley 1121, which are jaw pulleys, are formed to face each other, and are formed to be rotatable independently of each other around the rotation axis 1141, which is a jaw pulley rotation axis. In this regard, the drawings illustrate that the pulley 1111 and the pulley 1121 are formed to be rotated around one rotation axis 1141, but it is needless to say that each jaw pulley may be formed to be rotatable around a separate shaft. In this regard, the first jaw 1101 may be fixedly coupled to the pulley 1111 to be rotated together with the pulley 1111, and the second jaw 1102 may be fixedly coupled to the pulley 1121 to be rotated together with the pulley 1121. Yaw and actuation motions of the end tool 1100 are performed according to rotation of the pulley 1111 and the pulley 1121. That is, when the pulley 1111 and the pulley 1121 are rotated in the same direction around the rotation axis 1141, the yaw motion is performed, and when the pulley 1111 and the pulley 1121 are rotated in opposite directions around the rotation axis 1141, the actuation motion is performed.

In this regard, the first jaw 1101 and the pulley 1111 may be formed as separate members and coupled to each other, or the first jaw 1101 and the pulley 1111 may be formed as one body. Similarly, the second jaw 1102 and the pulley 1121 may be formed as separate members and coupled to each other, or the second jaw 1102 and the pulley 1121 may be formed as one body.

In this regard, a groove 1111a around which the wire 1301/wire 1305, which are first wires, are wound in the pulley 1111, which is a first jaw pulley, and a groove 1121a around which the wire 1302/wire 1306, which are second wires, are wound in the pulley 1121, which is a second jaw pulley, are arranged adjacent to each other. Thus, the wire 1301/wire 1305, which are first jaw wires, and the wire 1302 and the wire 1306, which are second jaw wires, are arranged adjacent to each other in the Z-axis direction, and thus, there may not be a space in which a separate structure is to be arranged, between the first jaw wires and the second jaw wires.

The pulley 1112 functions as a first jaw auxiliary pulley, the pulley 1122 functions as a second jaw auxiliary pulley, and these two components may be collectively referred to as a jaw auxiliary pulley.

In detail, the pulley 1112 and the pulley 1122, which are jaw auxiliary pulleys, may be additionally provided on one side of the pulley 1111 and the pulley 1121. In other words, the pulley 1112, which is a jaw auxiliary pulley, may be arranged between the pulley 1111 and the pulley 1113/pulley 1114. In addition, the pulley 1122, which is a jaw auxiliary pulley, may be arranged between pulley 1121 and pulley 1123/pulley 1124. The pulley 1112 and the pulley 1122 may be formed to be rotatable independently of each other around the rotation axis 1142. In this regard, the drawings illustrate that the pulley 1112 and the pulley 1122 are formed to be rotated around one rotation axis 1142, but it is needless to say that the pulley 1112 and the pulley 1122 may be formed to be rotatable around separate shafts, respectively. Such an auxiliary pulley will be described below in more detail.

The pulley 1113 and the pulley 1114 may function as first jaw pitch main pulleys, the pulley 1123 and the pulley 1124 may function as second jaw pitch main pulleys, and these two components may be collectively referred to as a pitch main pulley.

The pulley 1115 and the pulley 1116 may function as first jaw pitch sub-pulleys, the pulley 1125 and the pulley 1126 may function as second jaw pitch sub-pulleys, and these two components may be collectively referred to as a pitch sub-pulley.

Meanwhile, according to the present disclosure, the pulley 1118, and the pulley 1128, which are pitch redundant pulleys, are further arranged between the pulley 1112 and the pulley 1122, which are jaw auxiliary pulleys, and the pulley 1113, the pulley 1114, the pulley 1123, and the pulley 1124, which are pitch main pulleys.

The pulley 1118 may function as first jaw pitch redundant pulleys, the pulley 1128 may function as second jaw pitch redundant pulleys, and these two components may be collectively referred to as a pitch redundant pulley.

In addition, the rotation axis 1145 functioning as a pitch redundant rotation axis may be further provided, and the rotation axis 1145 may be inserted through the end tool hub 1106. In this regard, the rotation axis 1145 may be formed to be substantially parallel to the rotation axis 1143, which is a pitch main rotation axis, and the rotation axis 1144, which is a pitch sub-rotation axis. In this regard, the rotation axis 1145 is arranged between the rotation axis 1142, which is the second pin, and the rotation axis 1143, which is the third pin, and thus may be referred to as the two-and-a-halfth pin in terms of its position.

The pitch redundant pulleys may serve to change insertion/withdrawal paths of jaw wires entering from the proximal end of the end tool to the distal end, or coming out from the distal end to the proximal end. This will be described in more detail below.

Accordingly, the rotation axis 1141, the rotation axis 1142, the rotation axis 1145, the rotation axis 1143, and the rotation axis 1144 may be sequentially arranged from the distal end 1104 of the end tool 1100 toward the proximal end 1105.

In addition, the pulley 1111, the pulley 1112, the pulley 1118, the pulley 1113/pulley 1114, and the pulley 1115/pulley 1116, which are associated with rotation of the first jaw 1101, may be sequentially arranged from the distal end 1104 of the end tool 1100 toward the proximal end 1105.

In addition, the pulley 1121, the pulley 1122, the pulley 1128, the pulley 1123/pulley 1124, and the pulley 1125/pulley 1126, which are associated with rotation of the second jaw 1102, may be sequentially arranged from the distal end 1104 of the end tool 1100 toward the proximal end 1105.

Hereinafter, components associated with the rotation of the pulley 1111 will be described.

The pulley 1113 and the pulley 1114 are paired to function as first jaw pitch main pulleys. That is, the pulley 1113 and the pulley 1114 function as main rotation pulleys for a pitch motion of the first jaw 1101. In this regard, the wire 1301, which is a first jaw wire, is wound around the pulley 1113, and the wire 1305, which is a first jaw wire, is wound around the pulley 1114.

The pulley 1115 and the pulley 1116 are paired to function as first jaw pitch sub-pulleys. That is, the pulley 1115 and the pulley 1116 function as sub-rotation pulleys for a pitch motion of the first jaw 1101. In this regard, the wire 1301, which is a first jaw wire, is wound around the pulley 1115, and the wire 1305, which is a first jaw wire, is wound around the pulley 1116.

The pulley 1118 functions as first jaw redundant pulleys. That is, the pulley 1118 functions as redundant rotation pulleys for a pitch motion of the first jaw 1101. In this regard, the wire 1305, which is a first jaw wire, is wound around the pulley 1118.

In this regard, the pulley 1118 is arranged on one side of the pulley 1111 and the pulley 1112. In this regard, the pulley 1118 is formed to be rotatable around the rotation axis 1145, which is a pitch redundant rotation axis. In addition, the pulley 1113 and the pulley 1114 are arranged on one sides of the pulley 1118, respectively, to face each other. In this regard, the pulley 1113 and the pulley 1114 are formed to be rotatable independently of each other around the rotation axis 1143, which is a pitch main rotation axis. In addition, the pulley 1115 and the pulley 1116 are arranged on one sides of the pulley 1113 and the pulley 1114, respectively, to face each other. In this regard, the pulley 1115 and the pulley 1116 are formed to be rotatable independently of each other around the rotation axis 1144, which is a pitch sub-rotation axis. In this regard, the drawings illustrate that the pulley 1118, the pulley 1113, the pulley 1114, the pulley 1115, and the pulley 1116 are formed to be rotatable around the Y-axis direction, but the concept of the present disclosure is not limited thereto, and the rotation axes of the respective pulleys may be formed in various directions according to their configurations.

The wire 1301, which is a first jaw wire, is wound to sequentially come into contact with at least portions of the pulley 1115, the pulley 1113, and the pulley 1111. In addition, the wire 1305 connected to the wire 1301 by the coupling member 1323 is wound to sequentially come into contact with at least portions of the pulley 1111, the pulley 1112, the pulley 1118, the pulley 1114, and the pulley 1116.

In other words, the wire 1301 and the wire 1305, which are first jaw wires, are wound to sequentially come into contact with at least portions of the pulley 1115, the pulley 1113, the pulley 1111, the pulley 1112, the pulley 1118, the pulley 1114, and the pulley 1116, and are formed to move along the above pulleys while rotating the above pulleys.

Figure 77:
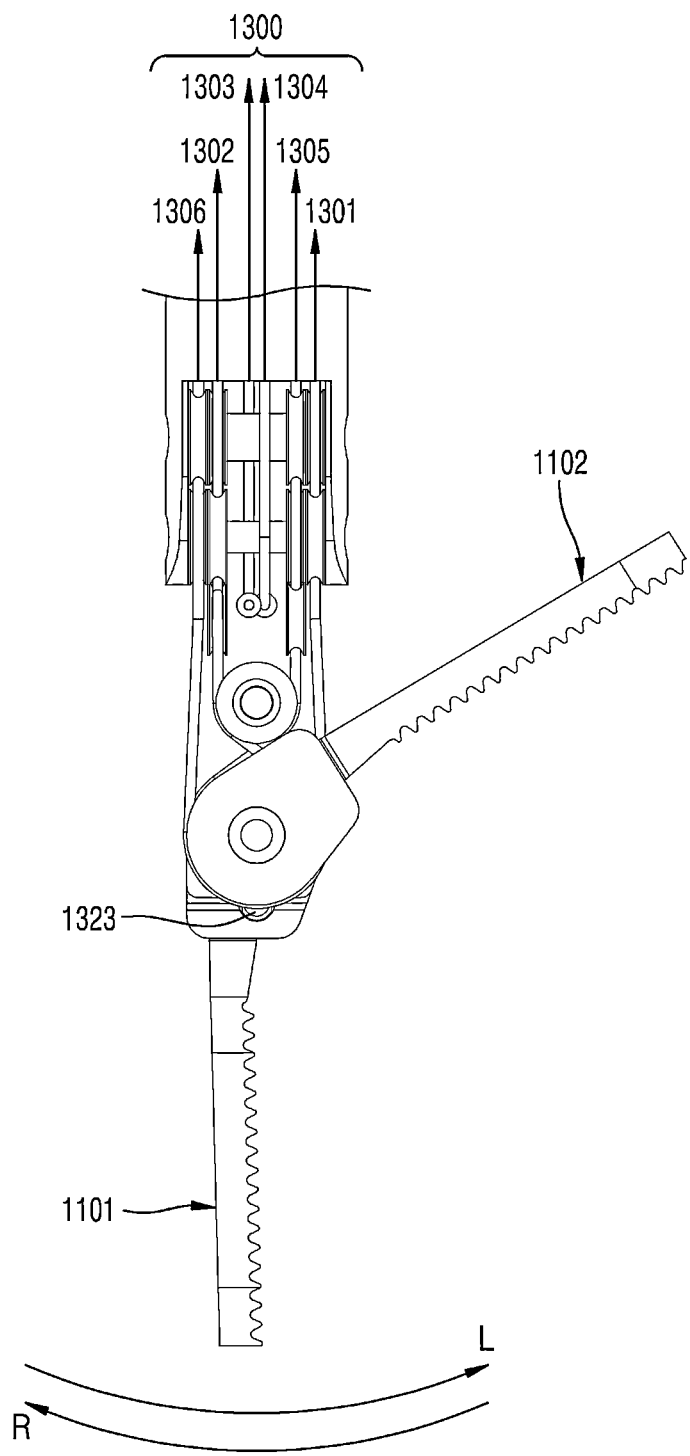
Figure 78:
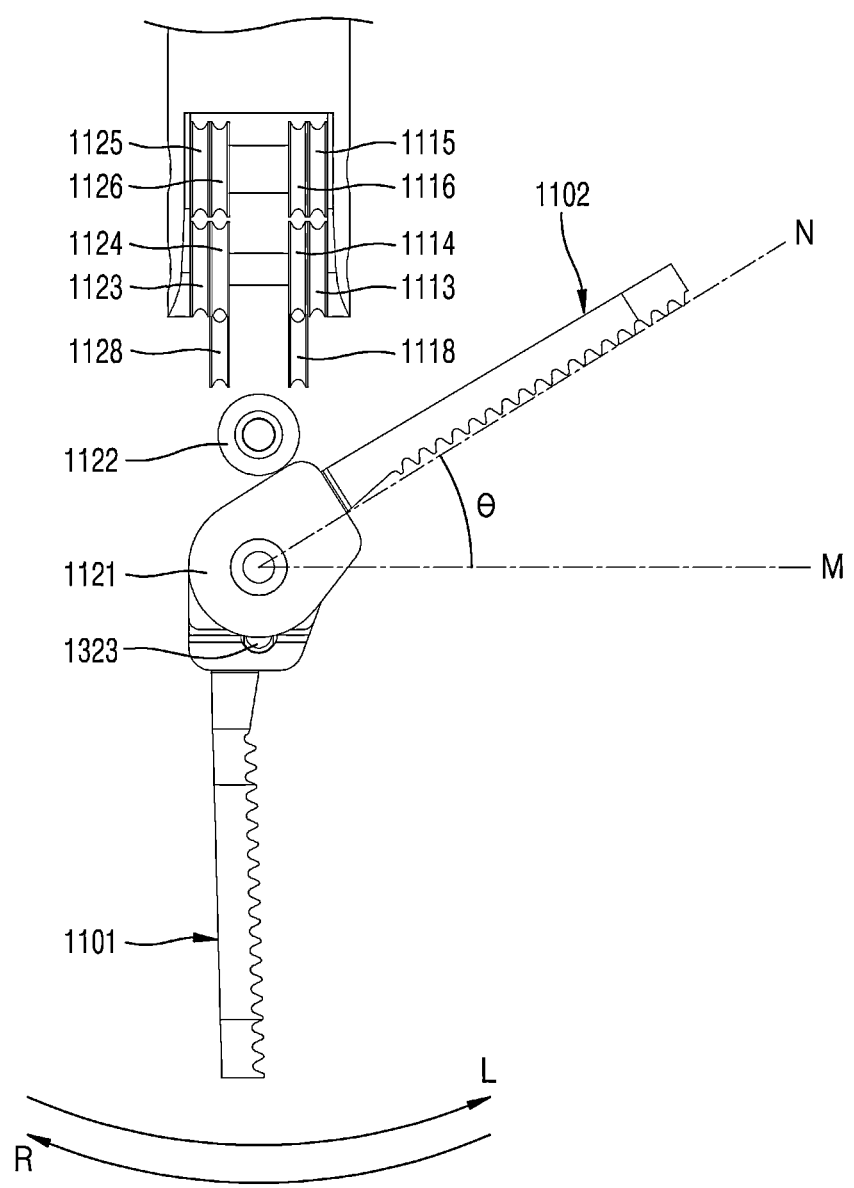

Accordingly, when the wire 1301 is pulled in the direction of an arrow 1301 of FIG. 77, the coupling member 1323 to which the wire 1301 is coupled and the pulley 1111 coupled to the coupling member 1323 are rotated in the direction of an arrow L of FIG. 77. On the contrary, when the wire 1305 is pulled in the direction of an arrow 1305 of FIG. 64, the coupling member 1323 to which the wire 1305 is coupled and the pulley 1111 coupled to the coupling member 1323 are rotated in the direction of an arrow R of FIG. 77.

Next, components associated with the rotation of the pulley 1121 will be described.

The pulley 1123 and the pulley 1124 are paired to function as second jaw pitch main pulleys. That is, the pulley 1123 and the pulley 1124 function as main rotation pulleys for a pitch motion of the second jaw 1102. In this regard, the wire 1306, which is a second jaw wire, is wound around the pulley 1123, and the wire 1302, which is a second jaw wire, is wound around the pulley 1124.

The pulley 1125 and the pulley 1126 are paired to function as second jaw pitch sub-pulleys. That is, the pulley 1125 and the pulley 1126 may function as sub-rotation pulleys for a pitch motion of the second jaw 1102. In this regard, the wire 1306, which is a second jaw wire, is wound around the pulley 1125, and the wire 1302, which is a second jaw wire, is wound around the pulley 1126.

The pulley 1128 functions as second jaw pitch redundant pulleys. That is, the pulley 1128 functions as redundant rotation pulleys for a pitch motion of the second jaw 1102. In this regard, the wire 1302, which is a second jaw wire, is wound around the pulley 1128.

In this regard, the pulley 1128 is arranged on one side of the pulley 1121 and the pulley 1122. In this regard, the pulley 1128 is formed to be rotatable around the rotation axis 1145, which is a pitch redundant rotation axis. In addition, the pulley 1123 and the pulley 1124 are arranged on one sides of the pulley 1128, respectively, to face each other. In this regard, the pulley 1123 and the pulley 1124 are formed to be rotatable independently of each other around the rotation axis 1143, which is a pitch main rotation axis. In addition, the pulley 1125 and the pulley 1126 are arranged on one sides of the pulley 1123 and the pulley 1124, respectively, to face each other. In this regard, the pulley 1125 and the pulley 1126 are formed to be rotatable independently of each other around the rotation axis 1144, which is a pitch sub-rotation axis. In this regard, the drawings illustrate that the pulley 1128, the pulley 1123, the pulley 1124, the pulley 1125, and the pulley 1126 are formed to be rotatable around the Y-axis direction, but the concept of the present disclosure is not limited thereto, and the rotation axes of the respective pulleys may be formed in various directions according to their configurations.

The wire 1306, which is a second jaw wire, is wound to sequentially come into contact with at least portions of the pulley 1125, the pulley 1123, and the pulley 1121. In addition, the wire 1302 connected to the wire 1306 by the coupling member 1326 is wound to sequentially come into contact with at least portions of the pulley 1121, the pulley 1122, the pulley 1128, the pulley 1124, and the pulley 1126.

In other words, the wire 1306 and the wire 1302, which are second jaw wires, are wound to sequentially come into contact with at least portions of the pulley 1125, the pulley 1123, the pulley 1121, the pulley 1122, the pulley 1128, the pulley 1124, and the pulley 1126, and are formed to move along the above pulleys while rotating the above pulleys.

Accordingly, when the wire 1306 is pulled in the direction of an arrow 1306 of FIG. 77, the coupling member 1326 to which the wire 1306 is coupled and the pulley 1121 coupled to the coupling member 1326 are rotated in the direction of the arrow R of FIG. 77. On the contrary, when the wire 1302 is pulled in the direction of an arrow 302 of FIG. 77, the coupling member 1326 to which the wire 1302 is coupled and the pulley 1121 coupled to the coupling member 1326 are rotated in the direction of an arrow L of FIG. 64.

In this regard, according to the present disclosure, two strands of jaw wires wound around one jaw pulley are wound around pitch main pulleys in opposite directions, such that a pitch motion is easily controlled.

In detail, when the side above, in the +Z-axis direction, a plane passing between the pulley 1111, which is a first jaw pulley, and the pulley 1121, which is a second jaw pulley (i.e., an XY plane) is defined as an upper side and the side below the plane in the −Z-axis direction is defined as a lower side, any one (e.g., the wire 1301) of the two strands of the first jaw wires may enter the pulley 1113, which is a first jaw pitch main pulley, from the lower side of the XY plane, and the other strand (e.g., the wire 1305) may come out of the pulley 1114, which is a first jaw pitch main pulley, from the upper side of the XY plane. In other words, it may be described as a structure in which the jaw wire enters the first jaw pitch main pulley from the lower side and comes out from the upper side. (The second jaw wire enters the second jaw pitch main pulley from the upper side and comes out from the lower side)

In other words, the wire 1301, which is one strand of the first jaw wires, sequentially comes into contact with the upper side of the pulley 1115, the lower side of the pulley 1113, and then comes into contact with the pulley 1111. Next, the wire 1305, which is the other strand of the first jaw wires, is wound around the pulley 1111 and the pulley 1112, and then sequentially comes into contact with the lower side of the pulley 1118, the upper side of the pulley 1114, and the lower side of the pulley 1116, and then comes out toward the connection part 400. Accordingly, the first jaw wire comes out of the connection part 400, enters the pulley 1113 from the lower side, then passes through each pulley, then passes through the upper side of the pulley 1114, and then enters back the connection part 400.

Similarly, the wire 1306, which is one strand of the second jaw wires, sequentially comes into contact with the lower side of the pulley 1125, the upper side of the pulley 1123, and then comes into contact with the pulley 1121. Next, the wire 1302, which is the other strand of the second jaw wires, is wound around the pulley 1121 and the pulley 1122, and then sequentially comes into contact with the upper side of the pulley 1128, the lower side of the pulley 1124, and the upper side of the pulley 1126, and then comes out toward the connection part 400. Accordingly, the second jaw wire comes out of the connection part 400, enters the pulley 1123 from the upper side, then passes through each pulley, then passes through the lower side of the pulley 1124, and then enters back the connection part 400.

In other words, it may also be described that, any one wire of the two strands of the first jaw wires is wound around the first jaw pitch main pulley in any one of the clockwise direction and the counterclockwise direction while moving toward the end tool 1100 from a connection part 1400, and the other wire is wound around the first jaw pitch main pulley in the other one of the clockwise direction and the counterclockwise direction while moving toward the end tool 1100 from the connection part 1400. That is, as illustrated in FIGS. 79, 80, and 81, the wire 1301 is wound in the clockwise direction while moving toward the end tool 1100 from the connection part 1400, and the wire 1305 is wound in the counterclockwise direction while moving toward the end tool 1100 from the connection part 400.

Similarly, it may also be described that, any one wire of the two strands of the second jaw wires is wound around the second jaw pitch main pulley in any one of the clockwise direction and the counterclockwise direction while moving toward the end tool 1100 from the connection part 1400, and the other wire is wound around the second jaw pitch main pulley in the other one of the clockwise direction and the counterclockwise direction while moving toward the end tool 1100 from the connection part 1400. That is, as illustrated in FIGS. 66, 67, and 68, the wire 1302 is wound in the clockwise direction while moving toward the end tool 1100 from the connection part 1400, and the wire 1306 is wound in the counterclockwise direction while moving toward the end tool 1100 from the connection part 400.

As such, the end tool 1100 of the surgical instrument according to an embodiment of the present disclosure may obtain an effect of facilitating control of the pitch motion as the two strands of the jaw wires wound around one jaw pulley are wound around the pitch main pulleys in opposite directions. That is, during a pitch motion, the drive part first jaw pulley (see 211, 212 of FIG. 21) and the drive part second jaw pulley (see 221, 222 of FIG. 21) are rotated to wind or unwind the jaw wires, and thus perform a kind of compensation for the pitch motion, enabling the pitch motion of the end tool 1100.

First Modified Example of Second Embodiment

Hereinafter, the end tool 1100 of the surgical instrument according to a first modified example of the second embodiment of the present disclosure will be described. In this regard, the end tool 1100 of the surgical instrument according to the first modified example of the second embodiment of the present disclosure is different from the end tool of the surgical instrument according to the first embodiment of the present disclosure described above in that some of the pulleys are omitted. Hereinafter, the configuration that is different from that of the first embodiment will be described in detail.

Figure 82:
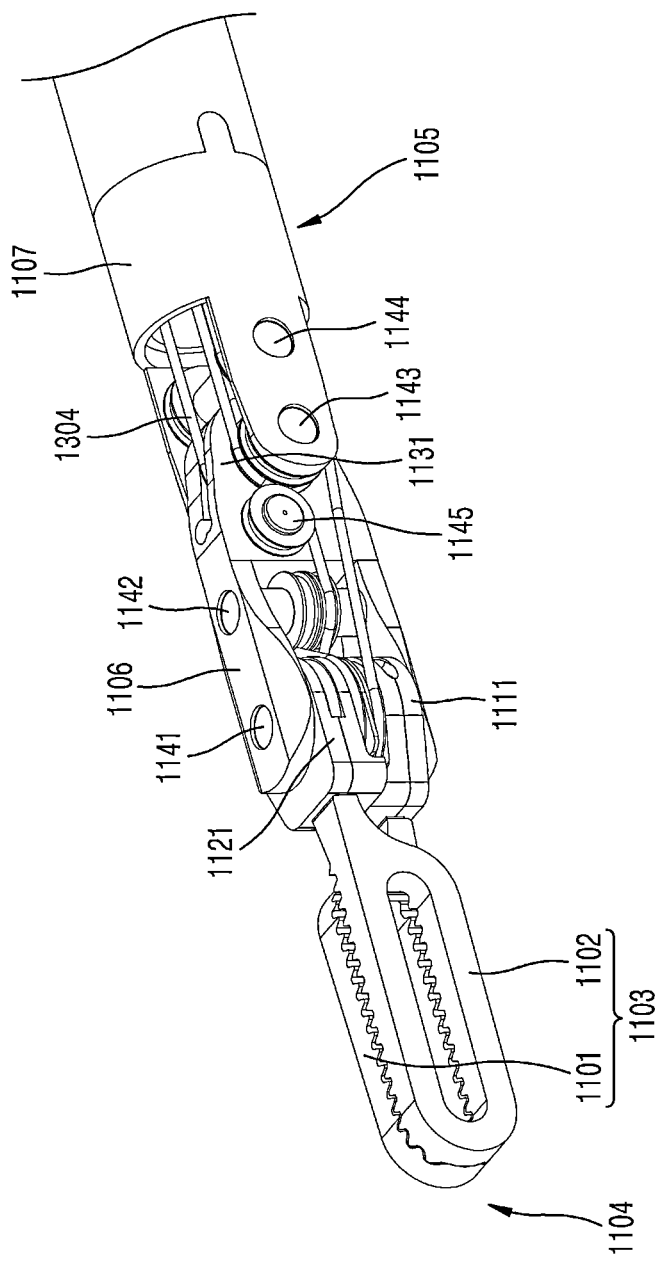
FIGS. 82 and 83 are perspective views illustrating an end tool of a surgical instrument according to a first modified example of the second embodiment of the present disclosure.
Figure 83:
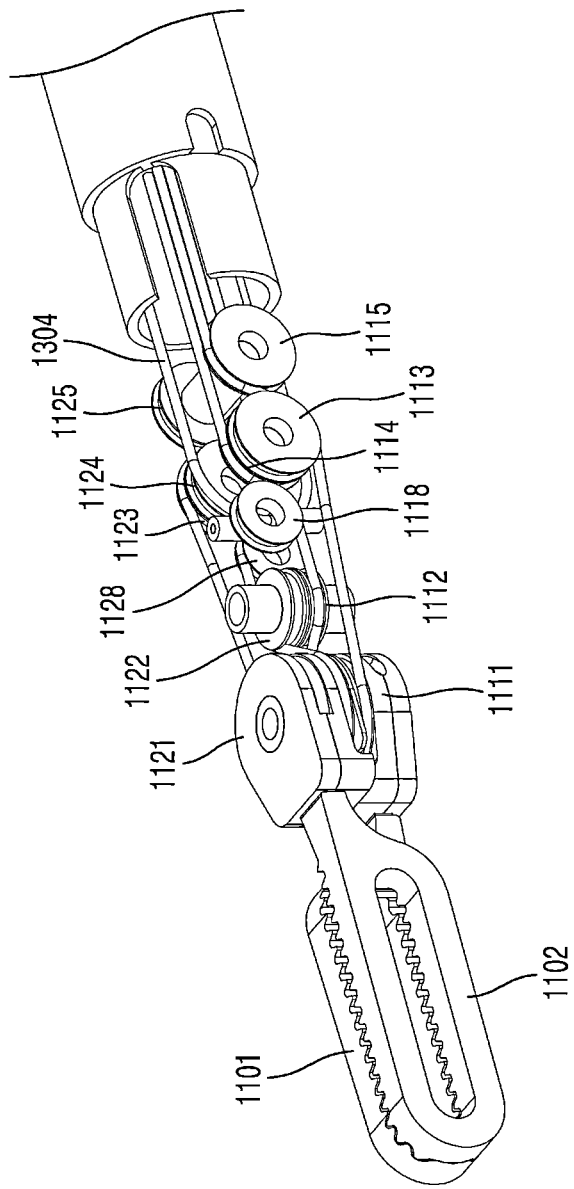
Figure 84:
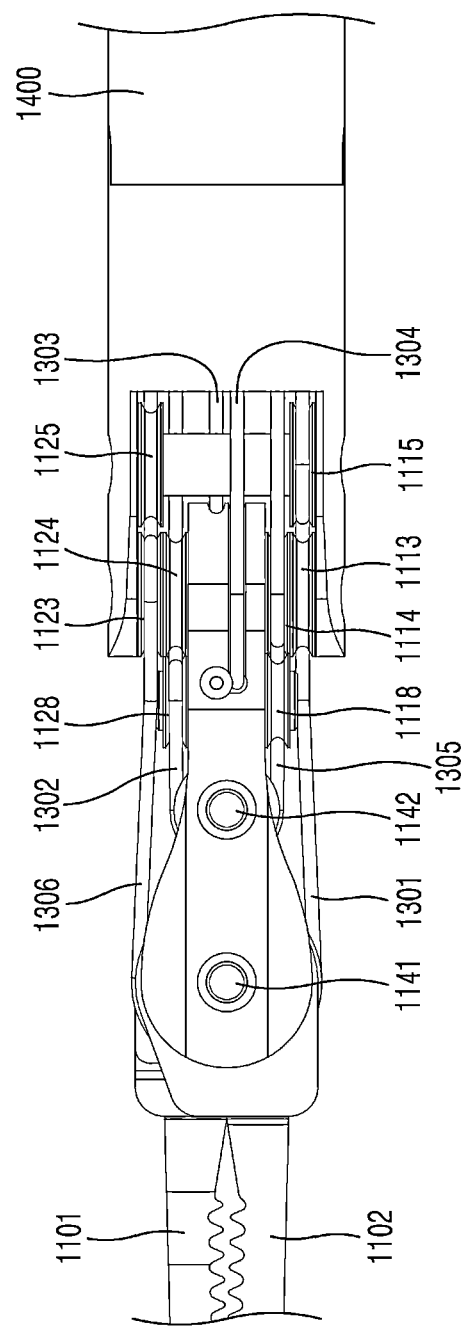
FIGS. 84 and 85 are plan views of the end tool of FIG. 82.
Figure 85:
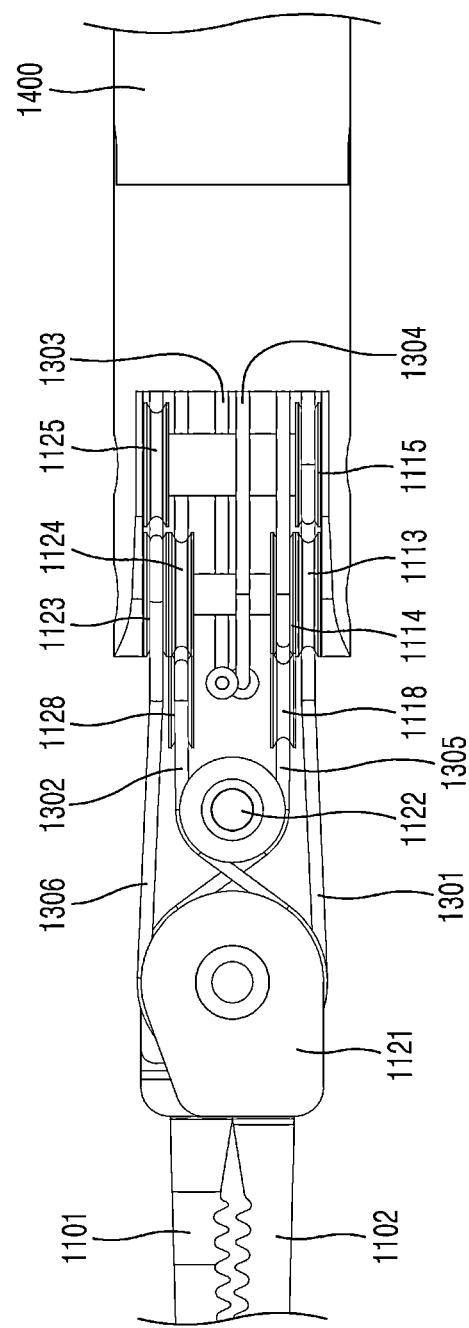
Figure 86:
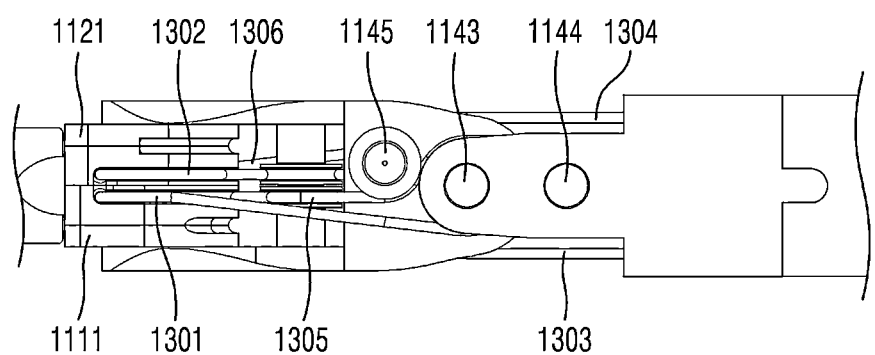
FIGS. 86, 87, and 88 are side views of the end tool of FIG. 82.
Figure 87:
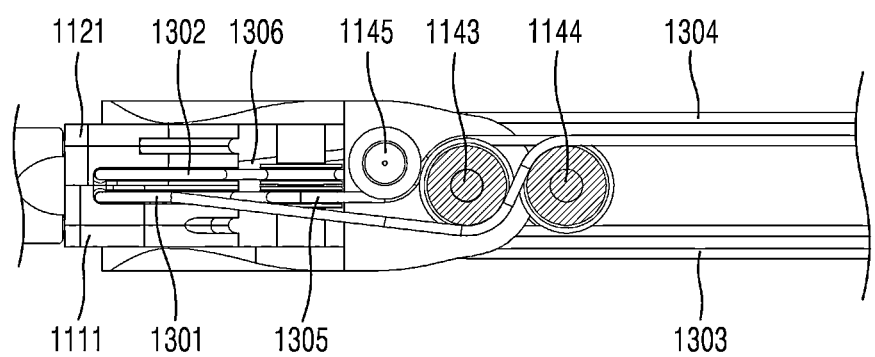
Figure 88:
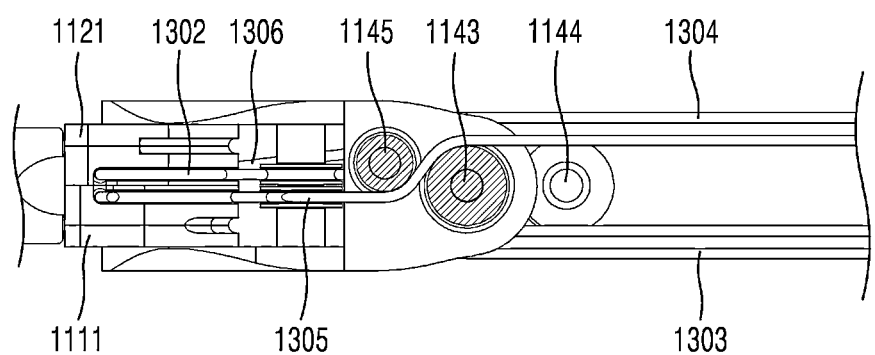
Figure 89:
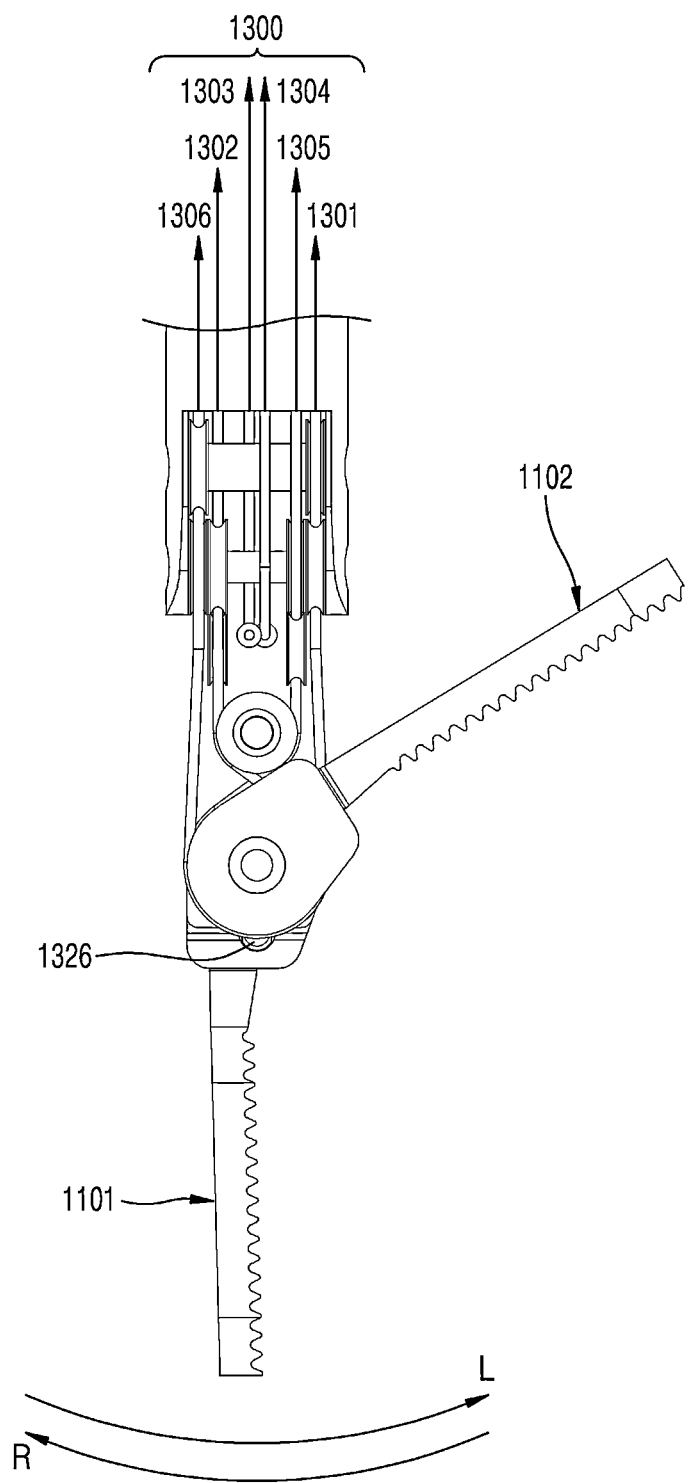
FIGS. 89 and 90 are plan views of the end tool of FIG. 82.
Figure 90:
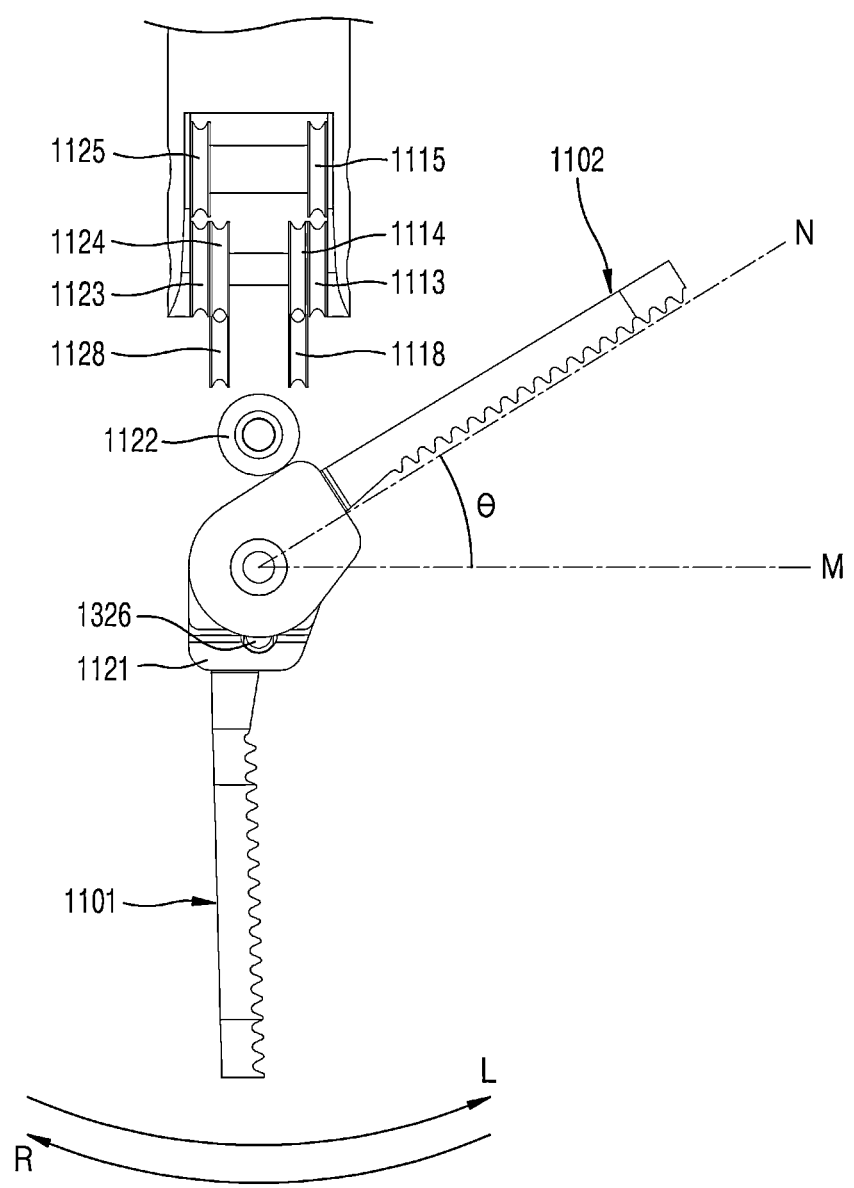

FIGS. 82 and 83 are perspective views illustrating an end tool of a surgical instrument according to the first modified example of the second embodiment of the present disclosure. FIGS. 84 and 85 are plan views of the end tool of FIG. 82. FIGS. 86, 87, and 88 are side views of the end tool of FIG. 82. FIGS. 89 and 90 are plan views of the end tool of FIG. 82.

Referring to FIGS. 82 to 90, the end tool 1100 according to the first modified example of the second embodiment of the present disclosure includes a pair of jaws for performing a grip motion, that is, the first jaw 1101 and the second jaw 1102. In this regard, a component encompassing each of the first jaw 1101 and the second jaw 1102 or both the first jaw 1101 and the second jaw 1102 may be referred to as the jaw 1103.

In addition, the end tool 1100 of the first modified example of the second embodiment of the present disclosure may include the end tool hub 1106 and the pitch hub 1107.

In addition, the end tool 1100 of the first modified example of the second embodiment of the present disclosure may include the rotation axis 1141, the rotation axis 1142, the rotation axis 1145, the rotation axis 1143, and the rotation axis 1144. As described above, the rotation axis 1141, the rotation axis 1142, and the rotation axis 1145 may be inserted through the end tool hub 1106, and the rotation axis 1143 and the rotation axis 1144 may be inserted through the pitch hub 1107.

In the present modified example, the end tool hub 1106, the pitch hub 1107, and the rotation axes 1141, 1142, 1143, 1144, and 1145 are substantially the same as the end tool hub 1106, the pitch hub 1107, and the respective rotation axes that are described above with reference to FIG. 73 and the like, respectively, and thus, detailed descriptions thereof will be omitted.

Meanwhile, the end tool 1100 may include the pulley 1111, the pulley 1112, the pulley 1113, the pulley 1114, the pulley 1115, and the pulley 1118, which are associated with a rotational motion of the first jaw 1101. In addition, the end tool 1100 may include the pulley 1121, the pulley 1122, the pulley 1123, the pulley 1124, the pulley 1125, and the pulley 1128, which are associated with a rotational motion of the second jaw 1102.

In this regard, in the end tool 1100 of the surgical instrument according to the first modified example of the second embodiment of the present disclosure, each of the first jaw pitch sub-pulley and the second jaw pitch sub-pulley includes only one pulley.

In detail, the end tool 1100 of the surgical instrument according to the second embodiment of the present disclosure illustrated in FIG. 73 and the like includes a pair of pulleys 1115 and 1116 as first jaw pitch sub-pulleys, and a pair of pulleys 1125 and 1126 as second jaw pitch sub-pulleys.

On the contrary, the end tool 1100 of the surgical instrument according to the first modified example of the second embodiment of the present disclosure is different from the second embodiment of the present disclosure illustrated in FIG. 60 and the like, in that it includes a single pulley 1115 as a first jaw pitch sub-pulley, and a single pulley 1125 as a second jaw pitch sub-pulley.

Accordingly, the pulley 1111, the pulley 1112, the pulley 1118, the pulley 1113/pulley 1114, and the pulley 1115, which are associated with rotation of the first jaw 1101, may be sequentially arranged from the distal end 1104 of the end tool 1100 toward the proximal end 1105.

In addition, the pulley 1121, the pulley 1122, the pulley 1128, the pulley 1123/pulley 1124, and the pulley 1125, which are associated with rotation of the second jaw 1102, may be sequentially arranged from the distal end 1104 of the end tool 1100 toward the proximal end 1105.

In this regard, the pulley 1116 and pulley 1126 of the end tool 1100 of the second embodiment of the present disclosure illustrated in FIG. 73 and the like are not pulleys around which wires are wound, but pulleys through which the wires pass in a straight line, and thus may be omitted as in the present modified example.

In other words, in the second embodiment of the present disclosure, two rows of first jaw pitch sub-pulleys and two rows of second jaw pitch sub-pulleys are provided, whereas in the first modified example of the second embodiment of the present disclosure, one row of a first jaw pitch sub-pulley and one row of a second jaw pitch sub-pulley are provided.

In this regard, the pulley 1118 is arranged on one side of the pulley 1111 and the pulley 1112. In this regard, the pulley 1118 are formed to be rotatable around the rotation axis 1145, which is a pitch redundant rotation axis. In addition, the pulley 1113 and the pulley 1114 are arranged on one side of the pulley 1117/pulley 1118 to face each other. In this regard, the pulley 1113 and the pulley 1114 are formed to be rotatable independently of each other around the rotation axis 1143, which is a pitch main rotation axis. In addition, the pulley 1115 is arranged on one side of the pulley 1113 and the pulley 1114. In this regard, the pulley 1115 is formed to be rotatable around the rotation axis 1144, which is a pitch sub-rotation axis. In this regard, the drawings illustrate that the pulley 1118, the pulley 1113, the pulley 1114, and the pulley 1115 are formed to be rotatable around the Y-axis direction, but the concept of the present disclosure is not limited thereto, and the rotation axes of the respective pulleys may be formed in various directions according to their configurations.

The wire 1301, which is a first jaw wire, is wound to sequentially come into contact with at least portions of the pulley 1115, the pulley 1113, and the pulley 1111. In addition, the wire 1305 connected to the wire 1301 by the coupling member 1323 is wound to sequentially come into contact with at least portions of the pulley 1111, the pulley 1112, the pulley 1118, and the pulley 1114.

In other words, the wire 1301 and the wire 1305, which are first jaw wires, are wound to sequentially come into contact with at least portions of the pulley 1115, the pulley 1113, the pulley 1111, the pulley 1112, the pulley 1118, and the pulley 1114, and are formed to move along the above pulleys while rotating the above pulleys.

Meanwhile, the pulley 1128 is arranged on one side of the pulley 1121 and the pulley 1122. In this regard, the pulley 1128 are formed to be rotatable around the rotation axis 1145, which is a pitch redundant rotation axis. In addition, the pulley 1123 and the pulley 1124 are arranged on one side of the pulley 1128 to face each other. In this regard, the pulley 1123 and the pulley 1124 are formed to be rotatable independently of each other around the rotation axis 1143, which is a pitch main rotation axis. In addition, the pulley 1125 is arranged on one side of the pulley 1123 and the pulley 1124. In this regard, the pulley 1125 is formed to be rotatable around the rotation axis 1144, which is a pitch sub-rotation axis. In this regard, the drawings illustrate that the pulley 1128, the pulley 1123, the pulley 1124, the pulley 1125, and the pulley 1126 are formed to be rotatable around the Y-axis direction, but the concept of the present disclosure is not limited thereto, and the rotation axes of the respective pulleys may be formed in various directions according to their configurations.

The wire 1306, which is a second jaw wire, is wound to sequentially come into contact with at least portions of the pulley 1125, the pulley 1123, and the pulley 1121. In addition, the wire 1302 connected to the wire 1306 by the coupling member 1326 is wound to sequentially come into contact with at least portions of the pulley 1121, the pulley 1122, the pulley 1128, and the pulley 1124.

In other words, the wire 1306 and the wire 1302, which are second jaw wires, are wound to sequentially come into contact with at least portions of the pulley 1125, the pulley 1123, the pulley 1121, the pulley 1122, the pulley 1128, and the pulley 1124, and are formed to move along the above pulleys while rotating the above pulleys.

Accordingly, in the second embodiment of the present disclosure, two rows of first jaw pitch sub-pulleys and two rows of second jaw pitch sub-pulleys are provided, whereas in the first modified example of the second embodiment of the present disclosure, one row of a first jaw pitch sub-pulley and one row of a second jaw pitch sub-pulley are provided, and thus, an effect of reducing the number of parts and simplifying a manufacturing process may be achieved.

<Third Embodiment of End Tool of Surgical Instrument>

Hereinafter, an end tool 2100 of a surgical instrument according to a third embodiment of the present disclosure will be described. In this regard, the end tool 2100 of the surgical instrument according to the third embodiment of the present disclosure is different from the end tool (see 100 of FIG. 5 and the like) of the surgical instrument according to the first embodiment of the present disclosure described above, in the arrangement of the jaw pulleys and the jaw wires. The configuration that is different from that of the first embodiment will be described in detail below.

Figure 91:
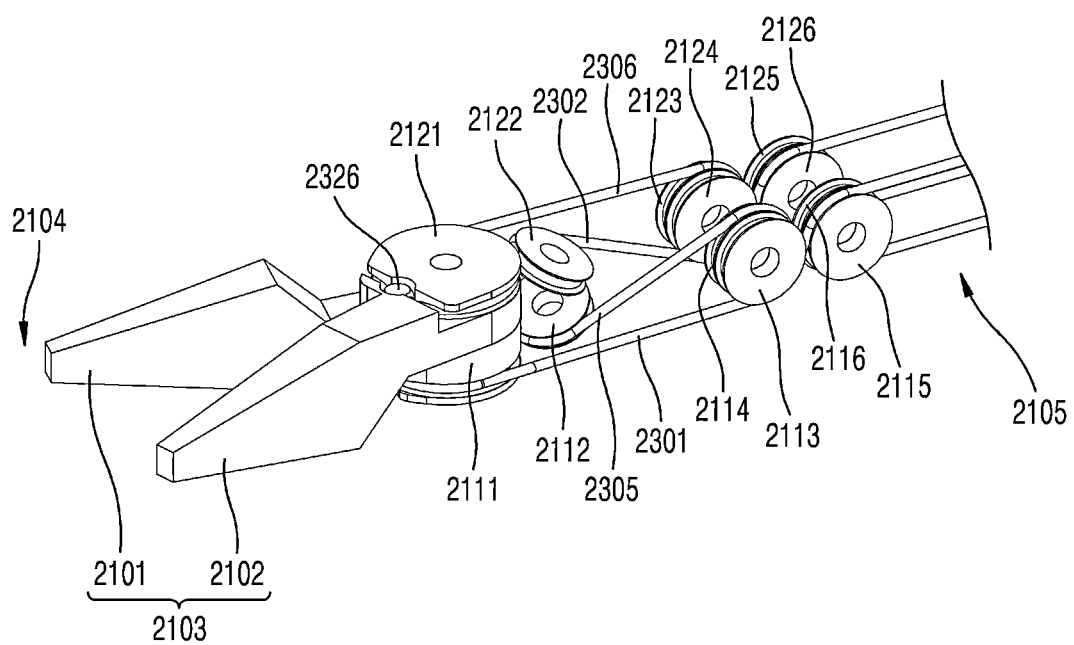
FIGS. 91, 92, 93, and 94 are perspective views illustrating an end tool of a surgical instrument according to a third embodiment of the present disclosure.
Figure 92:
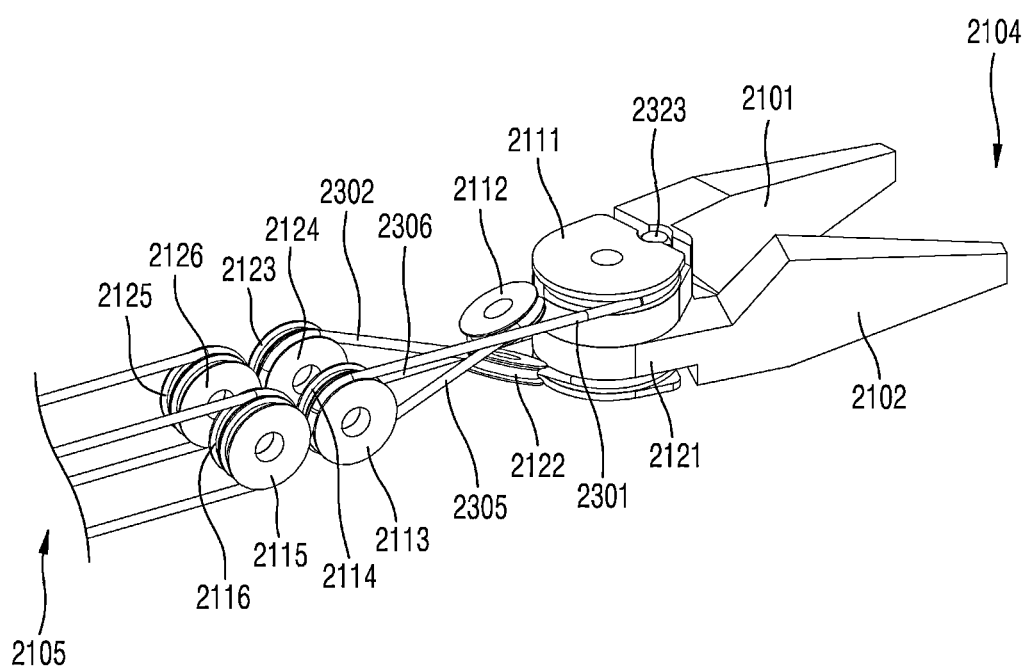
Figure 93:
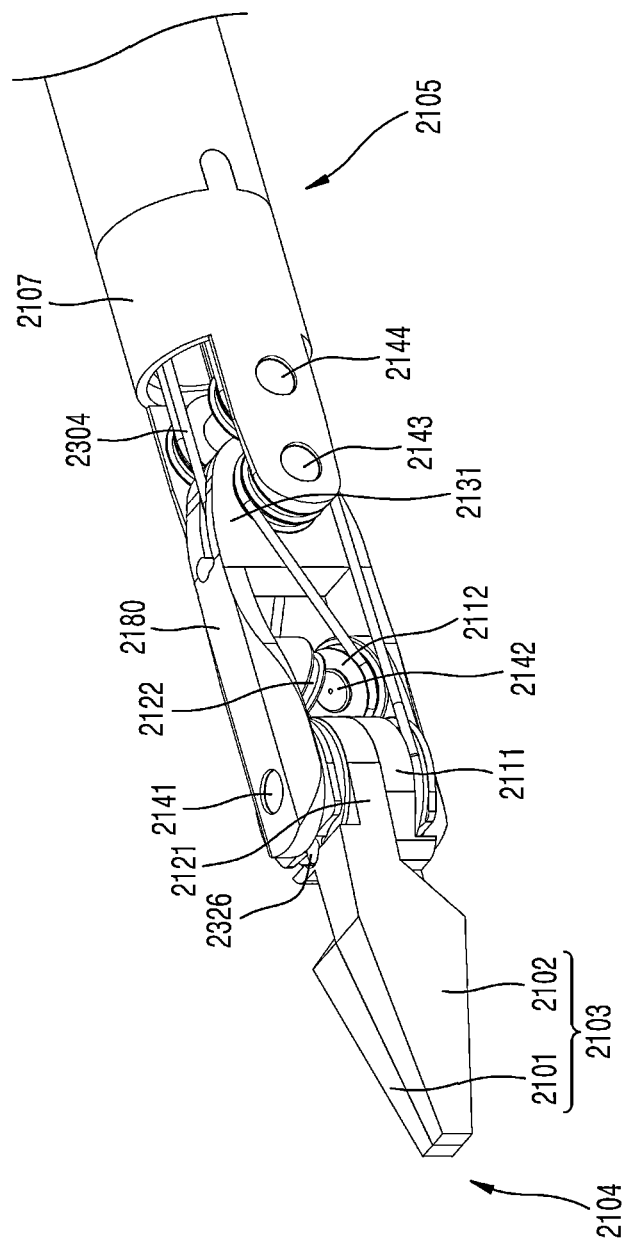
Figure 94:
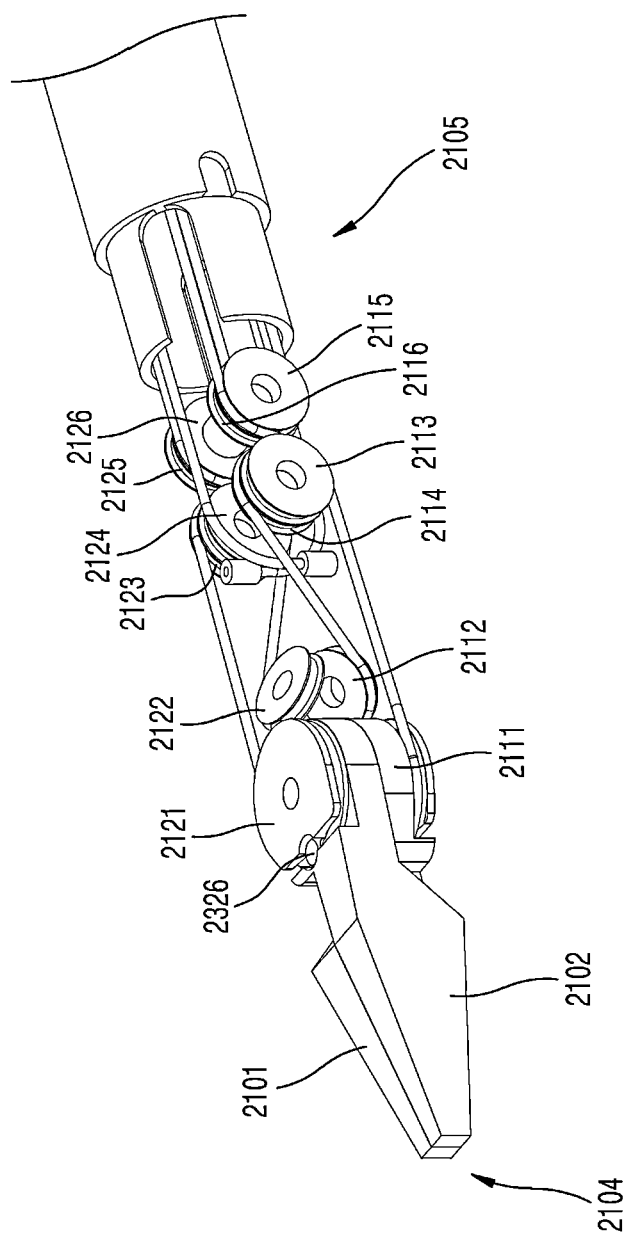
Figure 95:
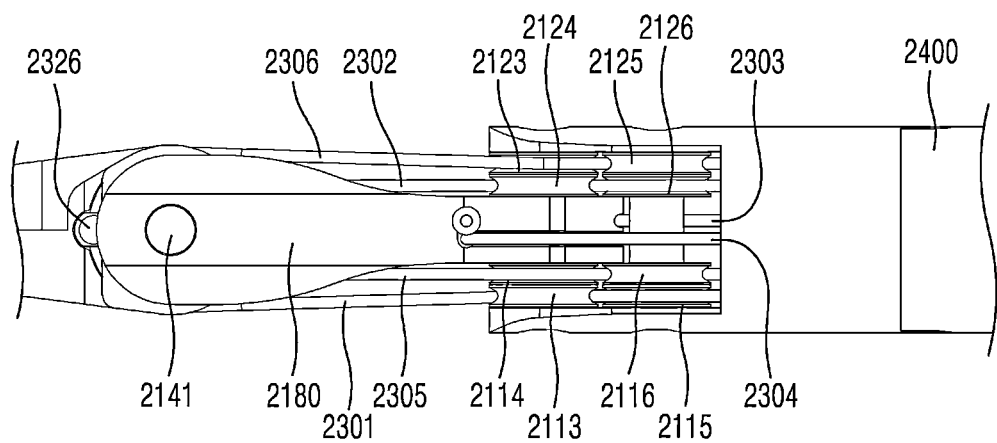
FIGS. 95 and 96 are plan views of the end tool of FIG. 91.
Figure 96:
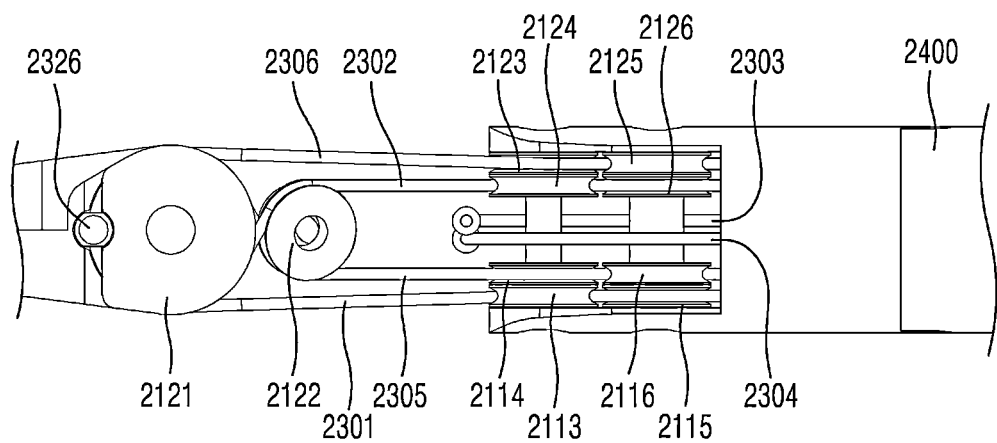
Figure 97:
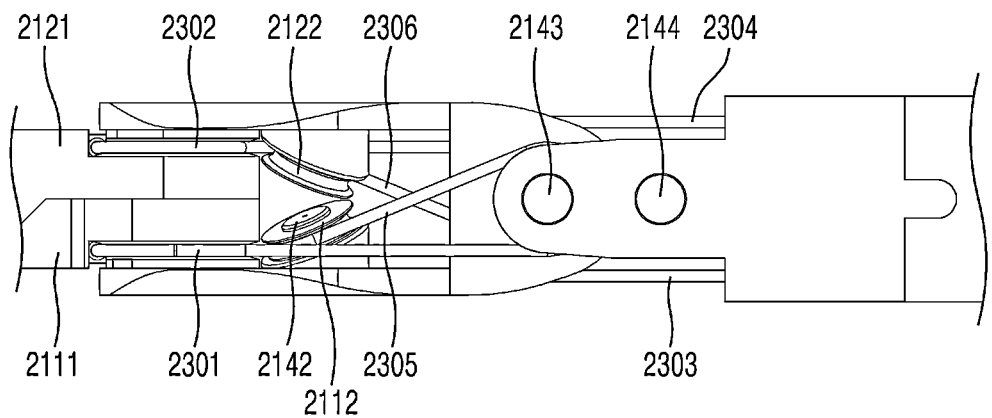
FIGS. 97, 98, and 99 are side views of the end tool of FIG. 91.
Figure 98:
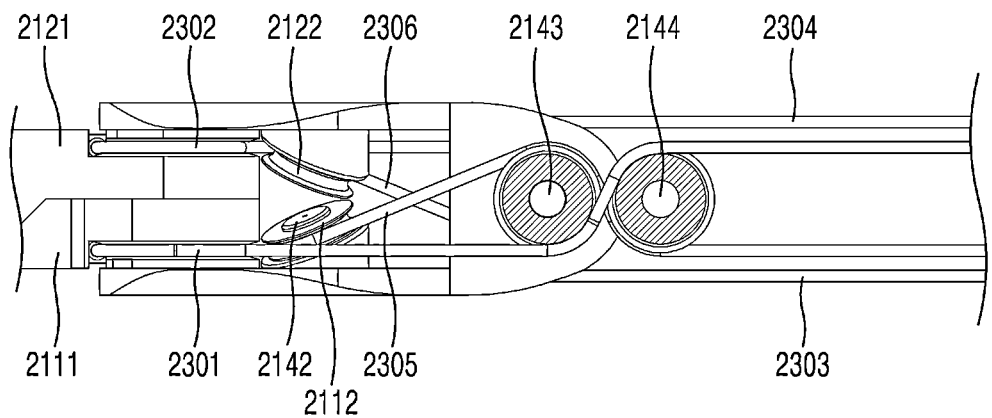
Figure 99:
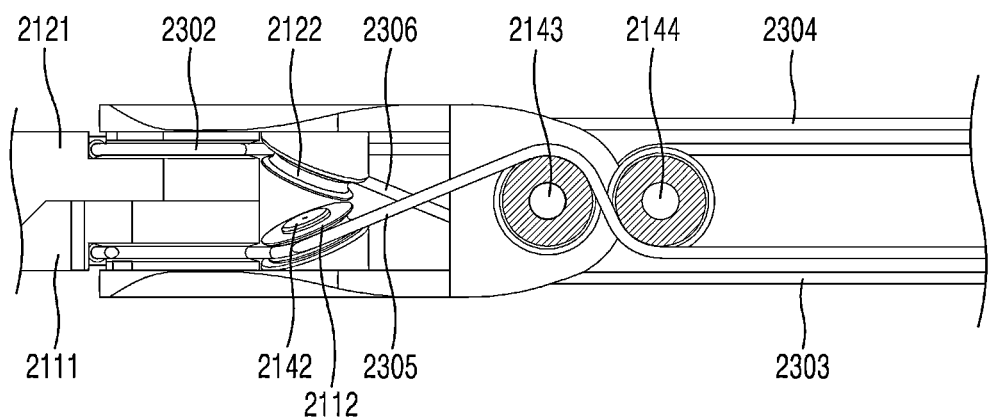
Figure 100:
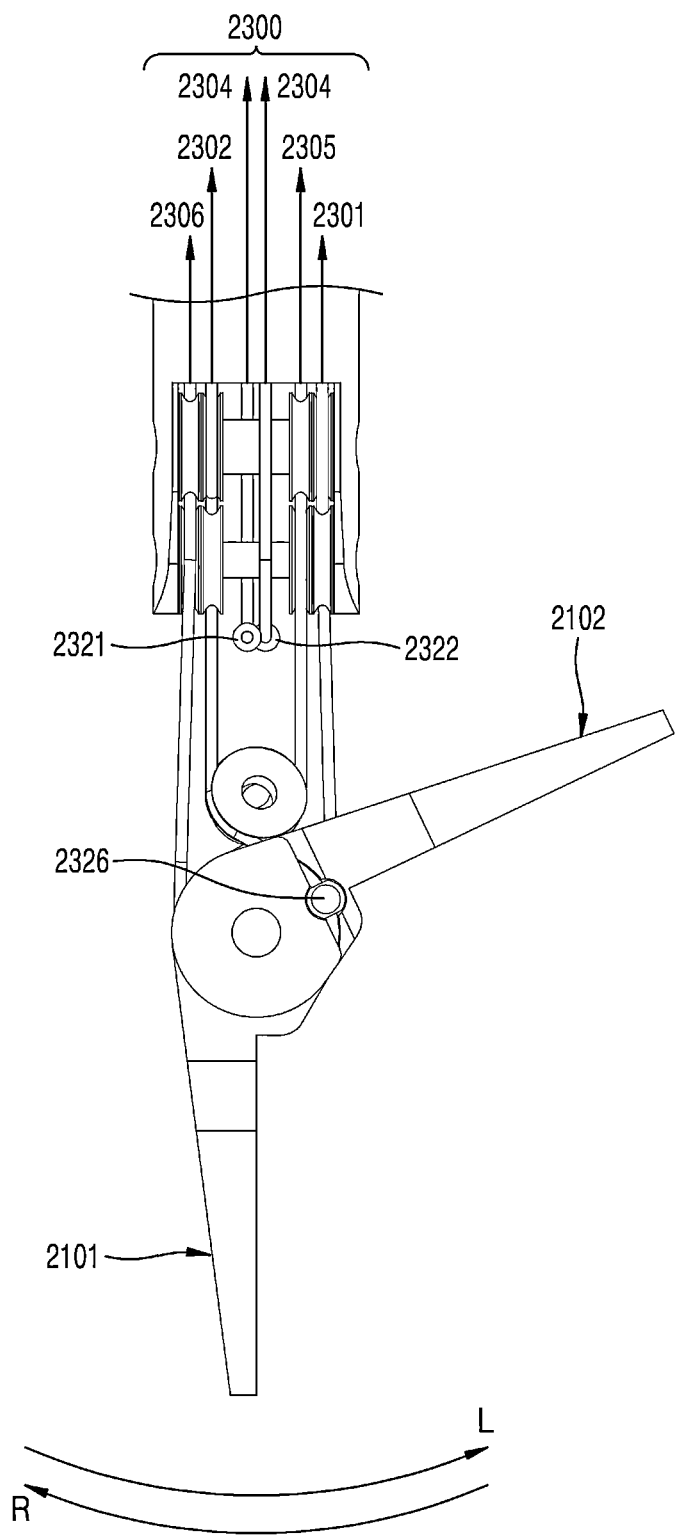
FIGS. 100 and 101 are plan views of the end tool of FIG. 91.
Figure 101:
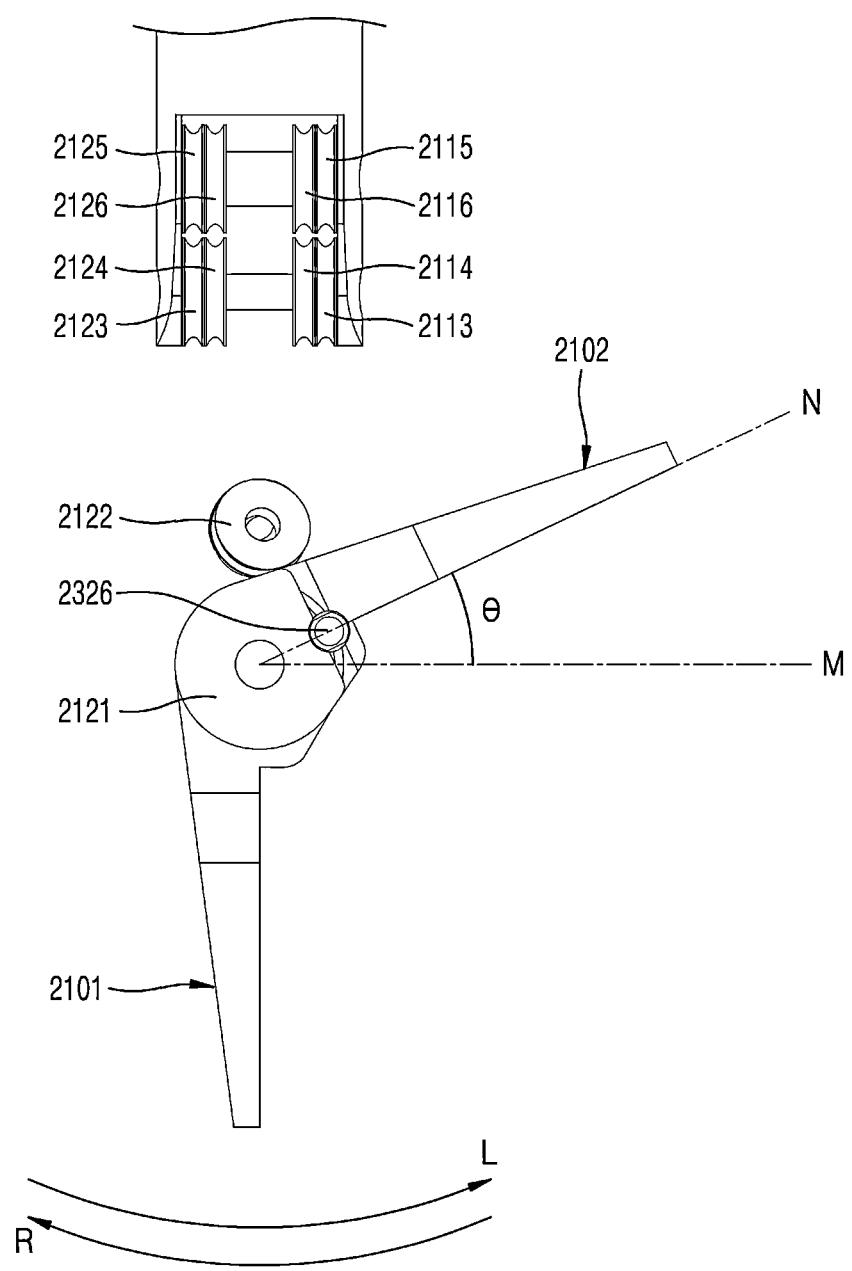
Figure 102:
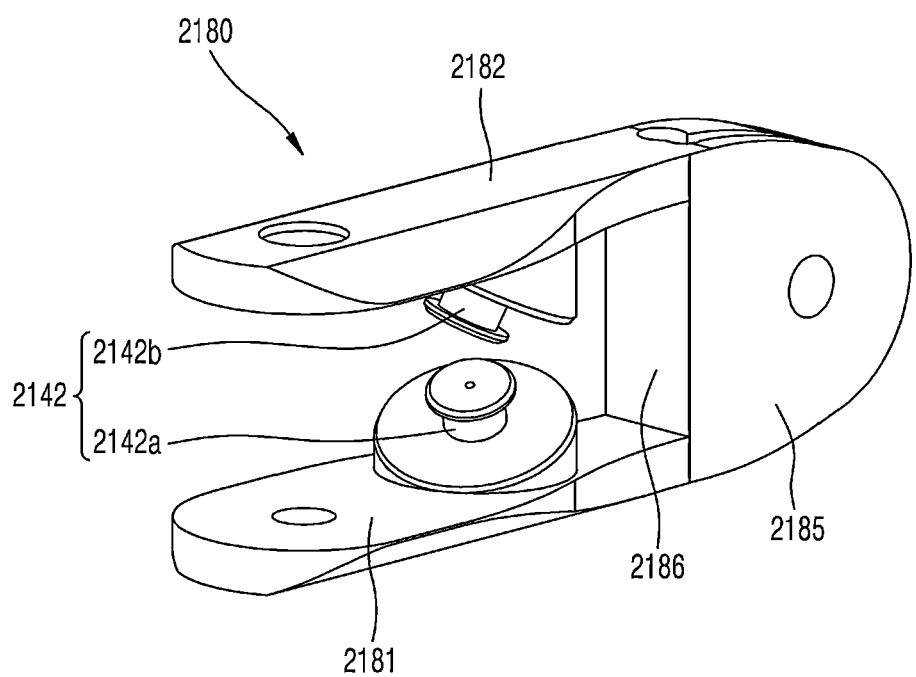
FIG. 102 is a perspective view of an end tool hub of the end tool of FIG. 91.
Figure 103:
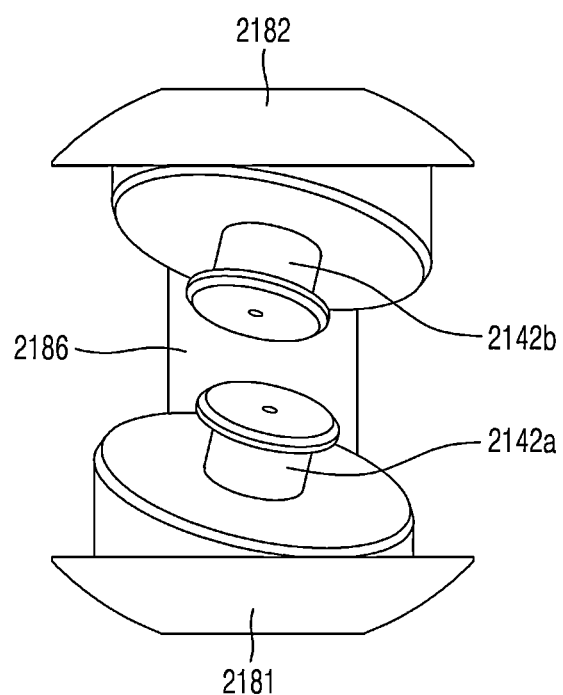
FIG. 103 is a front view of the end tool hub of the end tool of FIG. 91.
Figure 104:
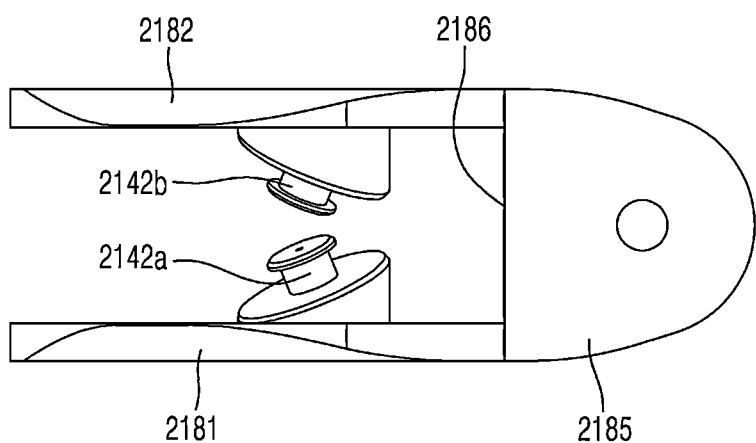
FIG. 104 is a side view of the end tool hub of the end tool of FIG. 91.

FIGS. 91, 92, 93, and 94 are perspective views illustrating an end tool of a surgical instrument according to the third embodiment of the present disclosure. FIGS. 95 and 96 are plan views of the end tool of FIG. 91. FIGS. 97, 98, and 99 are side views of the end tool of FIG. 91. FIGS. 100 and 101 are plan views of the end tool of FIG. 91. FIG. 102 is a perspective view of an end tool hub of the end tool of FIG. 91, FIG. 103 is a front view of the end tool hub of the end tool of FIG. 91, and FIG. 104 is a side view of the end tool hub of the end tool of FIG. 91.

Referring to FIGS. 91 to 104, a power transmission part 2300 of the end tool 2100 of the surgical instrument according to the third embodiment of the present disclosure may include a wire 2301, a wire 2302, a wire 2303, a wire 2304, a wire 2305, and a wire 2306. In the present embodiment, the wires are substantially the same as the wire 301, the wire 302, the wire 303, the wire 304, the wire 305, and the wire 306 of the first embodiment described above with reference to FIG. 9 and the like, and thus, detailed descriptions thereof will be omitted.

In addition, the power transmission part 2300 of the end tool 2100 of the surgical instrument according to the third embodiment of the present disclosure may include a coupling member 2321, a coupling member 2322, a coupling member 2323, a coupling member 2326, and the like, which are coupled to ends of the respective wires to combine the wires with the pulleys. In this regard, each of the coupling members may have various shapes as necessary, such as a ball shape, a tube shape, or the like. In the present embodiment, the coupling members are substantially the same as the coupling member 321, the coupling member 322, the coupling member 323, and the coupling member 326 of the first embodiment described above with reference to FIG. 9 and the like, and thus, detailed descriptions thereof will be omitted.

(End Tool)

Hereinafter, the end tool 2100 of the surgical instrument of FIG. 91 will be described in more detail.

Continuing to refer to FIGS. 91 to 104, the end tool 2100 of the third embodiment of the present disclosure includes a pair of jaws for performing a grip motion, that is, a first jaw 2101 and a second jaw 2102. In this regard, a component encompassing each of the first jaw 2101 and the second jaw 2102 or both the first jaw 2101 and the second jaw 2102 may be referred to as a jaw 2103.

In addition, the end tool 2100 may include a pulley 2111, a pulley 2112, a pulley 2113, a pulley 2114, a pulley 2115, and a pulley 2116, which are associated with a rotational motion of the first jaw 2101. In addition, the end tool 2100 may include a pulley 2121, a pulley 2122, a pulley 2123, a pulley 2124, a pulley 2125, and a pulley 2126, which are associated with a rotational motion of the second jaw 102. These pulleys will be described in more detail below.

In addition, the end tool 2100 of the third embodiment of the present disclosure may include an end tool hub 2180 and a pitch hub 2107. The end tool hub 2180 will be described in more detail below.

In this regard, the end tool hub 2180 may internally accommodate at least portions of the pulley 2111 and the pulley 2121 that are axially coupled to a rotation axis 2141. In addition, the end tool hub 2180 may internally accommodate at least portions of the pulley 2112 and the pulley 2122 that are axially coupled to a rotation axis 2142.

A rotation axis 2143 and a rotation axis 2144 may be inserted through the pitch hub 2107, and the pitch hub 2107 may be axially coupled to the end tool hub 2180 and a pulley 2131 by the rotation axis 2143. Thus, the end tool hub 2180 and the pulley 2131 (formed with the end tool hub 2180 as one body) may be formed to be rotatable around the rotation axis 2143 with respect to the pitch hub 2107.

In addition, the pitch hub 2107 may internally accommodate at least portions of the pulley 2113, the pulley 2114, the pulley 2123, and the pulley 2124 that are axially coupled to the rotation axis 2143. In addition, the pitch hub 2107 may internally accommodate at least portions of the pulley 2115, the pulley 2116, the pulley 2125, and the pulley 2126 that are axially coupled to the rotation axis 2144.

In addition, the end tool 2100 of the third embodiment of the present disclosure may include the rotation axis 2141, the rotation axis 2142, the rotation axis 2143, and the rotation axis 2144.

The rotation axis 2141, the rotation axis 2142, the rotation axis 2143, and the rotation axis 2144 may be sequentially arranged from a distal end 2104 of the end tool 2100 toward a proximal end 2105. Accordingly, starting from the distal end 2104, the rotation axis 2141 may be referred to as a first pin, the rotation axis 2142 may be referred to as a second pin, the rotation axis 2143 may be referred to as a third pin, and the rotation axis 2144 may be referred to as a fourth pin.

In this regard, the rotation axis 2141 may function as a jaw pulley rotation axis, the rotation axis 2142 may function as both a jaw auxiliary pulley rotation axis and a pitch redundant rotation axis, the rotation axis 2143 may function as a pitch main rotation axis, and the rotation axis 2144 may function as a pitch sub-rotation axis of the end tool 2100.

Hereinafter, the end tool hub 2180 of the third embodiment of the present disclosure will be described in more detail, and in particular, the rotation axis 2142 of the end tool hub 2180, which serves as a jaw auxiliary pulley rotation axis, will be mainly described.

Referring to FIGS. 102 to 104, and the like, the end tool hub 2180 includes a first jaw pulley coupling part 2181, a second jaw pulley coupling part 2182, the rotation axis 2142, a pitch pulley coupling part 2185, and a guide part 2186. In addition, the rotation axis 2142 may include a first sub-shaft 2142*a* and a second sub-shaft 2142*b*.

In detail, the first jaw pulley coupling part 2181 and the second jaw pulley coupling part 2182 are formed to face each other such that the pulley 2111, the pulley 2112, the pulley 2121, and the pulley 2122 are accommodated therein. In addition, a through hole is formed in each of the jaw pulley coupling parts 2181 and 2182 such that the rotation axis 2141 passes through and axially couples the jaw pulley coupling parts 2181 and 2182, the pulley 2111, and the pulley 2121.

The first jaw pulley coupling part 2181 and the second jaw pulley coupling part 2182 are connected to each other by the guide part 2186. That is, the first jaw pulley coupling part 2181 and the second jaw pulley coupling part 2182 parallel to each other are coupled by the guide part 2186 formed in a direction substantially perpendicular thereto, such that the first jaw pulley coupling part 2181, the second jaw pulley coupling part 2182, and the guide part 2186 form a substantially "C" shape in which the pulley 2111, the pulley 2112, the pulley 2121, and the pulley 2122 are accommodated.

In other words, it may also be described that the first jaw pulley coupling part 2181 and the second jaw pulley coupling part 2182 are formed to extend in the X-axis direction from both ends of the guide part 2186 that is elongated in the Z-axis direction.

The first sub-shaft 2142*a* may be formed on an inner surface of the first jaw pulley coupling part 2181, and the second sub-shaft 2142*b* may be formed on the second jaw pulley coupling part 2182. In other words, it may also be described that the second rotation axis 2142, which is a jaw auxiliary pulley rotation axis, is formed by being divided into the first sub-shaft 2142*a* and the second sub-shaft 2142*b*.

In detail, the first sub-shaft 2142*a* and the second sub-shaft 2142*b* may be formed to be inclined to a certain extent. In other words, the first sub-shaft 2142*a* and the second sub-shaft 2142*b* may be formed obliquely rather than parallel to any one of the X-axis, Y-axis, and Z-axis.

In addition, the pulley 2112 may be coupled to the first sub-shaft 2142*a*, and the pulley 2122 may be coupled to the second sub-shaft 2142*b*. In this regard, the pulley 2112 may function as both a first jaw auxiliary pulley and a first pitch redundant pulley. In addition, the pulley 2122 may function as both a second jaw auxiliary pulley and a second pitch redundant pulley. This will be described in detail below.

Meanwhile, the pulley 2131 that serves as an end tool pitch pulley may be formed in the pitch pulley coupling part 2185 at one end of the end tool hub 2180. In this regard, the pulley 2131 may be formed with the end tool hub 2180 as one body. That is, one end of the end tool hub 2180 may be formed in a disk shape or a semicircular shape, and a groove around which a wire may be wound may be formed on an outer circumferential surface of the groove, such that a kind of guide channel is formed. Alternatively, the pulley 2131 may be formed as a separate member from the end tool hub 2180 and coupled to the end tool hub 2180. The wire 2303 and the wire 2304 described above are coupled to the pulley 2131 serving as an end tool pitch pulley, and a pitch motion is performed as the pulley 2131 is rotated around the rotation axis 2143.

Meanwhile, one or more pulleys may be fit into each of the rotation axes 2141, 2142, 2143, and 2144, and this will be described in detail below.

The pulley 2111 functions as a first jaw pulley, the pulley 2121 functions as a second jaw pulley, and these two components may be collectively referred to as a jaw pulley.

The pulley 2111 and the pulley 2121, which are jaw pulleys, are formed to face each other, and are formed to be rotatable independently of each other around the rotation axis 2141, which is a jaw pulley rotation axis. In this regard, the drawings illustrate that the pulley 2111 and the pulley 2121 are formed to be rotated around one rotation axis 2141, but it is needless to say that each jaw pulley may be formed to be rotatable around a separate shaft. In this regard, the first jaw 2101 may be fixedly coupled to the pulley 2111 to be rotated together with the pulley 2111, and the second jaw 2102 may be fixedly coupled to the pulley 2121 to be rotated together with the pulley 2121. Yaw and actuation motions of the end tool 2100 are performed according to rotation of the pulley 2111 and the pulley 2121. That is, when the pulley 2111 and the pulley 2121 are rotated in the same direction around the rotation axis 2141, the yaw motion is performed, and when the pulley 2111 and the pulley 2121 are rotated in opposite directions around the rotation axis 2141, the actuation motion is performed.

In this regard, the first jaw 2101 and the pulley 2111 may be formed as separate members and coupled to each other, or the first jaw 2101 and the pulley 2111 may be formed as one body. Similarly, the second jaw 2102 and the pulley 2121 may be formed as separate members and coupled to each other, or the second jaw 2102 and the pulley 2121 may be formed as one body.

The pulley 2112 functions as a first jaw auxiliary pulley, the pulley 2122 functions as a second jaw auxiliary pulley, and these two components may be collectively referred to as a jaw auxiliary pulley. Simultaneously, the pulley 2112 may function as a first pitch redundant pulley, and the pulley 2122 may function as a second pitch redundant pulley.

In detail, the pulley 2112 and the pulley 2122, which are jaw auxiliary pulleys, may be additionally provided on one side of the pulley 2111 and the pulley 2121. In other words, the pulley 2112, which is a jaw auxiliary pulley, may be arranged between the pulley 2111 and the pulley 2113/pulley 2114. In addition, the pulley 2122, which is a jaw auxiliary pulley, may be arranged between pulley 2121 and pulley 2123/pulley 2124. The pulley 2112 may be formed to be rotatable around the first sub-shaft 2142*a* of the rotation axis 2142, and the pulley 2122 may be formed to be rotatable around the second sub-shaft 2142*b* of the rotation axis 2142.

The pulley 2113 and the pulley 2114 may function as first jaw pitch main pulleys, the pulley 2123 and the pulley 2124 may function as second jaw pitch main pulleys, and these two components may be collectively referred to as a pitch main pulley.

The pulley 2115 and the pulley 2116 may function as first jaw pitch sub-pulleys, the pulley 2125 and the pulley 2126 may function as second jaw pitch sub-pulleys, and these two components may be collectively referred to as a pitch sub-pulley.

Accordingly, the rotation axis 2141, the rotation axis 2142, the rotation axis 2143, and the rotation axis 2144 may be sequentially arranged from the distal end 2104 of the end tool 2100 toward the proximal end 2105.

In addition, the pulley 2111, the pulley 2112, the pulley 2113/pulley 2114, and the pulley 2115/pulley 2116, which are associated with rotation of the first jaw 2101, may be sequentially arranged from the distal end 2104 of the end tool 100 toward the proximal end 2105.

In addition, the pulley 2121, the pulley 2122, the pulley 2123/pulley 2124, and the pulley 2125/pulley 2126, which are associated with rotation of the second jaw 2102, may be sequentially arranged from the distal end 2104 of the end tool 100 toward the proximal end 2105.

Hereinafter, the pulley 2112 and the pulley 2122 will be described in more detail.

First, the pulley 2112 may function as a first jaw auxiliary pulley, and the pulley 2122 may function as a second jaw auxiliary pulley. The pulley 2112 and the pulley 2122 may come into contact with the wire 2305, which is a first jaw wire, and the wire 2302, which is a second jaw wire to change the arrangement path of the wire 2305 and the wire 2302 to a certain extent, and thus perform a function of increasing a rotation angle of each of the first jaw 2101 and the second jaw 2102. The role of the auxiliary pulley will be similar to that described in the first embodiment of the present disclosure.

Simultaneously, the pulley 2112 may function as a first pitch redundant pulley, and the pulley 2122 may function as a second pitch redundant pulley. The pitch redundant pulleys may serve to change insertion/withdrawal paths of jaw wires entering from the proximal end of the end tool to the distal end, or coming out from the distal end to the proximal end.

In this regard, a plane passing between the pulley 2111, which is a first jaw pulley, and the pulley 2121, which is a second jaw pulley, is defined as a first plane, the side above the first plane in the +Z-axis direction is defined as an upper side, and the side below the first plane in the −Z-axis direction is defined as a lower side.

The wire 2305, which is a first jaw wire, is located on the upper side of the first plane when passing through the pulley 2114, which is a first jaw pitch main pulley, then the path of the wire 2305 is changed as the wire 2305 passes through the pulley 2112, which is a first pitch redundant pulley, and when the wire 2305 passes through the pulley 2111, which is a first jaw pulley, the wire 2305 is located on the lower side of the first plane.

In this regard, the first sub-shaft 2142*a* and the pulley 2112 coupled thereto are formed to be inclined with respect to the first plane, to serve to guide the path of the wire 2305 such that the wire 2305, which is located on the upper side of the first plane when in contact with the pulley 2114, is located on the lower side of the first plane when in contact with the pulley 2111.

That is, as illustrated in FIG. 103, the first sub-shaft 2142*a* and the pulley 2112 coupled thereto may be formed to be inclined to a certain extent on a YZ plane. In addition, as illustrated in FIG. 104, the first sub-shaft 2142*a* and the pulley 2112 coupled thereto may be formed to be inclined to a certain extent on an XZ plane.

Similarly, the wire 2302, which is a second jaw wire, is located on the lower side of the first plane when passing through the pulley 2124, which is a second jaw pitch main pulley, then the path of the wire 2302 is changed as the wire 2302 passes through the pulley 2122, which is a second pitch redundant pulley, and when the wire 2302 passes through the pulley 2121, which is a second jaw pulley, the wire 2302 is located on the upper side of the first plane.

In this regard, the second sub-shaft 2142*b* and the pulley 2122 coupled thereto are formed to be inclined with respect to the first plane, to serve to guide the path of the wire 2302 such that the wire 2302, which is located on the lower side of the first plane when in contact with the pulley 2124, is located on the upper side of the first plane when in contact with the pulley 2121.

That is, as illustrated in FIG. 103, the second sub-shaft 2142*b* and the pulley 2122 coupled thereto may be formed to be inclined to a certain extent on a YZ plane. In addition, as illustrated in FIG. 104, the second sub-shaft 2142*b* and the pulley 2122 coupled thereto may be formed to be inclined to a certain extent on an XZ plane.

Hereinafter, components associated with the rotation of the pulley 2111 will be described.

The pulley 2113 and the pulley 2114 are paired to function as first jaw pitch main pulleys. That is, the pulley 2113 and the pulley 2114 function as main rotation pulleys for a pitch motion of the first jaw 2101. In this regard, the wire 2301, which is a first jaw wire, is wound around the pulley 2113, and the wire 2305, which is a first jaw wire, is wound around the pulley 2114.

The pulley 2115 and the pulley 2116 are paired to function as first jaw pitch sub-pulleys. That is, the pulley 2115 and the pulley 2116 function as sub-rotation pulleys for a pitch motion of the first jaw 2101. In this regard, the wire 2301, which is a first jaw wire, is wound around the pulley 2115, and the wire 2305, which is a first jaw wire, is wound around the pulley 2116.

In this regard, the pulley 2113 and the pulley 2114 are arranged on one side of the pulley 2111 and the pulley 2112 to face each other. In this regard, the pulley 2113 and the pulley 2114 are formed to be rotatable independently of each other around the rotation axis 2143, which is a pitch main rotation axis. In addition, the pulley 2115 and the pulley 2116 are arranged on one sides of the pulley 2113 and the pulley 2114, respectively, to face each other. In this regard, the pulley 2115 and the pulley 2116 are formed to be rotatable independently of each other around the rotation axis 2144, which is a pitch sub-rotation axis. In this regard, the drawings illustrate that the pulley 2113, the pulley 2114, the pulley 2115, and the pulley 2116 are formed to be rotatable around the Y-axis direction, but the concept of the present disclosure is not limited thereto, and the rotation axes of the respective pulleys may be formed in various directions according to their configurations.

The wire 2301, which is a first jaw wire, is wound to sequentially come into contact with at least portions of the pulley 2115, the pulley 2113, and the pulley 2111. In addition, the wire 2305 connected to the wire 2301 by the coupling member 2323 is wound to sequentially come into contact with at least portions of the pulley 2111, the pulley 2112, the pulley 2114, and the pulley 2116.

In other words, the wire 2301 and the wire 2305, which are first jaw wires, are wound to sequentially come into contact with at least portions of the pulley 2115, the pulley 2113, the pulley 2111, the pulley 2112, the pulley 2114, and the pulley 2116, and are formed to move along the above pulleys while rotating the above pulleys.

Accordingly, when the wire 2301 is pulled in the direction of an arrow 2301 of FIG. 100, the coupling member 2323 to which the wire 2301 is coupled and the pulley 2111 coupled to the coupling member 2323 are rotated in the direction of an arrow L of FIG. 100. On the contrary when the wire 2305 is pulled in the direction of an arrow 2305 of FIG. 100, the coupling member 2323 to which the wire 2305 is coupled and the pulley 2111 coupled to the coupling member 2323 are rotated in the direction of an arrow R of FIG. 100.

Next, components associated with the rotation of the pulley 2121 will be described.

The pulley 2123 and the pulley 2124 are paired to function as second jaw pitch main pulleys. That is, the pulley 2123 and the pulley 2124 function as main rotation pulleys for a pitch motion of the second jaw 2102. In this regard, the wire 2306, which is a second jaw wire, is wound around the pulley 2123, and the wire 2302, which is a second jaw wire, is wound around the pulley 2124.

The pulley 2125 and the pulley 2126 are paired to function as second jaw pitch sub-pulleys. That is, the pulley 2125 and the pulley 2126 may function as sub-rotation pulleys for a pitch motion of the second jaw 2102. In this regard, the wire 2306, which is a second jaw wire, is wound around the pulley 2125, and the wire 2302, which is a second jaw wire, is wound around the pulley 2126.

In this regard, the pulley 2123 and the pulley 2124 are arranged on one side of the pulley 2121 and the pulley 2122 to face each other. In this regard, the pulley 2123 and the pulley 2124 are formed to be rotatable independently of each other around the rotation axis 2143, which is a pitch main rotation axis. In addition, the pulley 2125 and the pulley 2126 are arranged on one sides of the pulley 2123 and the pulley 2124, respectively, to face each other. In this regard, the pulley 2125 and the pulley 2126 are formed to be rotatable independently of each other around the rotation axis 2144, which is a pitch sub-rotation axis. In this regard, the drawings illustrate that the pulley 2123, the pulley 2124, the pulley 2125, and the pulley 2126 are formed to be rotatable around the Y-axis direction, but the concept of the present disclosure is not limited thereto, and the rotation axes of the respective pulleys may be formed in various directions according to their configurations.

The wire 2306, which is a second jaw wire, is wound to sequentially come into contact with at least portions of the pulley 2125, the pulley 2123, and the pulley 2121. In addition, the wire 2302 connected to the wire 2306 by the coupling member 2326 is wound to sequentially come into contact with at least portions of the pulley 2121, the pulley 2122, the pulley 2124, and the pulley 2126.

In other words, the wire 2306 and the wire 2302, which are second jaw wires, are wound to sequentially come into contact with at least portions of the pulley 2125, the pulley 2123, the pulley 2121, the pulley 2122, the pulley 2124, and the pulley 2126, and are formed to move along the above pulleys while rotating the above pulleys.

Accordingly, when the wire 2306 is pulled in the direction of an arrow 2306 of FIG. 100, the coupling member 2326 to which the wire 2306 is coupled and the pulley 2121 coupled to the coupling member 2326 are rotated in the direction of an arrow R of FIG. 100. On the contrary, when the wire 2302 is pulled in the direction of an arrow 2302 of FIG. 100, the coupling member 2326 to which the wire 2302 is coupled and the pulley 2121 coupled to the coupling member 2326 are rotated in the direction of an arrow L of FIG. 100.

In this regard, according to the present disclosure, two strands of jaw wires wound around one jaw pulley are wound around pitch main pulleys in opposite directions, such that a pitch motion is easily controlled.

In detail, when the side above, in the +Z-axis direction, a plane passing between the pulley 2111, which is a first jaw pulley, and the pulley 2121, which is a second jaw pulley (i.e., an XY plane) is defined as an upper side and the side below the plane in the −Z-axis direction is defined as a lower side, any one (e.g., the wire 2301) of the two strands of the first jaw wires may enter the pulley 2113, which is a first jaw pitch main pulley, from the lower side of the XY plane, and the other strand (e.g., the wire 2305) may come out of the pulley 2114, which is a first jaw pitch main pulley, from the upper side of the XY plane. In other words, it may be described as a structure in which the first jaw wire enters the first jaw pitch main pulley from the lower side and comes out from the upper side. (The second jaw wire enters the second jaw pitch main pulley from the upper side and comes out from the lower side)

In other words, the wire 2301, which is one strand of the first jaw wires, sequentially comes into contact with the upper side of the pulley 2115 and the lower side of the pulley 2113, and then comes into contact with the pulley 2111. Next, the wire 2305, which is the other strand of the first jaw wires, is wound around the pulley 2111 and the pulley 2112, and then sequentially comes into contact with the upper side of the pulley 2114, and the lower side of the pulley 2116, and then comes out toward the connection part 400. Accordingly, the first jaw wire comes out of a connection part 2400, enters the pulley 2113 from the lower side, then passes through each pulley, then passes through the upper side of the pulley 2114, and then enters back the connection part 400.

Similarly, the wire 2306, which is one strand of the second jaw wires, sequentially comes into contact with the lower side of the pulley 2125 and the upper side of the pulley 2123, and then comes into contact with the pulley 2121. Next, the wire 2302, which is the other strand of the second jaw wires, is wound around the pulley 2121 and the pulley 2122, and then sequentially comes into contact with the lower side of the pulley 2124 and the upper side of the pulley 2126, and then comes out toward the connection part 400. Accordingly, the second jaw wire comes out of the connection part 400, enters the pulley 2123 from the upper side, then passes through each pulley, then passes through the lower side of the pulley 2124, and then enters back the connection part 2400.

In other words, it may also be described that, any one wire of the two strands of the first jaw wires is wound around the first jaw pitch main pulley in any one of the clockwise direction and the counterclockwise direction while moving toward the end tool 2100 from a connection part 2400, and the other wire is wound around the first jaw pitch main pulley in the other one of the clockwise direction and the counterclockwise direction while moving toward the end tool 2100 from the connection part 2400. That is, as illustrated in FIGS. 97, 98, and 99, the wire 2301 is wound in the clockwise direction while moving toward the end tool 2100 from the connection part 2400, and the wire 2305 is wound in the counterclockwise direction while moving toward the end tool 2100 from the connection part 400.

Similarly, it may also be described that, any one wire of the two strands of the second jaw wires is wound around the second jaw pitch main pulley in any one of the clockwise direction and the counterclockwise direction while moving toward the end tool 2100 from the connection part 2400, and the other wire is wound around the second jaw pitch main pulley in the other one of the clockwise direction and the counterclockwise direction while moving toward the end tool 2100 from the connection part 2400. That is, as illustrated in FIGS. 97, 98, and 99, the wire 2302 is wound in the clockwise direction while moving toward the end tool 2100 from the connection part 2400, and the wire 2306 is wound in the counterclockwise direction while moving toward the end tool 2100 from the connection part 400.

As such, the end tool 2100 of the surgical instrument according to an embodiment of the present disclosure may obtain an effect of facilitating control of the pitch motion as the two strands of the jaw wires wound around one jaw pulley are wound around the pitch main pulleys in opposite directions. That is, during a pitch motion, the drive part first jaw pulley (see 211, 212 of FIG. 21) and the drive part second jaw pulley (see 221, 222 of FIG. 21) are rotated to wind or unwind the jaw wires, and thus perform a kind of compensation for the pitch motion, enabling the pitch motion of the end tool 2100.

As such, the present disclosure has been described with reference to one embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL APPLICABILITY

The present disclosure relates to a surgical instrument, and more particularly, may be used in a surgical instrument capable of being mounted on a robot arm or operated manually for use in laparoscopic surgery or various surgeries.

The invention claimed is:
1. A surgical instrument comprising:
an end tool configured to allow at least a pitch rotation and a yaw rotation, the end tool including:
  a first jaw,
  a second jaw disposed to face the first jaw,
  a first jaw pulley coupled to the first jaw and configured to be rotatable around a first shaft, and
  a second jaw pulley coupled to the second jaw and disposed to face the first jaw pulley and configured to be rotatable around the first shaft or around an axis that is parallel to the first shaft,
  a pair of first jaw pitch main pulleys configured to be rotatable around a fourth shaft that forms a predetermined angle with the first shaft, and disposed on one side with respect to a plane perpendicular to the fourth shaft, passing between the first jaw and the second jaw, and
  a pair of second jaw pitch main pulleys configured to be rotatable around the fourth shaft or around an axis that is parallel to the fourth shaft, and disposed on another side with respect to the plane;
a jaw wire including a first jaw wire coupled to the first jaw pulley configured to rotate the first jaw pulley and a second jaw wire coupled to the second jaw pulley configured to rotate the second jaw pulley;
a connection portion disposed to extend in one direction, having the first jaw wire and the second jaw wire passing therethrough, and having one end portion to which the end tool is coupled; and a driving part coupled to another end portion of the connection portion and configured to control the pitch rotation and the yaw rotation of the end tool,
the driving part including:
  a driving part first jaw pulley coupled to the first jaw wire and configured to be rotatable around a second shaft and move the first jaw wire,
  a driving part second jaw pulley coupled to the second jaw wire and configured to be rotatable around the second shaft or an axis parallel to the second shaft and move the second jaw wire, and
  a driving part pitch pulley disposed adjacent to the driving part first jaw pulley and the driving part second jaw pulley and configured to be rotatable around a third shaft different from the second shaft,
wherein a relative position of the driving part first jaw pulley, the driving part second jaw pulley and the driving part pitch pulley remains constant,
wherein two strands of the first jaw wire coupled to the first jaw pulley are wound in opposite directions around the pair of first jaw pitch main pulleys,
wherein two strands of the second jaw wire coupled to the second jaw pulley are wound in opposite directions around the pair of second jaw pitch main pulleys, and
wherein when the driving part pitch pulley is rotated for the pitch rotation of the end tool, the driving part first jaw pulley and the driving part second jaw pulley are also rotated to compensate a movement of the first jaw wire and the second jaw wire respectively.

2. The surgical instrument of claim 1, wherein when the driving part pitch pulley is rotated around the third shaft, the driving part first jaw pulley is rotated around the second shaft to change a length of the first jaw wire in the driving part.

3. The surgical instrument of claim 2, wherein as the length of the first jaw wire in the driving part is changed due to a rotation of the driving part first jaw pulley, a length of the first jaw wire in the end tool is changed.

4. The surgical instrument of claim 2, wherein even when the length of the first jaw wire in the driving part is changed due to a rotation of the driving part first jaw pulley, an overall length of the first jaw wire remains constant.

5. The surgical instrument of claim 1, wherein the end tool includes:
  a first jaw pitch redundant pulley disposed between the first jaw pulley and the pair of first jaw pitch main pulleys and configured to be rotatable around a fifth shaft; and
  a second jaw pitch redundant pulley disposed between the second jaw pulley and the pair of second jaw pitch main pulleys and configured to be rotatable around a sixth shaft.

6. The surgical instrument of claim 5, wherein while moving from a proximal end of the end tool toward a distal end of the end tool, the first jaw wire sequentially comes into contact with the pair of first jaw pitch main pulleys and the first jaw pitch redundant pulley.

7. The surgical instrument of claim 6, wherein based on a plane perpendicular to the first shaft and passing between the first jaw pulley and the second jaw pulley, among the two strands of the first jaw wire coupled to the first jaw pulley, one strand of the first jaw wire sequentially comes into contact with a lower side of one of the pair of first jaw pitch main pulleys and a lower side of the first jaw pitch redundant pulley, and among the two strands of the first jaw wire coupled to the first jaw pulley, another strand of the first jaw wire sequentially comes into contact with an upper side of another of pair of first jaw pitch main pulleys and an upper side of the first jaw pitch redundant pulley.

8. The surgical instrument of claim 5, further comprising:
a first jaw auxiliary pulley disposed between the first jaw pulley and the first jaw pitch redundant pulley; and
a second jaw auxiliary pulley disposed between the second jaw pulley and the second jaw pitch redundant pulley.

9. The surgical instrument of claim 8,
wherein the first jaw wire is located on a common internal tangent of the first jaw pulley and the first jaw auxiliary pulley, and
wherein a rotation angle of the first jaw pulley is increased by the first jaw auxiliary pulley.

10. The surgical instrument of claim 5, further comprising:
an end tool hub formed to internally accommodate at least some of the first jaw and the second jaw; and
a pitch hub configured to be rotatable relative to the end tool hub by being axially coupled to the end tool hub.

11. The surgical instrument of claim 10,
wherein the first jaw and the second jaw are rotated around the first shaft to perform a yaw motion, and
wherein the end tool hub is rotated around the fourth shaft to perform a pitch motion.

12. The surgical instrument of claim 10, further comprising:
an end tool pitch pulley disposed on an end portion of the end tool hub at a proximal end side; and
a pitch wire coupled to the end tool pitch pulley to rotate the end tool pitch pulley.

13. The surgical instrument of claim 12, wherein when the end tool pitch pulley is rotated by the pitch wire, the end tool hub is rotated as a whole together with the end tool pitch pulley to change a length of the first jaw wire wound around the pair of first jaw pitch main pulleys and the pair of second jaw pitch main pulleys.

14. The surgical instrument of claim 13, wherein when the end tool pitch pulley is rotated by the pitch wire, the two strands of the first jaw wire is moved to a predetermined degree by an external force in order to compensate for an amount of change in the length by which the two strands of the first jaw wire is wound around each of the pair of first jaw pitch main pulleys, respectively.

15. The surgical instrument of claim 10, wherein the first jaw pitch redundant pulley or the second jaw pitch redundant pulley is integrally formed with the end tool hub.

16. The surgical instrument of claim 5, wherein the fifth shaft and the sixth shaft are substantially parallel to the fourth shaft.

17. The surgical instrument of claim 5, wherein the fifth shaft and the sixth shaft are formed to be inclined with respect to the first shaft and the fourth shaft, respectively.

18. The surgical instrument of claim 5, wherein the first jaw pitch redundant pulley or the second jaw pitch redundant pulley includes only one pulley.

19. The surgical instrument of claim 1, wherein while moving from a proximal end of the end tool toward a distal end of the end tool, among the two strands of the first jaw wire coupled to the first jaw pulley, one strand of the first jaw wire is wound in one direction of a clockwise direction and a counterclockwise direction around one of the pair of first jaw pitch main pulleys, and another strand of the first jaw wire is wound in another direction of the clockwise direction and the counterclockwise direction around another of the pair of first jaw pitch main pulleys.

20. The surgical instrument of claim 1, wherein based on a plane perpendicular to the first shaft and passing between the first jaw pulley and the second jaw pulley, among the two strands of the first jaw wire coupled to the first jaw pulley, one strand of the first jaw wire comes into contact with an upper side of one of the pair of first jaw pitch main pulleys, and another strand of the first jaw wire comes into contact with a lower side of another of the pair of first jaw pitch main pulleys.

21. The surgical instrument of claim 1, further comprising:
one or more first jaw pitch sub-pulleys formed on one side of the pair of first jaw pitch main pulleys and configured to be rotatable around a shaft substantially parallel to the fourth shaft; and
one or more second jaw pitch sub-pulleys formed on one side of the pair of second jaw pitch main pulleys and configured to be rotatable around a shaft substantially parallel to the fourth shaft.

22. The surgical instrument of claim 21, wherein the one or more first jaw pitch sub-pulleys or the one or more second jaw pitch sub-pulleys includes only one pulley.

23. The surgical instrument of claim 1, wherein a groove of the first jaw pulley around which the first jaw wire is wound and a groove of the second jaw pulley around which the second jaw wire is wound are formed to be spaced apart from each other by a predetermined degree.

24. The surgical instrument of claim 1, wherein a groove of the first jaw pulley around which the first jaw wire is wound and a groove of the second jaw pulley around which the second jaw wire is wound are formed to be adjacent to each other.

25. The surgical instrument of claim 1, wherein when the driving part pitch pulley of the driving part is rotated for a pitch motion, a driving part first jaw pulley and a driving part second jaw pulley of the driving part are rotated together to compensate for the pitch motion.

26. The surgical instrument of claim 1, comprising:
an end tool hub configured to internally accommodate at least some of the first jaw and the second jaw;
a pitch hub configured to be rotatable relative to the end tool hub by being axially coupled to the end tool hub;
a first pin configured to be inserted through the end tool hub, and formed to be the first shaft extending in a first direction;
a second pin configured to be inserted through the end tool hub, disposed to be parallel to the first pin, and disposed on one side of the first pin;
a 2.5th pin configured to be inserted through the end tool hub, disposed to extend in a second direction forming a predetermined angle with the first direction, and disposed on one side of the second pin;
a third pin configured to be inserted through the end tool hub and the pitch hub, disposed to be parallel to the 2.5th pin, and disposed on one side of the 2.5th pin;
a fourth pin configured to be inserted through the pitch hub, disposed to be parallel to the third pin, and formed to be the fourth shaft on one side of the third pin;
a first jaw auxiliary pulley disposed on one side of the first jaw pulley, and configured to be rotatable around the second pin;
a second jaw auxiliary pulley disposed on one side of the second jaw pulley, and configured to be rotatable around the second pin;
one or more first jaw pitch redundant pulleys disposed on one side of the first jaw auxiliary pulley, and configured to be rotatable around the 2.5th pin;

one or more second jaw pitch redundant pulleys disposed on one side of the second jaw auxiliary pulley, and configured to be rotatable around the 2.5th pin;

the pair of first jaw pitch main pulleys disposed on one side of the one or more first jaw pitch redundant pulleys, and configured to be rotatable around the third pin;

the pair of second jaw pitch main pulleys disposed on one side of the one or more second jaw pitch redundant pulleys, and configured to be rotatable around the third pin;

one or more first jaw pitch sub-pulleys formed on one side of the pair of first jaw pitch main pulleys, and configured to be rotatable around the fourth pin; and one or more second jaw pitch sub-pulleys formed on one side of the pair of second jaw pitch main pulleys, and configured to be rotatable around the fourth pin.

27. The surgical instrument of claim 1, comprising:

an end tool hub configured to internally accommodate at least some of the first jaw and the second jaw;

a pitch hub configured to be rotatable relative to the end tool hub by being axially coupled to the end tool hub;

a first pin configured to be inserted through the end tool hub, and formed to be the first shaft extending in a first direction;

a second pin configured to be inserted through the end tool hub, disposed to extend in a second direction forming a predetermined angle with the first direction, and disposed on one side of the first pin;

a third pin configured to be inserted through the end tool hub and the pitch hub, disposed to extend in a third direction forming a predetermined angle with the first direction and the second direction, and disposed on one side of the second pin;

a fourth pin configured to be inserted through the pitch hub, disposed to be parallel to the third pin, and formed to be the fourth shaft on one side of the third pin;

a first jaw auxiliary pulley disposed on one side of the first jaw pulley, and configured to be rotatable around the second pin;

a second jaw auxiliary pulley disposed on one side of the second jaw pulley, and configured to be rotatable around the second pin;

the pair of first jaw pitch main pulleys disposed on one side of the first jaw auxiliary pulley, and configured to be rotatable around the third pin;

the pair of second jaw pitch main pulleys disposed on one side of the second jaw auxiliary pulley, and configured to be rotatable around the third pin;

one or more first jaw pitch sub-pulleys formed on one side of the pair of first jaw pitch main pulleys, and configured to be rotatable around the fourth pin; and one or more second jaw pitch sub-pulleys formed on one side of the pair of second jaw pitch main pulleys, and configured to be rotatable around the fourth pin.

* * * * *